United States Patent
Jones et al.

(10) Patent No.: US 11,053,198 B2
(45) Date of Patent: *Jul. 6, 2021

(54) 1-CYANO-PYRROLIDINE COMPOUNDS AS USP30 INHIBITORS

(71) Applicant: MISSION THERAPEUTICS LIMITED, Cambridge (GB)

(72) Inventors: Alison Jones, Cambridge (GB); Mark Kemp, Cambridge (GB); Martin Stockley, Cambridge (GB); Karl Gibson, Sandwich (GB); Gavin Whitlock, Sandwich (GB)

(73) Assignee: MISSION THERAPEUTICS LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/297,937

(22) Filed: Mar. 11, 2019

(65) Prior Publication Data
US 2019/0270708 A1 Sep. 5, 2019

Related U.S. Application Data

(62) Division of application No. 15/558,632, filed as application No. PCT/GB2016/050851 on Mar. 24, 2016, now Pat. No. 10,343,992.

(30) Foreign Application Priority Data

Mar. 30, 2015 (GB) ...................................... 1505429
Jul. 21, 2015 (GB) ...................................... 1512829

(51) Int. Cl.
| | |
|---|---|
| C07D 211/56 | (2006.01) |
| C07D 403/12 | (2006.01) |
| C07D 401/14 | (2006.01) |
| C07D 413/14 | (2006.01) |
| C07D 401/12 | (2006.01) |
| C07D 403/14 | (2006.01) |
| C07D 413/12 | (2006.01) |
| C07D 417/12 | (2006.01) |
| C07D 417/14 | (2006.01) |
| C07D 471/04 | (2006.01) |
| C07D 487/04 | (2006.01) |
| C07D 207/14 | (2006.01) |

(52) U.S. Cl.
CPC .......... *C07D 211/56* (2013.01); *C07D 207/14* (2013.01); *C07D 401/12* (2013.01); *C07D 401/14* (2013.01); *C07D 403/12* (2013.01); *C07D 403/14* (2013.01); *C07D 413/12* (2013.01); *C07D 413/14* (2013.01); *C07D 417/12* (2013.01); *C07D 417/14* (2013.01); *C07D 471/04* (2013.01); *C07D 487/04* (2013.01)

(58) Field of Classification Search
CPC .................................................... C07D 211/56
USPC ..................................................... 514/210.18
See application file for complete search history.

(56) References Cited

U.S. PATENT DOCUMENTS

| | | | | |
|---|---|---|---|---|
| 6,835,727 | B2 * | 12/2004 | Okamoto | C07D 205/04 514/210.2 |
| 10,343,992 | B2 * | 7/2019 | Jones | C07D 211/56 |
| 10,689,345 | B2 * | 6/2020 | Jones | C07D 403/14 |
| 2004/0073029 | A1 | 4/2004 | Pruitt et al. | |
| 2009/0326020 | A1 | 12/2009 | Miller et al. | |

FOREIGN PATENT DOCUMENTS

| | | |
|---|---|---|
| WO | 2010051188 A1 | 5/2010 |
| WO | 2010111059 A1 | 9/2010 |
| WO | 2012040527 A2 | 3/2012 |
| WO | 2013106643 A2 | 7/2013 |
| WO | 2014152588 A1 | 9/2014 |

OTHER PUBLICATIONS

Dorwald F. A. Side Reactions in Organic Synthesis, 2005, Wiley: VCH, Weinheim p. IX of Preface p. 1-15.*
Venkatesh et al., J. Pharm. Sci. 89, 145-54 (2000).*
Cannon, Chapter Nineteen in Burger's Medicinal Chemistry and Drug Discovery, Fifth Edition, vol. I: Principles and Practice, Wiley-lnterscience 1995, pp. 783-802, 784.*
Laine, D. et al ACS Med. Chem. Lett. 2011 vol. 2 pp. 142-147.*
Falgueyret, Journal of Medicinal Chemistry (2001), 44(1), 94-104.*
Laine, ACS Medicinal Chemistry Letters (2011), 2(2), 142-147.*
Morgan, Organic Letters (2002), 4(4), 597-598.*
The US office actions, dated Nov. 19, 2019 and dated Jan. 30, 2020, in the related U.S. Appl. No. 16/419,558.
CAPLUS 2004:500870.

* cited by examiner

*Primary Examiner* — Nizal S Chandrakumar

(57) ABSTRACT

The present invention relates to novel compounds and method for the manufacture of inhibitors of deubiquitylating enzymes (DUBs). In particular, the invention relates to the inhibition of ubiquitin C-terminal hydrolase 30 (USP30). The invention further relates to the use of DUB inhibitors in the treatment of conditions involving mitochondrial dysfunction and cancer. Compounds of the invention include compounds having the formula (II) or a pharmaceutically acceptable salt thereof, wherein $R^1$, $R^2$, $R^3$, $R^4$, $R^5$, $R^8$, $R^9$, $R^{10}$, $R^{12}$, Z, Y and m are as defined herein.

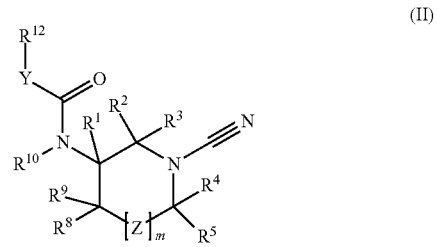

(II)

4 Claims, 1 Drawing Sheet

USP30 kinetic assay for high throughput screening of compounds using an isopeptide linked substrate
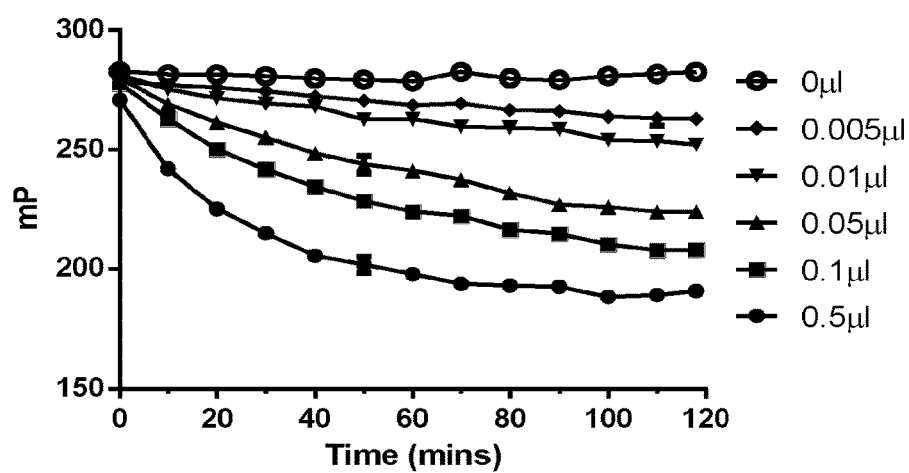

1-CYANO-PYRROLIDINE COMPOUNDS AS USP30 INHIBITORS

CROSS-REFERENCE TO RELATED APPLICATIONS

This application is a Divisional of U.S. patent application Ser. No. 15/558,632, filed Sep. 15, 2017, which in turn is a National Stage Application of PCT/GB2016/050851, filed Mar. 24, 2016, which claims priority from UK Patent Application No. 1505429.9, filed on Mar. 30, 2015 and UK Patent Application No. 1512829.1, filed on Jul. 21, 2015. The priority of said PCT and UK Patent Applications are claimed. Each of the prior mentioned applications is hereby incorporated by reference herein in its entirety.

The present invention relates to novel compounds and methods for the manufacture of inhibitors of deubiquitylating enzymes (DUBs). In particular, the invention relates to the inhibition of ubiquitin C-terminal hydrolase 30 (USP30). The invention further relates to the use of DUB inhibitors in the treatment of conditions involving mitochondrial dysfunction and in the treatment of cancer.

BACKGROUND TO THE INVENTION

The listing or discussion of an apparently prior-published document in this specification should not necessarily be taken as an acknowledgement that the document is part of the state of the art or is common general knowledge.

Ubiquitin is a small protein consisting of 76 amino acids that is important for the regulation of protein function in the cell. Ubiquitylation and deubiquitylation are enzymatically mediated processes by which ubiquitin is covalently bound or cleaved from a target protein by deubiquitylating enzymes (DUBs), of which there are approximately 95 DUBs in human cells, divided into sub-families based on sequence homology. The USP family are characterised by their common Cys and His boxes which contain Cys and His residues critical for their DUB activities. The ubiquitylation and deubiquitylation processes have been implicated in the regulation of many cellular functions including cell cycle progression, apoptosis, modification of cell surface receptors, regulation of DNA transcription and DNA repair. Thus, the ubiquitin system has been implicated in the pathogenesis of numerous disease states including inflammation, viral infection, metabolic dysfunction, CNS disorders, and oncogenesis (Clague et al., Physiol Rev 93:1289-1315, 2013).

Ubiquitin is a master regulator of mitochondrial dynamics. Mitochondria are dynamic organelles whose biogenesis, fusion and fission events are regulated by the post-translational regulation via ubiquitylation of many key factors such as mitofusins. While ubiquitin ligases such as parkin are known to ubiquitylate a number of mitochondrial proteins, until recently, deubiquitylating enzymes remained elusive. USP30 is a 517 amino acid protein which is found in the mitochondrial outer membrane (Nakamura et al., Mol Biol 19:1903-11, 2008). It is the sole deubiquitylating enzyme bearing a mitochondrial addressing signal and has been shown to deubiquitylate a number of mitochondrial proteins. It has been demonstrated that USP30 opposes parkin-mediated mitophagy and that reduction of USP30 activity can rescue parkin-mediated defects in mitophagy (Bingol et al., Nature 510:370-5, 2014).

Mitochondrial dysfunction can be defined as diminished mitochondrial content (mitophagy or mitochondrial biogenesis), as a decrease in mitochondrial activity and oxidative phosphorylation, but also as modulation of reactive oxygen species (ROS) generation. Hence a role for mitochondrial dysfunctions in a very large number of aging processes and pathologies including but not limited to, neurodegenerative diseases (e.g. Parkinson's disease (PD), Alzheimer's disease, Huntington's disease, Amylotrophic Lateral Sclerosis (ALS), muscular sclerosis), cancer, diabetes, metabolic disorders, cardio-vascular diseases, psychiatric diseases (e.g. Schizophrenia), and osteoarthritis.

For example, Parkinson's disease affects around 10 million people worldwide (Parkinson's Disease Foundation) and is characterised by the loss of dopaminergic neurons in the substantia nigra. The exact mechanisms underlying PD are unclear; however mitochondrial dysfunction is increasingly appreciated as a key determinant of dopaminergic neuronal susceptibility in PD and is a feature of both familial and sporadic disease, as well as in toxin-induced Parkinsonism. Parkin is one of a number of proteins that have been implicated with early onset PD. While most PD cases arw linked to defects in alpha-synuclein, 10% of Parkinson's cases are linked to specific genetic defects, one of which is in the ubiquitin E3 ligase parkin. Parkin and the protein kinase PTEN-induced putative kinase 1 (PINK1) collaborate to ubiquitylate mitochondrial membrane proteins of damaged mitochondria resulting in mitophagy. Dysregulation of mitophagy results in increased oxidative stress, which has been described as a characteristic of PD. Inhibition of USP30 could therefore be a potential strategy for the treatment of PD. For example, PD patients with parkin mutations leading to reduced activity could be therapeutically compensated by inhibition of USP30.

It has been reported that depletion of USP30 enhances mitophagic clearance of mitochondria and also enhances parkin-induced cell death (Liang et al., EMBO Reports 2015 DOI: 10.15252/embr.201439820). USP30 has also been shown to regulate BAX/BAK-dependent apoptosis independently of parkin over expression. Depletion of USP30 sensitises cancer cells to BH-3 mimetics such as ABT-737, without the need for parkin over expression. Thus, an anti-apoptotic role has been demonstrated for USP30 and USP30 is therefore a potential target for anti-cancer therapy.

To date, there have been no reports of DUB inhibitors that have successfully entered the clinic. Thus, there is a need for compounds and pharmaceutical compositions to inhibit DUBs such as USP30 for the treatment of indications where DUB activity is observed, including, although not limited to, conditions involving mitochondrial dysfunction, and cancer.

Lainé et al., Med Chem Lett. 2011, 2(2), 142-7 describes the compound N-[(3R)-1-cyano-3-pyrrolidinyl]-4-fluorobenzamide as an inhibitor of Cathepsin C. WO2001/077073 describes the compounds N-(1-cyano-3-pyrrolidinyl)-[1,1'-biphenyl]-4-carboxamide and N-(1-cyano-3-piperidinyl)-[1, 1'-biphenyl]-4-carboxamide as cathepsin inhibitors. WO2009/129371 describes the compounds N-[(3R)-1-cyano-3-pyrrolidinyl]-3-({[(3R)-1-cyano-3-pyrrolidinyl] amino}sulfonyl)benzamide and N-[(3R)-1-cyano-3-pyrrolidinyl]-3-([(3R)-3-pyrrolidinylamino]sulfonyl)-benzamide as Cathepsin C inhibitors. WO2016/021629 describes the compound 1-((3S,4R)-1-cyano-4-(3,4-difluorophenyl)pyrrolidin-3-yl)-3-(1',4-dimethyl-1-phenyl-1H,1'H-[3,4'-bipyrazol]-5-yl)ureayl)urea as a TrkA inhibitor. These compounds may be disclaimed for the appended claims.

SUMMARY OF THE INVENTION

In accordance with a first aspect of the invention there is provided a compound of formula (II)

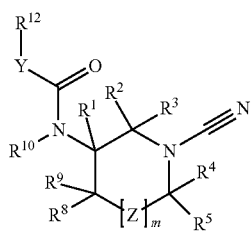

(II)

or a pharmaceutically acceptable salt thereof, wherein:
m is 0 or 1;
when m is 1, Z represents —C($R^6$)($R^7$)—;
$R^2$ represents a hydrogen atom, an optionally substituted $C_1$-$C_6$ alkyl, an optionally substituted $C_1$-$C_6$ alkoxy group, an optionally substituted 4 to 10 membered heteroaryl, heterocyclyl, aryl or 3 to 8 membered cycloalkyl ring;
$R^3$, $R^4$ and $R^5$ each independently represent a hydrogen atom, an optionally substituted $C_1$-$C_3$ alkyl or an optionally substituted $C_1$-$C_3$ alkoxy group;
$R^1$, $R^6$, $R^7$ and $R^8$ each independently represent a hydrogen atom, a fluorine atom, cyano, hydroxyl, an optionally substituted $C_1$-$C_3$ alkyl or an optionally substituted $C_1$-$C_3$ alkoxy group;
$R^9$ represents a hydrogen atom, a fluorine atom, cyano, hydroxyl, an optionally substituted $C_1$-$C_6$ alkyl, an optionally substituted $C_1$-$C_3$ alkoxy group, an optionally substituted 4 to 10 membered heteroaryl, heterocyclyl, aryl or 3 to 8 membered cycloalkyl ring, or forms an optionally substituted heterocyclic ring with $R^{10}$ wherein the ring optionally comprises one or more additional heteroatoms;
$R^{10}$ represents a hydrogen atom, optionally substituted $C_1$-$C_6$ alkyl, or forms an optionally substituted heterocyclic ring with $R^9$, or forms an optionally substituted monocyclic or bicyclic ring with $R^{11}$ with the proviso that when the ring is bicyclic the ring is not substituted with $NH_2$;
Y represents a covalent bond, —($C_0$-$C_3$) alkylene-$NR^{11}$—($C_0$-$C_3$) alkylene or optionally substituted $C_1$-$C_3$ alkylene;
$R^{11}$ represents a hydrogen atom, an optionally substituted $C_1$-$C_6$ alkyl, a 4 to 10 membered heteroaryl, heterocyclyl, aryl or 3 to 8 membered cycloalkyl ring, or forms an optionally substituted monocyclic or bicyclic heterocyclic ring with $R^{10}$ with the proviso that when the ring is bicyclic the ring is not substituted with $NH_2$;
$R^{12}$ represents a substituted monocyclic, optionally substituted bicyclic or optionally substituted tricyclic 3 to 14 membered heteroaryl, heterocyclyl, aryl or cycloalkyl ring; and
where the compound is not of the formula:

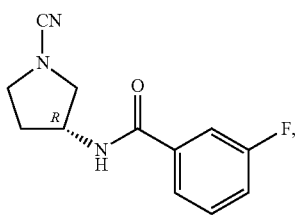

-continued

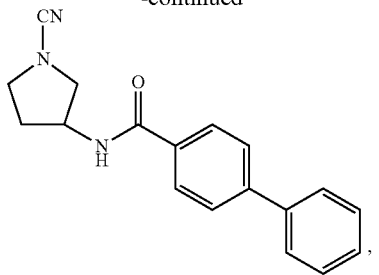

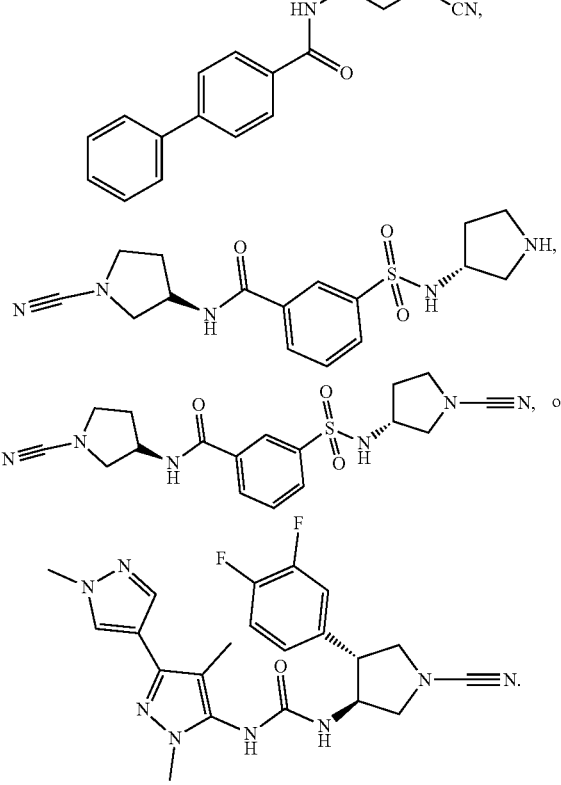

$R^{12}$ may represent a 3 to 14 membered heterocyclyl, heteroaryl, aryl or cycloalkyl ring substituted with one or more of $Q^1$-($R^{13}$)$_p$, wherein:
p is 0 or 1;
$Q^1$ represents a halogen atom, cyano, oxo, hydroxyl, a covalent bond, —$C_0$-$C_3$ alkylene-$NR^{14}$—, —$C_0$-$C_3$ alkylene-$NR^{14}R^{15}$, —$C_0$-$C_3$ alkylene-$CONR^{14}$—, —$C_0$-$C_3$ alkylene-$NR^{14}CO$—, —$C_0$-$C_3$ alkylene-$NR^{14}SO_2$—, —$C_0$-$C_3$ alkylene-O—$C_0$-$C_3$ alkylene, —$C_0$-$C_3$ alkylene-CO—, —$C_0$-$C_3$ alkylene-S(O)$_q$—, —$C_0$-$C_3$ alkylene-$SO_2NR^{14}$, —$C_1$-$C_6$ alkoxy, $C_1$-$C_6$ haloalkoxy, $C_1$-$C_6$ hydroxyalkyl, —$C_0$-$C_3$ alkylene-$SO_2R^{14}$, —$C_0$-$C_3$ alkylene-$NR^{14}COR^{15}$, —$C_0$-$C_3$ alkylene-$NR^{14}CONR^{15}R^{16}$, —$C_0$-$C_3$ alkylene-$NR^{14}SO_2NR^{15}R^{16}$, —$C_0$-$C_3$ alkylene-$CONR^{14}R^{15}$, —$C_0$-$C_3$ alkylene-$CO_2R^{14}$, —$C_0$-$C_3$ alkylene-$NR^{14}CO_2R^{15}$, —$C_0$-$C_3$ alkylene-$SO_2NR^{14}R^{15}$, —$C_0$-$C_3$ alkylene-$CONR^{14}$, —$C_0$-$C_3$ alkylene-C(O)$R^4$ and —$C_0$-$C_3$ alkylene-$NR^{14}SO_2R^{15}$, $NO_2$, or an optionally substituted $C_1$-$C_6$ alkylene, —$C_2$-$C_6$ alkenylene or —$C_1$-$C_6$ alkyl group;
q is 0, 1 or 2;

$R^{14}$, $R^{15}$ and $R^{16}$ each independently represent a hydrogen atom or an optionally substituted $C_1$-$C_6$ alkyl, or an optionally substituted $C_1$-$C_6$ alkylene group.

When p is 1, $R^{13}$ represents an optionally substituted 4 to 10 membered heterocyclyl, heteroaryl, aryl or 3 to 8 membered cycloalkyl ring (when p is 0, $Q^1$ is present and $R^{13}$ is absent).

$R^{13}$ may be optionally substituted with one or more substituents selected from halogen, optionally substituted $C_1$-$C_6$ haloalkyl, optionally substituted $C_1$-$C_6$ alkoxy, $C_1$-$C_6$ haloalkoxy, optionally substituted $C_1$-$C_6$ alkyl, optionally substituted $C_2$-$C_6$ alkenyl, optionally substituted $C_2$-$C_6$ alkynyl, $C_1$-$C_6$ hydroxyalkyl, oxo, cyano, optionally substituted heterocyclyl, optionally substituted cycloalkyl, optionally substituted heteroaryl, optionally substituted aryl, -$Q^2$-$R^{17}$, -$Q^2$-$NR^{17}CONR^{18}R^{19}$, -$Q^2$-$NR^{17}R^{18}$, -$Q^2$-$COR^{17}$, -$Q^2$-$NR^{17}COR^{18}$, -$Q^2$-$NR^{17}CO_2R^{18}$, -$Q^2$-$SO_2R^{17}$, $Q^2$-$CONR^{17}R^{18}$, -$Q^2$-$CO_2R^{17}$, -$Q^2$-$SO_2NR^{17}R^{18}$ and -$Q^2$-$NR^{17}SO_2R^{18}$; wherein $Q^2$ represents a covalent bond, an oxygen atom, carbonyl, or a $C_1$-$C_6$ alkylene or $C_2$-$C_6$ alkenylene group; and $R^{16}$, $R^{17}$, $R^{18}$ each independently represent hydrogen, optionally substituted $C_1$-$C_6$ alkyl, optionally substituted heterocyclyl, optionally substituted heteroaryl, optionally substituted aryl, or an optionally substituted cycloalkyl.

BRIEF DESCRIPTION OF THE FIGURES

FIG. 1 is a graph showing proteolytic activity of USP30 measured using a fluorescence polarisation assay. Various volumes of purified USP30 as indicated were incubated with a TAMRA labelled peptide linked to ubiquitin via an isopeptide bond.

DETAILED DESCRIPTION OF THE INVENTION

The definitions and explanations below are for the terms as used throughout this entire document including both the specification and the claims. Reference to compounds as described herein (e.g. a compound of formula I), includes reference to formula I, formula II and formula III including any sub-generic embodiments thereof.

Where any group of the compounds of formula (I) have been referred to as optionally substituted, this group may be substituted or unsubstituted. Substitution may be by one or more of the specified substituents which may be the same or different. It will be appreciated that the number and nature of substituents will be selected to avoid any sterically undesirable combinations.

In the context of the present specification, unless otherwise stated an alkyl, alkenyl, or alkynyl substituent group or an alkyl, alkenyl moiety in a substituent group may be linear or branched. Alkyl and alkenyl chains may also include intervening heteroatoms such as oxygen.

$C_x$-$C_y$ alkyl refers to a saturated aliphatic hydrocarbon group having x-y carbon atoms which may be linear or branched. For example $C_1$-$C_6$ alkyl contains from 1 to 6 carbon atoms. "Branched" means that at least one carbon branch point is present in the group. For example, tert-butyl and isopropyl are both branched groups. Examples of $C_1$-$C_6$ alkyl groups include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl.

A $C_x$-$C_y$ alkylene group or moiety may be linear or branched and refers to a divalent hydrocarbon group having one less hydrogen atom from $C_x$-$C_y$ alkyl as defined above. Examples of $C_1$-$C_6$ alkylene groups include methylene, ethylene, n-propylene, n-butylene, methylmethylene and dimethylmethylene.

$C_2$-$C_6$ alkenyl refers to a linear or branched hydrocarbon chain radical containing at least two carbon atoms and at least one double bond. Examples of alkenyl groups include ethenyl, propenyl, 2-propenyl, 1-butenyl, 2-butenyl, 1-hexenyl, 2-methyl-1-propenyl, 1,2-butadienyl, 1,3-pentadienyl, 1,4-pentadienyl and 1-hexadienyl.

$C_2$-$C_6$ alkynyl refers to a linear or branched hydrocarbon chain radical containing at least two carbon atoms and at least one triple bond. Examples of alkenyl groups include ethynyl, propynyl, 2-propynyl, 1-butynyl, 2-butynyl and 1-hexynyl.

$C_1$-$C_6$ alkoxy refers to a group or part of a group having an —O—$C_x$-$C_y$ alkyl group according to the definition of $C_x$-$C_y$ alkyl above. Examples of $C_1$-$C_6$ alkoxy include methoxy, ethoxy, propoxy, isopropoxy, butoxy, pentoxy and hexoxy.

$C_1$-$C_6$ haloalkyl and $C_1$-$C_6$ haloalkoxy refers to a $C_xC$ alkyl group as defined above wherein at least one hydrogen atom is replaced with a halogen atom. Examples of $C_1$-$C_6$ haloalkyl groups include fluoromethyl, difluoromethyl, trifluoromethyl, trifluoroethyl, pentafluoroethyl, fluoromethoxy, difluoromethoxy and trifluoromethoxy.

$C_1$-$C_6$ hydroxyalkyl refers to $C_x$-$C_y$ alkyl group as defined above wherein at least one hydrogen atom is replaced with a hydroxy (—OH) group. Examples of hydroxy $C_{1-6}$ alkyl groups include hydroxymethyl, hydroxyethyl, dihydroxyethyl, hydroxypropyl and hydroxyisopropyl.

The term "halogen" or "halo" refers to chlorine, bromine, fluorine or iodine atoms.

The term "oxo" means =O.

For the avoidance of doubt it will be understood that a 4 to 10 membered heteroaryl, heterocyclyl or aryl ring, or a 3 to 8 membered cycloalkyl ring as defined according to $R^2$, $R^9$, $R^{11}$ or $R^{13}$ or a 3 to 14 membered heteroaryl, heterocyclyl, cycloalkyl or aryl ring as defined according to $R^{12}$ does not include any unstable ring structures or, in the case of heteroaryl and heterocyclic rings systems, any O—O, O—S or S—S bonds. The ring systems may be monocyclic, bicyclic, or tricyclic where the definition allows. Bicyclic and tricyclic ring systems include bridged, fused and spiro ring systems, particularly fused ring systems. A substituent if present may be attached to any suitable ring atom which may be a carbon atom or, in the case of heteroaryl and heterocyclic ring systems, a heteroatom. Substitution on a phenyl ring may include a change in the ring atom at the position of substitution from carbon to nitrogen, resulting in a pyridine ring.

"$C_x$-$C_y$ cycloalkyl" refers to a cyclic non-aromatic hydrocarbon group of x-y carbon atoms. For example $C_3$-$C_8$ cycloalkyl refers to a hydrocarbon ring containing 3 to 8 carbon atoms. Examples of $C_3$-$C_8$ cycloalkyl are cyclopropyl, cyclobutyl, cyclopentyl, cyclohexyl, cyclopentyl, cyclohexyl cycloheptyl and cyclooctyl.

An "aryl" group/moiety refers to any monocyclic or bicyclic hydrocarbon group comprising at least one aromatic group, for example having up to 10 carbon atom ring members. Examples of aryl groups include phenyl, naphthyl and tetrahydronaphthyl.

"Heteroaryl" groups may be monocyclic, bicyclic or tricyclic. Bicyclic rings may be fused aromatic rings where both rings are aromatic or may be fused rings where one of the rings is non aromatic. In the case of $R^{12}$, the ring attached to the amide nitrogen may be an aromatic ring, which can be fused to a further aromatic or non-aromatic ring. Heteroaryl rings comprise 1, 2, 3 or 4 heteroatoms, in particular 1, 2, or 3 heteroatoms, selected from oxygen, sulphur and nitrogen. When the heteroatom is nitrogen it may be oxidised. Examples of heteroaryl groups include pyridinyl, pyrazinyl, pyrimidinyl, pyridazinyl, furyl, thiophenyl, pyrrolyl, oxazolyl, thiazolyl, pyrazolyl, triazolyl, tetrazolyl, indolyl, indolizinyl, isoindolyl, indolinyl, purinyl, furazanyl, imidazolyl, indazolyl, isothiazolyl, isoxazolyl, oxadiazolyl, oxazinanyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, 4H-quinolizinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, pyridazinyl, dihydrophyridinyl, benzopyrazolyl, quinoxalinyl, tetrahydropyridoindolyl, benzoimidazolyl, pyrrolopyridinyl, imidazopyrimidinyl, pyrazolopyrimidinyl, pyrrolopyrimidinyl and imidazopyrazinyl.

"Heterocyclyl" groups may also be monocyclic or comprise two or more fused rings which may be saturated or partially unsaturated comprising 1, 2, 3 or 4 heteroatoms, in particular 1, 2, or 3 heteroatoms, selected from oxygen, sulphur and nitrogen. Examples of heterocyclyl groups include azetidinyl, pyrrolidinyl, piperidinyl, azepanyl, diazepanyl, dihydrofuranyl (e.g. 2,3-dihydrofuranyl, 2,5-dihydrofuranyl), 4,5-dihydro-1H-maleimido, dioxolanyl, morpholinyl, oxazolidinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, pyridazinyl, 4H-quinolizinyl, quinuclinyl, tetrahydropyranyl, tetrahydropyridinyl, tetrahydropyrimidinyl, tetrahydrothiophenyl, tetramethylenesulfoxide, thiazolidinyl, hydantoinyl, benzopyranyl, tetrahydrothiazolopyridinyl, tetrahydroquinolinyl, tetrahydroisoquinolinyl, benzomorpholinyl and dihydroisoquinolinyl.

"Optionally substituted" as applied to any group means that the said group may if desired be substituted with one or more substituents, which may be the same or different. Examples of suitable substituents for "substituted" and "optionally substituted" moieties, include halo, deutero, $C_{1-6}$ alkyl or $C_{1-3}$ alkyl, hydroxy, $C_{1-6}$ alkoxy or $C_{1-3}$ alkoxy, cyano, amino, nitro or $SF_5$ (a known mimetic of $NO_2$), aryl, heteroaryl, heterocyclyl, $C_3$-$C_6$ cycloalkyl, $C_{1-3}$ alkylamino, $C_{2-6}$ alkenylamino, di-$C_{1-3}$ alkylamino, $C_{1-3}$ acylamino, di-$C_{1-3}$ acylamino, carboxy, $C_{1-3}$ alkoxycarbonyl, carbamoyl, mono-$C_{1-3}$ carbamoyl, di-$C_{1-3}$ carbamoyl or any of the above in which a hydrocarbyl moiety is itself substituted by halo. In groups containing an oxygen atom such as hydroxy and alkoxy, the oxygen atom can be replaced with sulphur to make groups such as thio (SH) and thio-alkyl (S-alkyl). Optional substituents therefore include groups such as S-methyl. In thio-alkyl groups, the sulphur atom may be further oxidised to make a sulfoxide or sulfone, and thus optional substituents therefore includes groups such as S(O)-alkyl and $S(O)_2$-alkyl.

Substituted groups thus include for example Cl, F, OMe, Me, $COCH_3$, $CONH_2$, $NHC(O)CH(CH_3)_2$, $CO_2CH_2CH_3$ etc. In the case of aryl groups, the substitutions may be in the form of rings from adjacent carbon atoms in the aryl ring, for example cyclic acetals such as O—$CH_2$—O.

The optional substituents for any alkyl, alkenyl, alkynyl, alkoxy, alkylene or alkenylene groups described herein may be selected from $C_1$-$C_3$ alkoxy, halogen, hydroxyl, thiol, cyano, amino, amido, nitro and $SF_5$, wherein the alkoxy may be optionally substituted with halogen. In particular, the optional substituents may be selected from halogen, hydroxyl, thiol, cyano, amino, amido, nitro and $SF_5$, more particularly fluorine or hydroxyl.

The term "treat" or "treating" or "treatment" includes prophylaxis and means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and non-human animals.

The dose of the compound is that amount effective to prevent occurrence of the symptoms of the disorder or to treat some symptoms of the disorder from which the patient suffers. By "effective amount" or "therapeutically effective amount" or "effective dose" is meant that amount sufficient to elicit the desired pharmacological or therapeutic effects, thus resulting in effective prevention or treatment of the disorder. Prevention of the disorder is manifested by delaying the onset of the symptoms of the disorder to a medically significant extent. Treatment of the disorder is manifested by a decrease in the symptoms associated with the disorder or an amelioration of the reoccurrence of the symptoms of the disorder.

Pharmaceutically acceptable salts of the compounds of the invention include but are not limited to addition salts (for example phosphates, nitrates, sulphates, borates, acetates, maleates, citrates, fumarates, succinates, methanesulphonates, benzoates, salicylates and hydrohalides), salts derived from organic bases (such as lithium, potassium and sodium), salts of amino acids (such as glycine, alanine, valine, leucine, isoleucine, cysteine, methionine and proline), inorganic bases (such as triethylamine, hydroxide, choline, thiamine and N—N'-diacetylethylenediamine). Other pharmaceutically acceptable salts include ammonium salts, substituted ammonium salts and aluminium salts. Further pharmaceutically acceptable salts include quaternary ammonium salts of the compounds of formula (I) or formula (II).

General methods for the production of salts are well known to the person skilled in the art. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Where compounds of the invention exist in different enantiomeric and/or diastereoisomeric forms, the invention relates to these compounds prepared as isomeric mixtures or racemates whether present in an optically pure form or as mixtures with other isomers. Enantiomers differ only in their ability to rotate plane-polarized light by equal amounts in opposite directions and are denoted as the (+)/(S) or (−)/(R) forms respectively. Individual enantiomers or isomers may be prepared by methods known in the art, such as optical resolution of products or intermediates (for example chiral chromatographic separation e.g. chiral HPLC, or an asymmetric synthesis approach). Similarly where compounds of the invention exist as alternative tautomeric forms e.g.

keto/enol, amide/imidic acid, the invention relates to the individual tautomers in isolation, and to mixtures of the tautomers in all proportions.

Included herein is the compound according to formula (IB):

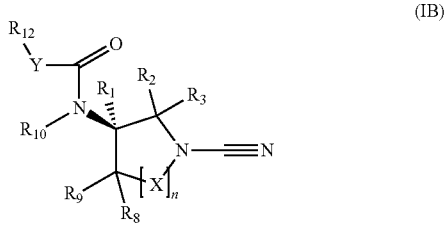

or a pharmaceutically acceptable salt thereof, wherein n, X, $R^1$, $R^2$, $R^3$, $R^8$, $R^9$, $R^{10}$, $R^{12}$ and Y are defined herein for compounds of formula (I).

Included herein is the compound according to formula (III):

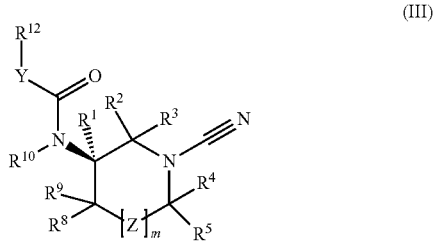

or a pharmaceutically acceptable salt thereof, wherein m, Z, $R^1$, $R^2$, $R^3$, $R^8$, $R^9$, $R^{10}$, $R^{12}$ and Y are defined above for compounds of formula (II).

Isotopes

The compounds described herein may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. Examples of isotopes include $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$ and $^{35}S$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment, the compounds contain no radioactive isotopes. Such compounds are preferred for therapeutic use. In another embodiment, however, the compounds may contain one or more radioisotopes. Compounds containing such radioisotopes may be useful in a diagnostic context.

Certain isotopically labelled compounds of formula (I) or formula (II), for example, those incorporating a radioactive isotope, are useful in drug and/or substrate tissue distribution studies. The radioactive isotopes i.e. $^3H$ and $^{14}C$ are particularly useful for this purpose in view of their ease of incorporation and ready means of detection. Substitution with heavier isotopes i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining receptor occupancy. Isotopically labelled compounds of formula (I) or formula (II) can generally be prepared by conventional techniques known to those skilled in the art or by processes analogous to those described in the accompanying examples and preparations using an appropriate isotopically labelled reagent in place of the non-labelled reagent previously employed.

Crystalline and Amorphous Forms

The compounds of formula (I) or formula (II) may exist in crystalline or amorphous form and some of the crystalline forms may exist as polymorphs, which are included within the scope of the present invention. Polymorphic forms of compounds of formula (I) or formula (II) may be characterised and differentiated using a number of conventional analytical techniques, including, but not limited to, infra-red spectra, Raman spectra, X-ray powder diffraction, differential scanning calorimetry, thermogravimetric analysis and solid state nuclear magnetic resonance.

Accordingly, in further embodiments, the invention provides a compound according to any described embodiments in a crystalline form. The compound may be from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline. The compound may alternatively be in an amorphous form.

The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

The invention relates to any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

The invention relates to pharmaceutically functional derivatives of compounds as defined herein including ester derivatives and/or derivatives that have, or provide for, the same biological function and/or activity as any relevant compound of the invention. Thus, for the purposes of this invention, the term also includes prodrugs of compounds as defined herein.

The term "prodrug" of a relevant compound includes any compound that, following oral or parenteral administration, is metabolised in vivo to form that compound in an experimentally-detectable amount, and within a predetermined time (e.g. within a dosing interval of between 6 and 24 hours (i.e. once to four times daily).

Prodrugs of compounds may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds wherein a hydroxyl, amino, sulfhydryl, carboxyl or carbonyl group in a compound is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, ester groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Compounds of the invention may be metabolised in vivo. Metabolites of compounds of formula (I) and formula (II) are also within the scope of the present invention. The term 'metabolites' refers to all molecules derived from any of the compounds according to the present invention in a cell or organism, preferably mammal. Preferably the term relates to molecules which differ from any molecule which is present in any such cell or organism under physiological conditions.

A treatment defined herein may be applied as a sole therapy of may involve, in addition to the compounds of the invention, conventional surgery or radiotherapy or chemotherapy. Furthermore, compounds of formula (I) or formula (II) can also be used in combination with existing therapeutic agents for the treatment of conditions associated with mitochondrial dysfunction and cancer, including small molecule therapeutics or antibody based therapeutics.

The compounds described herein are characterised by a cyanopyrrolidine or cyanopiperidine core.

The disclosure includes compounds having the formula (I)

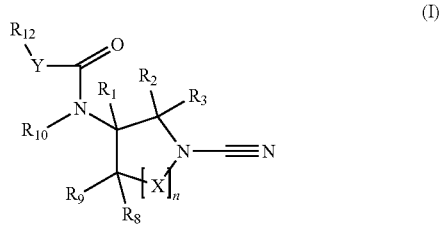

or a pharmaceutically acceptable salt thereof, wherein:
n is 1 or 2;

when n is 1, X is $CR^4R^5$ and when n is 2, X is $CR^6R^7CR^4R^5$ (wherein $CR^4R^5$ is adjacent to heterocycle N atom);

$R^2$ represents a hydrogen atom, cyano, an optionally substituted $C_1$-$C_6$ alkyl, an optionally substituted $C_1$-$C_6$ alkoxy group, an optionally substituted 4 to 10 membered heteroaryl, heterocyclyl, aryl or 3 to 8 membered cycloalkyl ring;

$R^1$, $R^3$, $R^4$ and $R^5$ each independently represent a hydrogen atom, cyano, an optionally substituted $C_1$-$C_3$ alkyl or an optionally substituted $C_1$-$C_3$ alkoxy group;

$R^6$, $R^7$ and $R^8$ each independently represent a hydrogen atom, a fluorine atom, cyano, an optionally substituted $C_1$-$C_3$ alkyl or an optionally substituted $C_1$-$C_3$ alkoxy group;

$R^9$ represents a hydrogen atom, a fluorine atom, cyano, an optionally substituted $C_1$-$C_6$ alkyl, an optionally substituted $C_1$-$C_3$ alkoxy group, an optionally substituted 4 to 10 membered heteroaryl, heterocyclyl, aryl or 3 to 8 membered cycloalkyl, or forms an optionally substituted heterocyclic ring with $R^{10}$ wherein the ring optionally comprises one or more additional heteroatoms;

$R^{10}$ represents a hydrogen atom, $C_{1-6}$ alkyl or forms an optionally substituted heterocyclic ring with $R^9$ or $R^{11}$ wherein the ring optionally comprises one or more additional heteroatoms;

Y represents a covalent bond, $NR^{11}$ or optionally substituted $C_1$-$C_3$ alkylene;

$R^{11}$ represents a hydrogen atom, an optionally substituted $C_1$-$C_6$ alkyl, a 4 to 10 membered heteroaryl, heterocyclyl, aryl or 3 to 8 membered cycloalkyl ring, or forms an optionally substituted heterocyclic ring with $R^{10}$ wherein the ring optionally comprises one or more additional heteroatoms;

$R^{12}$ represents a substituted 4 to 10 membered heteroaryl, heterocyclyl, aryl or 3 to 8 membered cycloalkyl ring.

In a first aspect the present invention provides a compound having the formula (II)

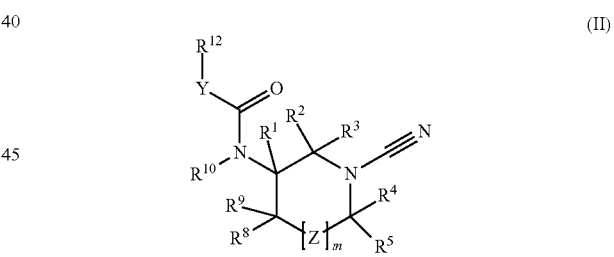

or a pharmaceutically acceptable salt thereof, wherein:
m is 0 or 1;
when m is 1, Z is —$C(R^6)(R^7)$—;

$R^2$ represents a hydrogen atom, an optionally substituted $C_1$-$C_6$ alkyl, an optionally substituted $C_1$-$C_6$ alkoxy group, an optionally substituted 4 to 10 membered heteroaryl, heterocyclyl, aryl or 3 to 8 membered cycloalkyl ring;

$R^3$, $R^4$ and $R^5$ each independently represent a hydrogen atom, an optionally substituted $C_1$-$C_3$ alkyl or an optionally substituted $C_1$-$C_3$ alkoxy group;

$R^1$, $R^6$, $R^7$ and $R^8$ each independently represent a hydrogen atom, a fluorine atom, cyano, hydroxyl, an optionally substituted $C_1$-$C_3$ alkyl or an optionally substituted $C_1$-$C_3$ alkoxy group;

$R^9$ represents a hydrogen atom, a fluorine atom, cyano, hydroxyl, an optionally substituted $C_1$-$C_6$ alkyl, an optionally substituted $C_1$-$C_3$ alkoxy group, an optionally substituted 4 to 10 membered heteroaryl, heterocyclyl, aryl or 3 to 8 membered cycloalkyl ring, or forms an optionally substituted heterocyclic ring with $R^{10}$;

$R^{10}$ represents a hydrogen atom, optionally substituted $C_{1-6}$ alkyl, or forms an optionally substituted heterocyclic ring with $R^9$, or forms an optionally substituted monocyclic or bicyclic ring with $R^{11}$ with the proviso that when the ring is bicyclic it is not substituted with $NH_2$;

Y represents a covalent bond, $-(C_0-C_3)$-alkylene-N $(R^{11})-(C_0-C_3)$-alkylene or optionally substituted $C_1-C_3$ alkylene;

$R^{11}$ represents a hydrogen atom, an optionally substituted $C_1-C_6$ alkyl, a 4 to 10 membered heteroaryl, heterocyclyl, aryl or 3 to 8 membered cycloalkyl ring or forms an optionally substituted monocyclic or bicyclic heterocyclic ring with $R^{10}$ with the proviso that when the ring is bicyclic it is not substituted with $NH_2$;

$R^{12}$ represents a substituted monocyclic, optionally substituted bicyclic or optionally substituted tricyclic 3 to 14 membered heteroaryl, heterocyclyl, cycloalkyl or aryl ring; and where the compound is not of the formula:

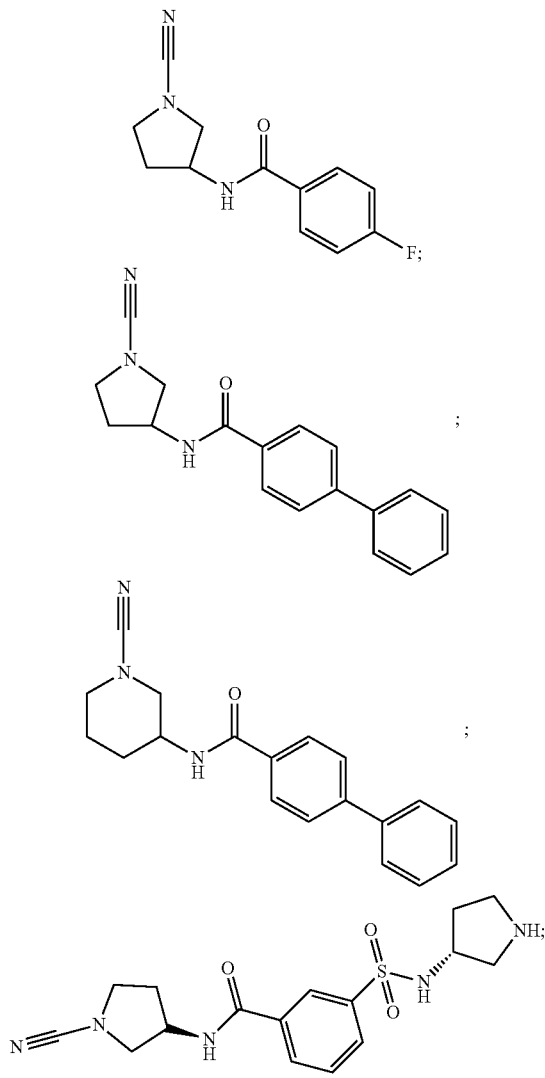

-continued

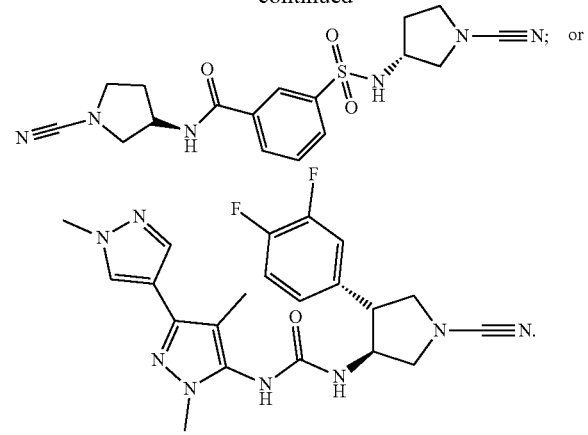

In one embodiment, $R^1$ represents a hydrogen atom. In another embodiment, $R^1$ represents $C_1-C_3$ methyl. In another embodiment, $R^1$ represents methyl.

In one embodiment, $R^2$ represents $C_1-C_3$ alkyl. In another embodiment $R^2$ represents $C_1-C_2$ (e.g. methyl or ethyl). In another embodiment, $R^2$ represents methyl. In another embodiment, $R^2$ represents hydroxyl. In another embodiment, $R^2$ represents $C_1-C_3$ alkyl, $C_1-C_2$ alkyl (e.g. methyl or ethyl) or hydroxyl and $R^1$, $R^3$, $R^4$, $R^5$, $R^8$, $R^9$, and $R^6$ and $R^7$ (if present), each independently represent a hydrogen atom In another embodiment $R^2$ represents $C_1-C_3$ alkyl or $C_1-C_2$ alkyl (e.g. methyl or ethyl) and $R^1$, $R^3$, $R^4$, $R^5$, $R^8$, $R^9$, and $R^6$ and $R^7$ (if present), each independently represent a hydrogen atom.

In one embodiment, $R^5$ represents $C_1-C_3$ alkyl. In another embodiment $R^5$ represents $C_1-C_2$ alkyl (e.g. methyl or ethyl). In another embodiment, $R^5$ represents methyl. In another embodiment $R^5$ represents $C_1-C_3$ alkyl or $C_1-C_2$ alkyl (e.g. methyl or ethyl) and $R^1$, $R^2$, $R^3$, $R^4$, $R^8$, $R^9$ and $R^6$ and $R^7$ (if present) each independently represent a hydrogen atom.

In one embodiment, $R^6$ and $R^7$ when present represent hydrogen.

In one embodiment, $R^8$ represents $C_1-C_3$ alkyl. In another embodiment $R^8$ represents $C_1-C_2$ alkyl (e.g. methyl or ethyl). In another embodiment, $R^8$ represents methyl. In another embodiment $R^8$ represents $C_1-C_3$ alkyl, $C_1-C_2$ alkyl (e.g. methyl or ethyl) or a fluorine atom and $R^1$, $R^2$, $R^3$, $R^4$, $R^5$, $R^9$ and $R^6$ and $R^7$ (if present) each independently represent a hydrogen atom.

In one embodiment, $R^9$ represents $C_1-C_3$ alkyl. In another embodiment $R^9$ represents $C_1-C_2$ alkyl (e.g. methyl or ethyl). In another embodiment, $R^9$ represents methyl. In another embodiment, $R^9$ represents $C_1-C_3$ alkoxy. In another embodiment, $R^9$ represents $C_1-C_2$ alkoxy (e.g. methoxy or ethoxy). In another embodiment, $R^9$ represents methoxy. In another embodiment, $R^9$ represents cyclopropyl. In another embodiment, $R^9$ represents a hydrogen atom, a fluorine atom, cyano, hydroxyl, an optionally substituted $C_1-C_6$ alkyl, an optionally substituted $C_1-C_3$ alkoxy group or an $C_3-C_4$ cycloalkyl. In another embodiment $R^9$ represents $C_1-C_3$ alkyl, $C_1-C_2$ alkyl (e.g. methyl or ethyl), a fluorine atom or cyclopropyl and $R^1$, $R^2$, $R^3$, R, $R^5$, $R^8$, and $R^6$ and $R^7$ (if present), each independently represent a hydrogen atom. In one embodiment, $R^9$ is not phenyl, in particular, not difluorophenyl.

The alkyl and alkoxy within the definitions of $R^1$, $R^2$, $R^3$, $R^4$, $R^5$, $R^6$, $R^7$, $R^8$ and $R^9$ may be optionally substituted with one or more substituents selected from halogen, hydroxyl, thiol, cyano, amino, nitro and $SF_5$.

In one embodiment, $R^9$ forms an optionally substituted heterocyclic ring with $R^{10}$ wherein the ring optionally comprises one or more additional heteroatoms. In one embodiment, $R^9$ forms a 5 membered heterocyclic ring with $R^{10}$. In another embodiment, $R^9$ forms a 6 membered heterocyclic ring with $R^{10}$ wherein the ring further comprises an oxygen heteroatom. In another embodiment, $R^9$ forms an optionally substituted heterocyclic ring with $R^{10}$ wherein the ring optionally comprises one or more additional heteroatoms and $R^1$, $R^2$, $R^3$, $R^4$, R, $R^8$ and $R^6$ and $R^7$ (if present) each independently represent a hydrogen atom. The ring formed by $R^9$ and $R^{10}$ may be optionally substituted with one or more of the substituents defined herein. In one embodiment, the optional substituents are selected from $C_1$-$C_3$ alkyl, $C_1$-$C_3$ alkoxy, halogen, hydroxyl, thiol, cyano, amino, amido, nitro and $SF_5$, wherein the alkyl and alkoxy may be optionally substituted with halogen.

In one embodiment, $R^{10}$ represents a hydrogen atom, optionally substituted $C_1$-$C_6$ alkyl or forms an optionally substituted heterocyclic ring with $R^9$ or $R^{11}$ wherein the ring optionally comprises one or more additional heteroatoms. In one embodiment, $R^{10}$ represents a hydrogen atom. In another embodiment $R^{10}$ represents $C_1$-$C_3$ alkyl. In another embodiment, $R^{10}$ represents methyl. In another embodiment, $R^{10}$ represents ethyl. In another embodiment, the $C_1$-$C_6$ alkyl may be optionally substituted. The optional substituents for the alkyl may be selected from $C_1$-$C_3$ alkoxy, halogen, hydroxyl, thiol, cyano, amino, amido, nitro and $SF_5$, wherein the alkoxy may be optionally substituted with halogen in particular fluorine. In particular, the $C_1$-$C_3$ may be optionally substituted with $C_1$-$C_3$ alkoxy, for example methoxy. In one embodiment, $R^{10}$ represents $CH_2CH_2OCH_3$. In yet another embodiment, $R^{10}$ forms a 5 membered heterocyclic ring with $R^9$. In another embodiment, $R^{10}$ forms a 6 membered heterocyclic ring with $R^9$ wherein the ring further comprises an oxygen heteroatom.

In one embodiment, Y is a covalent bond, —$NR^{11}$— or $C_1$-$C_3$ alkylene. In one embodiment, Y is a covalent bond or $C_1$-$C_3$ alkylene. In one embodiment, Y is a covalent bond. In another embodiment, Y represents $C_1$-$C_2$ alkylene (e.g. methylene or ethylene). In another embodiment, Y is methylene. In another embodiment, Y is —NH—.

$R^{11}$ represents a hydrogen atom, an optionally substituted $C_1$-$C_6$ alkyl, a 4 to 10 membered heteroaryl, heterocyclyl, aryl or 3 to 8 membered cycloalkyl ring or forms an optionally substituted monocyclic or bicyclic heterocyclic ring with $R^{10}$ with the proviso that when the ring is bicyclic it is not substituted with $NH_2$. In one embodiment, $R^{11}$ is hydrogen, $C_1$-$C_6$ alkyl or forms a 5 or 6 membered monocyclic ring with $R^{10}$.

In one embodiment, $R^{11}$ and $R^{10}$ together form a heterocyclyl ring. The ring may be monocyclic or bicyclic. In particular, when $R^{11}$ and $R^{10}$ together form a heterocyclyl ring, the ring is 5 or 6 membered monocyclic ring. In one embodiment, $R^{11}$ and $R^{10}$ together form a 5 membered heterocyclic ring. In another embodiment, $R^{11}$ and $R^{10}$ together form a 6 membered heterocyclic ring. In one embodiment, when $R^{11}$ and $R^{10}$ together form a heterocyclic ring, the ring is not dihydropurine.

The compounds of formula II may be in the form where m is 0, i.e. wherein the core structure is a cyanopyrrolidine. In such cases the compounds may be of the formula:

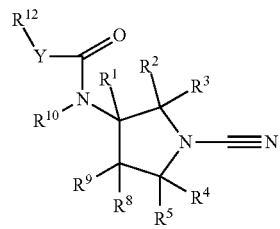

(IIA)

or a pharmaceutically acceptable salt thereof, wherein $R^1$, $R^2$, $R^3$, $R^4$, $R^5$, $R^8$, $R^9$, $R^{10}$, $R^{12}$ and Y are as defined herein for compounds of formula II.

Alternatively, the compounds of formula II may be in the form where m is 1, i.e. the core structure is a cyanopiperidine. In such cases the compounds may be of the formula:

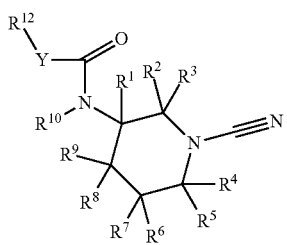

(IIB)

or a pharmaceutically acceptable salt thereof, wherein $R^1$, $R^2$, $R^3$, $R^4$, $R^5$, $R^6$, $R^7$, $R^8$, $R^9$, $R^{10}$, $R^{12}$ and Y are as defined herein for compounds of formula (II).

When m is 0, the compounds of formula II may be in the form where $R^9$ and $R^{10}$ together form a 5 membered heterocyclyl ring which is fused to the cyanopyrrolidine core to create an 8 membered bicyclic ring. In particular, Y may be a covalent bond, and $R^1$, $R^2$, $R^3$, $R^4$, $R^5$ and $R^8$ are each hydrogen. In such cases the compounds may be of the formula:

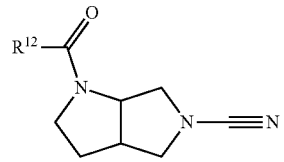

(IIC)

or a pharmaceutically acceptable salt thereof, wherein $R^{12}$ is as defined herein for compounds of formula (II).

In a further embodiment of the invention there is provided a compound of formula IID:

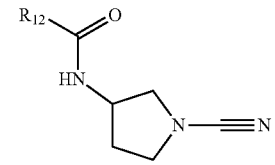

(IID)

or a pharmaceutically acceptable salt thereof, wherein $R^{12}$ is defined above for compounds of formula (I) or formula (II).

For compounds of formula (II), $R^{12}$ is a 3 to 14 membered (e.g. 3, 4, 5, 6, 7, 8, 9, 10, 11, 12, 13 or 14 membered) ring. When $R^{12}$ is a monocyclic ring, the ring must be substituted. When $R^{12}$ is a bicyclic or tricyclic ring then the ring can be either unsubstituted or substituted. In one embodiment, $R^{12}$ is a substituted ring.

When $R^{12}$ is a substituted heteroaryl or aryl ring, the ring may be monocyclic, bicyclic or tricyclic and, in the case of a heteroaryl ring, comprises one or more (e.g. 1, 2, or 3) heteroatoms selected from nitrogen, oxygen and sulphur, in particular nitrogen.

When $R^{12}$ is a substituted heteroaryl or aryl ring, the ring may be monocyclic or bicyclic and, in the case of a heteroaryl ring, comprises one or more (e.g. 1, 2 or 3) heteroatoms independently selected from nitrogen, oxygen and sulphur.

In one embodiment, $R^{12}$ is selected from phenyl, pyrrolidinyl, thiazolyl, pyridinyl, isoxazolyl, oxazolyl, imidazolyl, pyrazolyl, pyridazinyl, pyrimidinyl, indolyl, benzimidazolyl, quinolinyl, azetidinyl, indazolyl, pyrazolopyridinyl, imidazopyridinyl, indolinyl, piperazinyl, morpholinyl, diazepanyl, tetrahydropyridoindolyl, benzomorpholinyl and pyrrolopyridinyl.

In one embodiment, $R^{12}$ is selected from phenyl, pyrrolidinyl, thiazolyl, pyridinyl, isoxazolyl, oxazolyl, imidazolyl, pyrazolyl, pyridazinyl, pyrimidinyl, indolyl, benzimidazolyl and quinolinyl.

Typical examples of $R^{12}$ include phen-3-yl, phen-4-yl, pyrrolidin-1-yl, thiazol-2-yl, thiazol-5-yl, pyridin-2-yl, pyridin-3-yl, pyridin-4-yl, isoxazol-5-yl, oxazol-2-yl, pyrazol-4-yl, pyrazol-5-yl, pyrimidin-2-yl, pyridazin-3-yl, imidazol-4-yl, indol-2-yl, benzimidazol-2-yl, quinolin-4-yl and quinolin-6-yl.

In particular, $R^{12}$ may be selected from azetidinyl and pyrrolidinyl. In one embodiment, $R^{12}$ is azetidinyl. In another embodiment, $R^{12}$ is pyrrolidinyl. When $R^{12}$ is azetidinyl or pyrrolidinyl, preferably Y is a covalent bond which is attached to the nitrogen atom of the azetidinyl or pyrrolidinyl ring.

In one embodiment, when $R^{12}$ is pyridinyl, the pyridinyl is pyridin-2-yl.

Examples of $R^{12}$ include those shown below:

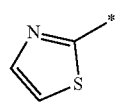

AA

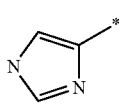

AB

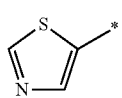

AC

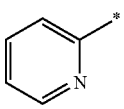

AD

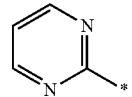

AE

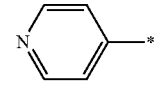

AF

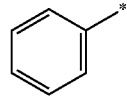

AG

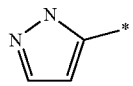

AH

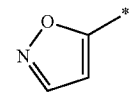

AI

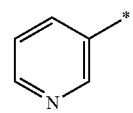

AJ

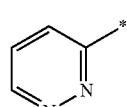

AK

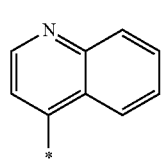

AL

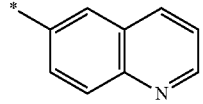

AM

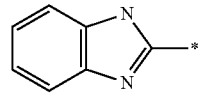

AN

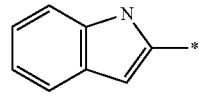

AO

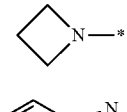

AP

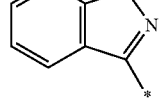

AQ

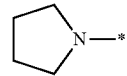

AR

-continued

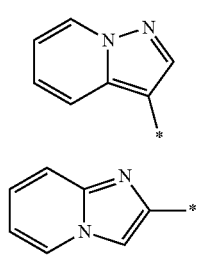 AS

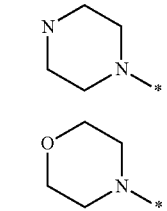 AT

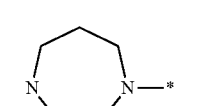 AU

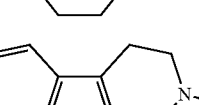 AV

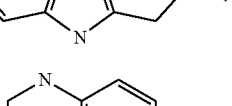 AW

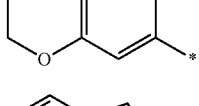 AX

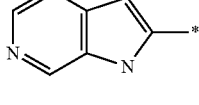 AY

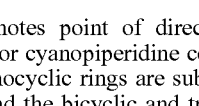 AZ

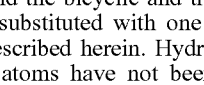

Wherein * denotes point of direct attachment to the cyanopyrrolidine or cyanopiperidine core via —Y—C(O)N(R$^{10}$)—. The monocyclic rings are substituted with at least one -Q$^1$-(R$^{13}$)$_p$ and the bicyclic and tricyclic rings may be unsubstituted or substituted with one or more -Q$^1$-(R$^{13}$)$_p$ substituents as described herein. Hydrogen atoms attached to ring nitrogen atoms have not been shown. It will be understood by the skilled person which ring nitrogen atoms are suitable for substitution and where not substituted the nitrogen may be bound to a hydrogen atom to complete its valency, where appropriate.

Further examples of R$^{12}$ include those shown below:

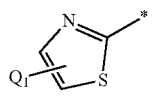 A

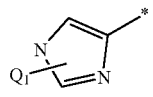 B

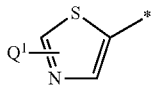 C

-continued

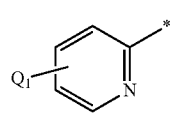 D

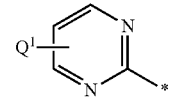 E

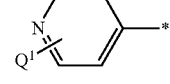 F

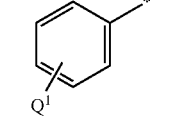 G

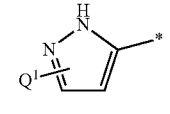 H

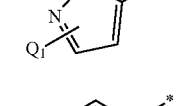 I

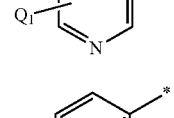 J

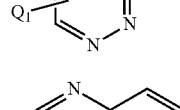 K

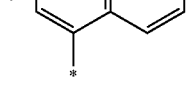 L

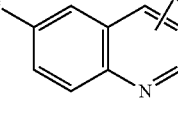 M

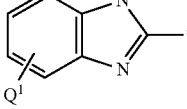 N

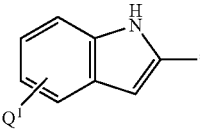 O

When substituted, R$^{12}$ may be substituted with one or more -Q$^1$-(R$^{13}$)$_p$, wherein each occurrence of -Q$^1$-(R$^{13}$)$_p$, may be the same or different.

p is 0 or 1 (when p is 1, $Q^1$ is a covalent bond or linker and $R^{13}$ is present, when p is 0, $Q^1$ is present and $R^{13}$ is absent).

Preferably, p is 1.

$Q^1$ represents a halogen atom, cyano, oxo, hydroxyl, a covalent bond, —$C_0$-$C_3$ alkylene-$NR^4$—, —$C_0$-$C_3$ alkylene-$NR^{14}R^{15}$, —$C_0$-$C_3$ alkylene-$CONR^{14}$—, —$C_0$-$C_3$ alkylene-$NR^{14}CO$—, —$C_0$-$C_3$ alkylene-$NR^{14}SO_2$—, —$C_0$-$C_3$-alkylene-O—$C_0$-$C_3$ alkylene, —$C_0$-$C_3$ alkylene-CO—, —$C_0$-$C_3$ alkylene-S(O)—, —$C_0$-$C_3$ alkylene-$SO_2NR^{14}$, —$C_1$-$C_6$ alkoxy, $C_1$-$C_6$ haloalkoxy, $C_1$-$C_6$ hydroxyalkyl, —$C_0$-$C_3$ alkylene-$SO_2R^{14}$, —$C_0$-$C_3$ alkylene-$NR^{14}COR^{15}$, —$C_0$-$C_3$ alkylene-$NR^{14}CONR^{15}R^{16}$, —$C_0$-$C_3$ alkylene-$NR^{14}SO_2NR^{15}R^{16}$, —$C_0$-$C_3$ alkylene-$CONR^{14}R^{15}$, —$C_0$-$C_3$ alkylene-$CO_2R^{14}$, —$C_0$-$C_3$ alkylene-$NR^{14}CO_2R^{15}$, —$C_0$-$C_3$ alkylene-$SO_2NR^{14}R^{15}$, —$C_0$-$C_3$ alkylene-$CONR^{14}$, —$C_0$-$C_3$ alkylene-$C(O)R^4$ and —$C_0$-$C_3$ alkylene-$NR^{14}SO_2R^{15}$, $NO_2$, or an optionally substituted $C_1$-$C_6$ alkylene, —$C_2$-$C_6$ alkenylene or —$C_1$-$C_6$ alkyl group; wherein q is 0, 1 or 2.

$Q^1$ may represent a halogen atom, cyano, oxo, a covalent bond, —$NR^{14}$—, —$NR^{14}R^{15}$, —$CONR^{14}$—, —$NR^{14}CO$—, an oxygen atom, —CO—, —$S(O)_q$—, —$SO_2NR^{14}$, —$C_1$-$C_6$ alkoxy, $C_1$-$C_6$ haloalkoxy, $C_1$-$C_6$ hydroxyalkyl, —$SO_2R^{14}$, —$NR^{14}COR^{15}$, —$NR^{14}CONR^{15}R^{16}$, —$NR^{14}SO_2NR^{15}R^{16}$ —$CONR^{14}R^{15}$, —$CO_2R^{14}$, —$NR^{14}CO_2R^{15}$, —$SO_2NR^{14}R^{15}$, —$CONR^{14}$, —$C(O)R^{14}$ and —$NR^{14}SO_2R^{15}$, $NO_2$, or an optionally substituted $C_1$-$C_6$ alkylene, —$C_2$-$C_6$ alkenylene or —$C_1$-$C_6$ alkyl group; wherein q is 0, 1 or 2.

In one embodiment, $Q^1$ represents a halogen atom, cyano, oxo, a covalent bond, an oxygen atom, —$C_0$-$C_3$-alkylene-O—$C_0$-$C_3$ alkylene, $C_1$-$C_6$ alkoxy, $C_1$-$C_4$ alkoxy, $C_1$-$C_2$ alkoxy, $C_1$-$C_6$ haloalkoxy, $C_1$-$C_4$ haloalkoxy, $C_1$-$C_2$ haloalkoxy, —$C_1$-$C_6$ hydroxyalkyl, $C_1$-$C_4$ hydroxyalkyl, $C_1$-$C_2$ hydroxyalkyl, $C_1$-$C_6$ alkylene, $C_1$-$C_4$ alkylene, $C_1$-$C_2$ alkylene, $C_2$-$C_6$ alkenylene or $C_2$-$C_4$ alkenylene group which may be optionally substituted with hydroxy, a halogen atom (e.g. fluorine, chlorine or bromine), $C_1$-$C_6$ alkyl, $C_1$-$C_4$ alkyl, $C_1$-$C_2$ alkyl, $C_1$-$C_6$ haloalkyl, $C_1$-$C_4$ haloalkyl, $C_1$-$C_2$ haloalkyl, $NR^{14}$—, —$NR^{14}R^{15}$—, —$CONR^{14}$—, —$NR^{14}CO$—, CO—, —$S(O)_q$—, —$SO_2NR^{14}$, —$NR^{14}SO_2$—, —$SO_2R^{14}$, —$NR^{14}COR^{15}$, —$NR^{14}CONR^{15}R^{16}$, —$NR^{14}SO_2NR^{15}R^{16}$—$CONR^{14}R^{15}$, —$CO_2R^{14}$, —$NR^{14}CO_2R^{15}$, —$SO_2NR^{14}R^{15}$, —$CONR^{14}$, —$C(O)R^{14}$, —$NR^{14}SO_2R^{15}$, or $NO_2$.

In one embodiment, $Q^1$ represents a halogen atom, cyano, oxo, a covalent bond, an oxygen atom, —O— methylene, —O-ethylene, $C_1$-$C_6$ alkoxy, $C_1$-$C_4$ alkoxy, $C_1$-$C_2$ alkoxy, $C_1$-$C_6$ haloalkoxy, $C_1$-$C_4$ haloalkoxy, $C_1$-$C_2$ haloalkoxy, —$C_1$-$C_6$ hydroxyalkyl, $C_1$-$C_4$ hydroxyalkyl, $C_1$-$C_2$ hydroxyalkyl, $C_1$-$C_6$ alkylene, $C_1$-$C_4$ alkylene, $C_1$-$C_2$ alkylene, $C_2$-$C_6$ alkenylene or $C_2$-$C_4$ alkenylene group which may be optionally substituted with hydroxy, a halogen atom (e.g. fluorine, chlorine or bromine), $C_1$-$C_6$ alkyl, $C_1$-$C_4$ alkyl, $C_1$-$C_2$ alkyl, $C_1$-$C_6$ haloalkyl, $C_1$-$C_4$ haloalkyl, $C_1$-$C_2$ haloalkyl, $NR^{14}$—, —$NR^{14}R^{15}$—, —$CONR^{14}$—, —$NR^{14}CO$—, CO—, —$S(O)_q$—, —$SO_2NR^{14}$, —$SO_2R^{14}$, —$NR^{14}COR^{15}$, —$NR^{14}CONR^{15}R^{16}$, —$NR^{14}SO_2NR^{15}R^{16}$—$CONR^{14}R^{15}$, —$CO_2R^{14}$, —$NR^{14}CO_2R^{15}$, —$SO_2NR^{14}R^{15}$, —$CONR^{14}$, —$C(O)R^{14}$, —$NR^{14}SO_2R^{15}$, or $NO_2$.

In another embodiment, $Q^1$ is selected from halogen, cyano, oxo, $C_1$-$C_6$ alkyl optionally substituted with fluorine, $C_1$-$C_6$ alkoxy optionally substituted with fluorine, —$NR^{14}COR^{15}$, a covalent bond, an oxygen atom, —$C_0$-$C_3$-alkylene-O—$C_0$-$C_3$ alkylene, —$NR^{14}$—, $C_1$-$C_6$ alkylene, —$NR^{14}SO_2$— and —$NR^{14}R^{15}$—.

In another embodiment, $Q^1$ is selected from halogen, oxo, a covalent bond, —$NR^{14}R^{15}$—, an oxygen atom, $C_1$-$C_6$ alkoxy, $C_1$-$C_4$ alkoxy, $C_1$-$C_2$ alkoxy, —$NR^{14}COR^{15}$ or $C_1$-$C_6$ alkyl, $C_1$-$C_4$ alkyl or $C_1$-$C_2$ alkyl.

$R^{14}$, $R^{15}$ and $R^{16}$ each independently represent a hydrogen atom or an optionally substituted $C_1$-$C_6$ alkyl, or an optionally substituted $C_1$-$C_6$ alkylene group. The alkyl or alkenylene group may be optionally substituted with halogen, hydroxyl, thiol, cyano, amino, amido, nitro and $SF_5$.

In a further embodiment, $Q^1$ may be selected from a fluorine atom, a chlorine atom, a bromine atom, cyano, oxo, methyl, butyl, $CF_3$, methoxy, $OCF_3$, $NMeC(O)CH(CH_3)_2$, —$NHCOCH(CH_3)_2$, a covalent bond, an oxygen atom, —O-methylene, —NH—, $C_1$-$C_2$ alkylene, —$NMeS(O)_2$—, —$OCH_2$— and —$N(CH_3)CH_2$—.

In a further embodiment, $Q^1$ may be selected from a fluorine atom, a chlorine atom, oxo, a covalent bond, an oxygen atom, methoxy, —$NHCOCH(CH_3)_2$, and —$N(CH_3)CH_2$—.

When $R^{12}$ is phenyl or pyridinyl, the phenyl or pyridinyl ring is preferably substituted with fluorine at one of the ortho positions on the ring. The phenyl or pyridinyl ring may be further substituted with -$Q^1$-($R^3$), as described above.

$R^{13}$ represents an optionally substituted 4 to 10 membered (e.g. 4, 5, 6, 7, 8, 9 or 10 membered) heteroaryl, heterocyclyl, aryl or 3 to 8 membered (e.g. 3, 4, 5, 6, 7 or 8 membered) cycloalkyl ring.

In one embodiment, $R^{13}$ represents a 4 to 10 membered heteroaryl, heterocyclyl, aryl or 3 to 8 membered cycloalkyl ring substituted with one or more substituents selected from halogen, optionally substituted $C_1$-$C_6$ haloalkyl, optionally substituted $C_1$-$C_6$ alkoxy, $C_1$-$C_6$ haloalkoxy, optionally substituted $C_1$-$C_6$ alkyl, optionally substituted $C_2$-$C_6$ alkenyl, optionally substituted $C_2$-$C_6$ alkynyl, $C_1$-$C_6$ hydroxyalkyl, oxo, cyano, optionally substituted heterocyclyl, optionally substituted cycloalkyl, optionally substituted heteroaryl, optionally substituted aryl, -$Q^2$-$R^{17}$, -$Q^2$-$NR^{17}CONR^{18}R^{19}$, -$Q^2$-$NR^{17}R^{18}$, -$Q^2$-$COR^7$, -$Q^2$-$NR^{17}COR^{18}$, -$Q^2$-$NR^{17}CO_2R^{18}$, -$Q^2$-$SO_2R^{17}$, $Q^2$-$CONR^{17}R^{18}$, -$Q^2$-$CO_2R^{17}$, -$Q^2$-$SO_2NR^{17}R^{18}$ and -$Q^2$-$NR^{17}SO_2R^{18}$.

$Q^2$ represents a covalent bond, an oxygen atom, carbonyl, or a $C_1$-$C_6$ alkylene or $C_2$-$C_6$ alkenylene group.

In one embodiment, $Q^2$ may be selected from a covalent bond, an oxygen atom, carbonyl, or an optionally substituted $C_1$-$C_6$ alkylene (e.g. $C_1$-$C_3$ alkylene, $C_1$-$C_4$ alkylene, $C_1$-$C_2$ alkylene) $C_2$-$C_6$ alkenylene or $C_2$-$C_4$ alkenylene. The alkylene and alkenylene may be optionally substituted with halogen, hydroxyl, thiol, cyano, amino, amido, nitro and $SF_5$.

In another embodiment $Q^2$ is selected from a covalent bond, an oxygen atom or carbonyl. In particular, $Q^2$ is a covalent bond.

$R^{17}$, $R^{18}$ and $R^{19}$ each independently represent hydrogen, optionally substituted $C_1$-$C_6$ alkyl, optionally substituted heterocyclyl, optionally substituted heteroaryl, optionally substituted aryl, or an optionally substituted cycloalkyl.

$R^{17}$, $R^{18}$ and $R^{19}$ may each independently represent hydrogen, $C_1$-$C_6$ alkyl or a 3 to 10 membered, in particular 3 to 6 membered, heterocyclyl, heteroaryl, aryl, or cycloalkyl ring, wherein the ring is optionally substituted with one or more substituents selected from $C_1$-$C_6$ alkyl, $C_1$-$C_6$ alkoxy, halogen, hydroxyl, thiol, cyano, amino, amido, nitro and $SF_5$, wherein the alkyl or alkoxy is optionally substituted with fluorine.

$R^{13}$ may be substituted with halogen, cyano, $C_1$-$C_3$ alkyl optionally substituted with fluorine, $C_1$-$C_3$ alkoxy optionally substituted with fluorine, or -$Q^2$-$R^{17}$, wherein $Q^2$ represents a covalent bond, an oxygen atom, carbonyl, or a $C_1$-$C_6$ alkylene or $C_2$-$C_6$ alkenylene group and $R^{17}$ represents an optionally substituted 3 to 10 membered heterocyclyl, heteroaryl, aryl, or cycloalkyl ring, wherein the optional substituents are selected from $C_1$-$C_6$ alkyl, $C_1$-$C_6$ alkoxy, halogen, hydroxyl, thiol, cyano, amino, amido, nitro and $SF_5$, wherein the alkyl or alkoxy is optionally substituted with fluorine.

In particular, $R^{13}$ may be substituted with fluorine, chlorine, cyano, methyl, $CF_3$, ethyl, methoxy or -$Q^2$-$R^{17}$, wherein $Q^2$ is a covalent bond, oxygen atom or carbonyl and $R^{17}$ is selected from optionally substituted morpholinyl, cyclopropyl, phenyl or pyridinyl and the optional substituents are one or more fluorine.

In one embodiment, $R^{13}$ is unsubstituted.

In one embodiment, $R^{13}$ is substituted with further optionally substituted 4 to 10 membered heteroaryl, heterocyclyl, aryl or 3 to 8 membered cycloalkyl rings, either directly attached or via a linking group.

The linking group may be an oxygen atom or carbonyl. The linking group may be an oxygen atom or —CO—.

In one embodiment, $R^{13}$ is selected from phenyl, pyridinyl, pyrazolyl, imidazolyl, isoxazolyl, morpholinyl, piperidinyl, piperazinyl, quinolinyl, pyrrolidinyl, benzopyrazolyl, isoindolinyl, tetrahydroquinolinyl, homopiperazinyl, pyrimidinyl, imidazopyrimidinyl, imidazopyridinyl, indazolyl, pyrrolopyridinyl, benzoimidazolyl, pyridazinyl, pyrazolopyrimidinyl, pyrrolopyrimidinyl, imidazopyrazinyl and dihydroisoquinolinyl.

In one embodiment, $R^{13}$ is selected from phenyl, pyridinyl, pyrazolyl, imidazolyl, isoxazolyl, morpholinyl, piperidinyl, piperazinyl, quinolinyl, pyrrolidinyl, benzopyrazolyl, isoindolinyl, tetrahydroquinolinyl and homopiperazinyl.

In the present invention, the compounds of the formulas described herein may not include compounds of the following structures:

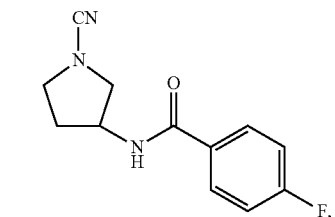

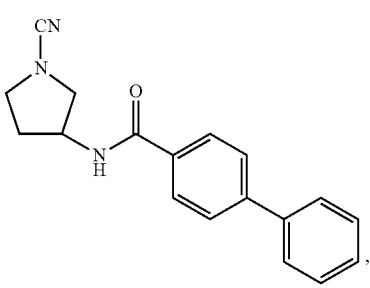

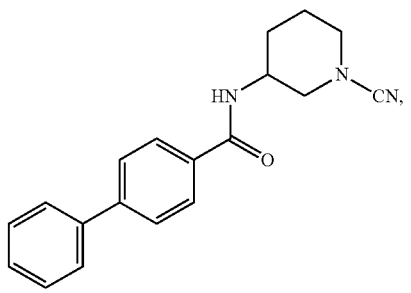

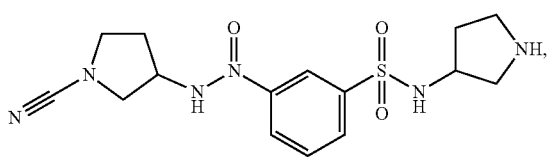

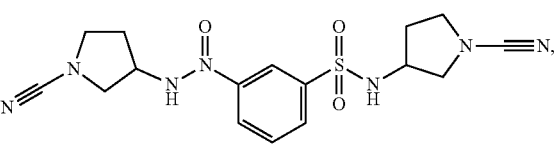

or

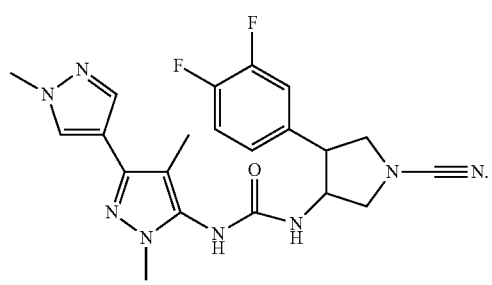

In particular, the compounds of the formulas described herein do not include the following compounds:

N-[(3R)-1-cyano-3-pyrrolidinyl]-4-fluoro-benzamide;

N-(1-cyano-3-pyrrolidinyl)-[1,1'-biphenyl]-4-carboxamide;

N-(1-cyano-3-piperidinyl)-[1,1'-biphenyl]-4-carboxamide;

N-[(3R)-1-cyano-3-pyrrolidinyl]-3-({[(3R)-1-cyano-3-pyrrolidinyl]amino}sulfonyl)benzamide;

N-[(3R)-1-cyano-3-pyrrolidinyl]-3-([(3R)-3-pyrrolidinylamino]sulfonyl)-benzamide; or 1-((3S,4R)-1-cyano-4-(3,4-difluorophenyl)pyrrolidin-3-yl)-3-(1',4-dimethyl-1-phenyl-1H, 1'H-[3,4'-bipyrazol]-5-yl)ureayl)urea, i.e. compounds of the following structures:

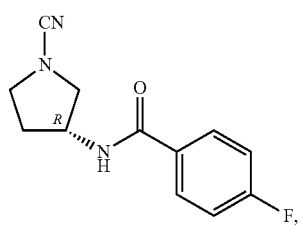

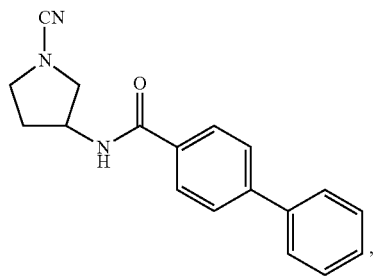

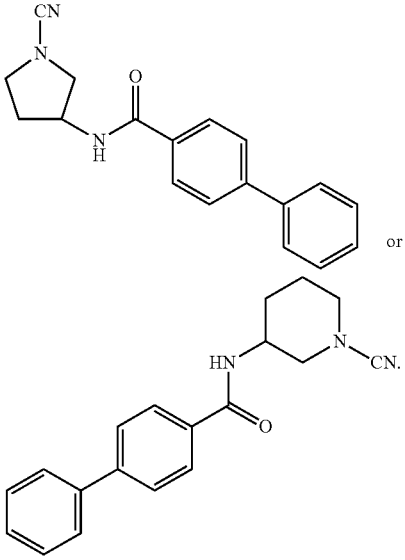

In the present invention, the compounds of formulae (I), (IB) and (IID), including any sub-generic embodiments thereof, do not include compounds of the following structures:

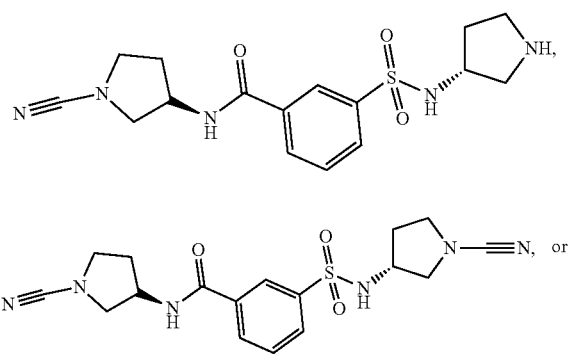

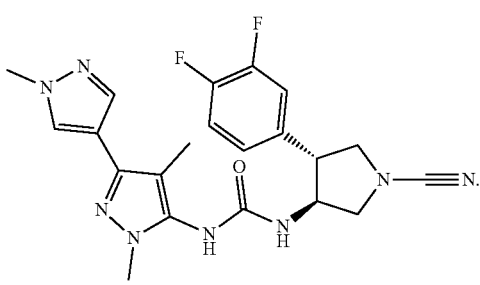

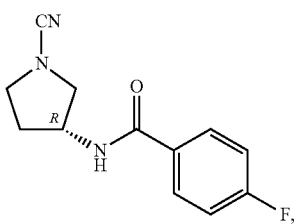

Embodiments of the invention that may be mentioned include compounds of formulae (I), (IB) and (IID) wherein:
n, X, $R^1$, $R^2$, $R^3$, $R^8$, $R^9$, $R^{10}$ and Y are defined above for compounds of formula (I);

$R^{12}$ represents either:
i) a 4 to 10 membered heteroaryl, heterocyclyl or 3 to 8 membered cycloalkyl ring substituted with one or more of $Q^1$-$(R^{13})_p$;
ii) a 4 to 10 membered aryl ring substituted with two or more $Q^1$-$(R^{13})_p$;
iii) a 5, 7, 8, 9 or 10 membered aryl ring singly substituted with $Q^{1'}$-$(R^{13})_p$; or
iv) a 6 membered aryl ring singly substituted with $Q^{1'}$-$(R^{13'})_p$;

wherein p is 0 or 1;

$Q^1$ represents a halogen atom, cyano, oxo, a covalent bond, —$NR^{14}$—, —$NR^{14}R^{15}$, —$CONR^{14}$—, —$NR^{14}CO$—, an oxygen atom, —CO—, —$S(O)_q$—, —$SO_2NR^{14}$—, $C_1$-$C_6$ alkoxy, $C_1$-$C_6$ haloalkoxy, $C_1$-$C_6$ hydroxyalkyl, —$SO_2R^{14}$, —$NR^{14}COR^5$, —$NR^{14}CONR^{15}R^{16}$, —$NR^{14}SO_2NR^{15}R^{16}$—, —$CONR^{14}R^{15}$, —$CO_2R^{14}$, —$NR^{14}CO_2R^{15}$, —$SO_2NR^{14}R^{15}$, —$CONR^{14}$—, —$C(O)R^{14}$ and —$NR^{14}SO_2R^{15}$, $NO_2$ or an optionally substituted $C_1$-$C_6$ alkylene, —$C_2$-$C_6$ alkenylene or —$C_1$-$C_6$ alkyl group;

$Q^{1'}$ represents a chlorine or bromine atom, cyano, oxo, a covalent bond, —$NR^{14}$—, —$NR^{14}R^{15}$, —$CONR^{14}$—, —$NR^{14}CO$—, an oxygen atom, —CO—, —$S(O)_q$—, $C_1$-$C_6$ alkoxy, $C_1$-$C_6$ haloalkoxy, $C_1$-$C_6$ hydroxyalkyl, —$SO_2R^{14}$, —$NR^{14}R^{15}$, —$NR^{14}COR^{15}$, —$NR^{14}CONR^{15}R^{16}$, —$CONR^{14}R^{15}$, —$CO_2R^{14}$, —$NR^{14}CO_2R^{15}$, $SO_2NR^{14}R^{15}$, —$CONR^{14}$—, —$C(O)R^{14}$ and —$NR^{14}SO_2R^{15}$ or an optionally substituted $C_1$-$C_6$ alkylene, —$C_2$-$C_6$ alkenylene or —$C_1$-$C_6$ alkyl group;

q is 0, 1 or 2;

$R^{14}$, $R^{15}$ and $R^{16}$ each independently represent a hydrogen atom or an optionally substituted $C_1$-$C_6$ alkyl, or an optionally substituted $C_1$-$C_6$ alkylene group; and when p is 1:
$R^{13}$ represents a 4 to 10 membered heteroaryl, heterocyclyl, aryl or 3 to 8 membered cycloalkyl ring (when p is 0, $Q^1$ is present and $R^{13}$ is absent), which is optionally substituted with one or more substituents selected from halogen, optionally substituted $C_1$-$C_6$ haloalkyl, optionally substituted $C_1$-$C_6$ alkoxy, $C_1$-$C_6$ haloalkoxy, optionally substituted $C_1$-$C_6$ alkyl, optionally substituted $C_2$-$C_6$ alkenyl, optionally substituted $C_2$-$C_6$ alkynyl, $C_1$-$C_6$ hydroxyalkyl, oxo, cyano, optionally substituted heterocyclyl, optionally substituted cycloalkyl, optionally substituted heteroaryl, optionally substituted aryl, -$Q^2$-$R^{17}$, -$Q^2$-$NR^{17}CONR^{18}R^{19}$, -$Q^2$-$NR^{17}R^{18}$, -$Q^2$-$COR^{17}$, -$Q^2$-$NR^{17}COR^{18}$, -$Q^2$-$NR^{17}CO_2R^{18}$, -$Q^2$-$SO_2R^{17}$, $Q^2$-$CONR^{17}R^{18}$, -$Q^2$-$CO_2R^{17}$, -$Q^2$-$SO_2NR^{17}R^{18}$ and -$Q^2$-$NR^{17}SO_2R^{18}$;

$R^{13'}$ represents an optionally substituted 4 to 10 membered heteroaryl, heterocyclyl or 3 to 8 membered cycloalkyl ring, an optionally substituted 5, 7, 8, 9 or 10 membered aryl ring, or a substituted 6 membered ring (when p is 0, $Q^{1'}$ is present and $R^{13'}$ is absent) substituted with one or more substituents selected from halogen, optionally substituted $C_1$-$C_6$ haloalkyl, optionally substituted $C_1$-$C_6$ alkoxy, $C_1$-$C_6$ haloalkoxy, optionally substituted $C_1$-$C_6$ alkyl, optionally substituted $C_2$-$C_6$ alkenyl, optionally substituted $C_2$-$C_6$ alkynyl, $C_1$-$C_6$ hydroxyalkyl, oxo, cyano, optionally substituted heterocyclyl, optionally substituted cycloalkyl, optionally substituted heteroaryl, optionally substituted aryl, -$Q^2$-$R^{17}$, -$Q^2$-$NR^{17}CONR^{18}R^{19}$, -$Q^2$-$NR^{17}R^{18}$, -$Q^2$-$COR^{17}$, -$Q^2$-$NR^{17}COR^{18}$, -$Q^2$-$NR^{17}CO_2R^{18}$, -$Q^2$-$SO_2R^{17}$, $Q^2$-$CONR^{17}R^{18}$, -$Q^2$-$CO_2R^{17}$, -$Q^2$-$SO_2NR^{17}R^{18}$ and -$Q^2$-$NR^{17}SO_2R^{18}$;

$Q^2$ represents a covalent bond, an oxygen atom, carbonyl, or a $C_1$-$C_6$ alkylene or $C_2$-$C_6$ alkenylene group; and $R^{17}$, $R^{18}$, $R^{19}$ each independently represent hydrogen, optionally substituted $C_1$-$C_6$ alkyl, optionally substituted heterocyclyl, optionally substituted heteroaryl, optionally substituted aryl, or an optionally substituted cycloalkyl.

In a particular embodiment of the invention there is provided a compound of formula (IID) wherein:

$R^{12}$ is selected from phenyl or pyridinyl and is substituted by one or two $Q^1(R^{13})_p$, wherein p is 1;

each $Q^1$ is independently selected from a covalent bond, a fluorine atom, $C_1$-$C_3$ alkoxy or $C_1$-$C_2$ alkoxy (e.g. methoxy or ethoxy); and $R^{13}$ is selected from a 5 or 6 membered heteroaryl or heterocyclyl which is optionally substituted with $C_1$-$C_3$ alkyl.

Embodiments of the invention that may be mentioned include compounds of formulae (II) or (III) wherein:

m, Z, $R^1$, $R^2$, $R^3$, $R^4$, $R^5$, $R^8$, $R^9$, $R^{10}$ and Y are defined above for compounds of formula (II);

$R^{12}$ represents either:

i) a 3 to 10 membered monocyclic heterocyclyl or cycloalkyl ring substituted with one or more of $Q^1$-$(R^{13})_p$, or bicyclic heterocyclyl or cycloalkyl ring optionally substituted with one or more of $Q^1$-$(R^{13})_p$;

ii) a 5 to 14 membered monocyclic aryl ring substituted with two or more $Q^1$-$(R^3)$, or bicyclic or tricyclic aryl ring optionally substituted with two or more $Q^1$-$(R^{13})_p$;

iii) a 5 or 7 to 14 membered monocyclic aryl ring substituted with one or more $Q^1$-$(R^{13})_p$, or bicyclic or tricyclic aryl ring optionally substituted with one or more $Q^1$-$(R^{13})$;

iv) a 6 membered aryl ring mono-substituted with $Q^{1'}$-$(R^{13'})_p$;

v) a 5 to 14 membered heteroaryl ring substituted with one or two $Q^1$-$(R^{13})_p$;

vi) a 6 to 14 membered heteroaryl ring substituted with one or more $Q^1$-$(R^{13})_p$; or vii) a 5 membered heteroaryl ring substituted with one or more $Q^{1''}$-$(R^{13''})_p$.

wherein p is 0 or 1;

$Q^1$ represents a halogen atom, cyano, oxo, hydroxyl, a covalent bond, —$C_0$-$C_3$ alkylene-$NR^{14}$—, —$C_0$-$C_3$ alkylene-$NR^{14}R^{15}$, —$C_0$-$C_3$ alkylene-$CONR^{14}$—, —$C_0$-$C_3$ alkylene-$NR^{14}CO$—, —$C_0$-$C_3$ alkylene-$NR^{14}SO_2$—, —$C_0$-$C_3$-alkylene-O—$C_0$-$C_3$ alkylene, —$C_0$-$C_3$ alkylene-CO—, —$C_0$-$C_3$ alkylene-S(O)$_q$—, —$C_0$-$C_3$ alkylene-$SO_2NR^{14}$, —$C_1$-$C_6$ alkoxy, $C_1$-$C_6$ haloalkoxy, $C_1$-$C_6$ hydroxyalkyl, —$C_0$-$C_3$ alkylene-$SO_2R^{14}$, —$C_0$-$C_3$ alkylene-$NR^{14}COR^{15}$, —$C_0$-$C_3$ alkylene-$NR^{14}CONR^{15}R^{16}$, —$C_0$-$C_3$ alkylene-$NR^{14}SO_2NR^{15}R^{16}$, —$C_0$-$C_3$ alkylene-$CONR^{14}R^{15}$, —$C_0$-$C_3$ alkylene-$CO_2R^{14}$, —$C_0$-$C_3$ alkylene-$NR^{14}CO_2R^{15}$, —$C_0$-$C_3$ alkylene-$SO_2NR^{14}R^{15}$, —$C_0$-$C_3$ alkylene-$CONR^{14}$, —$C_0$-$C_3$ alkylene-C(O)$R^{14}$ and —$C_0$-$C_3$ alkylene-$NR^{14}SO_2R^{15}$, $NO_2$, or an optionally substituted $C_1$-$C_6$ alkylene, —$C_2$-$C_6$ alkenylene or —$C_1$-$C_6$ alkyl group;

$Q^{1'}$ represents a chlorine or bromine atom, cyano, oxo, hydroxyl, a covalent bond, —$C_0$-$C_3$ alkylene-$NR^{14}$—, —$C_0$-$C_3$ alkylene-$NR^{14}R^{15}$, —$C_0$-$C_3$ alkylene-$CONR^{14}$—, —$C_0$-$C_3$ alkylene-$NR^{14}CO$—, —$C_0$-$C_3$ alkylene-$NR^{14}SO_2$—, —$C_0$-$C_3$-alkylene-O—$C_0$-$C_3$ alkylene, —$C_0$-$C_3$ alkylene-CO—, —$C_0$-$C_3$ alkylene-S(O)$_q$—, —$C_0$-$C_3$ alkylene-$SO_2NR^{14}$, —$C_1$-$C_6$ alkoxy, $C_1$-$C_6$ haloalkoxy, $C_1$-$C_6$ hydroxyalkyl, —$C_0$-$C_3$ alkylene-$SO_2R^{14}$, —$C_0$-$C_3$ alkylene-$NR^{14}COR^5$, —$C_0$-$C_3$ alkylene-$NR^{14}CONR^{15}R^{16}$, —$C_0$-$C_3$ alkylene-$NR^{14}SO_2NR^{15}R^{16}$, —$C_0$-$C_3$ alkylene-$CONR^{14}R^{15}$, —$C_0$-$C_3$ alkylene-$CO_2R^{14}$, —$C_0$-$C_3$ alkylene-$NR^{14}CO_2R^{15}$, —$C_0$-$C_3$ alkylene-$SO_2NR^{14}R^{15}$, —$C_0$-$C_3$ alkylene-$CONR^{14}$, —$C_0$-$C_3$ alkylene-C(O)$R^{14}$ and —$C_0$-$C_3$ alkylene-$NR^4SO_2R^{15}$, $NO_2$, or an optionally substituted $C_1$-$C_6$ alkylene, —$C_2$-$C_6$ alkenylene or —$C_1$-$C_6$ alkyl group;

$Q^{1''}$ represents halogen atom, cyano, oxo, hydroxyl, a covalent bond, —$C_0$-$C_3$ alkylene-$NR^{14}$—, —$C_0$-$C_3$ alkylene-$NR^{14}R^{15}$, —$C_0$-$C_3$ alkylene-$CONR^{14}$—, —$C_0$-$C_3$ alkylene-$NR^{14}CO$—, —$C_0$-$C_3$ alkylene-$NR^{14}SO_2$—, —$C_0$-$C_3$-alkylene-O—$C_0$-$C_3$ alkylene, —$C_0$-$C_3$ alkylene-CO—, —$C_0$-$C_3$ alkylene-S(O)$_q$—, —$C_0$-$C_3$ alkylene-$SO_2NR^{14}$, —$C_1$-$C_6$ alkoxy, $C_1$-$C_6$ haloalkoxy, $C_1$-$C_6$ hydroxyalkyl, —$C_0$-$C_3$ alkylene-$SO_2R^{14}$, —$C_0$-$C_3$ alkylene-$NR^{14}COR^{15}$, —$C_0$-$C_3$ alkylene-$NR^{14}CONR^{15}R^{16}$, —$C_0$-$C_3$ alkylene-$NR^{14}SO_2NR^{15}R^{16}$, —$C_0$-$C_3$ alkylene-$CONR^{14}R^{15}$, —$C_0$-$C_3$ alkylene-$CO_2R^{14}$, —$C_0$-$C_3$ alkylene-$NR^{14}CO_2R^{15}$, —$C_0$-$C_3$ alkylene-$SO_2NR^{14}R^{15}$, —$C_0$-$C_3$ alkylene-$CONR^{14}$, —$C_0$-$C_3$ alkylene-C(O)$R^{14}$ and —$C_0$-$C_3$ alkylene-$NR^{14}SO_2R^{15}$, $NO_2$, or an optionally substituted $C_1$-$C_6$ alkylene, —$C_2$-$C_6$ alkenylene or —$C_2$-$C_6$ alkyl group;

q is 0, 1 or 2;

$R^{14}$, $R^{15}$ and $R^{16}$ each independently represent a hydrogen atom or an optionally substituted $C_1$-$C_6$ alkyl, or an optionally substituted $C_1$-$C_6$ alkylene group; and when p is 1:

$R^{13}$ represents a 4 to 10 membered heteroaryl, heterocyclyl, aryl or 3 to 8 membered cycloalkyl ring, which is optionally substituted with one or more substituents selected from halogen, optionally substituted $C_1$-$C_6$ haloalkyl, optionally substituted $C_1$-$C_6$ alkoxy, $C_1$-$C_6$ haloalkoxy, optionally substituted $C_1$-$C_6$ alkyl, optionally substituted $C_2$-$C_6$ alkenyl, optionally substituted $C_2$-$C_6$ alkynyl, $C_1$-$C_6$ hydroxyalkyl, oxo, cyano, optionally substituted heterocyclyl, optionally substituted cycloalkyl, optionally substituted heteroaryl, optionally substituted aryl, -$Q^2$-$R^{17}$, -$Q^2$-$NR^{17}CONR^{18}R^{19}$, -$Q^2$-$NR^{17}R^{18}$, -$Q^2$-$COR^{17}$, -$Q^2$-$NR^{17}COR^{18}$, -$Q^2$-$NR^{17}CO_2R^{18}$, -$Q^2$-$SO_2R^{17}$, $Q^2$-$CONR^{17}R^{18}$, -$Q^2$-$CO_2R^{17}$, -$Q^2$-$SO_2NR^{17}R^{18}$ and $Q^2$-$NR^7SO_2R^{18}$;

$R^{13'}$ represents an optionally substituted 4 to 10 membered heteroaryl, heterocyclyl or 3 to 8 membered cycloalkyl ring, an optionally substituted 5, 7, 8, 9 or 10 membered aryl ring, or a substituted 6 membered aryl ring substituted with one or more substituents selected from halogen, optionally substituted $C_1$-$C_6$ haloalkyl, optionally substituted $C_1$-$C_6$ alkoxy, $C_1$-$C_6$ haloalkoxy, optionally substituted $C_1$-$C_6$ alkyl, optionally substituted $C_2$-$C_6$ alkenyl, optionally substituted $C_2$-$C_6$ alkynyl, $C_1$-$C_6$ hydroxyalkyl, oxo, cyano, optionally substituted heterocycyl, optionally substituted cycloalkyl, optionally substituted heteroaryl, optionally substituted aryl, -$Q^2$-$R^{17}$, -$Q^2$-$NR^{17}CONR^{18}R^{19}$, -$Q^2$-$NR^{17}R^{18}$, -$Q^2$-$COR^{17}$, -$Q^2$-$NR^{17}COR^{18}$, -$Q^2$-$NR^{17}CO_2R^{18}$, -$Q^2$-$SO_2R^{17}$, $Q^2$-$CONR^{17}R^{18}$, -$Q^2$-$CO_2R^{17}$, and -$Q^2$-$NR^{17}SO_2R^{18}$;

$R^{13''}$ represents an optionally substituted 4 to 10 membered heteroaryl, aryl or 3 to 8 membered cycloalkyl ring, an optionally substituted 6 to 10 membered heteroaryl ring, or a substituted 5 membered heterocyclyl ring wherein the substituents are selected from halogen, optionally substituted $C_1$-$C_6$ haloalkyl, optionally substituted $C_1$-$C_6$ alkoxy, $C_1$-$C_6$ haloalkoxy, optionally substituted $C_2$-$C_6$ alkyl, optionally substituted $C_2$-$C_6$ alkenyl, optionally substituted $C_2$-$C_6$ alkynyl, $C_1$-$C_6$ hydroxyalkyl, oxo, cyano, optionally substituted heterocycyl, optionally substituted cycloalkyl, optionally substituted heteroaryl, optionally substituted aryl, -$Q^2$-$R^{17}$, -$Q^2$-$NR^{17}CONR^{18}R^{19}$, -$Q^2$-$NR^{17}R^{18}$, -$Q^2$-$COR^{17}$, -$Q^2$-$NR^{17}COR^{18}$, -$Q^2$-$NR^{17}CO_2R^{18}$, -$Q^2$-$SO_2R^{17}$, $Q^2$-$CONR^{17}R^{18}$, -$Q^2$-$CO_2R^{17}$, and -$Q^2$-$NR^{17}SO_2R^{18}$ $Q^2$ represents a covalent bond, an oxygen atom, carbonyl, or a $C_1$-$C_6$ alkylene or $C_2$-$C_6$ alkenylene group; and $R^{17}$, $R^{18}$, $R^{19}$ each independently represent hydrogen, optionally substituted $C_1$-$C_6$ alkyl, optionally substituted heterocyclyl, optionally substituted heteroaryl, optionally substituted aryl, or an optionally substituted cycloalkyl.

Examples of novel compounds of formula (I) and/or formula (II) include:

(R)—N-(1-cyanopyrrolidin-3-yl)-5-phenylpicolinamide
(R)—N-(1-cyanopyrrolidin-3-yl)-3-methoxy-4-(1-methyl-1H-pyrazol-4-yl)benzamide
2'-chloro-N-(1-cyanopyrrolidin-3-yl)-[1,1'-biphenyl]-4-carboxamide
6-(benzyl(methyl)amino)-N-(1-cyanopyrrolidin-3-yl)nicotinamide
(R)—N-(1-cyanopyrrolidin-3-yl)-3-phenylazetidine-1-carboxamide
N—((R)-1-cyanopyrrolidin-3-yl)-4-((2S,6R)-2,6-dimethylmorpholino)-3-fluorobenzamide
N-(1-cyanopyrrolidin-3-yl)-4-phenylthiazole-2-carboxamide
3-(3-chlorophenyl)-N-(1-cyanopyrrolidin-3-yl)isoxazole-5-carboxamide
N-(1-cyanopyrrolidin-3-yl)-1-phenyl-1H-imidazole-4-carboxamide
N-(1-cyanopyrrolidin-3-yl)-1-(2,4-difluorobenzyl)-5-oxopyrrolidine-3-carboxamide
N-(1-cyanopyrrolidin-3-yl)-5-oxo-1-phenylpyrrolidine-3-carboxamide
N-(1-cyanopyrrolidin-3-yl)-4-(3,5-dimethylisoxazol-4-yl)benzamide
3'-chloro-N-(1-cyanopyrrolidin-3-yl)-[1,1'-biphenyl]-4-carboxamide
N-(1-cyanopyrrolidin-3-yl)-2'-methoxy-[1,1'-biphenyl]-4-carboxamide
N-(1-cyanopyrrolidin-3-yl)-4-phenoxybenzamide
2-([1,1'-biphenyl]-4-yl)-N-(1-cyanopyrrolidin-3-yl)acetamide
N-(1-cyanopyrrolidin-3-yl)-2-phenylquinoline-4-carboxamide
6-(4-carbamoylpiperidin-1-yl)-N-(1-cyanopyrrolidin-3-yl)nicotinamide
N-(1-cyanopyrrolidin-3-yl)-6-(4-(2,4-difluorophenyl)piperazin-1-yl)nicotinamide
ethyl 4-(5-((1-cyanopyrrolidin-3-yl)carbamoyl)pyridin-2-yl)piperazine-1-carboxylate
N-(1-cyanopyrrolidin-3-yl)-6-(2-(pyridin-3-yl)pyrrolidin-1-yl)nicotinamide
N-(1-cyanopyrrolidin-3-yl)-6-(4-phenoxypiperidine-1-yl)nicotinamide
N-(1-cyanopyrrolidin-3-yl)-6-(4-(pyridin-4-yl)piperidin-1-yl)nicotinamide
6-(benzyl(methyl)amino)-N-(1-cyanopyrrolidin-3-yl)picolinamide
N-(1-cyanopyrrolidin-3-yl)-6-(3,4-dihydroisoquinolin-2(1H)-yl)picolinamide
N-(1-cyanopyrrolidin-3-yl)-6-(4-phenoxypiperidine-1-yl)picolinamide
N-(1-cyanopyrrolidin-3-yl)-2-(3,4-dihydroisoquinolin-2(1H)-yl)isonicotinamide
2-(4-acetyl-1,4-diazepan-1-yl)-N-(1-cyanopyrrolidin-3-yl)isonicotinamide
(R)—N-(1-cyanopyrrolidin-3-yl)-6-phenylpicolinamide
(R)—N-(1-cyanopyrrolidin-3-yl)-4-phenylpicolinamide
(R)—N-(1-cyanopyrrolidin-3-yl)-4-morpholinobenzamide
(R)—N-(1-cyanopyrrolidin-3-yl)-3-fluoro-4-morpholinobenzamide
(R)—N-(1-cyanopyrrolidin-3-yl)-3-phenylisoxazole-5-carboxamide
(R)—N-(1-cyanopyrrolidin-3-yl)-5-(pyridin-4-yl)isoxazole-3-carboxamide
(R)—N-(1-cyanopyrrolidin-3-yl)-[1,1'-biphenyl]-4-carboxamide
(R)-6-(4-chlorophenyl)-N-(1-cyanopyrrolidin-3-yl)nicotinamide
(R)-2-(2-chlorophenyl)-N-(1-cyanopyrrolidin-3-yl)thiazole-5-carboxamide
(R)-4-(3-chloropyridin-4-yl)-N-(1-cyanopyrrolidin-3-yl)benzamide
(R)-4-(3-chloropyridin-4-yl)-N-(1-cyanopyrrolidin-3-yl)-3-methoxybenzamide
(R)—N-(1-cyanopyrrolidin-3-yl)-3-methoxy-4-(2-methylpyridin-4-yl)benzamide
(R)—N-(1-cyanopyrrolidin-3-yl)-3-methoxy-4-(2-morpholinopyridin-4-yl)benzamide
(R)—N-(1-cyanopyrrolidin-3-yl)-4-fluoro-3-(pyridin-4-yl)benzamide
(R)—N-(1-cyanopyrrolidin-3-yl)-4-fluoro-3-(1-methyl-1H-pyrazol-4-yl)benzamide
(R)—N-(1-cyanopyrrolidin-3-yl)-4-(1-methyl-1H-pyrazol-4-yl)benzamide
(R)—N-(1-cyanopyrrolidin-3-yl)-5-(1-methyl-1H-pyrazol-4-yl)pyrimidine-2-carboxamide
N—((R)-1-cyanopyrrolidin-3-yl)-3-phenylpyrrolidine-1-carboxamide
(S)—N-(1-cyanopyrrolidin-3-yl)-4-(pyridin-4-yl)benzamide
(S)—N-(1-cyanopyrrolidin-3-yl)-6-phenylpicolinamide
(R)-4-(3-chloropyridin-4-yl)-N-(1-cyanopyrrolidin-3-yl)-N-methylbenzamide
(R)-1-(1-cyanopyrrolidin-3-yl)-3-(imidazo[1,2-a]pyridin-2-yl)-1-methylurea
(3aR,6aR)-1-([1,1'-biphenyl]-3-carbonyl)hexahydropyrrolo[3,4-b]pyrrole-5(1H)-carbonitrile
(3aR,6aR)-1-(3-phenyl-1H-pyrazole-5-carbonyl)hexahydropyrrolo[3,4-b]pyrrole-5(1H)-carbonitrile (3aR,6aR)-1-(3-phenylisoxazole-5-carbonyl)hexahydropyrrolo[3,4-b]pyrrole-5 (1H)-carbonitrile
(3aR,6aR)-1-(1-phenyl-1H-imidazole-4-carbonyl)hexahydropyrrolo[3,4-b]pyrrole-5(1H)-carbonitrile
(3aR,6aR)-1-(3-(4-methoxyphenyl)-1H-pyrazole-5-carbonyl)hexahydropyrrolo[3,4-b]pyrrole-5(1H)-carbonitrile
(3aR,6aR)-1-(3-(4-methoxyphenyl)isoxazole-5-carbonyl)hexahydropyrrolo[3,4-b]pyrrole-5(1H)-carbonitrile
(3aR,6aR)-1-(4-fluoro-3-(pyridin-4-yl)benzoyl)hexahydropyrrolo[3,4-b]pyrrole-5(1H)-carbonitrile
(3aR,6aR)-1-(4-fluoro-3-(1-methyl-1H-pyrazol-4-yl)benzoyl)hexahydropyrrolo[3,4-b]pyrrole-5(1H)-carbonitrile
(3aR,6aR)-1-(4-(3-chloropyridin-4-yl)-3-methoxybenzoyl)hexahydropyrrolo[3,4-b]pyrrole-5(1H)-carbonitrile
(3aR,6aR)-1-(3-methoxy-4-(1-methyl-1H-pyrazol-4-yl)benzoyl)hexahydropyrrolo[3,4-b]pyrrole-5(1H)-carbonitrile
(3aR,6aR)-1-(2-oxo-6-phenyl-1,2-dihydropyridine-3-carbonyl)hexahydropyrrolo[3,4-b]pyrrole-5(1H)-carbonitrile
(R)—N-(1-cyanopyrrolidin-3-yl)-3-(N-methylisobutyramido)benzamide
(R)—N-(1-cyanopyrrolidin-3-yl)-5-phenylpyrimidine-2-carboxamide
(R)—N-(1-cyanopyrrolidin-3-yl)-3-(pyridin-4-yl)isoxazole-5-carboxamide
(R)—N-(1-cyanopyrrolidin-3-yl)-3-(pyridin-3-yl)isoxazole-5-carboxamide
(R)—N-(1-cyanopyrrolidin-3-yl)-3-(pyridin-2-yl)isoxazole-5-carboxamide
N-(1-cyanopyrrolidin-3-yl)-5-phenylpyridazine-3-carboxamide
N-(1-cyanopyrrolidin-3-yl)-N-methyl-[1,1'-biphenyl]-4-carboxamide
N-((3S,4R)-1-cyano-4-methylpyrrolidin-3-yl)-2-phenylthiazole-5-carboxamide
N-((3R,4S)-1-cyano-4-methylpyrrolidin-3-yl)-2-phenylthiazole-5-carboxamide
N-((3S,4R)-1-cyano-4-methylpyrrolidin-3-yl)-5-phenylthiazole-2-carboxamide
N-((3R,4S)-1-cyano-4-methylpyrrolidin-3-yl)-5-phenylthiazole-2-carboxamide
(R)—N-(1-cyanopyrrolidin-3-yl)-2-(isoindolin-2-yl)isonicotinamide
(R)—N-(1-cyanopyrrolidin-3-yl)-2-(3,4-dihydroisoquinolin-2(1H)-yl)isonicotinamide
(R)—N-(1-cyanopyrrolidin-3-yl)-2-fluoro-4-(4-methyl-1H-imidazol-1-yl)benzamide
(R)—N-(1-cyanopyrrolidin-3-yl)-3-fluoro-4-(1-methyl-1H-pyrazol-4-yl)benzamide
(R)—N-(1-cyanopyrrolidin-3-yl)-2-fluoro-4-(1-methyl-1H-pyrazol-4-yl)benzamide
(R)—N-(1-cyanopyrrolidin-3-yl)-2,5-difluoro-4-(1-methyl-1H-pyrazol-4-yl)benzamide
(R)—N-(1-cyanopyrrolidin-3-yl)-4-(1,3-dimethyl-1H-pyrazol-4-yl)-3-fluorobenzamide
(R)—N-(1-cyanopyrrolidin-3-yl)-4-(1,3-dimethyl-1H-pyrazol-4-yl)-2-fluorobenzamide
(R)—N-(1-cyanopyrrolidin-3-yl)-4-(1-ethyl-1H-pyrazol-4-yl)-2-fluorobenzamide
(R)—N-(1-cyanopyrrolidin-3-yl)-2-fluoro-4-(1-(2-methoxyethyl)-1H-pyrazol-4-yl)benzamide
(R)—N-(1-cyanopyrrolidin-3-yl)-6-(1-methyl-1H-pyrazol-4-yl)-1H-benzo[d]imidazole-2-carboxamide
(R)—N-(1-cyanopyrrolidin-3-yl)-6-(1-methyl-1H-pyrazol-4-yl)-1H-indole-2-carboxamide
(R)—N-(1-cyanopyrrolidin-3-yl)-2-fluoro-4-(5-(trifluoromethyl)-1H-pyrazol-4-yl)benzamide
(R)—N-(1-cyanopyrrolidin-3-yl)-2-fluoro-4-(1-methyl-1H-indazol-5-yl)benzamide
(R)—N-(1-cyanopyrrolidin-3-yl)-3-fluoro-N-methyl-4-(1-methyl-1H-pyrazol-4-yl)benzamide
(R)—N-(1-cyanopyrrolidin-3-yl)-N-methyl-6-(1-methyl-1H-pyrazol-4-yl)-1H-benzo[d]imidazole-2-carboxamide
(R)—N-(1-cyanopyrrolidin-3-yl)-N-methyl-3-phenoxyazetidine-1-carboxamide
(3aR,6aR)-5-cyano-N-(2-fluoro-4-(trifluoromethyl)phenyl)hexahydropyrrolo[3,4-b]pyrrole-1 (2H)-carboxamide
(R)—N-(1-cyanopyrrolidin-3-yl)-2-fluoro-4-(pyrimidin-2-ylamino)benzamide
N-((3R,4S)-1-cyano-4-methylpyrrolidin-3-yl)-2-fluoro-4-((R)-3-methoxypyrrolidin-1-yl)benzamide
2-(2-chlorophenyl)-N-((3R,4R)-1-cyano-4-hydroxypyrrolidin-3-yl)thiazole-5-carboxamide
N-(1-cyano-3-methylpyrrolidin-3-yl)-2-fluoro-4-(1-methyl-1H-pyrazol-4-yl)benzamide
(R)—N-(1-cyanopyrrolidin-3-yl)-5-(4-methoxyphenyl)-1H-pyrazole-3-carboxamide
(R)—N-(1-cyanopyrrolidin-3-yl)-5-(pyridin-2-yl)-1H-pyrazole-3-carboxamide
(R)—N-(1-cyanopyrrolidin-3-yl)-5-(2-methoxyphenyl)-1H-pyrazole-3-carboxamide
(R)—N-(1-cyanopyrrolidin-3-yl)-5-(2-fluorophenyl)-1H-pyrazole-3-carboxamide
(R)—N-(1-cyanopyrrolidin-3-yl)-6-morpholinonicotinamide
(R)—N-(1-cyanopyrrolidin-3-yl)-3-(4-methoxyphenyl)isoxazole-5-carboxamide
(R)—N-(1-cyanopyrrolidin-3-yl)-1H-indazole-3-carboxamide
(R)—N-(1-cyanopyrrolidin-3-yl)-5-phenyl-1H-pyrazole-3-carboxamide
(R)—N-(1-cyanopyrrolidin-3-yl)-5-(pyridin-3-yl)-1H-pyrazole-3-carboxamide
(R)—N-(1-cyanopyrrolidin-3-yl)-2-fluoro-3-(1-methyl-1H-pyrazol-4-yl)benzamide
(R)—N-(1-cyanopyrrolidin-3-yl)-2-fluoro-4-(2-methylpyrimidin-4-yl)benzamide
(R)—N-(1-cyanopyrrolidin-3-yl)-5-(1-methyl-1H-pyrazol-4-yl)picolinamide
(R)—N-(1-cyanopyrrolidin-3-yl)-2-fluoro-5-(1-methyl-1H-pyrazol-4-yl)benzamide
(R)—N-(1-cyanopyrrolidin-3-yl)-2-fluoro-4-(pyrimidin-4-yl)benzamide
(R)—N-(1-cyanopyrrolidin-3-yl)-2-fluoro-4-(imidazo[1,2-a]pyrimidin-6-yl)benzamide
(R)—N-(1-cyanopyrrolidin-3-yl)-2-methoxy-4-(1-methyl-1H-pyrazol-4-yl)benzamide
(R)—N-(1-cyanopyrrolidin-3-yl)-6-(1-methyl-1H-pyrazol-4-yl)nicotinamide
(R)—N-(1-cyanopyrrolidin-3-yl)-3,5-difluoro-4-(1-methyl-1H-pyrazol-4-yl)benzamide
(R)—N-(1-cyanopyrrolidin-3-yl)-2,6-difluoro-4-(1-methyl-1H-pyrazol-4-yl)benzamide
(R)—N-(1-cyanopyrrolidin-3-yl)-6-(1-methyl-1H-pyrazol-4-yl)pyrazolo[1,5-a]pyridine-3-carboxamide
(R)—N-(1-cyanopyrrolidin-3-yl)-2-fluoro-3-methoxy-4-(1-methyl-1H-pyrazol-4-yl)benzamide
(R)-6-(3-cyanophenyl)-N-(1-cyanopyrrolidin-3-yl)imidazo[1,2-a]pyridine-2-carboxamide
(R)-6-(4-cyanophenyl)-N-(1-cyanopyrrolidin-3-yl)imidazo[1,2-a]pyridine-2-carboxamide
(R)—N-(1-cyanopyrrolidin-3-yl)-2-fluoro-4-(imidazo[1,2-a]pyridin-6-yl)benzamide (R)—N-(1-cyanopyrrolidin-3-yl)-2-fluoro-4-(2-morpholinopyridin-4-yl)benzamide
(R)—N-(1-cyanopyrrolidin-3-yl)-3-fluoro-5-(1-methyl-1H-indazol-5-yl)picolinamide
(R)—N-(1-cyanopyrrolidin-3-yl)-3-fluoro-5-(1-methyl-1H-pyrrolo[2,3-b]pyridin-5-yl)picolinamide
(R)—N-(1-cyanopyrrolidin-3-yl)-5-(1,3-dimethyl-1H-pyrazol-4-yl)-3-fluoropicolinamide
(R)-3-chloro-N-(1-cyanopyrrolidin-3-yl)-5-(4-fluorophenyl)picolinamide
(R)—N-(1-cyanopyrrolidin-3-yl)-6-(1-methyl-1H-pyrazol-4-yl)imidazo[1,2-a]pyridine-2-carboxamide
(R)—N-(1-cyanopyrrolidin-3-yl)-6-(1,3-dimethyl-1H-pyrazol-4-yl)imidazo[1,2-a]pyridine-2-carboxamide
(R)—N-(1-cyanopyrrolidin-3-yl)-5-(1-methyl-1H-pyrazol-4-yl)-1H-indazole-3-carboxamide
(R)—N-(1-cyanopyrrolidin-3-yl)-6-(1-methyl-1H-pyrazol-4-yl)-1H-indazole-3-carboxamide
(R)—N-(1-cyanopyrrolidin-3-yl)-6-(3,5-dimethylisoxazol-4-yl)-1H-indole-2-carboxamide
(R)—N-(1-cyanopyrrolidin-3-yl)-6-(1,3-dimethyl-1H-pyrazol-4-yl)-1H-indole-2-carboxamide
(R)—N-(1-cyanopyrrolidin-3-yl)-5-(1-methyl-1H-pyrazol-4-yl)-1H-indole-2-carboxamide
(R)—N-(1-cyanopyrrolidin-3-yl)-2,3-difluoro-4-(1-methyl-1H-pyrazol-4-yl)benzamide
(R)—N-(1-cyanopyrrolidin-3-yl)-5-(1-ethyl-1H-pyrazol-4-yl)-4-methylpicolinamide
(R)—N-(1-cyanopyrrolidin-3-yl)-3-phenoxyazetidine-1-carboxamide
(R)-3-(1H-benzo[d]imidazol-2-yl)-N-(1-cyanopyrrolidin-3-yl)azetidine-1-carboxamide
(R)—N-(1-cyanopyrrolidin-3-yl)-4-phenylpiperazine-1-carboxamide
N—((R)-1-cyanopyrrolidin-3-yl)-2-phenylmorpholine-4-carboxamide
(R)-4-(2-chloro-6-fluorobenzyl)-N-(1-cyanopyrrolidin-3-yl)-1,4-diazepane-1-carboxamide
(R)-4-benzyl-N-(1-cyanopyrrolidin-3-yl)-1,4-diazepane-1-carboxamide
(R)—N-(1-cyanopyrrolidin-3-yl)-1,3,4,9-tetrahydro-2H-pyrido[3,4-b]indole-2-carboxamide
N—((R)-1-cyanopyrrolidin-3-yl)-2-((2S,6R)-2,6-dimethylmorpholino)-5-fluoroisonicotinamide
(R)—N-(1-cyanopyrrolidin-3-yl)-5-fluoro-2-(isoindolin-2-yl)isonicotinamide
(R)—N-(1-cyanopyrrolidin-3-yl)-3-fluoro-4-(pyrimidin-2-ylamino)benzamide
(R)—N-(1-cyanopyrrolidin-3-yl)-2-fluoro-4-(pyrrolidin-1-yl)benzamide
(R)—N-(1-cyanopyrrolidin-3-yl)-2,5-difluoro-4-morpholinobenzamide
(R)—N-(1-cyanopyrrolidin-3-yl)-2,5-difluoro-4-(pyrrolidin-1-yl)benzamide
N—((R)-1-cyanopyrrolidin-3-yl)-2-fluoro-4-((R)-3-methoxypyrrolidin-1-yl)benzamide
(R)—N-(1-cyanopyrrolidin-3-yl)-3-methoxy-4-(pyrimidin-2-ylamino)benzamide
(R)—N-(1-cyanopyrrolidin-3-yl)-3-methoxy-4-((4-methylpyrimidin-2-yl)amino)benzamide
(R)—N-(1-cyanopyrrolidin-3-yl)-2-fluoro-4-((4-methoxypyrimidin-2-yl)amino)benzamide
N—((R)-1-cyanopyrrolidin-3-yl)-5-methyl-1-(1-phenylethyl)-1H-pyrazole-3-carboxamide
(R)—N-(1-cyanopyrrolidin-3-yl)-5-methyl-1-(pyridin-2-ylmethyl)-1H-pyrazole-3-carboxamide
(R)—N-(1-cyanopyrrolidin-3-yl)-2-fluoro-4-(pyridazin-4-yl)benzamide
(R)—N-(1-cyanopyrrolidin-3-yl)-1-isobutyl-6-(1-methyl-1H-pyrazol-4-yl)-1H-indazole-3-carboxamide
(R)—N-(1-cyanopyrrolidin-3-yl)-6-(3,5-dimethylisoxazol-4-yl)-1-isobutyl-1H-indazole-3-carboxamide
(R)—N-(1-cyanopyrrolidin-3-yl)-1-(cyclopropylmethyl)-6-(3,5-dimethylisoxazol-4-yl)-1H-indazole-3-carboxamide
(R)—N-(1-cyanopyrrolidin-3-yl)-N-methyl-6-(1-methyl-1H-pyrazol-4-yl)imidazo[1,2-a]pyridine-2-carboxamide
(R)—N-(1-cyanopyrrolidin-3-yl)-N-methyl-5-(1-methyl-1H-pyrazol-4-yl)-1H-indole-2-carboxamide
(R)—N-(-cyanopyrrolidin-3-yl)-6-(3,5-dimethylisoxazxaol-4-yl)-N-methyl-1H-benzo[d]imidazole-2-carboxamide
(R)—N-(1-cyanopyrrolidin-3-yl)-7-(1-methyl-1H-pyrazol-4-yl)imidazo[1,2-a]pyridine-3-carboxamide
(R)-7-(3-cyanophenyl)-N-(1-cyanopyrrolidin-3-yl)imidazo[1,2-a]pyridine-3-carboxamide
(R)—N-(1-cyanopyrrolidin-3-yl)-N-methyl-7-(2-methylpyridin-4-yl)imidazo[1,2-a]pyridine-3-carboxamide
(R)—N-(1-cyanopyrrolidin-3-yl)-N-methyl-7-(6-methylpyridin-3-yl)imidazo[1,2-a]pyridine-3-carboxamide
(R)—N-(1-cyanopyrrolidin-3-yl)-7-(1,3-dimethyl-1H-pyrazol-4-yl)-N-methylimidazo[1,2-a]pyridine-3-carboxamide
(R)—N-(1-cyanopyrrolidin-3-yl)-7-(2,6-dimethylpyridin-4-yl)-N-methylimidazo[1,2-a]pyridine-3-carboxamide
(R)—N-(1-cyanopyrrolidin-3-yl)-N-ethyl-7-(2-methylpyridin-4-yl)imidazo[1,2-a]pyridine-3-carboxamide
(R)—N-(1-cyanopyrrolidin-3-yl)-7-morpholinoimidazo[1,2-a]pyridine-3-carboxamide
(R)-6-(3-cyanophenyl)-N-(1-cyanopyrrolidin-3-yl)-3-fluoroimidazo[1,2-a]pyridine-2-carboxamide
(R)—N-(1-cyanopyrrolidin-3-yl)-3-fluoro-6-(1-methyl-1H-pyrazol-4-yl)imidazo[1,2-a]pyridine-2-carboxamide
(R)—N-(1-cyanopyrrolidin-3-yl)-6-(1-ethyl-1H-pyrazol-4-yl)-3-fluoroimidazo[1,2-a]pyridine-2-carboxamide
(R)—N-(1-cyanopyrrolidin-3-yl)-6-(1,3-dimethyl-1H-pyrazol-4-yl)-3-fluoroimidazo[1,2-a]pyridine-2-carboxamide
(R)—N-(1-cyanopyrrolidin-3-yl)-6-(3,5-dimethylisoxazol-4-yl)-3-fluoroimidazo[1,2-a]pyridine-2-carboxamide
(R)—N-(1-cyanopyrrolidin-3-yl)-2-fluoro-4-(pyrazolo[1,5-a]pyrimidin-5-yl)benzamide
(R)—N-(1-cyanopyrrolidin-3-yl)-5-(4-fluorophenyl)picolinamide
N-((2R,3R)-1-cyano-2-methylpyrrolidin-3-yl)-5-(4-fluorophenyl)picolinamide
3-chloro-N-((3R,4S)-1-cyano-4-methylpyrrolidin-3-yl)-4-morpholinobenzamide
N-((3R,4R)-1-cyano-4-fluoropyrrolidin-3-yl)-[1,1'-biphenyl]-4-carboxamide
N-((3R,4R)-1-cyano-4-cyclopropylpyrrolidin-3-yl)-3-fluoro-4-(1-methyl-1H-pyrazol-4-yl)benzamide
N-((3S,4S)-1-cyano-4-methoxypyrrolidin-3-yl)-N-methyl-4-(1-methyl-1H-pyrazol-4-yl)benzamide
(R)—N-(1-cyanopyrrolidin-3-yl)-5-(1,3-dimethyl-1H-pyrazol-4-yl)picolinamide
(R)—N-(1-cyanopyrrolidin-3-yl)-5-(2-methyl-6-(trifluoromethyl)pyrimidin-4-yl)picolinamide
(R)—N-(1-cyanopyrrolidin-3-yl)-4-(2,6-dimethylpyrimidin-4-yl)-2-fluorobenzamide
(R)—N-(1-cyanopyrrolidin-3-yl)-2-fluoro-4-(5-fluoro-2-methylpyrimidin-4-yl)benzamide
(R)—N-(1-cyanopyrrolidin-3-yl)-2-fluoro-4-(2-(trifluoromethyl)pyrimidin-4-yl)benzamide
(R)—N-(1-cyanopyrrolidin-3-yl)-2-fluoro-4-(2-methyl-3H-pyrrolo[2,3-d]pyrimidin-4-yl)benzamide (R)—N-(1-cyanopyrrolidin-3-yl)-2-fluoro-4-(imidazo[1,2-a]pyrazin-3-yl)benzamide
(R)—N-(1-cyanopyrrolidin-3-yl)-3-fluoro-5-(pyrazolo[1,5-a]pyrimidin-5-yl)picolinamide
(R)—N-(1-cyanopyrrolidin-3-yl)-3-fluoro-5-(imidazo[1,2-a]pyridin-6-yl)picolinamide
(R)—N-(1-cyanopyrrolidin-3-yl)-3-methoxy-3-phenylazetidine-1-carboxamide
(R)—N-(1-cyanopyrrolidin-3-yl)-N-methyl-3-phenylazetidine-1-carboxamide
(R)—N-(1-cyanopyrrolidin-3-yl)-3-(4-methoxyphenyl)azetidine-1-carboxamide
(R)-3-(4-chlorophenyl)-N-(1-cyanopyrrolidin-3-yl)azetidine-1-carboxamide
(R)-3-(3-chlorophenyl)-N-(1-cyanopyrrolidin-3-yl)azetidine-1-carboxamide
(3aR,6aR)-1-(3-phenylazetidine-1-carbonyl)hexahydropyrrolo[3,4-b]pyrrole-5 (1H)-carbonitrile
(R)-1-(1-cyanopyrrolidin-3-yl)-1-methyl-3-(4-(1-methyl-1H-pyrazol-4-yl)phenyl)urea
(R)-1-(1-cyanopyrrolidin-3-yl)-1-methyl-3-(4-(trifluoromethyl)phenyl)urea
(3aR,6aR)-N-(4-chloro-2-fluorophenyl)-5-cyanohexahydropyrrolo[3,4-b]pyrrole-1(2H)-carboxamide
(3aR6aR)-5-cyano-N-(2-fluoro-4-(trifluoromethoxy)phenyl)hexahydropyrrolo[3,4-b]pyrrole-1(2H)-carboxamide
(3aR,6aR)-5-cyano-N-(4-cyano-2-fluorophenyl)hexahydropyrrolo[3,4-b]pyrrole-1(2H)-carboxamide
(3aR,6aR)-5-cyano-N-(4-cyano-2,5-difluorophenyl)hexahydropyrrolo[3,4-b]pyrrole-1(2H)-carboxamide
(3aR,6aR)-N-(5-chloro-2-fluorophenyl)-5-cyanohexahydropyrrolo[3,4-b]pyrrole-1(2H)-carboxamide
(3aR,6aR)-5-cyano-N-(2-fluoro-5-(trifluoromethyl)phenyl)hexahydropyrrolo[3,4-b]pyrrole-1(2H)-carboxamide
(3aR,6aR)-5-cyano-N-(5-phenylpyridin-2-yl)hexahydropyrrolo[3,4-b]pyrrole-1 (2H)-carboxamide
(3aR,6aR)-5-cyano-N-(4-(trifluoromethyl)phenyl)hexahydropyrrolo[3,4-b]pyrrole-1(2H)-carboxamide
(R)-1-(1-cyanopyrrolidin-3-yl)-1-ethyl-3-(4-(trifluoromethyl)phenyl)urea
1-(1-cyanopyrrolidin-3-yl)-1-(2-methoxyethyl)-3-(4-(trifluoromethyl)phenyl)urea
(R)—N-(1-cyanopyrrolidin-3-yl)-N-ethyl-3-fluoro-4-(-methyl-1H-pyrazol-4-yl)benzamide
(R)—N-(1-cyanopyrrolidin-3-yl)-N-ethyl-3-phenylazetidine-1-carboxamide
(R)-3-(2-oxo-3-(4-phenylthiazol-2-yl)imidazolidin-1-yl)pyrrolidine-1-carbonitrile
(R)-3-(2-oxo-3-(4-phenylthiazol-2-yl)tetrahydropyrimidin-1(2H)-yl)pyrrolidine-1-carbonitrile
(R)-3-(3-(3-morpholinophenyl)-2-oxoimidazolidin-1-yl)pyrrolidine-1-carbonitrile
(R)—N-(1-cyanopyrrolidin-3-yl)-4-(pyrimidin-2-yl)-3,4-dihydro-2H-benzo[b][1,4]oxazine-7-carboxamide
(R)—N-(1-cyanopyrrolidin-3-yl)-4-(4-cyclopropylpyrimidin-2-yl)-3,4-dihydro-2H-benzo[b][1,4]oxazine-7-carboxamide
(R)—N-(1-cyanopyrrolidin-3-yl)-4-((4-cyclopropylpyrimidin-2-yl)amino)-3-fluorobenzamide
(R)—N-(1-cyanopyrrolidin-3-yl)-4-((4-cyclopropylpyrimidin-2-yl)amino)-2,3-difluorobenzamide
(R)—N-(1-cyanopyrrolidin-3-yl)-4-(N-methylisobutyramido)picolinamide
(R)—N-(1-cyanopyrrolidin-3-yl)-[2,3'-bipyridine]-6'-carboxamide
(R)—N-(1-cyanopyrrolidin-3-yl)-[2,4'-bipyridine]-2'-carboxamide
(R)-3-(4-chlorophenyl)-N-(1-cyanopyrrolidin-3-yl)isoxazole-5-carboxamide
(R)—N-(1-cyanopyrrolidin-3-yl)-3-(4-(trifluoromethyl)phenyl)isoxazole-5-carboxamide
(R)—N-(1-cyanopyrrolidin-3-yl)-3-(3,4-dimethoxyphenyl)isoxazole-5-carboxamide
(R)—N-(1-cyanopyrrolidin-3-yl)-3-(3-methoxyphenyl)isoxazole-5-carboxamide
N—((R)-1-cyanopyrrolidin-3-yl)-1-phenylpyrrolidine-3-carboxamide
(R)—N-(1-cyanopyrrolidin-3-yl)-3-fluoro-4-(4-methyl-1H-imidazol-1-yl)benzamide
(R)—N-(1-cyanopyrrolidin-3-yl)-3-fluoro-N-methyl-4-(4-methyl-1H-imidazol-1-yl)benzamide
N—((R)-1-cyanopyrrolidin-3-yl)-3-(pyridin-2-yl)pyrrolidine-1-carboxamide
N—((R)-1-cyanopyrrolidin-3-yl)-3-(1-methyl-1H-pyrazol-4-yl)pyrrolidine-1-carboxamide
(R)—N-(1-cyanopyrrolidin-3-yl)-3-(2-methoxypyridin-4-yl)-N-methylisoxazole-5-carboxamide
(R)—N-(1-cyanopyrrolidin-3-yl)-2-fluoro-4-(N-methylphenylsulfonamido)benzamide
(R)—N-(1-cyanopyrrolidin-3-yl)-1-methyl-6-(1-methyl-1H-pyrazol-4-yl)-1H-indole-2-carboxamide
(R)—N-(1-cyanopyrrolidin-3-yl)-1-methyl-5-(1-methyl-1H-pyrazol-4-yl)-1H-indole-2-carboxamide
(R)—N-(1-cyanopyrrolidin-3-yl)-3-(2-(isoindolin-2-yl)pyridin-4-yl)-1-methylurea
(R)—N-(1-cyanopyrrolidin-3-yl)-3-fluoro-1-methyl-5-(1-methyl-1H-pyrazol-4-yl)-1H-indole-2-carboxamide
(R)—N-(1-cyanopyrrolidin-3-yl)-7-(1-methyl-1H-pyrazol-4-yl)imidazo[1,5-a]pyridine-3-carboxamide
(R)—N-(1-cyanopyrrolidin-3-yl)-3-(1-phenyl-1H-pyrazol-3-yl)azetidine -1-carboxamide
(R)—N-(1-cyanopyrrolidin-3-yl)-3-(1-(pyrazin-2-yl)-1H-pyrazol-3-yl)azetidine-1-carboxamide
(R)—N-(1-cyanopyrrolidin-3-yl)-3-(2-phenylpyrimidin-4-yl)azetidine-1-carboxamide
(R)-3-(2-(4-chlorophenyl)pyrimidin-4-yl)-N-(1-cyanopyrrolidin-3-yl)azetidine-1-carboxamide
(R)-3-(benzyloxy)-N-(1-cyanopyrrolidin-3-yl)-3-phenylazetidine-1-carboxamide
(R)—N-(1-cyanopyrrolidin-3-yl)-1-(4-cyclopropylpyrimidin-2-yl)indoline-5-carboxamide
(R)—N-(1-cyanopyrrolidin-3-yl)-1-(4-cyclopropylpyrimidin-2-yl)-N-methylindoline-5-carboxamide
(3aR,6aR)-5-cyano-N-(3-(2-methylpyridin-4-yl)phenyl)hexahydropyrrolo[3,4-b]pyrrole-1(2H)-carboxamide
(3aR,6aR)-5-cyano-N-(4-(2-methylpyridin-4-yl)phenyl)hexahydropyrrolo[3,4-b]pyrrole-1(2H)-carboxamide
(3aR,6aR)-5-cyano-N-(2-fluoro-4-(2-methylpyridin-4-yl)phenyl)hexahydropyrrolo[3,4-b]pyrrole-1(2H)-carboxamide
(3aR,6aR)-5-cyano-N-(2'-methyl-[3,4'-bipyridin]-6-yl)hexahydropyrrolo[3,4-b]pyrrole-1(2H)-carboxamide
(3aR,6aR)-5-cyano-N-(2-fluoro-4-(1-methyl-1H-pyrazol-4-yl)phenyl)hexahydropyrrolo[3,4-b]pyrrole-1(2H)-carboxamide
1-(3-phenyl-1H-pyrazole-5-carbonyl)hexahydropyrrolo[3,4-b]pyrrole-5 (1H)-carbonitrile
(3aR,6aR)-1-(3-phenoxyazetidine-1-carbonyl)hexahydropyrrolo[3,4-b]pyrrole-5 (1H)-carbonitrile
N-(1-cyanopiperidin-3-yl)-[1,1'-biphenyl]-3-carboxamide
1-(3-benzylphenyl)-3-(1-cyanopiperidin-3-yl)urea
1-(1-cyanopiperidin-3-yl)-3-(3-phenoxyphenyl)urea
1-(1-cyanopyrrolidin-3-yl)-3-(2,4-dichlorophenyl)urea 1-(1-cyanopyrrolidin-3-yl)-3-(4-(trifluoromethyl)phenyl) urea
1-(3-benzylphenyl)-3-(1-cyanopyrrolidin-3-yl)urea
1-([1,1'-biphenyl]-4-yl)-3-(1-cyanopyrrolidin-3-yl)urea
1-(1-cyanopyrrolidin-3-yl)-3-(3-phenoxyphenyl)urea
3-(3-benzylphenyl)-1-(1-cyanopyrrolidin-3-yl)-1-methyl-urea
3-(3-chlorophenyl)-1-(1-cyanopyrrolidin-3-yl)-1-methyl-urea
1-(1-cyanopyrrolidin-3-yl)-1-methyl-3-(3-phenoxyphenyl) urea
3-([1,1'-biphenyl]-4-yl)-1-(1-cyanopyrrolidin-3-yl)-1-methylurea
1-(1-cyanopyrrolidin-3-yl)-3-(2,4-dichlorophenyl)-1-methylurea
1-(1-cyanopyrrolidin-3-yl)-1-methyl-3-(4-(trifluoromethyl) phenyl)urea
(R)—N-(1-cyanopyrrolidin-3-yl)-6-(3,5-dimethylisoxazol-4-yl)-N -methyl-1H-indole-2-carboxamide
(R)—N-(1-cyanopyrrolidin-3-yl)-N-methyl-5-(1-methyl-1H-pyrazol-4-yl)-1H-pyrrolo[2,3-c]pyridine-2-carboxamide
N—((R)-1-cyanopyrrolidin-3-yl)-N-methyl-2-phenylmorpholine-4-carboxamide
(R)—N-(1-cyanopyrrolidin-3-yl)-N-methylindoline-1-carboxamide
(R)-1-(1-cyanopyrrolidin-3-yl)-1-methyl-3-(6-(trifluoromethyl)pyridin-3-yl)urea
(R)-3-(5-chloropyridin-2-yl)-1-(1-cyanopyrrolidin-3-yl)-1-methylurea
(3aR,6aR)-1-(3-chloro-4-morpholinobenzoyl)hexahydropyrrolo[3,4-b]pyrrole-5 (1H)-carbonitrile
(3aR,6aR)-1-(indoline-1-carbonyl)hexahydropyrrolo[3,4-b]pyrrole-5(1H)-carbonitrile
(R)—N-(1-cyanopyrrolidin-3-yl)-3-(2-methylpyridin-4-yl) isoxazole-5-carboxamide
(R)—N-(1-cyanopyrrolidin-3-yl)-3-(3,4-dimethylphenyl) isoxazole-5-carboxamide
(R)—N-(1-cyanopyrrolidin-3-yl)-3-(2,4-difluorophenyl) isoxazole-5-carboxamide
(R)—N-(1-cyanopyrrolidin-3-yl)-N-methyl-3-(2-methylpyridin-4-yl)isoxazole-5-carboxamide It should be noted that each of the chemical compounds listed above represents a particular and independent aspect of the invention.

Described herein is a process for the preparation of a compound of formula (I) or a pharmaceutically acceptable salt thereof comprising the steps of reacting an amine of formula (IV) with a compound $R^{12}$—Y—COOH to form an amide:

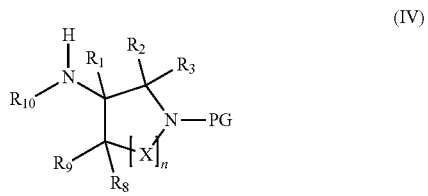

(IV)

Where $R^1$, $R^2$, $R^3$, $R^8$, $R^9$, $R^{10}$, X and n, are as defined elsewhere and PG is an amine protecting group. The protecting group may be but is not limited to BOC. It is clear to a person skilled in the art to combine or adjust such a protecting chemical group. After coupling of $R^{12}$—Y—COOH to form an amide, the protecting group may be removed to leave the free amine according to formula (V) which can then be treated with cyanogen bromide to form compounds according to formula (I).

Also described is provided a process for the preparation of a compound of formula (I) or a pharmaceutically acceptable salt thereof comprising the steps of reacting an amine of formula (V) with cyanogen bromide to form N—CN compounds:

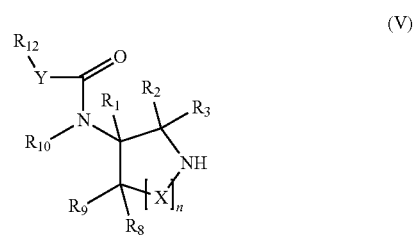

(V)

According to a further aspect of the invention there is provided a process for the preparation of a compound of formula (IT) or a pharmaceutically acceptable salt thereof comprising the steps of reacting an amine of formula (IVA) with a compound $R^{12}$—Y—COOH to form an amide:

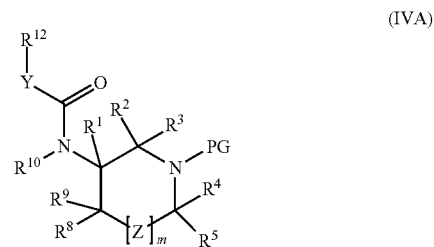

(IVA)

Where $R^1$, $R^2$, $R^3$, $R^4$, $R^5$, $R^8$, $R^9$, $R^{10}$, $R^{12}$, Z and m, are as defined elsewhere for formula II and PG is an amine protecting group. The protecting group may be but is not limited to BOC. It is clear to a person skilled in the art to combine or adjust such a protecting chemical group. After coupling of $R^{12}$—Y—COOH to form an amide, the protecting group may be removed to leave the free amine according to formula (VA) which can then be treated with cyanogen bromide to form compounds according to formula (II).

According to a further aspect of the invention there is provided a process for the preparation of a compound of formula (II) or a pharmaceutically acceptable salt thereof comprising the steps of reacting an amine of formula (VA) with cyanogen bromide to form N—CN compounds:

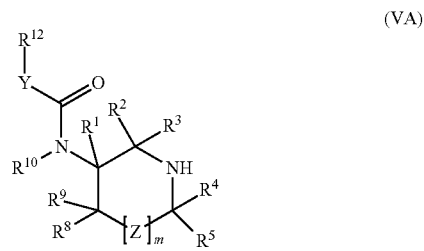

(VA)

Where $R^1$, $R^2$, $R^3$, $R^4$, $R^5$, $R^8$, $R^9$, $R^{10}$, Z and m, are as defined elsewhere for formula II.

According to a further aspect of the invention there is provided a pharmaceutical composition comprising a compound of formula (I) or formula (II).

Pharmaceutical compositions of this invention comprise any of the compounds of the invention combined with any pharmaceutically acceptable carrier, adjuvant or vehicle. Examples of pharmaceutically acceptable carriers, are known to those skilled in the art and include but are not limited to preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may be in the form of, for example, tablets, capsules, powders, granules, elixirs, lozenges, suppositories, syrups and liquid preparations including suspensions and solutions. The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

According to a further aspect of the invention there is provided a compound of formula (I) or formula (II) or pharmaceutical composition thereof for use in therapy.

There is also provided a compound of formula (IA) or a pharmaceutical composition thereof for use in the treatment cancer and conditions involving mitochondrial dysfunction

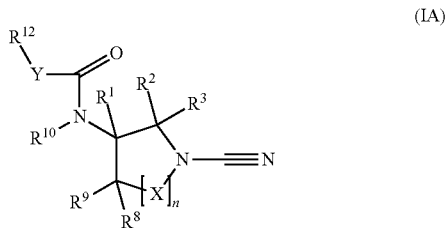

(IA)

or a pharmaceutically acceptable salt thereof, wherein:
n is 1 or 2;
when n is 1, X is $CR^4R^5$ and when n is 2, X is $CR^6R^7CR^4R^5$ (wherein $CR^4R^5$ is adjacent to heterocycle N atom);
$R^2$ represents a hydrogen atom, cyano, an optionally substituted $C_1$-$C_6$ alkyl, an optionally substituted $C_1$-$C_6$ alkoxy group, an optionally substituted 4 to 10 membered heteroaryl, heterocyclyl, aryl or 3 to 8 membered cycloalkyl ring;
$R^1$, $R^3$, $R^4$ and $R^5$ each independently represent a hydrogen atom, cyano, an optionally substituted $C_1$-$C_3$ alkyl or an optionally substituted $C_1$-$C_3$ alkoxy group;
$R^6$, $R^7$ and $R^8$ each independently represent a hydrogen atom, a fluorine atom, cyano, an optionally substituted $C_1$-$C_3$ alkyl or an optionally substituted $C_1$-$C_3$ alkoxy group;
$R^9$ represents a hydrogen atom, a fluorine atom, cyano, an optionally substituted $C_1$-$C_6$ alkyl, an optionally substituted $C_1$-$C_3$ alkoxy group, an optionally substituted 4 to 10 membered heteroaryl, heterocyclyl, aryl or 3 to 8 membered cycloalkyl ring, or forms an optionally substituted heterocyclic ring with $R^{10}$ wherein the ring optionally comprises one or more additional heteroatoms;
$R^{10}$ represents a hydrogen atom, $C_1$-$C_6$ alkyl, or forms an optionally substituted heterocyclic ring with $R^9$ or $R^{11}$ wherein the ring optionally comprises one or more additional heteroatoms;
Y represents a covalent bond, $NR^{11}$ or optionally substituted $C_1$-$C_3$ alkylene;
$R^{11}$ represents a hydrogen atom, an optionally substituted $C_1$-$C_6$ alkyl, a 4 to 10 membered heteroaryl, heterocyclyl, aryl or 3 to 8 membered cycloalkyl ring, or forms an optionally substituted heterocyclic ring with $R^{10}$ wherein the ring optionally comprises one or more additional heteroatoms;
$R^{12}$ represents an optionally substituted 4 to 10 membered heteroaryl, heterocyclyl, aryl or 3 to 8 membered cycloalkyl ring.

Further definitions of $R^1$, $R^2$, $R^3$, $R^4$, $R^5$, $R^6$, $R^7$, $R^8$, $R^9$, $R^{10}$, $R^{11}$, $R^{12}$ and Y include those described in the embodiments above for formulae (I), (IB) and (IID).

Conditions Involving Mitochondrial Dysfunction

The compounds of the invention according to formulae (I), (IA) and (II) can be used in the treatment of disorders or diseases having a component relating to mitochondrial dysfunction, particularly disorders or diseases linked to DUB activity. More particularly, disorders or diseases link to USP30 activity.

The compounds of formulae (I), (IA) and (II) as described herein may be used in the manufacture of a medicament for the treatment of conditions involving mitochondrial dysfunction.

In a further aspect of the invention there is provided a method of treatment or prevention of a condition involving mitochondrial dysfunction, the method comprising administering a pharmaceutically effective amount of a compound of formulae (I), (IA) and (II) or a pharmaceutical composition thereof to an individual diagnosed with a condition involving mitochondrial dysfunction.

Mitochondrial dysfunctions result from defects of the mitochondria, which are specialized compartments present in every cell of the body except red blood cells. When mitochondria fail, less and less energy is generated within the cell and cell injury or even cell death will follow. If this process is repeated throughout the body the life of the subject in whom this is happening is severely compromised. Diseases of the mitochondria appear most often in organs that are very energy demanding such as the brain, heart, liver, skeletal muscles, kidney and the endocrine and respiratory system.

The condition involving mitochondrial dysfunction may be selected from a condition involving a mitophagy defect, a condition involving a mutation in mitochondrial DNA, a condition involving mitochondrial oxidative stress, a condition involving a defect in mitochondrial membrane potential, mitochondrial biogenesis, a condition involving a defect in mitochondrial shape or morphology, and a condition involving a lysosomal storage defect.

In particular, the condition involving mitochondrial dysfunction may be selected from a neurodegenerative disease; mitochondrial myopathy, encephalopathy, lactic acidosis, and stroke-like episodes (MELAS) syndrome; Leber's hereditary optic neuropathy (LHON); cancer; neuropathy, ataxia, retinitis pigmentosa-maternally inherited Leigh syndrome (NARP-MILS); Danon disease; diabetes; metabolic disorders; ischemic heart disease leading to myocardial infarction; psychiatric diseases, for example schizophrenia;

multiple sulfatase deficiency (MSD); mucolipidosis II (ML II); mucolipidosis III (ML III); mucolipidosis IV (ML IV); GM1-gangliosidosis (GM1); neuronal ceroid-lipofuscinoses (NCL1); Alpers disease; Barth syndrome; Beta-oxidation defects; camitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; and very long-chain acyl-CoA dehydrogenase (VLCAD) deficiency.

The condition involving mitochondrial dysfunction may be a CNS disorder, for example a neurodegenerative disease.

Neurodegenerative diseases include, but are not limited to, Parkinson's disease, Alzheimer's disease, amyotrophic lateral sclerosis (ALS), Huntington's disease, ischemia, stroke, dementia with Lewy bodies, and frontotcmporal dementia.

In a particular embodiment, the compounds of the invention are useful in the treatment of Parkinson's disease, including, but not limited to, PD related to mutations in α-synuclein, parkin and PINK1, autosomal recessive juvenile Parkinson's disease (AR-JP) where parkin is mutated.

The compounds of formulae (I), (IA) and (II) or pharmaceutical compositions thereof as described herein may be combined with one or more additional agents when used for the treatment of conditions involving mitochondrial dysfunction. The compounds may be combined with one or more additional agents selected from levodopa, a dopamine agonist, a monoamino oxygenase (MAO) B inhibitor, a catechol O-methyltransferase (COMT) inhibitor, an anticholinergic, riluzole, amantadine, a cholinesterase inhibitor, memantine, tetrabenazine, an antipsychotic, diazepam, clonazepam, an antidepressant, and an anti-convulsant.

Cancer

Compounds of formulae (I) and (IA) also have use in the treatment of cancer and more particularly in the treatment of cancer linked to DUB activity, especially USP30 activity.

The compounds of the invention according to formula (II) also have use in the treatment of cancer and more particularly in the treatment of cancer linked to DUB activity or desumoylation activity. The compounds of the invention may be useful against any DUB or desumoylating enzyme, including but not limited to USP30 and USP10.

The compounds described herein may be used in the manufacture of a medicament for the treatment of cancer linked to DUB activity.

The compounds of formulae (I), (IB) and (II) as described herein may also be used in the manufacture of a medicament for the treatment of a cancer. In a further aspect of the invention there is provided a method of treatment or prevention of a cancer, the method comprising administering a pharmaceutically effective amount of a compound of formulae (I), (IB) and (II) or a pharmaceutical composition thereof to an individual suffering from a cancer.

The compounds of the invention also have use in the treatment of cancer linked to mitochondrial dysfunction.

In one embodiment, the compounds of the invention according have use in the treatment of cancer where apoptotic pathways are dysregulated and more particularly where proteins of the BCL-2 family arc mutated, or over or under expressed.

References to "cancer" or "tumour" include but are not limited to breast, ovarian, prostate, lung, kidney, gastric, colon, testicular, head and neck, pancreas, brain, melanoma, bone or other cancers of tissue organs and cancers of the blood cells such as lymphomas and leukaemias. Particular cancers include lymphoma, multiple myeloma, colorectal cancer, and non-small cell lung carcinoma.

The compounds of formulae (I), (IA) and (II) or pharmaceutical compositions thereof as described herein may be combined with one or more additional agents when used for the treatment of cancer. The compounds may be combined with an additional anti-tumour therapeutic agent, for example chemotherapeutic drugs or inhibitors of other regulatory proteins. In one embodiment the additional anti-tumour therapeutic agent is a BH-3 mimetic. In a further embodiment BH-3 mimetics may be selected from but not limited to one or more of ABT-737, ABT-199, ABT-263, and Obatoclax. In a further embodiment the additional anti-tumour agent is a chemotherapeutic agent. Chemotherapeutic agents may be selected from but not limited to, olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin.

For treating a mitochondrial dysfunction disorder, the pharmaceutical compositions of the invention may be designed for administration by the oral, parenteral or mucosal route and the choice or the specific form of composition is dependent on the administration route. Thus for oral administration the composition may be in the form, for example, of tablets, lozenges, dragees, films, powders, elixirs, syrups, liquid preparations including dispersions, suspensions, emulsions, solutions or sprays, eachets, granules, capsules, etc. For administration to mucosa the composition may be in the form of sprays, inhalants, dispersions, suspensions, emulsions, solutions, gels, patches, films, ointments, creams, lotions, suppositories etc. For parenteral administration the composition is in the form of a liquid preparation such as a solution, dispersion, emulsion or suspension including liposome compositions.

For treating a CNS disorder, the compounds of the invention must have the ability to pass across the blood-brain barrier. As such, such compounds have the ability to enter the central nervous system of a patient. Alternatively, the pharmaceutical compositions of the present invention can bypass the blood brain barrier through use of compositions and methods known in the art for bypassing the blood brain barrier or can be injected directly into the brain. Suitable areas for injection include the cerebral cortex, cerebellum, midbrain, brainstem, hypothalamus, spinal cord and ventricular tissue, and areas of the PNS including the carotid body and the adrenal medulla. Further dosage forms include those suitable for oral delivery including, but not limited to tablets, dragees, powders, elixirs, syrups, liquid preparations including suspensions, sprays, inhalants, tablets, lozenges, emulsions, solutions, eachets, granules and capsules. For parenteral administration, preparations include sterile aqueous, aqueous-organic, and organic solutions, suspensions and emulsions.

For treating a cancer, the pharmaceutical compositions of the invention may be administered in any effective manner suitable for targeting cancer cells, for example orally in any orally acceptable dosage form including, but not limited to tablets, dragees, powders, elixirs, syrups, liquid preparations including suspensions, sprays, inhalants, tablets, lozenges, emulsions, solutions, eachets, granules and capsules. Preparations according to the invention for parenteral administration include sterile aqueous, aqueous-organic, and organic solutions, suspensions and emulsions.

Such dosage forms are prepared according to techniques known in the art of pharmaceutical formulation. When in the form of sprays or inhalants the pharmaceutical compositions may be administered nasally. Suitable formulations for this purpose are known to those skilled in the art.

The pharmaceutical compositions of the invention may be administered by injection and may be in the form of a sterile liquid preparation for injection, including liposome preparations.

The pharmaceutical compositions of the invention may also be in the form of suppositories for rectal administration. These are formulated so that the pharmaceutical composition is solid at room temperature and liquid at body temperature to allow release of the active compound.

The dosages may be varied depending upon the requirements of the patient, the severity of the condition being treated, and the compound being employed. Determination of the proper dosage for a particular situation is within the remit of the person skilled in the skill of the art. Generally, treatment is initiated with smaller dosages which are less than the optimal dose of the compound. Thereafter the dosage is increased by small increments until the optimum effect under the circumstances is reached.

The magnitude of an effective dose of a compound will, of course, vary with the nature of the severity of the condition to be treated and with the particular compound and its route of administration. The selection of appropriate dosages is within the ability of one of ordinary skill in this art, without undue burden. The daily dose range is about 10 g to about 100 mg per kg body weight of a human and non-human animal and in general may be around 10 µg to 30 mg per kg body weight per dose. The above dose may be given from one to three times per day.

Synthetic Methodologies

Compounds of the invention may be prepared via a variety of synthetic routes. Exemplary routes to certain compounds of the invention are shown below. Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art. Those skilled in the art appreciate that, where appropriate, the individual transformations within a scheme can be completed in a different order. The following schemes describe general synthetic methods whereby intermediate and target compounds of the present invention may be prepared. Additional representative compounds and stereoisomers, racemic mixtures, diastereomers and enantiomers thereof can be synthesized using the intermediates prepared in accordance to the general schemes and other materials, compounds and reagents known to those skilled in the art. All such compounds, stereoisomers, racemic mixtures, diastereomers and enantiomers thereof are intended to be encompassed within the scope of the present invention.

The compounds were characterised by liquid chromatography-mass spectroscopy (LCMS) and/or $^1$H NMR.

Abbreviations:
aq Aqueous
Ar Aryl
BOC Tert-butyloxycarbonyl
br Broad (NMR signal)
d Doublet (NMR signal)
CDI Carbonyldiimidazole
DCM Dichloromethane
DCE 1,2-Dichloroethane
DIPEA Diisopropylethylamine
DMA Dimethylacetamide
DMAP Dimethylaminopyridine
DMF N,N-Dimethylformamide
DMSO Dimethylsulphoxide
dppf 1,1'-Bis(diphenylphosphino)ferrocene
EDC 1-Ethyl-3-(3-dimethylaminopropyl)carbodiimide
ES Electrospray
EtOAc Ethyl acetate
EtOH Ethanol
Fmoc Fluorenylmethyloxycarbonyl
h Hour(s)
HATU 1-[Bis(dimethylamino)methylene]-1H-1,2,3-triazolo[4,5-b]pyridinium 3-oxide hexafluorophosphate
HBTU O-Benzotriazole-N,N,N',N'-tetramethyl-uronium-hexafluoro-phosphate
HOAt 1-Hydroxy-7-azabenzotriazole
HOBT 1-Hydroxybenzotriazole
IPA Isopropyl alcohol
LDA Lithium diisopropylamide
LiHMDS Lithium hexamethyldisilazide
m Multiplet (NMR signal)
MeCN Acetonitrile
MeOH Methanol
min Minute(s)
NCS N-chlorosuccinimide
PE Petroleum Ether
rt Room temperature
RT Retention Time
s Singlet (NMR signal)
t Triplet (NMR signal)
T3P 2,4,6-Tripropyl-1,3,5,2,4,6-trioxatriphosphorinane-2,4,6-trioxide
TBAI Tetrabutylammonium Iodide
TBD 1,5,7-Triazabicyclo[4.4.0]dec-5-ene
TEA Triethylamine
TFAA Trifluoroacetic anhydride
TFA Trifluoroacetic acid
THF Tetrahydrofuran
TLC Thin layer chromatography
Xantphos 4,5-Bis(diphenylphosphino)-9,9-dimethylxanthene
X-Phos 2-Dicyclohexylphosphino-2',4',6'-triisopropylbiphenyl Analytical Methods:

| Method A | |
|---|---|
| Column | X-bridge C18, 50 × 4.6 mm, 3.5 µm or equivalent |

Method A

| | | |
|---|---|---|
| Mobile Phase | (A) 0.1% Ammonia in water; | |
| | (B) 0.1% Ammonia in MeCN | |
| Flow Rate | 1.0 ml/min | |

| | Time | % B |
|---|---|---|
| Gradient | 0.01 | 5 |
| | 5.00 | 90 |
| | 5.80 | 95 |
| | 7.20 | 95 |

Method B

| | | |
|---|---|---|
| Column | BEH C18, 50 × 2.1 mm, 1.7 μm or equivalent | |
| Mobile Phase | (A) 5 mM Ammonium acetate + 0.1% formic acid in water | |
| | (B) 0.1% Formic acid in MeCN | |
| Flow Rate | 0.45 ml/min | |

| | Time | % B |
|---|---|---|
| Gradient | 0.01 | 2 |
| | 0.50 | 2 |
| | 5.00 | 90 |
| | 6.00 | 95 |
| | 7.00 | 95 |

Method C

| | | |
|---|---|---|
| Column | BEH C18, 50 × 2.1 mm, 1.7 μm or equivalent | |
| Mobile Phase | (A) 5 mM Ammonium acetate + 0.1% formic acid in water | |
| | (B) 0.1% Formic acid in MeCN | |
| Flow Rate | 0.55 ml/min | |

| | Time | % B |
|---|---|---|
| Gradient | 0.01 | 5 |
| | 0.40 | 5 |
| | 0.80 | 35 |
| | 1.20 | 55 |
| | 2.50 | 100 |
| | 3.30 | 100 |

Method D

| | | |
|---|---|---|
| Column | Agilent TC-C18, 50 × 2.1 mm, 5 μm | |
| Mobile Phase | (A) 0.04% TFA in water; (B) 0.02% TFA in MeCN | |
| Flow Rate | 0.8 ml/min | |

| | Time | % B |
|---|---|---|
| Gradient | 0 | 0 |
| | 0.4 | 1 |
| | 3.4 | 100 |
| | 4 | 100 |
| Temperature | 50° C. | |

Method E

| | | |
|---|---|---|
| Column | XBridge ShieldRP18, 50 × 2.1 mm, 5 μm | |
| Mobile Phase | (A) 0.05% Ammonia in water; (B) MeCN | |
| Flow Rate | 0.8 ml/min | |

| | Time | % B |
|---|---|---|
| Gradient | 0 | 0 |
| | 0.4 | 5 |
| | 3.4 | 100 |
| | 4 | 100 |
| Temperature | 40° C. | |

Method F

| | | |
|---|---|---|
| Column | Agilent TC-C18, 50 × 2.1 mm, 5 μm | |
| Mobile Phase | (A) 0.04% TFA in water; (B) 0.02% TFA in MeCN | |
| Flow Rate | 0.6 ml/min | |

| | Time | % B |
|---|---|---|
| Gradient | 0 | 0 |
| | 0.4 | 0 |
| | 3.4 | 100 |
| | 4 | 100 |
| Temperature | 40° C. | |

Method G

| | | |
|---|---|---|
| Column | YMC Triart C18, 150 × 4.6 mm, 5 μm | |
| Mobile Phase | (A) 10 mM Ammonium acetate in water; (B) MeCN | |
| Flow Rate | 1.0 ml/min | |

| | Time | % B |
|---|---|---|
| Gradient | 0.01 | 10 |
| | 5.00 | 90 |
| | 7.00 | 100 |
| | 11.00 | 100 |

Method H

| | | |
|---|---|---|
| Column | X-bridge C18, 250 × 4.6 mm, 5 μm or equivalent | |
| Mobile Phase | (A) 0.1% Ammonia in water; | |
| | (B) 0.1% Ammonia in MeCN | |
| Flow Rate | 1.0 ml/min | |

| | Time | % B |
|---|---|---|
| Gradient | 0.01 | 5 |
| | 5.00 | 5 |
| | 10.00 | 30 |
| | 15.00 | 30 |
| | 25.00 | 60 |
| | 30.00 | 90 |
| | 35.00 | 90 |

Chiral HPLC Method X

| | |
|---|---|
| Column | CHIRALPAK_IC, 250 × 4.6 mm, 5 μm |
| Mobile Phase | (A) 0.1% TFA in hexane; |
| | (B) 0.1% TFA in 50% IPA/MeOH |
| Flow Rate | 1.00 ml/min |

| Chiral HPLC Method X | | |
|---|---|---|
| | Time | % B |
| Gradient | 0.01 | 20 |
| | 3.00 | 20 |
| | 5.00 | 55 |
| | 15.00 | 85 |
| | 25.00 | 85 |

| Chiral HPLC Method Y | | |
|---|---|---|
| Column | CHIRALPAK_IB, 250 × 4.6 mm, 5 μm | |
| Mobile Phase | (A) 0.1% TFA in hexane; (B) 0.1% TFA in EtOH | |
| Flow Rate | 1.00 ml/min | |
| | Time | % B |
| Gradient | 0.01 | 20 |
| | 3.00 | 20 |
| | 10.00 | 55 |
| | 15.00 | 85 |
| | 25.00 | 85 |

| Chiral HPLC Method Z | | |
|---|---|---|
| Column | CHIRALPAK_IB, 250 × 4.6 mm, 5 μm | |
| Mobile Phase | (A) 0.1% TFA in hexane; (B) 0.1% TFA in IPA | |
| Flow Rate | 1.00 ml/min | |

| Chiral HPLC Method Z | | |
|---|---|---|
| | Time | % B |
| Gradient | 0.01 | 20 |
| | 3.00 | 20 |
| | 10.00 | 55 |
| | 15.00 | 70 |
| | 20.00 | 70 |

General Method A

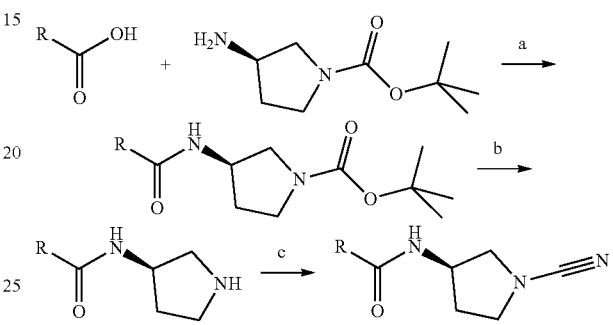

Reagents and conditions: a) EDC.HCl, HOBT, DIPEA, THF, rt, 15 h; b) TFA, DCM, 0° C. then at 50° C., 12 h; c) cyanogen bromide, $K_2CO_3$, THF, 0° C. then at rt, 30 min General Method B

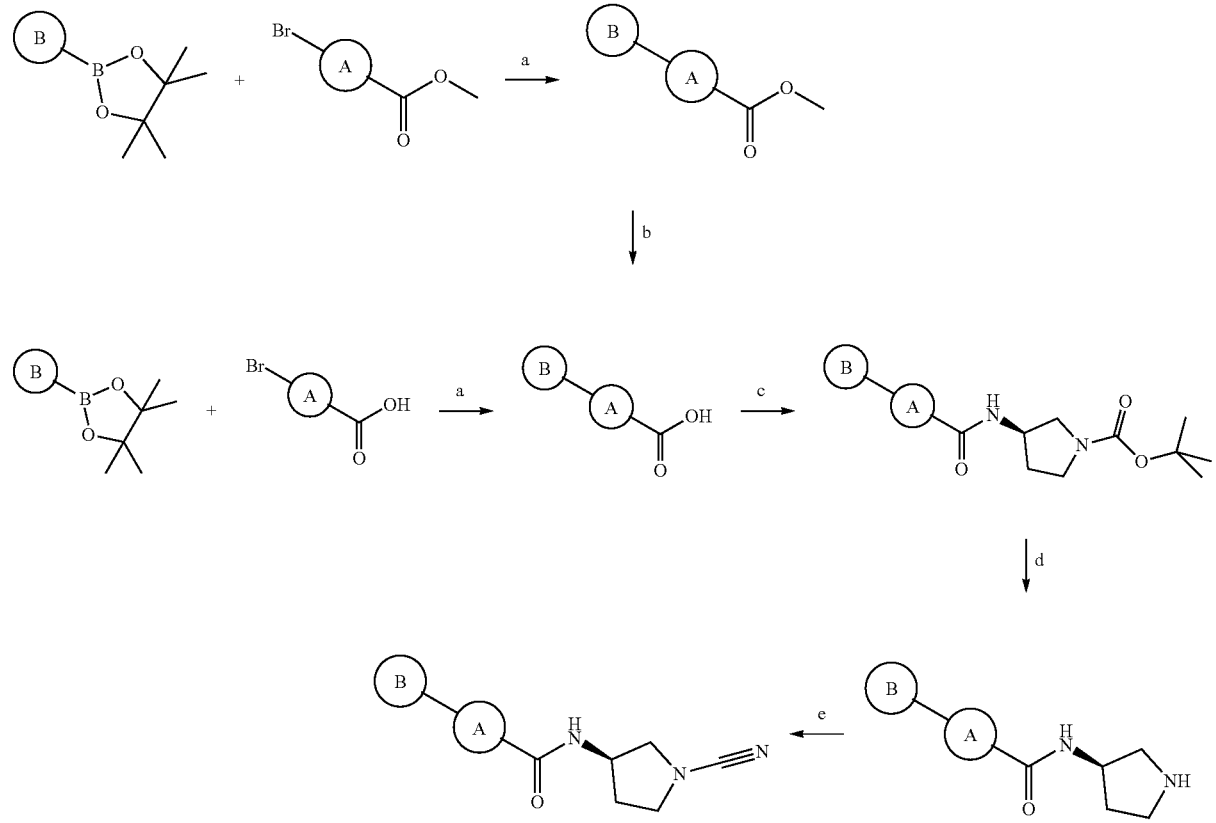

Reagents and conditions: a) Pd(PPh$_3$)$_4$, Na$_2$CO$_3$, 1,4-dioxane:water (2:1), 90° C., 8 h; b) LiOH.H$_2$O, THF, water (1:1), rt, 3 h; c) HATU, DIPEA, THF, 0° C. then at rt, 2 h; d) TFA, DCM, 0° C. then at rt, 2 h; e) cyanogen bromide, K$_2$CO$_3$, THF, 0° C. then at rt, 1 h General Method C

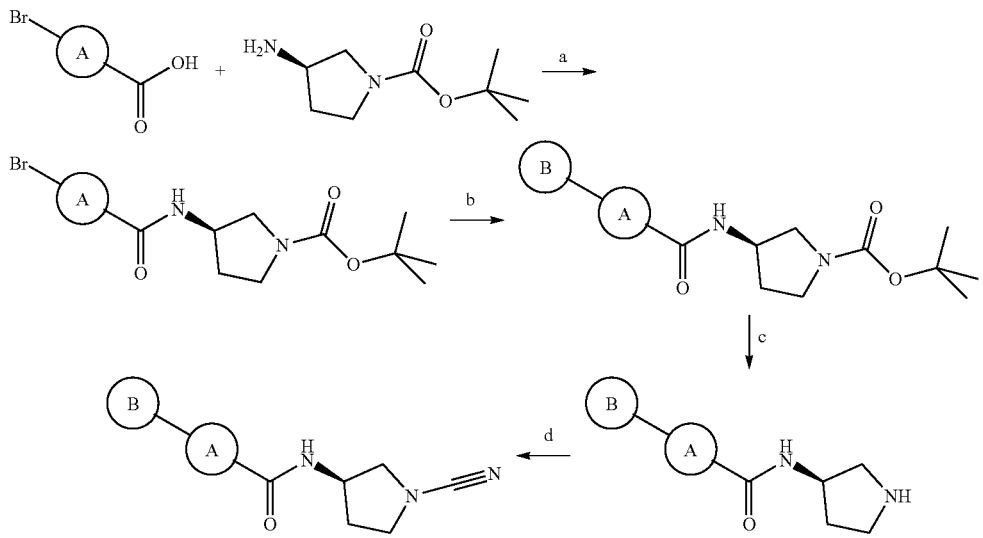

Reagents and conditions: a) T3P (50% in EtOAc), DIPEA, THF, 0° C. then at rt, 1.5 h; b) ArB(OH)$_2$, Pd(PPh$_3$)$_4$, K$_2$CO$_3$, 1,4-dioxane:water (5:1), 80° C., 2 h; c) TFA, DCM, 0° C. then at rt, 2 h; d) cyanogen bromide, K$_2$CO$_3$, THF, 0° C. then at rt, 20 min General Method D

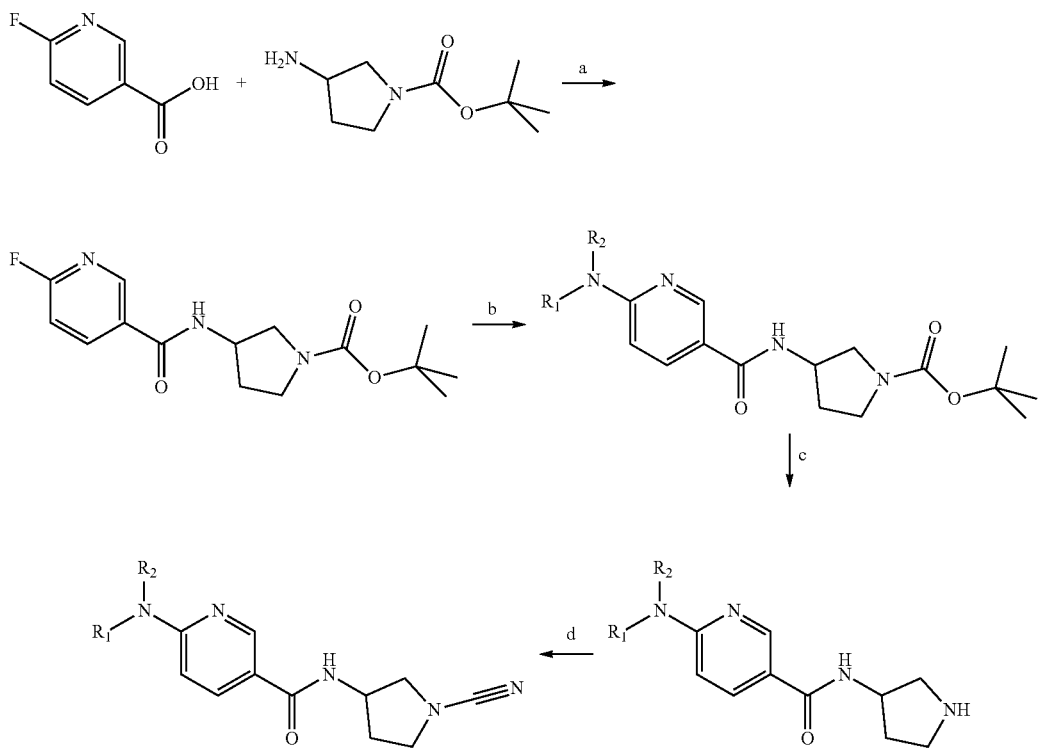

Reagents and conditions: a) HATU, DIPEA, DCM, 0° C. then rt, 16 h; b) R₁R₂NH, Cs₂CO₃, DMF, 120° C., 16 h; c) HCl/EtOAc, rt, 2 h; d) cyanogen bromide, NaHCO₃, EtOH, rt, 16 h
General Method E

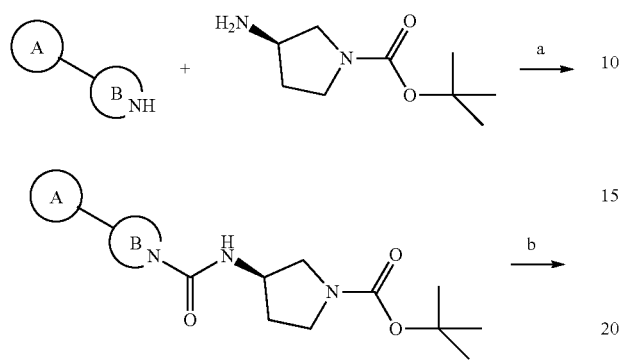

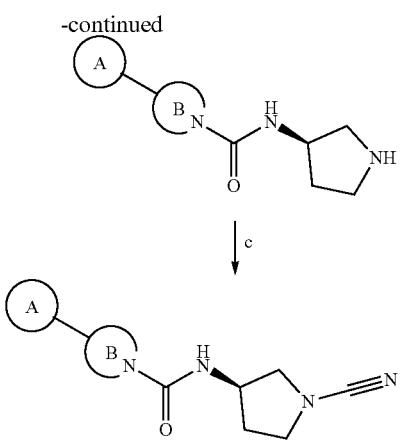

Reagents and conditions: a) CDI, water, (or THF or DCM), 0° C., 30 min then rt, 18 h (or triphosgene, TEA, DCM, 0° C.); b) TFA, DCM, rt, 3 h; c) cyanogen bromide, DIPEA, DCM, 0° C., 30 min
General Method F

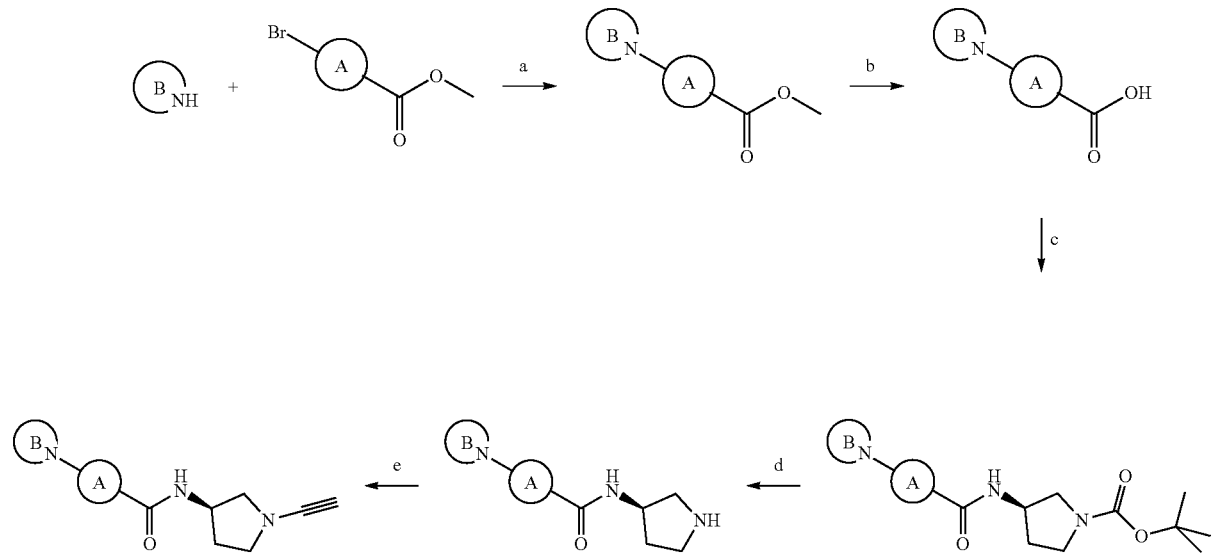

Reagents and conditions: a) (optionally substituted) cis-2,6-dimethylmorpholine, NaOtBu, Xantphos, Pd₂(dba)₃, toluene, 110° C., 1 h; b) LiOH.H₂O, THF, water, 50° C. 4 h, then at rt, 15 h; c) HATU, DIPEA, DMF, rt, 2 h; d) TFA, DCM, rt, 1 h; e) cyanogen bromide, K₂CO₃, THF, rt, 30 min
General Method G

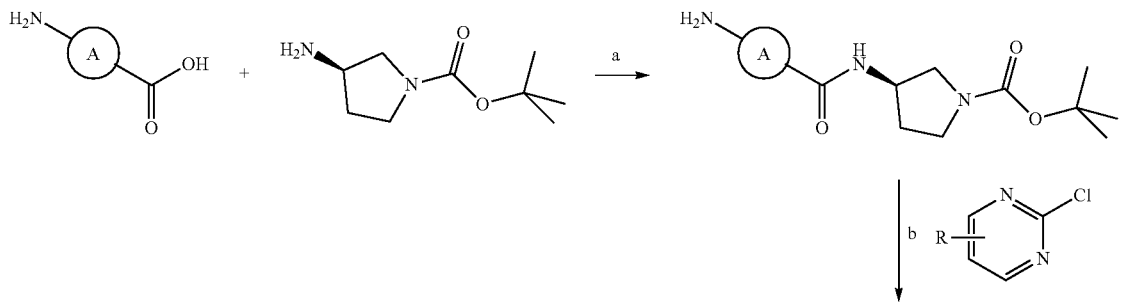

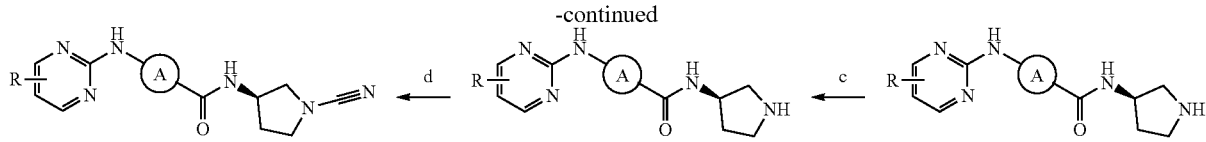

Reagents and conditions: a) HATU, DIPEA, THF, rt, 4 h; b) NaOtBu, DBU, BINAP, Pd$_2$(dba)$_3$, toluene, 110° C., 1 h; c) TFA, DCM, rt 1 h; d) cyanogen bromide, K$_2$CO$_3$, THF, rt, 30 min General Method H

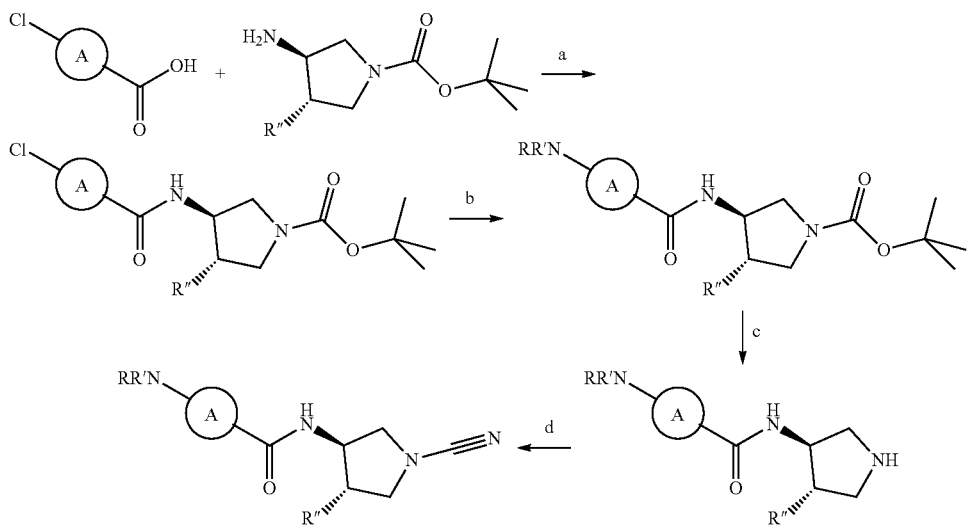

Reagents and conditions: a) HATU, DIPEA, THF, rt, 4 h; b) R$_1$R$_2$NH, NaOtBu or Cs$_2$CO$_3$, BINAP or Xantphos, Pd$_2$(dba)$_3$, toluene or dioxane:water, 110° C., 1 h; c) TFA, DCM, rt 1 h; d) cyanogen bromide, K$_2$CO$_3$, THF, rt, 30 min Example 1 (R)—N-(1-cyanopyrrolidin-3-yl)-5-phenylpicolinamide (Prepared According to General Method A)

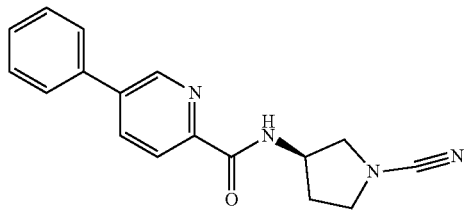 [SMILES: N#CN1CC[C@@H](NC(=O)c2ccc(-c3ccccc3)cn2)C1]

Step a.

To a solution of (R)-3-amino-1N—BOC-pyrrolidine (0.24 mmol) in THF (10 ml) was added EDC.HCl (0.33 mmol), HOBt (0.33 mmol) and DIPEA (0.45 mmol) at rt. The reaction mixture was stirred at rt for 15 min. 5-Phenylpyridine-2-carboxylic acid (0.22 mmol) was added to the reaction mixture at rt and stirred for 15 h. The resulting reaction mixture was poured into water (50 ml) and extracted with EtOAc (3×10 ml). The combined organic phase was collected, dried over Na$_2$SO$_4$, filtered and concentrated under reduced pressure yielding tert-butyl (R)-3-(5-phenylpicolinamido) pyrrolidine-1-carboxylate (quantitative). This material was used directly for the next step without further purification. MS: ES+ 312.2 (M-tBu).

Step b.

To a solution of tert-butyl (R)-3-(5-phenylpicolinamido) pyrrolidine-1-carboxylate (0.27 mmol) in DCM (10 ml) was added TFA (1 ml) at 0° C. The reaction mixture was stirred at rt for 3 h and then heated at 50° C. for 12 h. The resulting reaction mixture was concentrated under reduced pressure. The obtained residue was azeotropically distilled using DCM (2×10 ml) and dried under reduced pressure yielding (R)-5-phenyl-N-(pyrrolidin-3-yl) picolinamide TFA salt (quantitative). This material was used directly for the next step without further purification. MS: ES+ 268.2

Step c.

To a solution of (R)-5-phenyl-N-(pyrrolidin-3-yl) picolinamide TFA salt (0.26 mmol) in THF (15 m) was added K$_2$CO$_3$ (1.3 mmol) at 0° C. The reaction mixture was stirred at 0° C. for 30 min. Cyanogen bromide (0.31 mmol) was added to the reaction mixture at 0° C. Then reaction mixture was stirred at rt for 30 min. The resulting reaction mixture was poured in to water (50 ml) and extracted with EtOAc (3×10 ml). The combined organic phase was collected, dried over Na$_2$SO$_4$, filtered and concentrated under reduced pressure. The resulting residue was purified by column chromatography (40% EtOAc in hexane) yielding the title compound (0.11 mmol). LCMS: Method B, RT 3.68 min, MS: ES+ 293.5; $^1$H NMR (400 MHz, DMSO-d$_6$) δ ppm 9.05 (d, J=7.2 Hz, 1H), 8.95-8.96 (m, 1H), 8.29 (dd, J=1, 2.4 Hz, 1H), 8.10 (d, J=8.4 Hz, 1H), 7.81 (dd, J=1.6, 6.8 Hz, 2H), 7.55-7.57 (m, 2H), 7.47-7.50 (m, 1H), 4.53-4.58 (m, 1H), 3.55-3.65 (m, 2H), 3.40-3.49 (m, 2H), 2.12-2.15 (m, 1H), 2.05-2.10 (m, 1H)

Example 2 (R)—N-(1-cyanopyrrolidin-3-yl)-3-methoxy-4-(1-methyl-1H-pyrazol-4-yl)benzamide (Prepared According to General Method B)

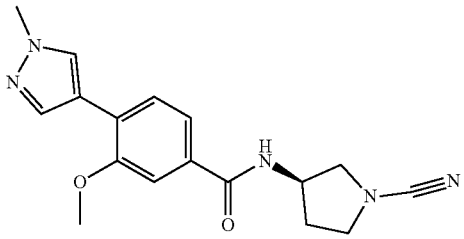 [SMILES: COc1cc(C(=O)N[C@@H]2CCN(C#N)C2)ccc1-c1cnn(C)c1]

Step a.

To a solution of methyl 4-bromo-3-methoxybenzoate (1.02 mmol), 1-methylpyrazole-4-boronic acid pinacol ester (1.52 mmol) in 1,4-dioxane:water (2:1) (6 ml) was added $Na_2CO_3$ (3.35 mmol) at rt. The reaction mixture was purged with nitrogen for 10 min. $Pd(PPh_3)_4$ (0.04 mmol) was added to the reaction mixture. The reaction mixture was heated at 90° C. for 8 h. The resulting reaction mixture was poured in to water (100 ml) and extracted with EtOAc (2×50 ml). The combined organic layer was washed with brine (100 ml), dried over $Na_2SO_4$, filtered and concentrated under reduced pressure yielding methyl 3-methoxy-4-(1-methyl-1H-pyrazol-4-yl)benzoate (quantitative). This material was used for next step without further purification. MS: ES+ 247.1

Step b.

To a solution of 3-methoxy-4-(1-methyl-1H-pyrazol-4-yl)benzoate (3.65 mmol) in THF:water (1:1, 10 ml) was added $LiOH.H_2O$ (14.60 mmol) portion wise at rt. The reaction mixture was stirred at rt for 3 h. The resulting mixture was poured into water (50 ml) and extracted with EtOAc (2×50 ml). The resulting aqueous layer containing the product was cooled to 0° C. and neutralised by slow addition of dilute aqueous HCl solution. The resulting mixture was extracted with EtOAc (2×50 ml). The combined organic phase was dried over $Na_2SO_4$, filtered and concentrated under reduced pressure yielding 3-methoxy-4-(1-methyl-1H-pyrazol-4-yl)benzoic acid (1.63 mmol). MS: ES+ 233.2

Step c.

To a solution of (R)-3-amino-1N—BOC-pyrrolidine (0.86 mmol) and 3-methoxy-4-(1-methyl-1H-pyrazol-4-yl)benzoic acid (0.86 mmol) in THF (7 ml) added HATU (1.29 mmol) and DIPEA (2.5 mmol) at 0° C. The reaction mixture was stirred at rt for 2 h. The resulting reaction mixture was poured into water (100 ml) and extracted with EtOAc (2×50 ml). The combined organic phase was collected and washed with dilute citric acid solution (2×50 ml), brine (1×100 ml), dried over $Na_2SO_4$, filtered and concentrated under reduced pressure yielding tert-butyl (R)-3-(3-methoxy-4-(1-methyl-1H-pyrazol-4-yl)benzamido)-pyrrolidine-1-carboxylate (0.9 mmol). MS: ES+ 401.3

Step d.

To a solution of tert-butyl (R)-3-(3-methoxy-4-(1-methyl-1H-pyrazol-4-yl)-benzamido) pyrrolidine-1-carboxylate (0.9 mmol) in DCM (10 ml) was added TFA (29.4 mmol) at 0° C. The reaction mixture was stirred at rt for 2 h. The resulting reaction mixture was concentrated under reduced pressure. The obtained residue was azeotropically distilled with DCM (3×25 ml) and dried to yield (R)-3-methoxy-4-(1-methyl-1H-pyrazol-4-yl)-N-(pyrrolidin-3-yl) benzamide TFA salt (0.57 mmol). MS: ES+ 301.24

Step e.

To a solution of (R)-3-methoxy-4-(1-methyl-1H-pyrazol-4-yl)-N-(pyrrolidin-3-yl) benzamide TFA salt (0.57 mmol) in THF (10 ml) was added $K_2CO_3$ (4.7 mmol) and cyanogen bromide (0.79 mmol) at 0° C. The reaction mixture was stirred at rt for 1 h. The reaction mixture was poured into water (50 ml) and extracted with ethyl acetate (2×50 ml). The combined organic layer was washed with brine (100 ml), dried over $Na_2SO_4$, filtered and concentrated under reduced pressure. The resulting residue was purified by flash chromatography (1-5% MeOH in DCM) yielding (R)—N-(1-cyanopyrrolidin-3-yl)-3-methoxy-4-(1-methyl-1H-pyrazol-4-yl)benzamide (0.29 mmol). LCMS: Method B, RT 2.97 min, MS: ES+ 326.27; $^1$H NMR (400 MHz, DMSO-$d_6$) δ ppm 8.56 (d, J=6.4 Hz, 1H), 8.21 (s, 1H), 7.98 (s, 1H), 7.70 (d, J=8.4 Hz, 1H), 7.48-7.50 (m, 2H), 4.45-4.53 (m, 1H), 3.94 (s, 3H), 3.88 (s, 3H), 3.63-3.67 (m, 1H), 3.54-3.60 (m, 1H), 3.43-3.49 (m, 1H), 3.30-3.33 (m, 1H), 2.10-2.18 (m, 1H), 1.94-2.00 (m, 1H)

Example 3 2'-chloro-N-(1-cyanopyrrolidin-3-yl)-[1,1'-biphenyl]-4-carboxamide (Prepared According to General Method C)

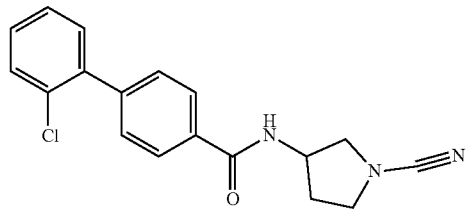 [SMILES: N#CN1CCC(NC(=O)c2ccc(-c3ccccc3Cl)cc2)C1]

Step a.

To a solution of 4-bromobenzoic acid (4.97 mmol) in THF (20 ml) was added T3P (50% in EtOAc) (14.9 mmol) at 0° C. The reaction mixture was stirred at 0° C. for 20 min. 3-Amino-1N—BOC-pyrrolidine (5.93 mmol) and DIPEA (14.96 mmol) were added to the reaction mixture at 0° C. The reaction mixture was stirred at rt for 1.5 h. The resulting mixture was poured into saturated $NaHCO_3$ solution (80 ml) and extracted with EtOAc (2×40 ml). The organic layer was washed with M HCl (40 ml), dried over $Na_2SO_4$, filtered and concentrated under reduced pressure. The resulting mixture was purified by trituration using $Et_2O$:hexane (1:1) yielding tert-butyl-3-(4-bromobenzamido) pyrrolidine-1-carboxylate (1.90 mmol). MS: ES+ 369.13

Step b.

To a solution of tert-butyl-3-(4-bromobenzamido)pyrrolidine-1-carboxylate (0.67 mmol) and 2-chloro-phenylboronic acid (1.01 mmol) in 1,4-dioxane:water (5:1) (7.5 ml) was added $K_2CO_3$ (2.03 mmol) at rt. The reaction mixture was purged with nitrogen for 30 min. $Pd(PPh_3)_4$ (0.03 mmol) was added to the reaction mixture under nitrogen atmosphere. The reaction was heated to 80° C. for 2 h. The resulting mixture was poured into water (20 ml) and extracted with EtOAc (3×20 ml). The combined organic layer was dried over $Na_2SO_4$, filtered and concentrated under reduced pressure. The resulting residue was purified by flash chromatography (0.5% MeOH in DCM) yielding tert-butyl 3-(2'-chloro-[1,1'-biphenyl]-4-carboxamido)pyrrolidine-1-carboxylate (0.5 mmol). MS: ES+ 401.18, $^1$H NMR (400 MHz, DMSO-$d_6$) δ ppm 8.65 (d, J=6.8 Hz, 1H), 7.94 (d, J=8.4 Hz, 2H), 7.65-7.58 (m, 2H), 7.53 (d, J=8.4 Hz, 2H), 7.44 (dd, J=2, 5.6 Hz, 2H), 4.44-4.45 (m, 1H), 3.51-3.60 (m, 1H), 3.16-3.30 (m, 1H), 2.08-2.10 (m, 2H), 1.92-1.93 (m, 2H), 1.41 (s, 9H).

Steps c, d.

The title compound was synthesised from the intermediate above using a procedure similar to that described for Example 2. LCMS: Method B, RT 4.01 min, MS: ES+ 326.23; $^1$H NMR (400 MHz, DMSO-$d_6$) δ ppm 8.70 (d, J=6.4 Hz, 1H), 7.94 (d, J=8.00 Hz, 2H), 7.59-7.62 (m, 1H), 7.54 (d, J=8.00 Hz, 2H), 7.42-7.46 (m, 3H), 4.49-4.53 (m, 1H), 3.60-3.68 (m, 1H), 3.54-3.58 (m, 1H), 3.45-3.56 (m, 1H), 3.34-3.44 (m, 1H), 2.01-2.17 (m, 1H), 1.95-2.01 (m, 1H)

Example 4 6-(benzyl(methyl)amino)-N-(1-cyanopyrrolidin-3-yl)nicotinamide (Prepared According to General Method D)

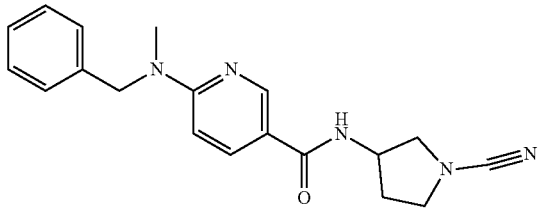 [SMILES: CN(Cc1ccccc1)c1ccc(C(=O)NC2CCN(C#N)C2)cn1]

Step a.

To a solution of 6-fluoropyridine-3-carboxylic (5.32 mmol) in DCM (20 ml) was added HATU (15.9 mmol). The reaction mixture was stirred at 0° C. for 20 min. 3-Amino-1N—BOC-pyrrolidine (5.33 mmol) and DIPEA (15.96 mmol) were added to the reaction mixture at rt. The reaction mixture was stirred at rt for 16 h. The resulting mixture was poured into saturated NaHCO$_3$ solution (80 ml) and extracted with EtOAc (2×40 ml). The organic layer was washed with 1M HCl (40 ml), dried over anhydrous Na$_2$SO$_4$, filtered and concentrated under reduced pressure. The resulting mixture was purified by column chromatography (0 to 20% EtOAc in PE) yielding tert-butyl 3-[(6-fluoropyridine-3-carbonyl)amino]pyrrolidine-1-carboxylate (3.88 mmol). MS: ES+ 310.10; $^1$H NMR (400 MHz, DMSO-$d_6$) δ ppm 8.75 (d, J=6.0 Hz, 1H), 8.71 (d, J=2.0 Hz, 1H), 8.35-8.46 (m, 1H), 7.26-7.37 (m, 1H), 4.34-4.51 (m, 1H), 3.49-3.63 (m, 1H), 3.33-3.43 (m, 2H), 3.16-3.27 (m, 1H), 2.05-2.18 (m, 1H), 1.84-1.96 (m, 1H), 1.37-1.46 (m, 9H)

Step b.

To a solution of tert-butyl 3-[(6-fluoropyridine-3-carbonyl)amino]pyrrolidine-1-carboxylate (0.2 mmol) and N-methyl-1-phenyl-methanamine (0.24 mmol) in DMF (1 ml) was added Cs$_2$CO$_3$ (0.6 mmol) at rt. The reaction was heated to 120° C. for 16 h. The resulting mixture was concentrated under reduced pressure and the residue was purified by prep-TLC (PE/EtOAc=1:2) yielding tert-butyl 3-(6-(benzyl(methyl)amino)-nicotinamido)pyrrolidine-1-carboxylate. MS: ES+ 411.2

Steps c, d.

The title compound was synthesised from the intermediate above using a procedure similar to that described for Example 2 to provide the title compound (23.2 mg, 0.069 mmol). LCMS: Method F, RT 2.39 min, MS: ES+ 336.2

Example 5 (R)—N-(1-cyanopyrrolidin-3-yl)-3-phenylazetidine-1-carboxamide (Prepared According to General Method E)

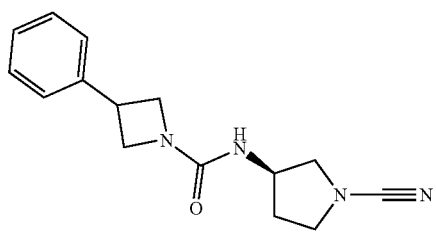 [SMILES: N#CN1CC[C@@H](NC(=O)N2CC(c3ccccc3)C2)C1]

Step a.

To a solution of (R)-3-amino-1N—BOC-pyrrolidine (1.34 mmol) in water (5 ml) was added CDI (2.68 mmol) at 0° C. The reaction mixture was stirred at 0° C. for 30 min. 3-phenylazetidine (1.61 mmol) was added to the reaction mixture at 0° C. The reaction mixture was stirred at rt for 18 h. The resulting reaction mixture was poured into water (150 ml) and extracted with DCM (3×100 ml). The organic phase was collected, dried over Na$_2$SO$_4$, filtered and concentrated under reduced pressure. The resulting residue was purified by flash chromatography (1.5% MeOH in DCM) yielding tert-butyl (R)-3-(3-phenylazetidine-1-carboxamido) pyrrolidine-1-carboxylate (0.60 mmol). MS: ES+ 346.1

Step b.

To a solution of tert-butyl (R)-3-(3-phenylazetidine-1-carboxamido) pyrrolidine-1-carboxylate (0.60 mmol) in DCM (5 ml) was added TFA (3.0 mmol) at rt. The reaction mixture was stirred at rt for 3 h. The resulting reaction mixture was concentrated under reduced pressure and azeotroped with DCM (3×10 ml). The resulting residue was purified by triturating with diethylether (5 ml). The obtained material was dried under reduced pressure yielding (R)-3-phenyl-N-(pyrrolidin-3-yl)azetidine-1-carboxamide TFA salt (0.25 mmol). This material was directly used for the next step without further purification. MS: ES+ 246.53

Step c.

To a solution of (R)-3-phenyl-N-(pyrrolidin-3-yl)azetidine-1-carboxamide TFA salt (0.25 mmol) in DCM (5 ml) was added DIPEA (0.75 mmol) at 0° C. and stirred for 10 min. Cyanogen bromide (0.37 mmol) was added to the reaction mixture at 0° C. and stirred for a further 30 min. The resulting reaction mixture was poured into ice water (100 ml) and extracted with DCM (3×50 ml). The organic phase was collected, dried over Na$_2$SO$_4$, filtered and concentrated under reduced pressure. The resulting residue was purified by flash chromatography (2.0% MeOH in DCM) yielding the title compound (0.08 mmol). LCMS: Method B, RT 3.26 min, MS: ES+ 271.38; $^1$H NMR: (400 MHz, DMSO-$d_6$) δ ppm 7.32-7.38 (m, 4H), 7.23-7.27 (m, 1H), 6.58 (d, J=6.4 Hz, 1H), 4.13-4.21 (m, 3H), 3.74-3.81 (m, 3H), 3.47-3.54 (m, 2H), 3.36-3.45 (m, 1H), 3.14-3.17 (m, 1H), 1.96-2.05 (m, 1H), 1.76-1.84 (m, 1H).

Example 6 N—((R)-1-cyanopyrrolidin-3-yl)-4-((cis)-2,6-dimethylmorpholino)-3-fluorobenzamide (Prepared According to General Method F)

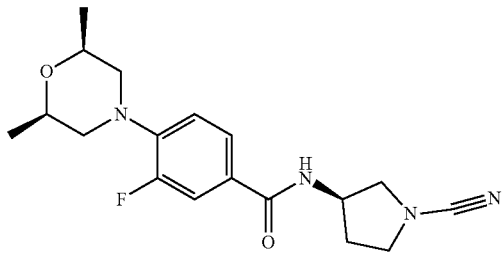 [SMILES: C[C@@H]1CN(c2ccc(C(=O)N[C@@H]3CCN(C#N)C3)cc2F)C[C@H](C)O1]

Step a.

A mixture of methyl 4-bromo-3-fluorobenzoate (0.42 mmol), cis-2,6-dimethylmorpholine (0.42 mmol) and NaOtBu (0.42 mmol) in dry toluene (2 ml) was stirred at rt in a glass tube. The reaction mixture was purged with nitrogen for 10 min. Xantphos (0.021 mmol) and Pd$_2$(dba)$_3$ (0.009 mmol) were added to the reaction mixture and the glass tube was sealed. The resulting reaction mixture was heated at 110° C. (external temperature) for 1 h. Upon completion the reaction mixture was cooled to rt and diluted with EtOAc (30 ml). The resulting reaction mixture was poured into water (40 ml). The mixture was extracted with EtOAc (2×20 ml). The combined organic layer was washed with brine (25 ml), dried over Na$_2$SO$_4$, filtered and concentrated under reduced pressure. The resulting residue was purified by flash chromatography (50% EtOAc in hexane) yielding methyl 4-((cis)-2,6-dimethylmorpholino)-3-fluorobenzoate (0.37 mmol). MS: ES+ 268.3.

Step b.

To a solution of methyl 4-((cis)-2,6-dimethylmorpholino)-3-fluorobenzoate (1.49 mmol) in THF:water (1:1, 8 ml) was added LiOH (14.98 mmol) at rt. The reaction mixture was stirred at 50° C. for 4 h and then at rt for 15 h. The resulting reaction mixture was adjusted to pH 4 using 1 M aqueous HCl solution and the mixture was extracted with EtOAc (3×100 ml). The combined organic phase was collected, dried over Na$_2$SO$_4$, filtered and concentrated under reduced pressure yielding 4-((cis)-2,6-dimethylmorpholino)-3-fluorobenzoic acid (0.95 mmol). This material was directly used for the next step without further purification. MS: ES+ 254.26.

Step c.

To a solution of 4-((cis)-2,6-dimethylmorpholino)-3-fluorobenzoic acid (0.95 mmol) in DMF (3 ml) was added HATU (1.42 mmol) at rt. The reaction mixture was stirred at rt for 30 min. A solution of tert-butyl (R)-3-aminopyrrolidine-1-carboxylate (0.85 mmol) in DMF (1 ml) was added to the reaction mixture at rt. DIPEA (2.85 mmol) was added to the reaction mixture at rt. The resulting reaction mixture was stirred at rt for 2 h. The resulting reaction mixture was poured into water (150 ml) and extracted with EtOAc (3×100 ml). The combined organic phase was collected, washed with saturated NaHCO$_3$ solution (100 ml), brine (100 ml), dried over Na$_2$SO$_4$, filtered and concentrated under reduced pressure yielding tert-butyl (R)-3-(4-((cis)-2,6-dimethylmorpholino)-3-fluorobenzamido)pyrrolidine-1-carboxylate (quantitative). This material was directly used for the next step without further purification. MS: ES+ 422.4.

Steps d, e.

The title compound was synthesised from the intermediate above using a procedure similar to that described for Example 2 to provide the title compound (0.25 mmol). LCMS: Method A, RT 3.87 min, MS: ES+ 346.98; $^1$H NMR (400 MHz, DMSO-d$_6$) δ ppm 8.48 (d, J=6.4 Hz, 1H), 7.64-7.67 (m, 2H), 7.08 (t, J=8.4 Hz, 1H), 4.43-4.47 (m, 1H), 3.71-3.75 (m, 2H), 3.60-3.64 (m, 1H), 3.51-3.55 (m, 1H), 3.43-3.47 (m, 1H), 3.27-3.38 (m, 3H), 2.39-2.45 (m, 2H), 2.11-2.15 (m, 1H), 1.90-1.95 (m, 1H), 1.13 (d, J=6.4 Hz, 6H)

Compounds in Table 1 were synthesised using the general methods A-F as exemplified by Examples 1-6 using (rac)-tert-butyl 3-aminopyrrolidine-1-carboxylate (CAS Number 186550-13-0).

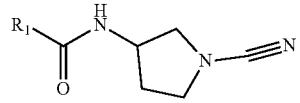

TABLE 1

| Ex | R1 | Name | Synthetic Method | LCMS Method | LCMS RT (min) | MS |
|---|---|---|---|---|---|---|
| 7 | (4-phenylthiazol-2-yl) | N-(1-cyanopyrrolidin-3-yl)-4-phenylthiazole-2-carboxamide | A | B | 3.87 | ES+ 299.2 |
| 8 | (3-(3-chlorophenyl)isoxazol-5-yl) | 3-(3-chlorophenyl)-N-(1-cyanopyrrolidin-3-yl)isoxazole-5-carboxamide | A | B | 3.95 | ES+ 317.23 |

TABLE 1-continued

| Ex | R1 | Name | Synthetic Method | LCMS Method | LCMS RT (min) | MS |
|---|---|---|---|---|---|---|
| 9 | 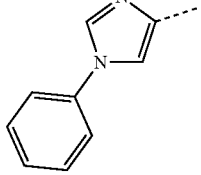 | N-(1-cyanopyrrolidin-3-yl)-1-phenyl-1H-imidazole-4-carboxamide | A | A | 3.25 | ES+ 282.15 |
| 10 | 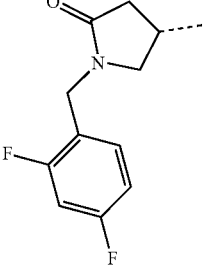 | N-(1-cyanopyrrolidin-3-yl)-1-(2,4-difluorophenyl)-5-oxopyrrolidine-3-carboxamide | A | A | 3.27 | ES+ 348.99 |
| 11 | 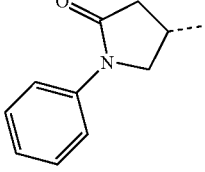 | N-(1-cyanopyrrolidin-3-yl)-5-oxo-1-phenylpyrrolidine-3-carboxamide | A | A | 3.03 | ES+ 299.10 |
| 12 | 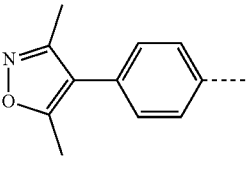 | N-(1-cyanopyrrolidin-3-yl)-4-(3,5-dimethylisoxazol-4-yl)benzamide | B | A | 3.51 | ES+ 311.00 |
| 13 | 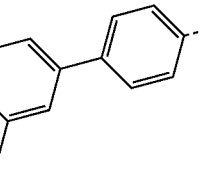 | 3'-chloro-N-(1-cyanopyrrolidin-3-yl)-[1,1'-biphenyl]-4-carboxamide | C | A | 4.58 | ES+ 325.92 |
| 14 | 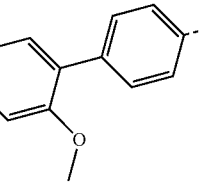 | N-(1-cyanopyrrolidin-3-yl)-2'-methoxy-[1,1'-biphenyl]-4-carboxamide | C | A | 4.24 | ES+ 321.91 |
| 15 | 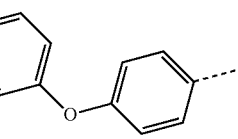 | N-(1-cyanopyrrolidin-3-yl)-4-phenoxybenzamide | A | D | 2.69 | ES+ 308.2 |
| 16 | 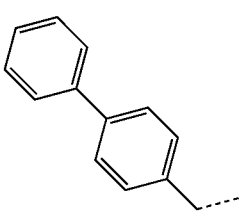 | 2-([1,1'-biphenyl]-4-yl)-N-(1-cyanopyrrolidin-3-yl)acetamide | A | D | 2.96 | ES+ 306.1 |

TABLE 1-continued

| Ex | R1 | Name | Synthetic Method | LCMS Method | LCMS RT (min) | MS |
|----|----|------|------------------|-------------|---------------|-----|
| 17 | | N-(1-cyanopyrrolidin-3-yl)-2-phenylquinoline-4-carboxamide | A | D | 2.80 | ES+ 343.1 |
| 18 | | 6-(4-carbamoylpiperidin-1-yl)-N-(1-cyanopyrrolidin-3-yl)nicotinamide | D | E | 1.69 | ES+ 343.2 |
| 19 | | N-(1-cyanopyrrolidin-3-yl)-6-(4-(2,4-difluorophenyl)piperazin-1-yl)nicotinamide | D | D | 2.52 | ES+ 413.1 |
| 20 | | ethyl 4-(5-((1-cyanopyrrolidin-3-yl)carbamoyl)pyridin-2-yl)piperazin-1-carboxylate | D | E | 2.10 | ES+ 373.3 |
| 21 | | N-(1-cyanopyrrolidin-3-yl)-6-(2-(pyridin-3-yl)pyrrolidin-1-yl)nicotinamide | D | D | 1.72 | ES+ 363.1 |

TABLE 1-continued

| Ex | R1 | Name | Synthetic Method | LCMS Method | LCMS RT (min) | MS |
|----|----|------|------------------|-------------|---------------|-----|
| 22 | | N-(1-cyanopyrrolidin-3-yl)-6-(4-phenoxypiperidin-1-yl)nicotinamide | D | D | 2.42 | ES+ 392.2 |
| 23 | | N-(1-cyanopyrrolidin-3-yl)-6-(4-(pyridin-4-yl)piperidin-1-yl)nicotinamide | D | F | 1.82 | ES+ 377.3 |
| 24 | | 6-(benzyl(methyl)amino)-N-(1-cyanopyrrolidin-3-yl)picolinamide | D | D | 2.87 | ES+ 336.1 |
| 25 | | N-(1-cyanopyrrolidin-3-yl)-6-(3,4-dihydroisoquinolin-2(1H)-yl)picolinamide | D | D | 2.95 | ES+ 348.1 |

TABLE 1-continued

| Ex | R1 | Name | Synthetic Method | LCMS Method | LCMS RT (min) | MS |
|---|---|---|---|---|---|---|
| 26 | 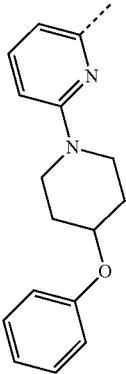 | N-(1-cyanopyrrolidin-3-yl)-6-(4-phenoxypiperidin-1-yl)picolinamide | D | D | 3.06 | ES+ 392.3 |
| 27 | 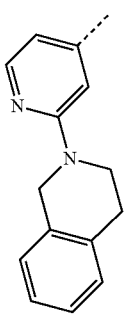 | N-(1-cyanopyrrolidin-3-yl)-2-(3,4-dihydroisoquinolin-2(1H)-yl)isonicotinamide | D | D | 1.97 | ES+ 348.2 |
| 28 | 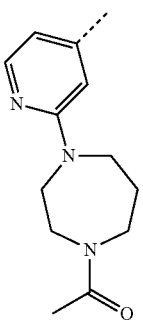 | 2-(4-acetyl-1,4-diazepan-1-yl)-N-(1-cyanopyrrolidin-3-yl)isonicotinamide | D | E | 1.68 | ES+ 357.3 |

Compounds in Table 2 were synthesised using the general methods A-F as exemplified by Examples 1-6 using (R)-tert-butyl 3-aminopyrrolidine-1-carboxylate (CAS Number 147081-49-0).

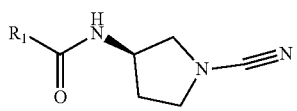

TABLE 2

| Ex | R1 | Name | Synthetic Method | LCMS Method | LCMS RT (min) | MS |
|---|---|---|---|---|---|---|
| 29 | 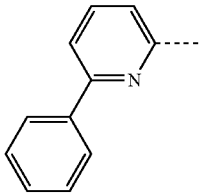 | (R)-N-(1-cyanopyrrolidin-3-yl)-6-phenylpicolinamide | A | A | 4.22 | ES+ 292.90 |
| 30 | 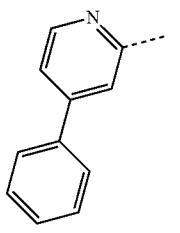 | (R)-N-(1-cyanopyrrolidin-3-yl)-4-phenylpicolinamide | A | B | 3.65 | ES+ 293.16 |
| 31 | 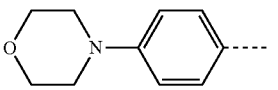 | (R)-N-(1-cyanopyrrolidin-3-yl)-4-morpholinobenzamide | A | B | 2.85 | ES+ 302.32 |
| 32 | 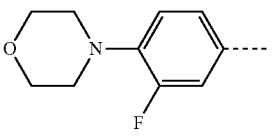 | (R)-N-(1-cyanopyrrolidin-3-yl)-3-fluoro-4-morpholinobenzamide | A | B | 3.03 | ES+ 319.52 |
| 33 | 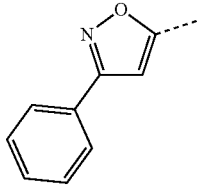 | (R)-N-(1-cyanopyrrolidin-3-yl)-3-phenylisoxazole-5-carboxamide | A | B | 3.50 | ES+ 283.20 |
| 34 | 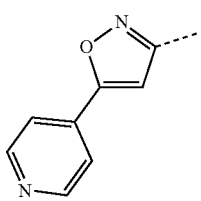 | (R)-N-(1-cyanopyrrolidin-3-yl)-5-(pyridin-4-yl)isoxazole-3-carboxamide | A | B | 2.42 | ES+ 284.20 |
| 35 | 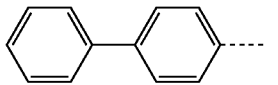 | (R)-N-(1-cyanopyrrolidin-3-yl)-[1,1'-biphenyl]-4-carboxamide | A | A | 4.20 | ES+ 291.94 |
| 36 | 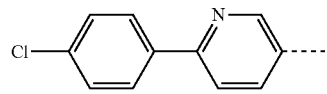 | (R)-6-(4-chlorophenyl)-N-(1-cyanopyrrolidin-3-yl)nicotinamide | B | A | 4.19 | ES+ 327.05 |
| 37 | 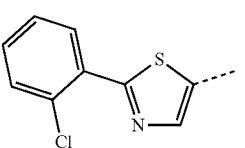 | (R)-2-(2-chlorophenyl)-N-(1-cyanopyrrolidin-3-yl)thiazole-5-carboxamide | B | B | 3.81 | ES+ 333.13 |

TABLE 2-continued

| Ex | R1 | Name | Synthetic Method | LCMS Method | LCMS RT (min) | MS |
|---|---|---|---|---|---|---|
| 38 | 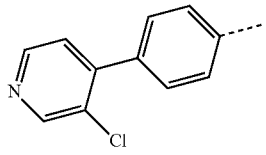 | (R)-4-(3-chloropyridin-4-yl)-N-(1-cyanopyrrolidin-3-yl)benzamide | B | B | 3.22 | ES+ 327.20 |
| 39 | 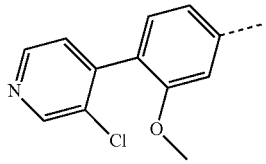 | (R)-4-(3-chloropyridin-4-yl)-N-(1-cyanopyrrolidin-3-yl)-3-methoxybenzamide | B | B | 3.28 | ES+ 357.27 |
| 40 | 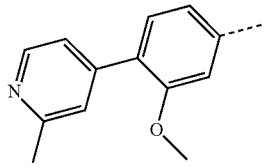 | (R)-N-(1-cyanopyrrolidin-3-yl)-3-methoxy-4-(2-methylpyridin-4-yl)benzamide | B | B | 2.43 | ES+ 337.27 |
| 41 | 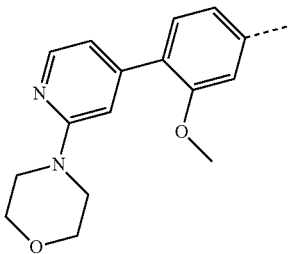 | (R)-N-(1-cyanopyrrolidin-3-yl)-3-methoxy-4-(2-morpholinopyridin-4-yl)benzamide | B | B | 2.60 | ES+ 408.36 |
| 42 | 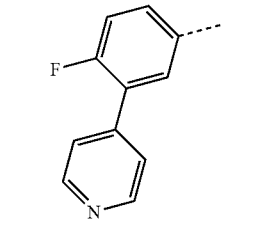 | (R)-N-(1-cyanopyrrolidin-3-yl)-4-fluoro-3-(pyridin-4-yl)benzamide | B | A | 3.36 | ES+ 311.00 |
| 43 | 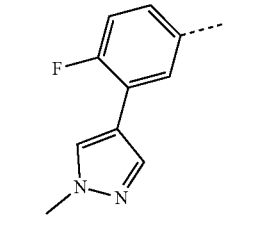 | (R)-N-(1-cyanopyrrolidin-3-yl)-4-fluoro-3-(1-methyl-1H-pyrazol-4-yl)benzamide | B | B | 3.07 | ES+ 314.26 |
| 44 | 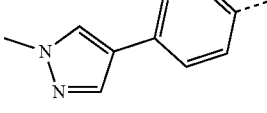 | (R)-N-(1-cyanopyrrolidin-3-yl)-4-(1-methyl-1H-pyrazol-4-yl)benzamide | B | B | 2.79 | ES+ 296.17 |
| 45 | 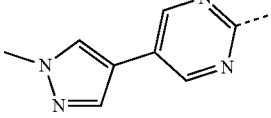 | (R)-N-(1-cyanopyrrolidin-3-yl)-5-(1-methyl-1H-pyrazol-4-yl)pyrimidine-2-carboxamide | C | A | 3.01 | ES+ 298.00 |

TABLE 2-continued

| Ex | R1 | Name | Synthetic Method | LCMS Method | LCMS RT (min) | MS |
|---|---|---|---|---|---|---|
| 46 | (3-phenylpyrrolidin-1-yl) | N-((R)-1-cyanopyrrolidin-3-yl)-3-phenylpyrrolidine-1-carboxamide | E | A | 3.67 | ES+ 285.04 |
| 76 | 2-fluoro-4-(1-methyl-1H-pyrazol-4-yl)phenyl | (R)-N-(1-cyanopyrrolidin-3-yl)-3-fluoro-4-(1-methyl-1H-pyrazol-4-yl)benzamide | B | B | 3.12 | ES+ 314.31 |
| 77 | 3-fluoro-4-(1-methyl-1H-pyrazol-4-yl)phenyl | (R)-N-(1-cyanopyrrolidin-3-yl)-2-fluoro-4-(1-methyl-1H-pyrazol-4-yl)benzamide | C | B | 3.06 | ES+ 314.26 |
| 78 | 2,5-difluoro-4-(1-methyl-1H-pyrazol-4-yl)phenyl | (R)-N-(1-cyanopyrrolidin-3-yl)-2,5-difluoro-4-(1-methyl-1H-pyrazol-4-yl)benzamide | C | A | 3.35 | ES+ 332.01 |
| 79 | 2-fluoro-4-(1,3-dimethyl-1H-pyrazol-4-yl)phenyl | (R)-N-(1-cyanopyrrolidin-3-yl)-4-(1,3-dimethyl-1H-pyrazol-4-yl)-3-fluorobenzamide | C | A | 3.27 | ES+ 328.02 |
| 80 | 3-fluoro-4-(1,3-dimethyl-1H-pyrazol-4-yl)phenyl | (R)-N-(1-cyanopyrrolidin-3-yl)-4-(1,3-dimethyl-1H-pyrazol-4-yl)-2-fluorobenzamide | C | B | 3.19 | ES+ 328.54 |
| 81 | 3-fluoro-4-(1-ethyl-1H-pyrazol-4-yl)phenyl | (R)-N-(1-cyanopyrrolidin-3-yl)-4-(1-ethyl-1H-pyrazol-4-yl)-2-fluorobenzamide | C | B | 3.33 | ES+ 328.64 |
| 82 | 3-fluoro-4-(1-(2-methoxyethyl)-1H-pyrazol-4-yl)phenyl | (R)-N-(1-cyanopyrrolidin-3-yl)-2-fluoro-4-(1-(2-methoxyethyl)-1H-pyrazol-4-yl)benzamide | C | A | 3.23 | ES+ 358.03 |

TABLE 2-continued

| Ex | R1 | Name | Synthetic Method | LCMS Method | LCMS RT (min) | MS |
|---|---|---|---|---|---|---|
| 83 | (pyrazole-benzimidazole structure) | (R)-N-(1-cyanopyrrolidin-3-yl)-6-(1-methyl-1H-pyrazol-4-yl)-1H-benzo[d]imidazole-2-carboxamide | C | B | 3.02 | ES+ 336.64 |
| 84 | (pyrazole-indole structure) | (R)-N-(1-cyanopyrrolidin-3-yl)-6-(1-methyl-1H-pyrazol-4-yl)-1H-indole-2-carboxamide | C | A | 3.37 | ES+ 335.0 |
| 85 | (trifluoromethyl pyrazole-fluorophenyl structure) | (R)-N-(1-cyanopyrrolidin-3-yl)-2-fluoro-4-(5-(trifluoromethyl)-1H-pyrazol-4-yl)benzamide | C | A | 3.42 | ES+ 368.01 |
| 86 | (methylindazole-fluorophenyl structure) | (R)-N-(1-cyanopyrrolidin-3-yl)-2-fluoro-4-(1-methyl-1H-indazol-5-yl)benzamide | C | A | 3.82 | ES+ 364.08 |

Compounds in Table 3 were synthesised using the general methods A-F as exemplified by Examples 1-6 using (S)-tert-butyl 3-aminopyrrolidine-1-carboxylate (CAS Number 147081-44-5).

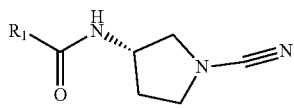

TABLE 3

| Ex | R1 | Name | Synthetic Method | LCMS Method | LCMS RT (min) | MS |
|---|---|---|---|---|---|---|
| 47 | (pyridinyl-phenyl structure) | (S)-N-(1-cyanopyrrolidin-3-yl)-4-(pyridin-4-yl)benzamide | A | A | 3.01 | ES+ 293.00 |
| 48 | (phenyl-pyridine structure) | (S)-N-(1-cyanopyrrolidin-3-yl)-6-phenylpicolinamide | A | A | 4.25 | ES+ 292.96 |

Compounds in Table 4 were synthesised using the general methods A-F as exemplified by Examples 1-6 using (R)-tert-butyl 3-(methylamino)pyrrolidine-1-carboxylate (CAS Number 199336-83-9).

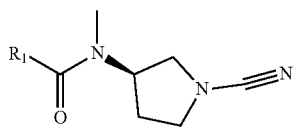

TABLE 4

| Ex | R1 | Name | Synthetic Method | LCMS Method | LCMS RT (min) | MS |
|---|---|---|---|---|---|---|
| 49 | | (R)-4-(3-chloropyridin-4-yl)-N-(1-cyanopyrrolidin-3-yl)-N-methylbenzamide | B | B | 3.283 | ES+ 341.20 |
| 50 | | (R)-1-(1-cyanopyrrolidin-3-yl)-3-(imidazo[1,2-a]pyridin-2-yl)-1-methylurea | E | B | 2.19 | ES+ 285.24 |
| 87 | | (R)-N-(1-cyanopyrrolidin-3-yl)-3-fluoro-N-methyl-4-(1-methyl-1H-pyrazol-4-yl)benzamide | B | B | 3.22 | ES+ 328.44 |
| 88 | | (R)-N-(1-cyanopyrrolidin-3-yl)-N-methyl-6-(1-methyl-1H-pyrazol-4-yl)-1H-benzo[d]imidazole-2-carboxamide | C | A | 2.97 | ES+ 349.97 |
| 262 | | (R)-N-(1-cyanopyrrolidin-3-yl)-6-(3,5-dimethylisoxazol-4-yl)-N-methyl-1H-indole-2-carboxamide | C | A | 3.98 | ES+ 364.21 |
| 263 | | (R)-N-(1-cyanopyrrolidin-3-yl)-N-methyl-5-(1-methyl-1H-pyrazol-4-yl)-1H-pyrrolo[2,3-c]pyridine-2-carboxamide | C | B | 2.55 | ES+ 350.25 |
| 264 | | N-((R)-1-cyanopyrrolidin-3-yl)-N-methyl-2-phenylmorpholine-4-carboxamide | E | B | 3.70 | ES+ 315.51 |

TABLE 4-continued

| Ex | R1 | Name | Synthetic Method | LCMS Method | LCMS RT (min) | MS |
|---|---|---|---|---|---|---|
| 265 | 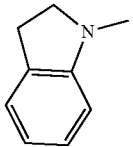 | (R)-N-(1-cyanopyrrolidin-3-yl)-N-methylindoline-1-carboxamide | E | A | 3.85 | ES+ 271.08 |
| 266 | 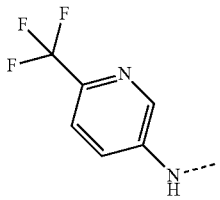 | (R)-1-(1-cyanopyrrolidin-3-yl)-1-methyl-3-(6-(trifluoromethyl)pyridin-3-yl)urea | E | A | 3.61 | ES+ 313.93 |
| 267 | 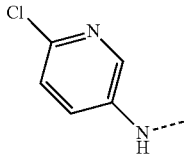 | (R)-3-(5-chloropyridin-2-yl)-1-(1-cyanopyrrolidin-3-yl)-1-methylurea | E | A | 3.57 | ES+ 279.95 |

Compounds in Table 5 were synthesised using the general methods A-F as exemplified by Examples 1-6 using tert-butyl rac-(3 aR,6aR)-hexahydropyrrolo[3,4-b]pyrrole-5 (1H)-carboxylate (CAS Number 180975-51-3).

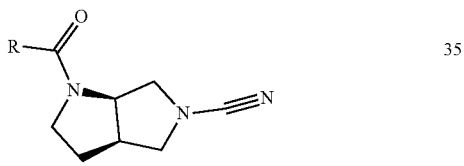

TABLE 5

| Ex | R1 | Name | Synthetic Method | LCMS Method | LCMS RT (min) | MS |
|---|---|---|---|---|---|---|
| 51 | 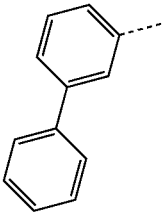 | rac-(3aR,6aR)-1-([1,1'-biphenyl]-3-carbonyl)hexahydropyrrolo[3,4-b]pyrrole-5(1H)-carbonitrile | A | B | 3.94 | ES+ 318.27 |
| 52 | 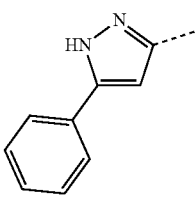 | rac-(3aR,6aR)-1-(3-phenyl-1H-pyrazole-5-carbonyl)hexahydropyrrolo[3,4-b]pyrrole-5(1H)-carbonitrile | A | B | 3.30 | ES+ 308.27 |

TABLE 5-continued

| Ex | R1 | Name | Synthetic Method | LCMS Method | LCMS RT (min) | MS |
|---|---|---|---|---|---|---|
| 53 | 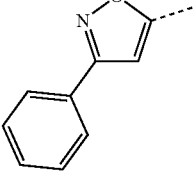 | rac-(3aR,6aR)-1-(3-phenylisoxazole-5-carbonyl)hexahydropyrrolo[3,4-b]pyrrole-5(1H)-carbonitrile | A | A | 3.99 | ES+ 308.99 |
| 54 | 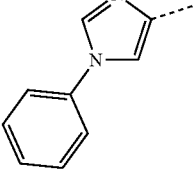 | rac-(3aR,6aR)-1-(1-phenyl-1H-imidazole-4-carbonyl)hexahydropyrrolo[3,4-b]pyrrole-5(1H)-carbonitrile | A | A | 3.32 | ES+ 308.00 |
| 55 | 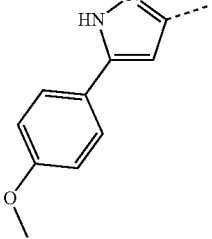 | rac-(3aR,6aR)-1-(3-(4-methoxyphenyl)-1H-pyrazole-5-carbonyl)hexahydropyrrolo[3,4-b]pyrrole-5(1H)-carbonitrile | A | A | 3.59 | ES+ 337.93 |
| 56 | 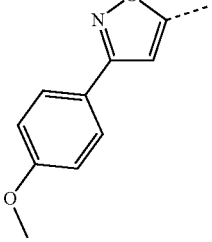 | rac-(3aR,6aR)-1-(3-(4-methoxyphenyl)isoxazole-5-carbonyl)hexahydropyrrolo[3,4-b]pyrrole-5(1H)-carbonitrile | A | A | 4.02 | ES+ 338.93 |
| 57 | 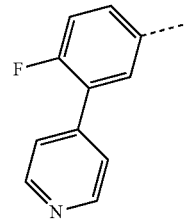 | rac-(3aR,6aR)-1-(4-fluoro-3-(pyridin-4-yl)benzoyl)hexahydropyrrolo[3,4-b]pyrrole-5(1H)-carbonitrile | B | A | 3.34 | ES+ 337.00 |
| 58 | 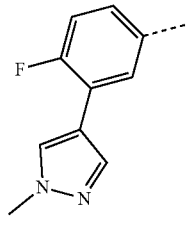 | rac-(3aR,6aR)-1-(4-fluoro-3-(1-methyl-1H-pyrazol-4-yl)benzoyl)hexahydropyrrolo[3,4-b]pyrrole-5(1H)-carbonitrile | B | B | 3.17 | ES+ 340.00 |
| 59 | 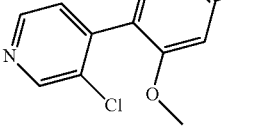 | rac-(3aR,6aR)-1-(4-(3-chloropyridin-4-yl)-3-methoxybenzoyl)hexahydropyrrolo[3,4-b]pyrrole-5(1H)-carbonitrile | B | B | 3.41 | ES+ 383.28 |

TABLE 5-continued

| Ex | R1 | Name | Synthetic Method | LCMS Method | LCMS RT (min) | MS |
|---|---|---|---|---|---|---|
| 60 | | rac-(3aR,6aR)-1-(3-methoxy-4-(1-methyl-1H-pyrazol-4-yl)benzoyl)hexahydropyrrolo[3,4-b]pyrrole-5(1H)-carbonitrile | B | A | 3.24 | ES+ 351.97 |
| 61 | | (3aR,6aR)-1-(2-oxo-6-phenyl-1,2-dihydropyridine-3-carbonyl)hexahydropyrrolo[3,4-b]pyrrole-5(1H)-carbonitrile | A | E | 1.88 | ES+ 335.20 |
| 268 | | (3aR,6aR)-1-(3-chloro-4-morpholinobenzoyl)hexahydropyrrolo[3,4-b]pyrrole-5(1H)-carbonitrile | A | A | 3.64 | ES+ 361.02 |
| 269 | | (3aR,6aR)-1-(indoline-1-carbonyl)hexahydropyrrolo[3,4-b]pyrrole-5(1H)-carbonitrile | E | A | 3.75 | ES+ 383.12 |

Example 62 (R)—N-(1-cyanopyrrolidin-3-yl)-3-(N-methylisobutyramido)benzamide

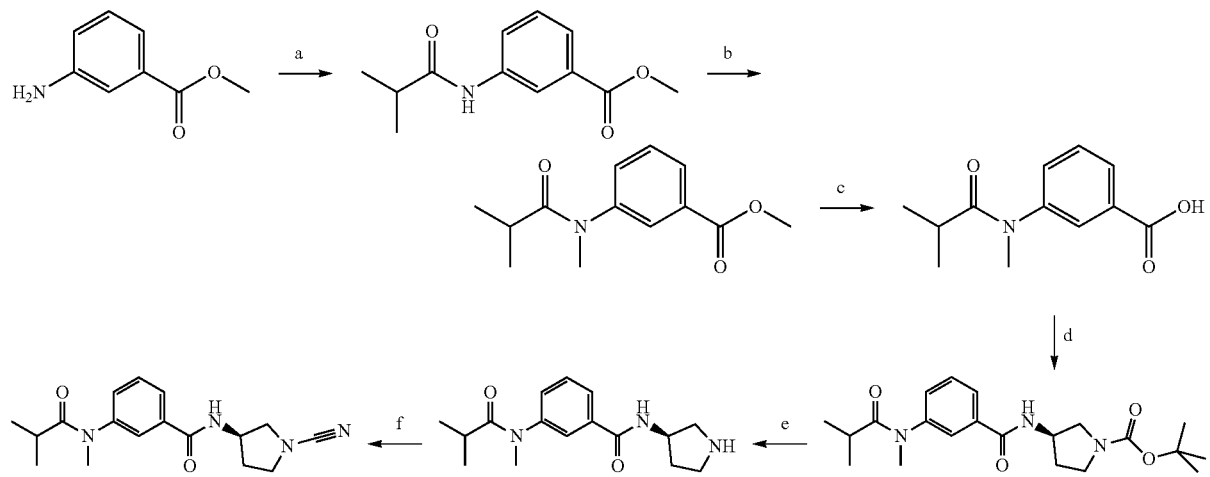

Step a.

To a solution of methyl 3-aminobenzoate (3.31 mmol) in DCM (10 ml) was added TEA (9.93 mmol) at rt and the reaction mixture was stirred at rt for 30 min. Isobutyryl chloride (4.96 mmol) was added to the reaction mixture at 0° C. The reaction mixture was then stirred at rt for 1 h. The resulting reaction mixture was poured into water (100 ml) and extracted with DCM (2×50 ml). The combined organic phase was collected, dried over $Na_2SO_4$, filtered and concentrated under reduced pressure yielding methyl 3-isobutyramidobenzoate (quantitative). This material was directly used for the next step without further purification. MS: ES+ 222.2.

Step b.

To a solution of methyl 3-isobutyramidobenzoate (1.80 mmol) in THF (10 ml) was added NaH (60% mineral oil, 3.61 mmol) at 0° C. The reaction mixture was stirred at rt for 30 min. Methyl iodide (3.61 mmol) was added to the reaction mixture at rt. The reaction mixture was stirred at rt for 2 h. The resulting reaction mixture was poured into ice cold water (50 ml) and extracted with EtOAc (3×20 ml). The combined organic phase was collected, dried over $Na_2SO_4$, filtered and concentrated under reduced pressure yielding methyl 3-(N methylisobutyramido) benzoate (1.65 mmol). This material was directly used for the next step without further purification. MS: ES+ 236.6.

Step c.

To a solution of 3-(N methylisobutyramido) benzoate (1.61 mmol) in THF:water (10:2, 12 ml) was added LiOH.H₂O (4.85 mmol) at 0° C. The reaction mixture was stirred at rt for 5 h. The resulting reaction mixture was adjusted to pH 3 by slow addition of aqueous citric acid solution. The resulting mixture was extracted with EtOAc (3×20 ml). The combined organic phase was collected, dried over Na₂SO₄, filtered and concentrated under reduced pressure yielding 3-(N-methylisobutyramido)benzoic acid (1.44 mmol). This material was directly used for the next step without further purification. MS: ES+ 222.2 lected, dried over Na₂SO₄, filtered and concentrated under reduced pressure. The resulting residue was purified by column chromatography (77% EtOAc in hexane) yielding the title compound (0.28 mmol). LCMS: Method B, RT 3.15 min, MS: ES+ 315.1; ¹H NMR (400 MHz, DMSO-d₆) δ ppm 8.64 (d, J=6 Hz, 1H), 7.81-7.86 (m, 2H), 7.53-7.57 (m, 2H), 4.46-4.49 (m, 1H), 3.63-3.67 (m, 1H), 3.52-3.58 (m, 1H), 3.42-3.48 (m, 2H), 3.17 (s, 3H), 2.33-2.39 (m, 1H), 2.09-2.18 (m, 1H), 1.93-1.98 (m, 1H), 0.88-1.0 (m, 6H)

Example 63 (R)—N-(1-cyanopyrrolidin-3-yl)-5-phenylpyrimidine-2-carboxamide

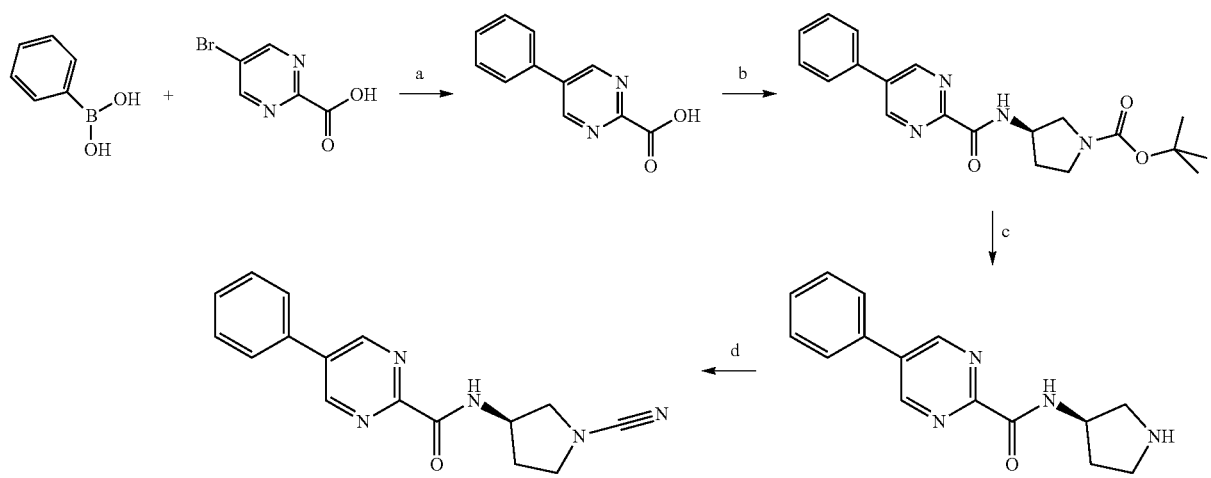

Step d.

To a solution of 3-(N-methylisobutyramido)benzoic acid (1.26 mmol) in THF (15 ml) was added HATU (1.90 mmol) and DIPEA (2.53 mmol) at 0° C. The reaction mixture was stirred at rt for 30 min. (R)-3-Amino-1N—BOC-pyrrolidine (1.52 mmol) was added to the reaction mixture at rt and stirred for 2 h. The resulting reaction mixture was poured into water (100 ml) and extracted with EtOAc (2×50 ml). The combined organic phase was collected, dried over Na₂SO₄, filtered and concentrated under reduced pressure, yielding tert-butyl (R)-3-(3-(N-methylisobutyramido)benzamido)pyrrolidine-1-carboxylate (quantitative). This material was directly used for the next step without further purification. MS: ES-388.6.

Step e.

To a solution of tert-butyl (R)-3-(3-(N-methylisobutyramido)benzamido)pyrrolidine-1-carboxylate (1.02 mmol) in DCM (15 ml) was added TFA (4 ml) at 0° C. The reaction mixture was stirred at rt for 1 h. The resulting reaction mixture was concentrated under reduced pressure yielding (R)-3-(N-methylisobutyramido)-N-(pyrrolidin-3-yl) benzamide TFA salt (0.99 mmol). This material was used directly for the next step without further purification. MS: ES+ 290.4.

Step f.

To a solution of (R)-3-(N-methylisobutyramid)-N-(pyrrolidin-3-yl) benzamide TFA salt (0.99 mmol) in THF (15 ml) was added K₂CO₃ (3.97 mmol) at rt. The reaction mixture was stirred at rt for 15 min. Cyanogen bromide (1.48 mmol) was added to the reaction mixture at 0° C. The reaction mixture was stirred at rt for 30 min. The resulting reaction mixture was poured into water (100 ml) and extracted with EtOAc (2×50 ml). The combined organic phase was col- Step a.

To a solution of 5-bromopyrimidine-2-carboxylic acid (1.47 mmol) in 1,4-dioxane:water (3:1, 7 ml) was added phenylboronic acid (2.19 mmol) and Na₂CO₃ (2.79 mmol) at rt in a glass tube. The reaction mixture and purged with nitrogen for 10 min. Pd(PPh₃)₄(0.14 mol) was added to the reaction mixture under nitrogen atmosphere and the glass tube was sealed. The reaction mixture was heated at 100° C. (external temperature) for 2 h. The resulting reaction mixture was poured into 1M NaOH solution (50 ml) and washed with diethyl ether (50 ml). The resulting aqueous layer containing the product was acidified with 1 M HCl and extracted with EtOAc (3×20 ml). The combined organic phase was dried over Na₂SO₄, filtered and concentrated under reduced pressure yielding 5-phenylpyrimidine-2-carboxylic acid (1.25 mmol). MS: ES+ 201.02, 1H NMR (400 MHz, DMSO-d₆) δ ppm 13.62 (s, 1H), 9.30 (s, 2H), 7.89-7.91 (m, 2H), 7.51-7.60 (m, 3H).

Step b.

To a solution of 5-phenylpyrimidine-2-carboxylic acid (0.60 mmol) in DCM (5 ml) was added HATU (0.90 mmol), TEA (1.20 mmol) and tert-butyl (R)-3-aminopyrrolidine-1-carboxylate (0.60 mmol) at rt. The reaction mixture was stirred at rt for 16 h. The resulting reaction mixture was poured into water (50 ml) and extracted with EtOAc (3×20 ml). The combined organic phase was collected, dried over Na₂SO₄, filtered and concentrated under reduced pressure yielding tert-butyl (R)-3-(5-phenylpyrimidine-2-carboxamido)pyrrolidine-1-carboxylate (0.35 mmol). This material was directly used for the next step without further purification. MS: ES+ 369.40.

Step c.

To a solution of tert-butyl (R)-3-(5-phenylpyrimidine-2-carboxamido) pyrrolidine-1-carboxylate (0.33 mmol) in DCM (5 ml) was added TFA (0.5 ml) at 0° C. The reaction mixture was stirred at rt for 6 h. The resulting reaction mixture was concentrated under reduced pressure. The resulting crude material was triturated with diethyl ether (5 ml) yielding (R)-5-phenyl-N-(pyrrolidin-3-yl) pyrimidine-2-carboxamide TFA salt (0.30 mmol). This material was used directly for the next step without further purification. MS: ES+ 269.30.

Step d.

To a solution of (R)-5-phenyl-N-(pyrrolidin-3-yl) pyrimidine-2-carboxamide TFA salt (0.27 mmol) in DCM (5 ml) was added $K_2CO_3$ (0.54 mmol) at 0° C. Cyanogen bromide (0.40 mmol) was added to the reaction mixture at 0° C. The reaction mixture was stirred at rt for 2 h. The resulting reaction mixture was poured into water (50 ml) and extracted with DCM (3×20 ml). The combined organic phase was collected, dried over $Na_2SO_4$, filtered and concentrated under reduced pressure. The obtained residue was triturated with diethyl ether (10 ml) yielding title compound (0.15 mmol). LCMS: Method A, RT 3.34 min, MS: ES+ 294.10; $^1$H NMR (400 MHz, DMSO-$d_6$) δ ppm 9.29 (s, 2H), 9.22 (d, J=7.20 Hz, 1H), 7.89-7.91 (m, 2H), 7.51-7.61 (m, 3H), 4.52-4.57 (m, 1H), 3.60-3.67 (m, 1H), 3.54-3.58 (m, 1H), 3.51-3.53 (m, 1H), 3.40-3.45 (m, 1H), 2.12-2.19 (m, 1H), 1.99-2.08 (m, 1H)

Example 64 (R)—N-(1-cyanopyrrolidin-3-yl)-3-(pyridin-4-yl)isoxazole-5-carboxamide 0° C. The reaction mixture was stirred at rt for 3 h. The resulting reaction mixture was poured into water (100 ml) and extracted with EtOAc (3×30 ml). The combined organic phase was collected, dried over $Na_2SO_4$, filtered and concentrated under reduced pressure. The resulting residue was purified by flash chromatography (26% EtOAc in hexane) yielding methyl 3-(pyridin-4-yl) isoxazole-5-carboxylate (2.45 mmol). MS: ES+ 205.19.

Step c.

To a solution of methyl 3-(pyridin-4-yl) isoxazole-5-carboxylate (1.96 mmol) in THF (5 ml) was added TBD (3.79 mmol) at rt. Tert-butyl (R)-3-aminopyrrolidine-1-carboxylate (1.96 mmol) was added to the reaction mixture. The reaction mixture was stirred at rt for 3 h. The resulting reaction mixture was poured into water (100 ml) and extracted with EtOAc (3×30 ml). The combined organic phase was collected, dried over $Na_2SO_4$, filtered and concentrated under reduced pressure. The resulting residue was purified by flash chromatography (2% MeOH in DCM) yielding the tert-butyl (R)-3-(3-(pyridin-4-yl)isoxazole-5-carboxamido) pyrrolidine-1-carboxylate (0.33 mmol). MS: ES+358.90.

Step d.

To a solution of tert-butyl (R)-3-(3-(pyridin-4-yl) isoxazole-5-carboxamido) pyrrolidine-1-carboxylate (0.31 mmol) in DCM (2 ml) was added TFA (0.8 ml) at 0° C. The reaction mixture was stirred at rt for 1 h. The resulting reaction mixture was concentrated under reduced pressure. The resulting crude material was triturated with diethyl ether (5 ml) yielding (R)-3-(pyridin-4-yl)-N-(pyrrolidin-3-yl)

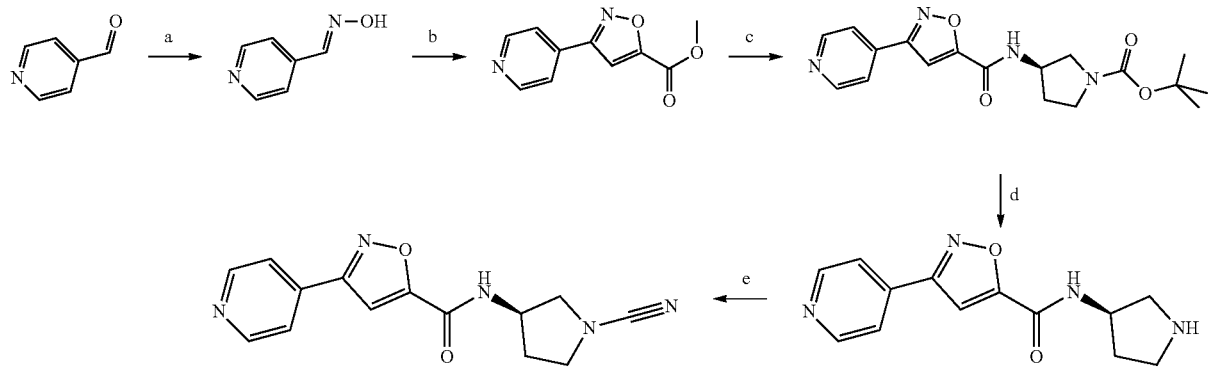

isoxazole-5-carboxamide TFA salt (0.20 mmol). This material was used directly for the next step without further purification. MS: ES+ 259.20

Step e.

To a solution of (R)-3-(pyridin-4-yl)-N-(pyrrolidin-3-yl) isoxazole-5-carboxamide TFA salt (0.18 mmol) in DCM (2 ml) was added $K_2CO_3$ (0.55 mmol) at 0° C. Cyanogen bromide (0.27 mmol) was added to the reaction mixture at 0° C. The reaction mixture was stirred at rt for 2 h. The resulting reaction mixture was poured into water (50 ml) and extracted with DCM (3×20 ml). The combined organic phase was collected, dried over $Na_2SO_4$, filtered and concentrated under reduced pressure. The resulting residue was purified by flash chromatography (2% MeOH in DCM) yielding the title compound (0.07 mmol). LCMS: Method A, RT 2.90 min, MS: ES+ 283.90; $^1$H NMR (400 MHz, DMSO-$d_6$) δ ppm 9.37 (d, J=6.80 Hz, 1H), 8.77 (dd, J=4.80, Step a.

To a solution of 4-pyridine carboxaldehyde (28.04 mmol) in MeOH (30 ml) was added $NH_2OH.HCl$ (55.94 mmol) at rt. The reaction mixture was heated at 60° C. for 30 min. Precipitation was observed in the reaction mixture. The obtained precipitates were collected by filtration and dried under reduced pressure to yield isonicotinaldehyde oxime (23.77 mmol). This material was used directly for the next step without further purification. MS: ES+ 122.8; $^1$H NMR (400 MHz, DMSO-$d_6$) δ ppm 12.78 (s, 1H), 8.89 (d, J=6.40 Hz, 2H), 8.42 (s, 1H), 8.14 (d, J=6.80 Hz, 2H)

Step b.

To a solution of isonicotinaldehyde oxime (22.95 mmol) in DMF (30 ml) was added NCS (34.36 mmol) at rt and stirred for 1 h. The reaction mixture was cooled to 0° C. and a solution of methyl propiolate (21.90 mmol) in DCM (5 ml) was added to the reaction mixture at 0° C. all at once. TEA (43.56 mmol) was added dropwise to the reaction mixture at 1.60 Hz, 2H), 7.92 (dd, J=4.40, 1.60 Hz, 2H), 7.82 (s, 1H), 4.48-4.52 (m, 1H), 3.63-3.67 (m, 1H), 3.53-3.59 (m, 1H), 3.44-3.49 (m, 1H), 3.34-3.38 (m, 1H), 2.11-2.17 (m, 1H), 1.96-2.02 (m, 1H)

Compounds in Table 6 were synthesised using a procedure similar to that described for Example 64.

Example 273 (R)—N-(1-cyanopyrrolidin-3-yl)-N-methyl-3-(2-methylpyridin-4-yl)isoxazole-5-carboxamide

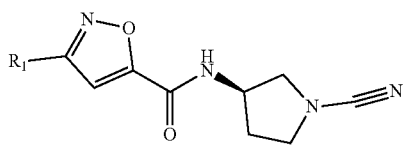

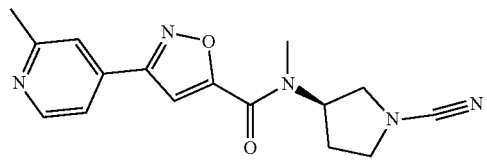 [SMILES: Cc1cc(-c2cc(C(=O)N(C)[C@@H]3CCN(C#N)C3)on2)ccn1]

TABLE 6

| Ex | R1 | Name | ¹H NMR (400 MHz) δ ppm | LCMS Method | LCMS RT (min) | MS |
|---|---|---|---|---|---|---|
| 65 | pyridin-3-yl | (R)-N-(1-cyanopyrrolidin-3-yl)-3-(pyridin-3-yl)isoxazole-5-carboxamide | DMSO-$d_6$ 9.36 (d, J = 6.80 Hz, 1 H), 9.14 (s, 1 H), 8.73-8.74 (m, 1 H), 8.32-8.35 (m, 1 H), 7.79 (s, 1 H), 7.58-7.61 (m, 1 H), 4.48-4.52 (m, 1 H), 3.63-3.67 (m, 1 H), 3.53-3.59 (m, 1 H), 3.44-3.49 (m, 1 H), 3.35-3.37 (m, 1 H), 2.10-2.19 (m, 1 H), 1.94-2.02 (m, 1 H) | B | 2.57 | ES+ 284.2 |
| 66 | pyridin-2-yl | (R)-N-(1-cyanopyrrolidin-3-yl)-3-(pyridin-2-yl)isoxazole-5-carboxamide | DMSO-$d_6$ 9.26 (d, J = 6.40 Hz, 1 H), 8.75-8.76 (m, 1 H), 7.98-8.10 (m, 2 H), 7.68 (s, 1 H), 7.56-7.59 (m, 1 H), 4.47-4.51 (m, 1 H), 3.63-3.68 (m, 1 H), 3.53-3.59 (m, 1 H), 3.44-3.50 (m, 1 H), 3.35-3.37 (m, 1 H), 2.10-2.19 (m, 1 H), 1.94-2.01 (m, 1 H) | B | 2.90 | ES+ 283.9 |
| 270 | 2-methylpyridin-4-yl | (R)-N-(1-cyanopyrrolidin-3-yl)-3-(2-methylpyridin-4-yl)isoxazole-5-carboxamide | MeOD 8.58 (d, J = 5.2 Hz, 1 H), 7.84 (s, 1 H), 7.75 (d, J = 5.2 Hz, 1 H), 7.56 (s, 1 H), 4.62-4.65 (m, 1 H), 3.75-3.79 (m, 1 H), 3.63-3.69 (m, 1 H), 3.54-3.59 (m, 2 H), 3.44-3.48 (m, 1 H), 2.64 (s, 3 H), 2.29-2.34 (m, 1 H), 2.09-2.14 (m, 1 H) | A | 3.04 | ES+ 297.89 |
| 271 | 3,4-dimethylphenyl | (R)-N-(1-cyanopyrrolidin-3-yl)-3-(3,4-dimethylphenyl)isoxazole-5-carboxamide | DMSO-$d_6$ 9.27 (d, J = 6.8 Hz, 1 H), 7.72 (s, 1 H), 7.63-7.65 (m, 2 H), 7.30 (d, J = 8.0 Hz, 1 H), 4.45-4.52 (m, 1 H), 3.62-3.66 (m, 1 H), 3.52-3.58 (m, 1 H), 3.43-3.51 (m, 1 H), 3.30-3.32 (m, 1 H), 2.29 (s, 3 H), 2.28 (s, 3 H), 2.09-2.18 (m, 1 H), 1.93-2.01 (m, 1 H) | A | 4.43 | ES+ 310.99 |
| 272 | 2,4-difluorophenyl | (R)-N-(1-cyanopyrrolidin-3-yl)-3-(2,4-difluorophenyl)isoxazole-5-carboxamide | MeOD 8.06 (t, J = 6.4 Hz, 1 H), 7.41 (d, J = 2.8 Hz, 1 H), 7.15-7.24 (m, 2 H), 4.63-4.65 (m, 1 H), 3.74-3.78 (m, 1 H), 3.63-3.66 (m, 1 H), 3.53-3.59 (m, 1 H), 3.44-3.47 (m, 1 H), 2.28-2.33 (m, 1 H), 2.11-2.14 (m, 1 H) | A | 4.01 | ES+ 318.97 |

Synthesised using a procedure similar to that described for Example 64. LCMS: Method A, RT 3.22 min, MS: ES+ 311.99; $^1$H NMR (400 MHz, MeOD) δ ppm: 8.58 (d, J=5.2 Hz, 1H), 7.86 (s, 1H), 7.77 (d, J=5.2 Hz, 1H), 7.45-7.48 (m, 1H), 3.68-3.74 (m, 3H), 3.53-3.59 (m, 2H), 3.22 (s, 3H), 3.65 (s, 3H), 2.26-2.33 (m, 2H).

Example 67 (R)—N-(1-cyanopyrrolidin-3-yl)-5-phenylpyridazine-3-carboxamide

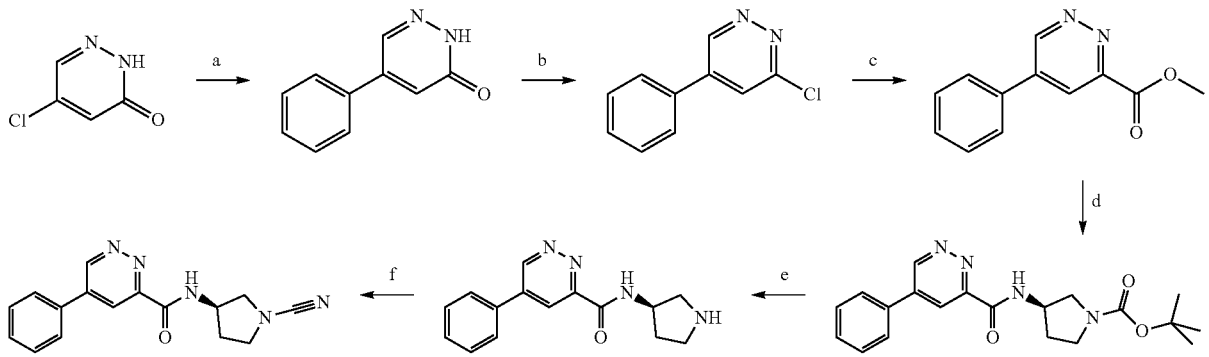

Step a.

A solution of 5-chloropyridazin-3(2H)-one (9.96 mmol) and phenylboronic acid (11.95 mmol) in 1,4-dioxane (10 ml) was taken in a glass tube. Na$_2$CO$_3$ (19.92 mmol) was added to the reaction mixture at rt as a 2M aqueous solution. The reaction mixture was purged with nitrogen for 10 min. Pd(dppf)Cl$_2$ (4.98 mmol) was added to the reaction mixture at rt. The glass tube was tightly sealed and heated at 110° C. (external temperature) for 24 h. The resulting mixture was filtered through celite hyflow and washed with EtOAc (3×50 ml). Water (2×50 ml) was added to the filtrate. The organic layer phase was separated and washed with brine (100 ml), dried over Na$_2$SO$_4$, filtered and concentrated under reduced pressure. The resulting residue was purified by flash chromatography (27% EtOAc in hexane) yielding 5-phenylpyridazin-3(2H)-one (6.25 mmol). MS: ES+ 172.79; $^1$H NMR (400 MHz, DMSO-d$_6$) δ ppm 13.14 (s, 1H), 8.31 (d, J=2.4 Hz, 1H), 7.81-7.84 (m, 2H), 7.53-7.54 (m, 3H), 7.14 (d, J=2.4 Hz, 1H)

Step b.

POCl$_3$ (22 ml) was added very slowly to a 100 ml round bottomed flask containing 5-phenylpyridazin-3(2H)-one (12.19 mmol) at rt. The reaction mixture was heated at 90° C. for 1 h. The resulting reaction mixture was carefully poured into ice cooled water (50 ml), basified using solid NaHCO$_3$ (pH adjusted 8 to 9) and extracted with EtOAc (3×100 ml). The combined organic phase was washed with brine (100 ml), dried over Na$_2$SO$_4$, filtered and concentrated under reduced pressure. The resulting residue was triturated with hexane (3×20 ml) and dried to yield 3-chloro-5-phenylpyridazine (12.06 mmol). This material was directly used for the next step without further purification. MS: ES+ 192.1.

Step c.

A solution of 3-chloro-5-phenylpyridazine (2.63 mmol) in MeOH:DMF (1:1, 10 ml) was taken in a 25 ml glass tube at rt. TEA (3.95 mmol) was added to the reaction mixture at rt and stirred for 5 min. The reaction mixture was treated with dppf (0.26 mmol) and purged with nitrogen for 10 min. The resulting reaction mixture was transferred to an autoclave under nitrogen atmosphere. Pd(OAc)$_2$ (0.13 mmol) was added to the reaction mixture at rt under nitrogen atmosphere. The reaction mixture was stirred in an autoclave under 10 psi CO$_2$ pressure at 70° C. for 18 h. The resulting reaction mixture was carefully filtered through celite hyflow and washed with EtOAc (2×50 ml). Water (2×50 ml) was added to the filtrate. The organic phase was separated, dried over Na$_2$SO$_4$, filtered and concentrated under reduced pressure. The resulting residue was purified by flash chromatography (40% EtOAc in hexane) yielding methyl 5-phenylpyridazine-3-carboxylate (0.65 mmol). MS: ES+ 215.18; $^1$H NMR (400 MHz, DMSO-d$_6$) δ ppm 9.86 (d, J=2.4 Hz, 1H), 8.44 (d, J=2.4 Hz, 1H), 7.99-8.04 (m, 2H), 7.57-7.64 (m, 3H), 4.00 (s, 3H)

Step d.

To a solution of methyl 5-phenylpyridazine-3-carboxylate (0.51 mmol) in THF (4 ml) was added TBD (0.77 mmol) at rt. A solution of (R)-3-amino-1N—BOC-pyrrolidine (0.51 mmol) in THF (1 ml) was added dropwise to the reaction mixture at rt. The reaction mixture was heated at 70° C. for 12 h. The resulting reaction mixture was poured into water (50 ml), extracted with EtOAc (2×30 ml). The combined organic phase was washed with brine (50 ml), dried over Na$_2$SO$_4$, filtered and concentrated under reduced pressure. The resulting residue was purified by flash chromatography (30% EtOAc in hexane) yielding tert-butyl 3-(5-phenylpyridazine-3-carboxamido)pyrrolidine-1-carboxylate (0.19 mmol). MS: ES+ 369.19.

Steps e, f.

The title compound was synthesised from the intermediate above using a procedure similar to that described for steps d, e of Example 64. LCMS: Method B, RT 3.25 min, MS: ES+ 294.27; $^1$H NMR (400 MHz, DMSO-d$_6$) δ ppm 9.85 (d, J=2.4 Hz, 1H), 9.62 (d, J=7.2 Hz, 1H), 8.41 (d, J=2 Hz, 1H), 8.00-8.07 (m, 2H), 7.56-7.61 (m, 3H), 4.60-4.65 (m, 1H), 3.57-3.69 (m, 2H), 3.45-3.50 (m, 2H), 2.07-2.21 (m, 2H)

Example 68 N-(1-cyanopyrrolidin-3-yl)-N-methyl-[1,1'-biphenyl]-4-carboxamide

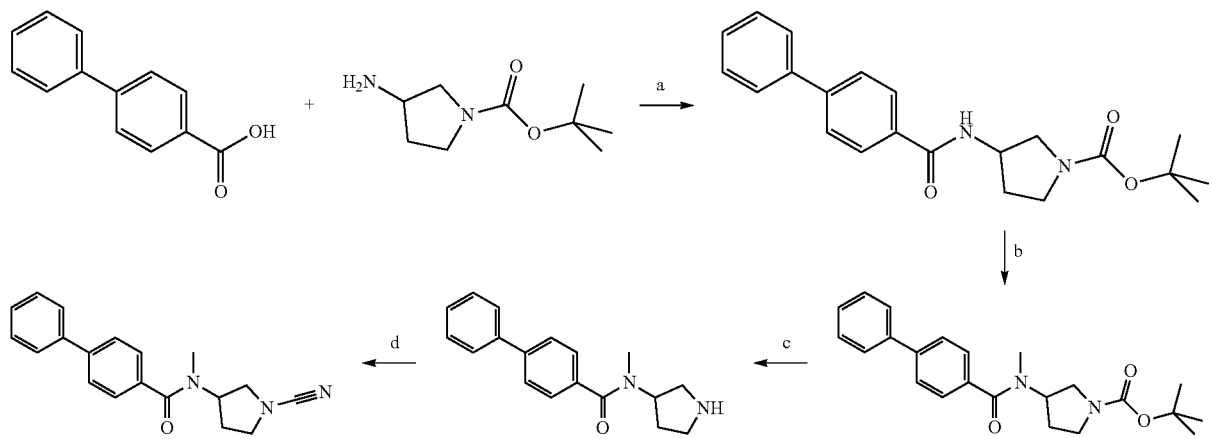

Step a.

To a solution of 4-phenylbenzoic acid (2.52 mmol) in THF (12.5 ml) was added T3P (50% in EtOAc) (7.56 mmol) at 0° C. The reaction mixture was stirred at 0° C. for 20 min. Tert-butyl 3-aminopyrrolidine-1-carboxylate (2.52 mmol) and DIPEA (7.56 mmol) were added to the reaction mixture at rt. The reaction mixture was stirred at rt for 16 h. The resulting reaction mixture was poured into water (50 ml) and extracted with EtOAc (3×30 ml). The combined organic layer was washed with 1M HCl (30 ml), aqueous NaHCO$_3$ solution (30 ml), brine (50 ml), dried over Na$_2$SO$_4$, filtered and concentrated under reduced pressure. The resulting mixture was purified by column chromatography (25% EtOAc in hexane) yielding tert-butyl 3-([1,1'-biphenyl]-4-carboxamido)pyrrolidine-1-carboxylate (1.03 mmol) MS: ES+ 367.28.

Step b.

To a solution of tert-butyl 3-([1,1'-biphenyl]-4-carboxamido)pyrrolidine-1-carboxylate (0.96 mmol) in DMF (9 ml) was added NaH (60% mineral oil, 1.95 mmol) at 0° C. The reaction mixture was stirred at 0° C. for 15 min. Methyl iodide (1.45 mmol) was added to the reaction mixture at 0° C. The reaction mixture was stirred at rt for 10 min. The resulting reaction mixture was poured into water (100 ml) and extracted with EtOAc (3×30 ml). The combined organic layer was washed with brine (50 ml), dried over Na$_2$SO$_4$, filtered and concentrated under reduced pressure yielding tert-butyl 3-(N-methyl-[1,1'-biphenyl]-4-carboxamido)pyrrolidine-1-carboxylate (1.18 mmol) MS: ES+ 381.4

Steps c, d.

The title compound was synthesised from the intermediate above using a procedure similar to that described for steps b, c of Example 1. LCMS: Method A, RT 4.27 min, MS: ES+ 305.94; $^1$H NMR (400 MHz, DMSO-d$_6$) δ ppm 7.63-7.68 (m, 2H), 7.61-7.62 (m, 2H), 7.47-7.51 (m, 4H), 7.40-7.43 (m, 1H), 5.13 (br s, 1H), 3.63-3.68 (m, 2H), 3.45-3.48 (m, 2H), 3.03 (s, 3H), 2.13-2.21 (m, 2H)

Example 69 N-((3R,4S)-1-cyano-4-methylpyrrolidin-3-yl)-5-phenylthiazole-2-carboxamide Example 70 N-((3S,4R)-1-cyano-4-methylpyrrolidin-3-yl)-5-phenylthiazole-2-carboxamide

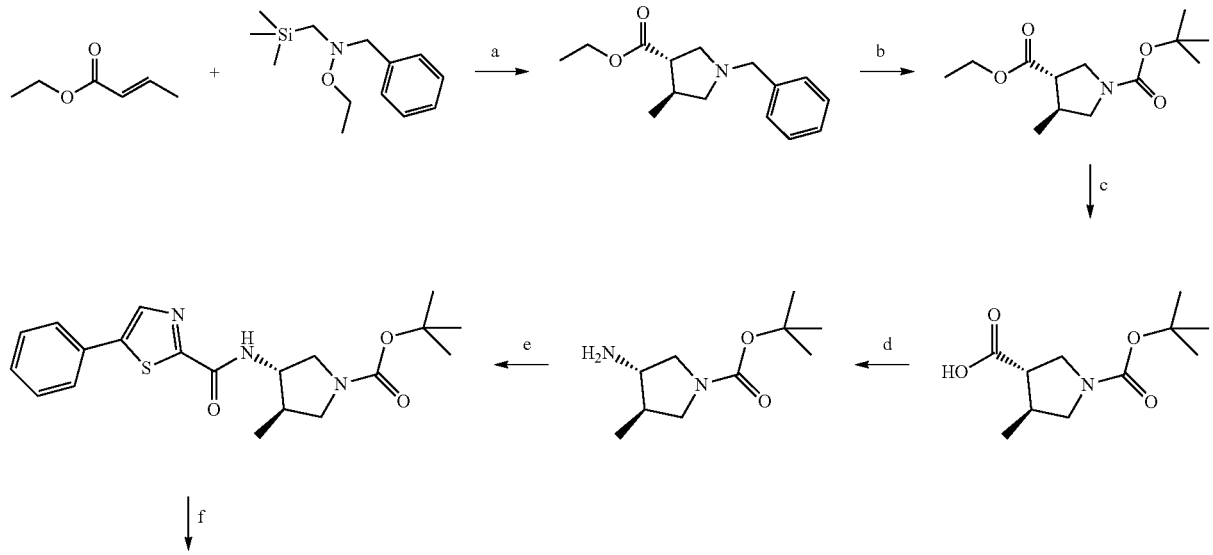

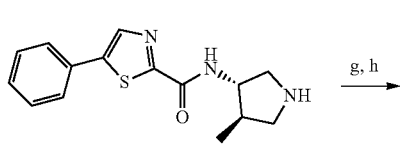 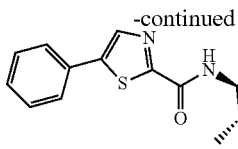 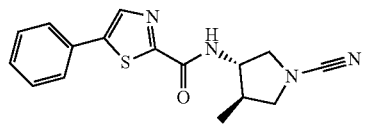

69     70

Step a.

A solution of ethyl crotonate (17.5 mmol) and N-benzyl-O-ethyl-N-((trimethylsilyl)methyl) hydroxyl amine (19.2 mmol) in toluene (40 ml) was stirred at rt for 5 min. TFA (17.5 mmol) was added dropwise to the reaction mixture at rt. The reaction mixture was then heated at 50° C. for 16 h. The resulting reaction mixture was poured into water (100 ml) and basified with solid NaHCO$_3$. The resulting mixture was extracted with EtOAc (2×180 ml). The combined organic phase was collected, dried over Na$_2$SO$_4$, filtered and concentrated under reduced pressure. The resulting residue was purified by column chromatography (0-9% EtOAc in hexane) yielding ethyl-(+)-trans-1-benzyl-4-methylpyrrolidine-3-carboxylate (9.0 mmol). MS: ES+ 248.33; $^1$H NMR (400 MHz, CDCl$_3$) δ ppm 7.24-7.36 (m, 5H), 4.13 (q, J=8.0, 5.2 Hz 2H), 3.67 (d, J=12.8 Hz, 1H), 3.58 (d, J=13.2 Hz, 1H), 2.77-2.91 (m, 3H), 2.47-2.59 (m, 2H), 2.21-2.26 (m, 1H), 1.27 (t, J=7.2 Hz, 3H), 1.16 (d, J=6.71 Hz, 3H).

Step b

To a solution of ethyl-(±)-trans-1-benzyl-4-methylpyrrolidine-3-carboxylate (10 mmol) in EtOH (30 ml) were added polymethyl hydrosiloxane (1.0 w/w), 20% Pd(OH)$_2$ on carbon (0.5 w/w) and BOC anhydride (20 mmol) at 0° C. The reaction mixture was stirred at rt for 1.5 h. The resulting reaction mixture was carefully filtered through celite hyflow and the filtrate was concentrated under reduced pressure. The resulting residue was purified by column chromatography (0-10% EtOAc in hexane) yielding 1-tert-butyl 3-ethyl (±)-4-methylpyrrolidine-1,3-dicarboxylate (8.5 mmol). MS: ES+202.2 (M-tBu)

Step c.

A solution of 1-tert-butyl 3-ethyl (+)-4-methylpyrrolidine-1,3-dicarboxylate (8.5 mmol) in THF (15 ml) was stirred at 0° C. for 5 min. A solution of NaOH (34.0 mmol) in water (15 ml) was added dropwise to the reaction mixture at 0° C. The reaction mixture was stirred at rt for 16 h. The resulting reaction mixture was poured into water (200 ml) and acidified to pH 4.0 with dilute HCl. The obtained mixture was extracted with EtOAc (2×150 ml). The combined organic phase was collected, dried over Na$_2$SO$_4$, filtered and concentrated under reduced pressure yielding 1-[(tert-butoxy)carbonyl]-(+)-trans-4-methylpyrrolidine-3-carboxylic acid (7.1 mmol). This material was used directly for the next step without further purification. MS: ES-228.28; $^1$H NMR (400 MHz, DMSO-d$_6$) δ ppm 12.51 (br s, 1H), 3.47-3.56 (m, 2H), 3.28-3.34 (m, 1H), 2.78-2.86 (m, 1H), 2.58-2.64 (m, 1H), 2.27-2.34 (m, 1H), 1.38 (s, 9H), 1.04 (d, J=4.8 Hz, 3H).

Step d.

To a solution of 1-[(tert-butoxy)carbonyl]-(±)-trans-4-methylpyrrolidine-3-carboxylic acid (2.62 mmol) in toluene (7 ml) were added DIPEA (5.24 mmol) and diphenyl phosphorylazide (3.93 mmol) dropwise at 0° C. The reaction mixture was heated at 80° C. for 3 h. The resulting reaction mixture was cooled to rt followed by addition of 8M NaOH (2 ml). The reaction mixture was further heated at 80° C. for 30 minutes. The resulting reaction mixture was poured into water (70 ml) and extracted with diethyl ether (2×70 ml) to remove non polar impurities. The resulting aqueous layer was further extracted with DCM (3×70 ml). The combined DCM organic layer was dried over Na$_2$SO$_4$ and evaporated under reduced pressure to yield 1-[(tert-butoxy)carbonyl]-(+)-trans-3-amino-4-methylpyrrolidine (1.17 mmol, quantitative). This material was used directly for the next step without further purification. MS: ES+ 145.09 (M-tBu).

Steps e, f, g.

The title compound was synthesised as a racemic mixture from the intermediate above using a procedure similar to that described for steps a, b, c of Example 1.

Step h.

The enantiomers were separated by preparative chiral HPLC; mobile phase: (A) 0.1% TFA in hexane (B) 0.1% TFA in EtOH, column: Chiralpak IB, 250×4.6 mm, 5 μm, flow rate: 1 ml/min.

Example 69 N-((3R,4S)-1-cyano-4-methylpyrrolidin-3-yl)-5-phenylthiazole-2-carboxamide LCMS: Method B, RT 3.78 min, MS: ES+ 313.22; Chiral HPLC: Method Y, RT 12.90 min; $^1$H NMR (400 MHz, DMSO-d$_6$) δ ppm 8.82 (d, J=7.2 Hz, 1H), 8.49 (s, 1H), 7.99-8.016 (m, 2H), 7.52-7.55 (m, 3H), 4.11-4.15 (m, 1H), 3.73-3.77 (m, 1H), 3.66-3.70 (m, 1H), 3.25-3.29 (m, 1H), 3.09-3.13 (m, 1H), 2.26-2.33 (m, 1H), 1.02 (d, J=6.8 Hz, 3H).

Example 70 N-((3S,4R)-1-cyano-4-methylpyrrolidin-3-yl)-5-phenylthiazole-2-carboxamide LCMS: Method B, RT 3.78 min, MS: ES+ 313.22; Chiral HPLC: Method Y, RT 15.61 min; $^1$H NMR (400 MHz, DMSO-d$_6$) δ ppm 8.82 (d, J=7.2 Hz, 1H), 8.49 (s, 1H), 7.99-8.016 (m, 2H), 7.52-7.55 (m, 3H), 4.11-4.15 (m, 1H), 3.73-3.77 (m, 1H), 3.66-3.70 (m, 1H), 3.25-3.29 (m, 1H), 3.09-3.13 (m, 1H), 2.26-2.33 (m, 1H), 1.02 (d, J=6.8 Hz, 3H).

Example 71 N-((3R,4S)-1-cyano-4-methylpyrrolidin-3-yl)-2-phenylthiazole-5-carboxamide Example 72 N-((3S,4R)-1-cyano-4-methylpyrrolidin-3-yl)-2-phenylthiazole-5-carboxamide

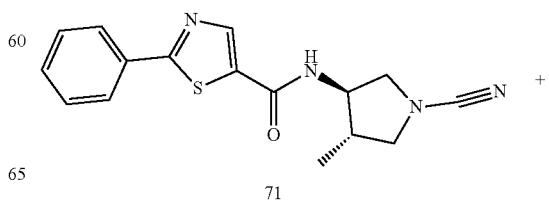

71

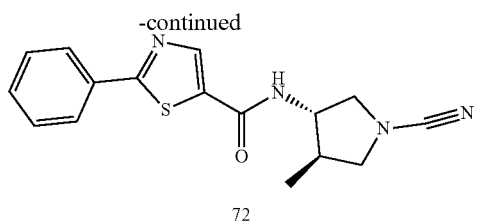

72

The title compounds were synthesised as a racemic mixture from the intermediate above using a procedure similar to that described for Examples 69/70 and the enantiomers were separated by preparative chiral HPLC; mobile phase: (A) 0.1% TFA in hexane (B) 0.1% TFA in IPA, column: Chiralpak IB, 250×4.6 mm, 5 μm, flow rate: 1 ml/min.

Example 71 N-((3R,4S)-1-cyano-4-methylpyrrolidin-3-yl)-2-phenylthiazole-5-carboxamide LCMS: Method B, RT 4.21 min, MS: ES+ 312.96; Chiral HPLC: Method Z, RT 14.29 min; $^1$H NMR (400 MHz, DMSO-d$_6$) δ ppm 9.16 (d, J=8.4 Hz, 1H), 8.46 (s, 1H), 7.79 (d, J=7.2 Hz, 2H), 7.42-7.52 (m, 3H), 4.15-4.23 (m, 1H), 3.64-3.72 (m, 2H), 3.33-3.38 (m, 1H), 3.07-3.12 (m, 1H), 2.34-2.42 (m, 1H), 0.99 (d, J=6.8 Hz, 3H).

Example 72 N-((3S,4R)-1-cyano-4-methylpyrrolidin-3-yl)-2-phenylthiazole-5-carboxamide LCMS: Method B, RT 4.21 min, MS: ES+ 312.96; Chiral HPLC: Method Z, RT 12.49 min; $^1$H NMR (400 MHz, DMSO-d$_6$) δ ppm 9.16 (d, J=8.4 Hz, 1H), 8.46 (s, 1H), 7.79 (d, J=7.2 Hz, 2H), 7.42-7.52 (m, 3H), 4.15-4.23 (m, 1H), 3.64-3.72 (m, 2H), 3.33-3.38 (m, 1H), 3.07-3.12 (m, 1H), 2.34-2.42 (m, 1H), 0.99 (d, J=6.8 Hz, 3H).

Example 73 (R)—N-(1-cyanopyrrolidin-3-yl)-2-(isoindolin-2-yl)isonicotinamide (Prepared According to General Method D)

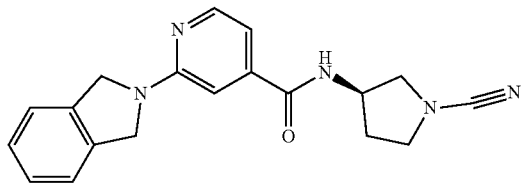 [SMILES: N#CN1CC[C@@H](NC(=O)c2ccnc(N3Cc4ccccc4C3)c2)C1]

Step a.

To a solution of 2-fluoropyridine-4 carboxylic acid (0.5 g, 3.50 mmol) in DCM (8 ml) was added HATU (2.01 g, 5.30 mmol) and DIPEA (0.91 g, 7.08 mmol) at 0° C. The reaction mixture was stirred at stirred for 0° C. 20 min before adding tert-butyl (R)-3-aminopyrrolidine-1-carboxylate (CAS Number 147081-49-0) (0.52 g, 2.83 mmol). The reaction mixture was stirred at rt for 4 h. The resulting reaction mixture was poured into water (100 ml) and extracted with DCM (3×50 ml). The combined organic phase was collected, dried over Na$_2$SO$_4$, filtered and concentrated under reduced pressure yielding tert-butyl (R)-3-(2-fluoroisonicotinamido)pyrrolidine-1-carboxylate (1.5 g, quantitative). MS: ES+ 254.2 (M-56).

Step b.

To a solution of tert-butyl (R)-3-(2-fluoroisonicotinamido)pyrrolidine-1-carboxylate (1.5 g, 4.84 mmol) in DMF (4 ml) was added K$_2$CO$_3$ (1.33 g, 9.6 mmol) at rt and stirred for 10 min. A solution of isoindoline (CAS Number 496-12-8) (0.63 g, 5.33 mmol) in DMF (1 ml) was added dropwise to the reaction mixture at rt. The reaction mixture was heated at 120° C. for 18 h. The resulting reaction mixture was poured into water (100 ml) and extracted with EtOAc (3×40 ml). The combined organic phase was collected, washed with brine (2×50 ml), dried over Na$_2$SO$_4$, filtered and concentrated under reduced pressure. The resulting residue was purified by flash chromatography (40% EtOAc in hexane) yielding tert-butyl (R)-3-(2-(isoindolin-2-yl)isonicotinamido)pyrrolidine-1-carboxylate (0.35 g, 0.85 mmol). MS: ES+ 409.3

Step c.

To a solution of tert-butyl (R)-3-(2-(isoindolin-2-yl)isonicotinamido)pyrrolidine-1-carboxylate (0.35 g, 0.85 mmol) in DCM (6 ml) was added TFA (2 ml) at 0° C. The reaction mixture was stirred at rt for 2 h and then concentrated under reduced pressure. The resulting residue was azeotropically distilled using DCM (2×20 ml). The resulting material was triturated with n-pentane (2×20 ml), diethyl ether (2×20 ml) and finally dried yielding (R)-2-(isoindolin-2-yl)-N-(pyrrolidin-3-yl)isonicotinamide TFA salt (0.18 g, 0.42 mmol) MS: ES+ 309.3

Step d.

To a solution of (R)-2-(isoindolin-2-yl)-N-(pyrrolidin-3-yl) isonicotinamide TFA salt (0.18 g, 0.42 mmol) in THF (6 ml) was added K$_2$CO$_3$ (0.23 g, 1.70 mmol) at 0° C. The reaction mixture was stirred at 0° C. for 20 min before adding cyanogen bromide (0.045 g, 0.42 mmol). The reaction mixture was stirred at rt for 3 h. The resulting reaction mixture was poured into water (50 ml) and extracted with 5% MeOH in DCM (2×50 ml). The combined organic layer was dried over Na$_2$SO$_4$, filtered and concentrated under reduced pressure. The resulting material was triturated with n-pentane (2×30 ml), diethyl ether (2×30 ml) and further purified by preparative TLC using 3% MeOH in DCM as mobile phase. The obtained material was further purified by preparative HPLC (mobile phase: 0.1% formic acid in water/MeCN; column: YMC ACTUS TRIART C18 (250×20 mm), 5 μm; flow rate: 18 ml/min) yielding the title compound (0.033 g, 0.099 mmol). LCMS: Method A, RT 3.92 min, MS: ES+ 334.01; $^1$H NMR (400 MHz, DMSO-d$_6$) δ ppm 8.76 (d, J=6.8 Hz, 1H), 8.26 (d, J=5.2 Hz, 1H), 7.32-7.44 (m, 4H), 7.01 (d, J=4.8 Hz, 1H), 6.95 (s, 1H), 4.8 (s, 4H), 4.47-4.52 (m, 1H), 3.64-3.68 (m, 1H), 3.54-3.60 (m, 1H), 3.34-3.49 (m, 1H), 3.30-3.31 (m, 1H), 2.13-2.18 (m, 1H), 1.94-1.99 (m, 1H).

Example 74 (R)—N-(1-cyanopyrrolidin-3-yl)-2-(3,4-dihydroisoquinolin-2(H)-yl)isonicotinamide

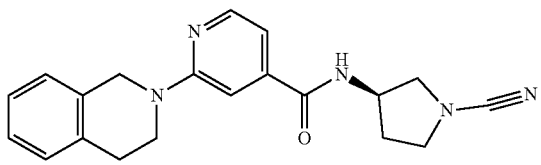 [SMILES: N#CN1CC[C@@H](NC(=O)c2ccnc(N3CCc4ccccc4C3)c2)C1]

Synthesised using a procedure similar to that described for Example 73 using 1,2,3,4-tetrahydro-isoquinoline (CAS Number 91-21-4). LCMS: Method B, RT 3.34 min, MS: ES+ 348.35

Example 75 (R)—N-(1-cyanopyrrolidin-3-yl)-2-fluoro-4-(4-methyl-1H-imidazol-1-yl)benzamide

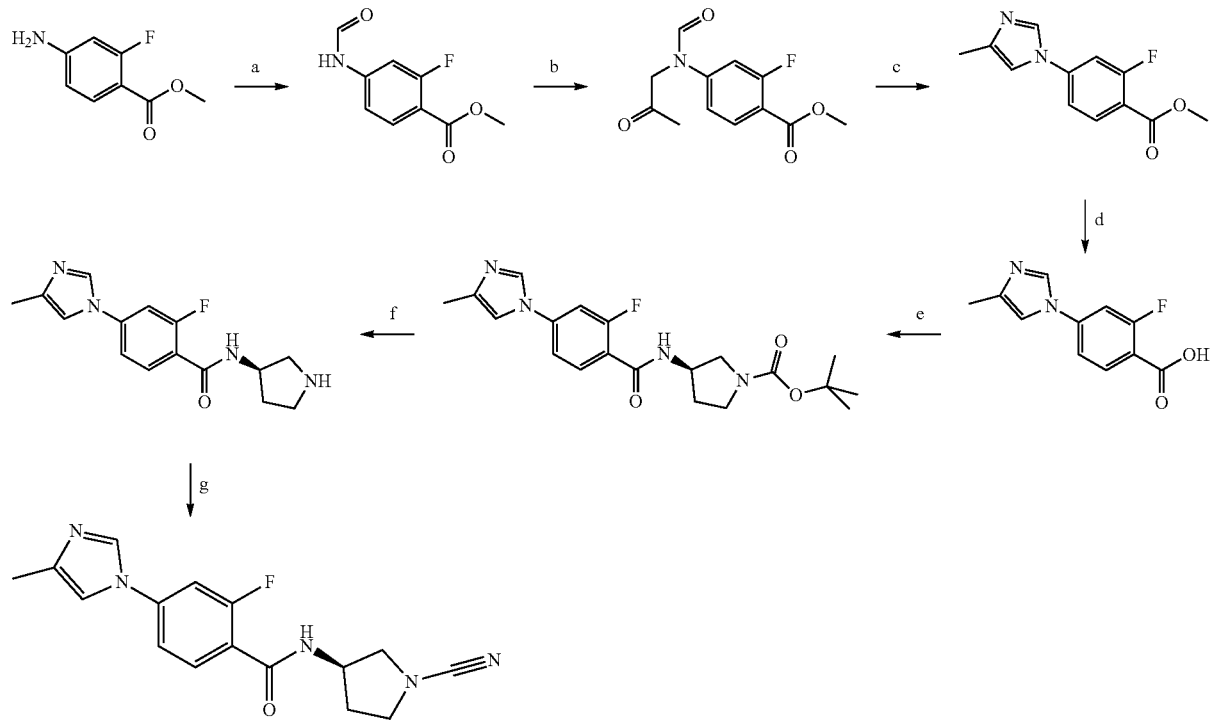

Step a.

A solution of acetic anhydride (0.89 g, 8.74 mmol) in formic acid (1.3 ml) was stirred at rt for 30 min. A solution of 4-amino-2-fluoro-benzoic acid methyl ester (CAS Number 73792-08-2) (0.4 g, 2.36 mmol) in THF (4 ml) was added dropwise and the reaction mixture was then heated to 60° C. for 16 h. The reaction mixture was poured into water (150 ml) and stirred at rt for 30 min. The precipitated solids were collected by filtration under vacuum, washed with water (2×25 ml) and finally dried under vacuum yielding methyl 2-fluoro-4-formamidobenzoate (0.31 g, 1.56 mmol) MS: ES+ 198.28

Step b.

To a solution of methyl 2-fluoro-4-formamidobenzoate (0.31 g, 1.56 mmol) in DMF (4 ml) was added $K_2CO_3$ (0.32 g, 2.34 mmol) and KI (0.025 g, 0.15 mmol) at rt. Chloroacetone (0.36 g, 3.90 mmol) was added dropwise to the reaction mixture and stirred at rt for 16 h. The reaction mixture was poured into water (150 ml) and extracted with EtOAc (3×100 ml). The combined organic phase was collected washed with brine (100 ml), dried over $Na_2SO_4$, filtered and concentrated under reduced pressure yielding methyl 2-fluoro-4-(N-(2-oxopropyl)formamido) benzoate (0.3 g, 1.18 mmol) MS: ES+ 254.5.

Step c.

To a solution of 2-fluoro-4-(N-(2-oxopropyl)formamido) benzoate (0.3 g, 1.18 mmol) in glacial acetic acid (4 ml) was added ammonium acetate (0.54 g, 7.10 mmol) at rt. The reaction mixture was heated at 130° C. for 3 h. The resulting reaction mixture was allowed to cool to rt and was basified using aqueous ammonium hydroxide to adjust to pH 7. The resulting aqueous solution was extracted with EtOAc (3×120 ml). The combined organic phase was collected, washed with water (100 ml), brine (150 ml), dried over $Na_2SO_4$, filtered and concentrated under reduced pressure yielding methyl 2-fluoro-4-(4-methyl-1H-imidazol-1-yl) benzoate (0.32 g, 1.38 mmol) MS: ES+ 235.2.

Step d.

To a solution of methyl 2-fluoro-4-(4-methyl-1H-imidazol-1-yl) benzoate (0.32 g, 1.38 mmol) in THF:water (1:1) was added $LiOH.H_2O$ (0.58 g, 13.80 mmol) at rt. The reaction mixture was stirred at rt for 8 h. The resulting reaction mixture was acidified using 1M HCl to adjust to pH 4. The resulting aqueous solution was extracted with EtOAc (3×150 ml). The desired product remained in the aqueous layer which was evaporated. The desired product was extracted from the obtained residue by using 10% MeOH in DCM (40 ml). The obtained organic layer was dried over $Na_2SO_4$, filtered and concentrated under reduced pressure yielding 2-fluoro-4-(4-methyl-1H-imidazol-1-yl)benzoic acid (0.29 g, 1.31 mmol) MS: ES+ 221.14.

Step e.

To a solution 2-fluoro-4-(4-methyl-1H-imidazol-1-yl) benzoic acid (0.29 g, 1.31 mmol) in DMF (5 ml) was added HATU (0.8 g, 2.1 mmol) at rt. The reaction mixture was stirred at rt for 30 min. A solution of tert-butyl (R)-3-aminopyrrolidine-1-carboxylate (CAS Number 186550-13-0) (0.19 g, 1.05 mmol) in DMF (1 ml) was added to the reaction mixture at rt followed by addition of DIPEA (0.51 g, 3.9 mmol) at rt. The reaction mixture was stirred at rt for 1 h. The resulting reaction mixture was poured into chilled water (100 ml) and extracted with EtOAc (3×100 ml). The combined organic phase was collected and washed with saturated $NaHCO_3$ solution (100 ml), brine (100 ml). The resulting organic phase was dried over $Na_2SO_4$, filtered and concentrated under reduced pressure yielding tert-butyl (R)-3-(2-fluoro-4-(4-methyl-1H-imidazol-1-yl)benzamido)pyrrolidine-1-carboxylate (0.3 g, 0.77 mmol) MS: ES+ 389.4

Step f.

To a solution of tert-butyl (R)-3-(2-fluoro-4-(4-methyl-1H-imidazol-1-yl)benzamido)-pyrrolidine-1-carboxylate (0.3 g, 0.77 mmol) in DCM (4 ml) was added TFA (0.586 ml, 7.73 mmol) at rt. The reaction mixture was stirred at rt for 2 h. The resulting reaction mixture was concentrated under reduced pressure. The obtained residue was triturated with diethyl ether (3×25 ml) and dried yielding (R)-2-fluoro-4-(4-methyl-1H-imidazol-1-yl)-N-(pyrrolidin-3-yl)benzamide TFA salt (0.15 g, 0.37 mmol). This material was used directly for the next step without further purification.

Step g.

To a solution of (R)-2-fluoro-4-(4-methyl-1H-imidazol-1-yl)-N-(pyrrolidin-3-yl)benzamide TFA salt (0.15 g, 0.37 mmol) in THF (3 ml) was added $K_2CO_3$ (0.206 g, 1.49 mmol) and cyanogen bromide (0.039 g, 0.37 mmol) at rt. The reaction mixture was stirred at rt for 30 min. The reaction mixture was poured into water (70 ml) and extracted with EtOAc (3×50 ml). The combined organic layer was washed with brine (50 ml), dried over $Na_2SO_4$, filtered and concentrated under reduced pressure. The resulting residue was purified by flash chromatography (100% EtOAc) yielding the title compound (0.020 g, 0.06 mmol) LCMS: Method A, RT 2.97 min, MS: ES+ 313.98; $^1$H NMR (400 MHz, DMSO-$d_6$) δ ppm 8.68 (d, J=6.8 Hz, 1H), 8.33 (s, 1H), 7.67-7.75 (m, 2H), 7.57-7.60 (m, 2H), 4.44-4.47 (m, 1H), 3.61-3.65 (m, 1H), 3.43-3.55 (m, 2H), 3.28-3.31 (m, 1H), 2.16 (s, 3H), 2.08-2.13 (m, 1H), 1.88-1.96 (m, 1H).

Example 89 (R)—N-(1-cyanopyrrolidin-3-yl)-N-methyl-3-phenoxyazetidine-1-carboxamide (Prepared According to General Method E)

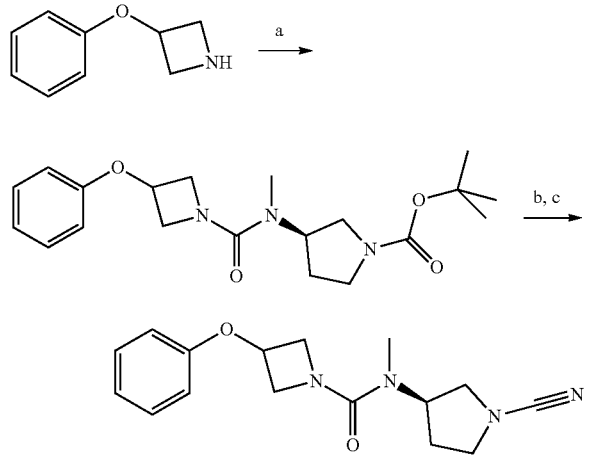

Step a.

To a solution of tert-butyl (R)-3-(methylamino)pyrrolidine-1-carboxylate (CAS Number 199336-83-9) (0.22 g, 1.08 mmol) and TEA (0.5 ml, 3.59 mmol) in DCM (5 ml) was added triphosgene (0.1 g, 0.355 mmol) at 0° C. The reaction mixture was stirred at 0° C. for 30 min. A solution of 3-phenoxy-azetidine hydrochloride (CAS Number 301335-39-7) (0.2 g, 1.08 mmol) and TEA (0.25 ml, 1.80 mmol) was added to the reaction mixture at 0° C. The reaction mixture was allowed to warm to rt and stirred for 1 hr. The resulting reaction mixture was poured into saturated $NaHCO_3$ solution (50 ml) and extracted with DCM (3×25 ml). The combined organic layer was washed with brine (25 ml), dried over $Na_2SO_4$, filtered and concentrated under reduced pressure. The resulting residue was purified by flash chromatography (5% MeOH in DCM) yielding tert-butyl (R)-3-(N-methyl-3-phenoxyazetidine-1-carboxamido)pyrrolidine-1-carboxylate (0.3 g, 0.80 mmol). LCMS: Method C, RT 2.25 min, MS: ES+ 376.69.

Steps b, c.

The title compound was synthesised from the intermediate above using a procedure similar to that described for steps b, c of Example 5 to provide the title compound. LCMS: Method A, RT 3.84 min, MS: ES+ 301.21; $^1$H NMR (400 MHz, DMSO-$d_6$) δ ppm 7.30 (t, J=7.6 Hz, 2H), 6.97 (t, 7.6 Hz, 1H), 6.83 (d, J=8.4 Hz, 2H), 4.96-4.98 (m, 1H), 4.56-4.60 (m, 1H), 4.31-4.38 (m, 2H), 3.83-3.89 (m, 2H), 3.37-3.52 (m, 3H), 3.24-3.28 (m, 1H), 2.68 (s, 3H), 1.89-1.98 (m, 2H).

Example 90 (3aR,6aR)-5-cyano-N-(2-fluoro-4-(trifluoromethyl)phenyl)hexahydropyrrolo[3,4-b]pyrrole-1 (2H)-carboxamide

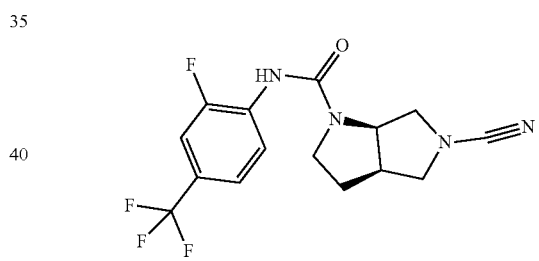

Synthesised using a procedure similar to that described for Example 89 using (3aR,6aR)-5-N—BOC-hexahydropyrrolo[3,4-b]pyrrole (CAS Number 370882-39-6) in step a. LCMS: Method A, RT 4.19 min, MS: ES+ 343.05; $^1$H NMR (400 MHz, DMSO-$d_6$) δ ppm 8.34 (s, 1H), 8.46 (t, J=8.0 Hz, 1H), 7.68 (d, J=10.8 Hz, 1H), 7.52 (d, J=7.6 Hz, 1H), 4.37 (m, 1H), 3.51-3.61 (m, 4H), 3.41-3.45 (m, 1H), 3.24-3.28 (m, 1H), 2.96-2.98 (m, 1H), 2.02-207 (m, 1H), 1.80-1.86 (m, 1H).

Example 91 (R)—N-(1-cyanopyrrolidin-3-yl)-2-fluoro-4-(pyrimidin-2-ylamino)benzamide (Prepared According to General Method G)

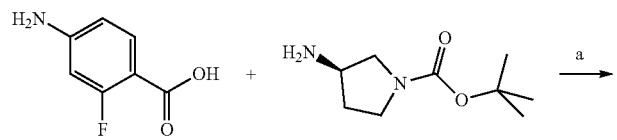

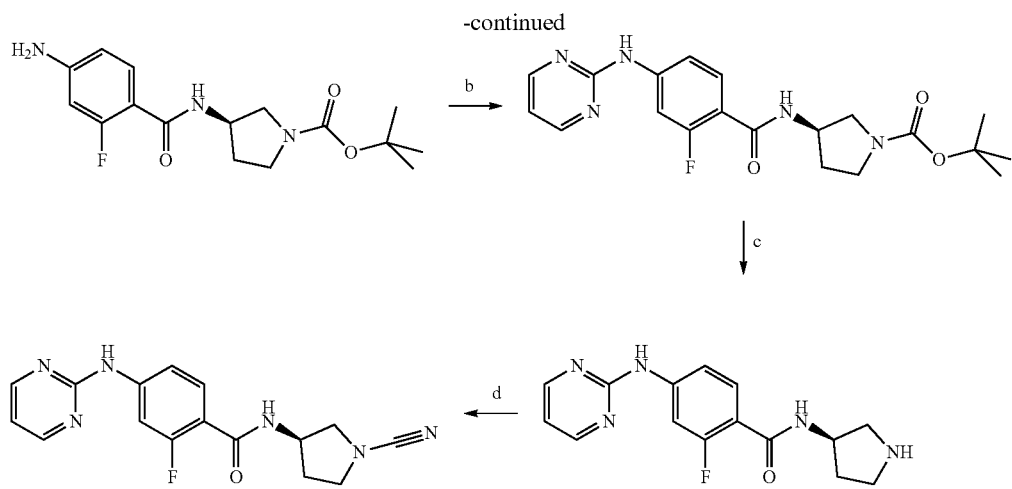

Step a.

To a solution of 4-amino-2-fluorobenzoic acid (0.4 g, 2.58 mmol) in THF (10 ml) was added HATU (1.46 g, 3.868 mmol) and DIPEA (1.3 ml, 7.74 mmol) at rt and stirred for 20 min. (R)-3-Amino-1N—BOC-pyrrolidine (0.52 g, 2.84 mmol) was added to the reaction mixture at rt and stirred for 4 h. The resulting reaction mixture was poured into water (30 ml) and extracted with EtOAc (2×50 ml). The combined organic phase was collected, dried over $Na_2SO_4$, filtered and concentrated under reduced pressure yielding tert-butyl (R)-3-(4-amino-2-fluorobenzamido)pyrrolidine-1-carboxylate (1.2 g, 3.71 mmol). LCMS: Method C, RT 1.99 min, MS: ES+ 324.29.

Step b.

A mixture of tert-butyl (R)-3-(4-amino-2-fluorobenzamido)pyrrolidine-1-carboxylate (0.7 g, 2.16 mmol), 2-chloropyrimidine (0.24 g, 2.16 mmol), DBU (0.03 g, 1.73 mmol) and sodium tert-butoxide (0.31 g, 3.25 mmol) was prepared in toluene (15 ml) at rt. The reaction mixture was degassed for 10 min at rt and then racemic BINAP (0.013 g, 0.021 mmol) and $Pd_2(dba)_3$ (0.02 g, 0.021 mmol) were added to the reaction mixture. The reaction mixture was heated at 110° C. for 12 h. The resulting reaction mixture was allowed to cool at rt and poured into water (100 ml) and extracted with EtOAc (2×100 ml). The combined organic phase was collected, dried over $Na_2SO_4$, filtered and concentrated under reduced pressure. The resulting residue was purified by flash chromatography (1.5% MeOH in DCM) yielding tert-butyl (R)-3-(2-fluoro-4-(pyrimidin-2-ylamino)benzamido)pyrrolidine-1-carboxylate (0.3 g, 0.75 mmol). LCMS: Method C, RT 2.04 min, MS: ES+ 402.5.

Steps c, d.

The title compound was synthesised from the intermediate above using a procedure similar to that described for steps b, c of Example 1. LCMS: Method B, RT 2.98 min, MS: ES+ 305.94; $^1$H NMR (400 MHz, DMSO-$d_6$) δ ppm 10.14 (s, 1H), 8.58 (d, J=5 Hz, 2H), 8.35 (d, J=5 Hz, 1H), 7.88-7.92 (m, 1H), 7.54-7.57 (m, 2H), 6.97 (t, J=5 Hz, 1H), 4.42-4.46 (m, 1H), 3.60-3.64 (m, 1H), 3.39-3.53 (m, 2H), 3.26-3.30 (m, 1H), 2.09-2.13 (m, 1H), 1.89-1.94 (m, 1H)

Example 92 N-((trans)-1-cyano-4-methylpyrrolidin-3-yl)-2-fluoro-4-((R)-3-methoxypyrrolidin-1-yl)benzamide (Prepared According to General Method H)

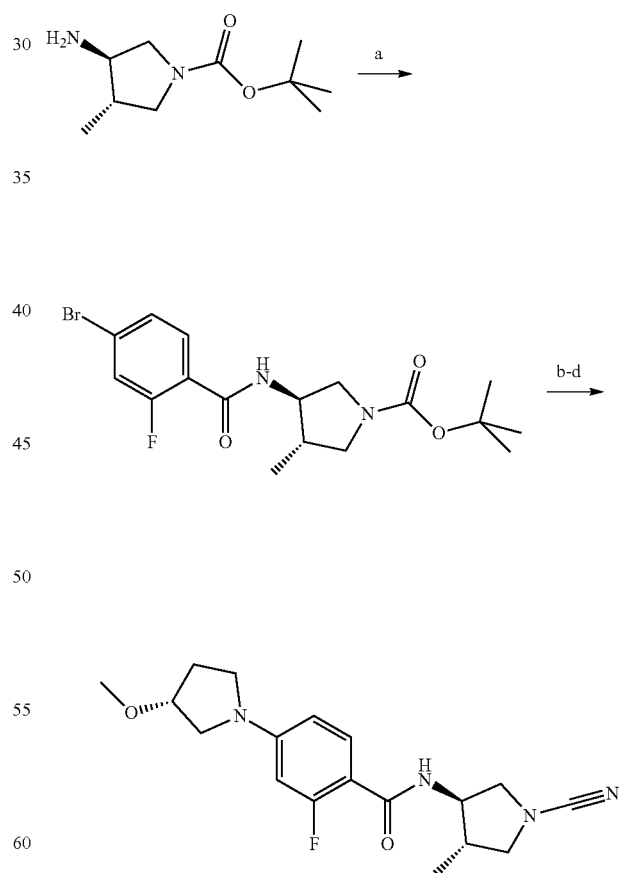

Step a was carried out using a procedure similar to that described for step a of Example 91 using 1-[(tert-butoxy)carbonyl]-(±)-trans-3-amino-4-methylpyrrolidine (described in the synthesis of Examples 69/70).

Step b was carried out using a procedure similar to step a of Example 6

Steps c-d were carried out using a procedure similar to steps c-d of Example 91. LCMS: Method B, RT 3.74 min, MS: ES+ 347.32; $^1$H NMR (400 MHz, DMSO-$d_6$) δ ppm 7.86-7.89 (m, 1H), 7.51 (t, J=8.8 Hz, 1H), 6.30-6.41 (m, 2H), 4.11-4.15 (m, 2H), 3.61-3.68 (m, 2H), 3.43-3.45 (m, 1H), 3.27-3.33 (m, 2H), 3.25 (s, 3H), 3.21-3.24 (m, 2H), 3.05-3.10 (m, 1H), 2.23-2.31 (m, 1H), 2.04-2.09 (m, 2H), 1.03 (d, J=6.8 Hz, 3H).

Example 93 2-(2-chlorophenyl)-N-((trans)-1-cyano-4-hydroxypyrrolidin-3-yl) thiazole-5-carboxamide

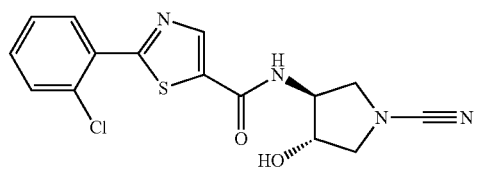 [SMILES: N#CN1C[C@H](NC(=O)c2cnc(-c3ccccc3Cl)s2)[C@@H](O)C1]

Synthesised using a procedure similar to that described for Example 2, using ethyl 2-bromothiazole-5-carboxylate (CAS Number 41731-83-3) in step a and (3R,4R)-rel-tert-butyl 3-amino-4-hydroxypyrrolidine-1-carboxylate (CAS Number 148214-90-8) in step c. LCMS: Method A, RT 3.76 min, MS: ES+ 348.84; 1H NMR (400 MHz, DMSO-$d_6$) δ ppm 8.86 (d, J=6.8 Hz, 1H), 8.60 (s, 1H), 8.25-8.27 (m, 1H), 7.68-7.70 (m, 1H), 7.50-7.61 (m, 2H), 5.65 (dd, J=16.4, 4.0 Hz, 1H), 4.16-4.26 (m, 2H), 3.75-3.79 (m, 1H), 3.64-3.68 (m, 1H), 3.40-3.43 (m, 1H), 3.24-3.27 (m, 1H).

Example 94 N-(1-cyano-3-methylpyrrolidin-3-yl)-2-fluoro-4-(1-methyl-1H-pyrazol-4-y)benzamide

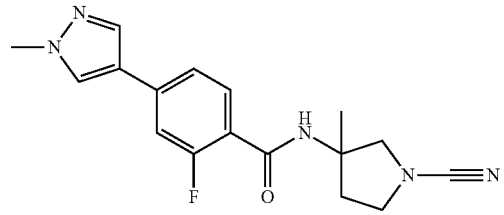 [SMILES: Cn1cc(-c2ccc(C(=O)NC3(C)CCN(C#N)C3)c(F)c2)cn1]

Synthesised using a procedure similar to that described for Example 2 using tert-butyl 3-amino-3-methylpyrrolidine-1-carboxylate (CAS Number 1158758-59-8) in step c. LCMS: Method A, RT 3.43 min, MS: ES+ 328.15; $^1$H NMR (400 MHz, CDCl$_3$) δ ppm 8.04 (t, J=8.4 Hz, 1H), 7.82 (s, 1H), 7.71 (s, 1H), 7.38 (d, J=7.2 Hz, 1H), 7.22 (d, J=13.6 Hz, 1H), 6.73 (d, J=16 Hz, 1H), 3.98 (s, 3H), 3.89 (d, J=10.4 Hz, 1H), 3.58-3.66 (m, 2H), 3.52 (d, J=10 Hz, 1H), 2.44-2.46 (m, 1H), 2.00-2.04 (m, 1H), 1.65 (s, 3H).

Compounds in Table 7 were synthesised either using the general methods A-F as exemplified by Examples 1-6 and Example 89 or by general method G as exemplified by Example 91 or by general method H as exemplified by Example 92 using (R)-tert-butyl 3-aminopyrrolidine-1-carboxylate (CAS Number 147081-49-0).

TABLE 7

| Ex | R1 | Name | Synthetic Method | $^1$H NMR: (400 MHz, DMSO-$d_6$) δ ppm | LCMS Method | LCMS RT (min) | MS |
|---|---|---|---|---|---|---|---|
| 95 | | (R)-N-(1-cyanopyrrolidin-3-yl)-5-(4-methoxyphenyl)-1H-pyrazole-3-carboxamide | A | 13.49 (s, 1 H), 8.43 (s, 1 H), 7.72 (d, J = 7.6 Hz, 2 H), 7.02 (d, J = 8.0, 3 H), 4.46-4.50 (m, 1 H), 3.79 (s, 3 H), 3.52-3.60 (m, 2 H), 3.44-3.50 (m, 1 H), 3.10 3.22 (m, 1 H), 2.06-2.15 (m, 1 H), 1.94-2.01 (m, 1 H) | A | 3.38 | ES+ 312.0 |
| 96 | | (R)-N-(1-cyano-pyrrolidin-3-yl)-5-(pyridin-2-yl)-1H-pyrazole-3-carboxamide | A | 13.99 (s, 1 H), 8.50-8.72 (m, 2 H), 7.85-7.98 (m, 2 H), 7.58 (s, 1 H), 7.29-7.39 (m, 1 H), 4.49 (s, 1 H), 3.54-3.65 (m, 2 H), 3.42-3.44 (m, 2 H), 1.97-2.11 (m, 2 H) | A | 2.63 | ES+ 283.0 |

TABLE 7-continued

| Ex | R1 | Name | Synthetic Method | ¹H NMR: (400 MHz, DMSO-d₆) δ ppm | LCMS Method | LCMS RT (min) | MS |
|---|---|---|---|---|---|---|---|
| 97 | 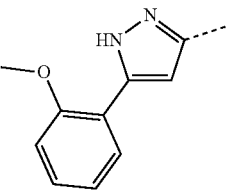 | (R)-N-(1-cyano-pyrrolidin-3-yl)-5-(2-methoxyphenyl)-1H-pyrazole-3-carboxamide | A | 13.17 (s, 1 H), 8.14-8.21 (m, 1 H), 7.65-7.75 (m, 1 H), 7.33-7.40 (m, 1 H), 7.16 (d, J = 8.0 Hz, 1H), 7.03-7.06 (m, 2 H), 4.48-4.53 (m, 1 H), 3.91 (s, 3 H), 3.53-3.65 (m, 2 H), 3.41-3.47 (m, 1 H), 3.33-3.37 (m, 1 H), 2.13-2.18 (m, 1 H), 1.98-2.05 (m, 1 H) | A | 3.44 | ES+ 312.3 |
| 98 | 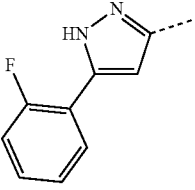 | (R)-N-(1-cyano-pyrrolidin-3-yl)-5-(2-fluorophenyl)-1H-pyrazole-3-carboxamide | A | 10.95 (s, 1 H), 6.95-7.73 (m, 1 H), 7.37-7.43 (m, 1 H), 7.23-7.31 (m, 3 H), 7.06 (d, J = 7.2 Hz, 1 H), 4.69-4.76 (m, 1 H), 3.76-3.80 (m, 1 H), 3.55-3.68 (m, 2 H), 3.42-3.46 (m, 1 H), 2.28-2.37 (m, 1 H), 2.03-2.11 (m, 1 H) | H | 3.37 | ES+ 300.2 |
| 99 | 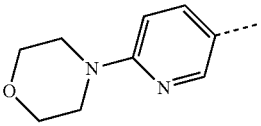 | (R)-N-(1-cyano-pyrrolidin-3-yl)-6-morpholino-nicotinamide | A | 8.61 (dd, J = 12.4, 2.0 Hz, 1 H), 8.38 (d, J = 6.4 Hz, 1 H), 7.93-8.00 (m, 1 H), 6.86-6.88 (m 1 H), 4.41-4.46 (m, 1 H), 4.68-4.70 (m, 4 H), 3.51-3.64 (m, 6 H), 3.39-3.47 (m, 1 H), 3.26-3.30 (m, 1 H), 2.06-2.18 (m, 1 H), 1.88-1.96 (m, 1 H) | B | 2.50 | ES+ 302.29 |
| 100 | 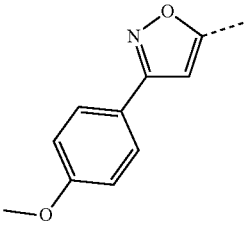 | (R)-N-(1-cyano-pyrrolidin-3-yl)-3-(4-methoxyphenyl)isoxazole-5-carboxamide | A | 9.25 (d, J = 6.4 Hz, 1 H), 7.85-7.89 (m, 2 H), 7.61 (s, 1 H), 7.08-7.11 (m, 2 H), 4.46-4.53 (m, 1 H), 3.83 (s, 3 H), 3.63-3.67 (m, 1 H), 3.53-3.59 (m, 1 H), 3.43-3.49 (m, 1 H), 3.34-3.38 (m, 1 H), 2.10-2.19 (m, 1 H), 1.94-2.01 (m, 1 H) | C | 2.01 | ES+ 313.43 |
| 101 | 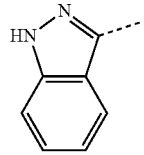 | (R)-N-(1-cyano-pyrrolidin-3-yl)-1H-indazole-3-carboxamide | A | 13.64 (s, 1 H), 8.71 (d, J = 6.8 Hz, 1 H), 8.16 (d, J = 8.4 Hz, 1 H), 7.62 (d, J = 8.8 Hz, 1 H), 7.40-7.44 (m, 1 H), 7.23-7.27 (m, 1 H), 4.54-4.59 (m, 1 H), 3.55-3.66 (m, 2 H), 3.37-3.48 (m, 2 H), 2.12-2.17 (m, 1 H), 2.02-2.10 (m, 1 H) | B | 3.11 | ES+ 256.37 |
| 102 | 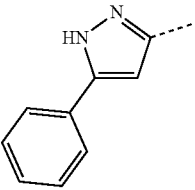 | (R)-N-(1-cyano-pyrrolidin-3-yl)-5-phenyl-1H-pyrazole-3-carboxamide | A | 13.65 (s, 1 H), 8.44-8.65 (m, 1 H), 7.79-7.81 (m, 2 H), 7.29-7.50 (m, 3 H), 7.09 (s, 1 H), 4.47-4.50 (m, 1 H), 3.52-3.68 (m, 3 H), 3.36-3.46 (m, 1 H), 2.06-2.16 (m, 1 H), 1.95-2.03 (m, 1 H) | B | 3.30 | ES+ 282.39 |
| 103 | 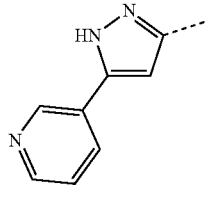 | (R)-N-(1-cyano-pyrrolidin-3-yl)-5-(pyridin-3-yl)-1H-pyrazole-3-carboxamide | A | 13.83-13.86 (m, 1 H), 8.99-9.04 (m, 1 H), 8.51-8.72 (m, 2 H), 8.13-8.20 (m, 1 H), 7.45-7.53 (m, 1 H), 7.23-7.37 (m, 1 H), 4.49-4.52 (m, 1 H), 3.52-3.68 (m, 2 H), 3.35-3.49 (m, 2 H), 2.07-2.17 (m, 1 H), 1.91-2.01 (m, 1 H) | B | 2.32 | ES+ 283.32 |

TABLE 7-continued

| Ex | R1 | Name | Synthetic Method | ¹H NMR: (400 MHz, DMSO-d$_6$) δ ppm | LCMS Method | LCMS RT (min) | MS |
|---|---|---|---|---|---|---|---|
| 104 | | (R)-N-(1-cyano-pyrrolidin-3-yl)-2-fluoro-3-(1-methyl-1H-pyrazol-4-yl)benzamide | B | 8.77 (d, J = 6.8 Hz, 1 H), 8.19 (d, J = 2.0 Hz, 1 H), 7.93 (s, 1 H), 7.79-7.83 (m, 1 H), 7.34-7.37 (m, 1 H), 7.26 (t, J = 7.6 Hz, 1 H), 4.44-4.48 (m, 1 H), 3.90 (s, 3 H), 3.64-3.66 (m, 1 H), 3.43-3.55 (m, 2 H), 3.27-3.34 (m, 1 H), 2.09-2.17 (m, 1 H), 1.87-1.95 (m, 1 H) | A | 3.11 | ES+ 314.0 |
| 105 | | (R)-N-(1-cyano-pyrrolidin-3-yl)-2-fluoro-4-(2-methyl-pyrimidin-4-yl)benzamide | B | 8.82-8.84 (m, 2 H), 8.10-8.15 (m, 2 H), 8.01 (d, J = 5.2 Hz, 1 H), 7.74 (t, J = 7.6 Hz, 1 H), 3.46-4.50 (m, 1H), 3.63-3.67 (m, 1 H), 3.45-3.56 (m, 2 H), 3.30-3.33 (m 1 H), 2.71 (s, 3 H), 2.12-2.17 (m, 1 H), 1.91-1.96 (m, 1 H) | A | 3.11 | ES+ 326.0 |
| 106 | | (R)-N-(1-cyano-pyrrolidin-3-yl)-5-(1-methyl-1H-pyrazol-4-yl)picolinamide | B | 8.93 (d, J = 7.6 Hz, 1 H), 8.77 (d, J = 1.6 Hz, 1 H), 8.39 (s, 1 H), 8.15 (dd, J = 8.4, 2.4 Hz, 1 H), 8.08 (s, 1 H), 8.00 (d, J = 8.0 Hz, 1 H), 4.51-4.55 (m, 1 H), 3.90 (s, 3 H), 3.54-3.64 (m, 2 H), 3.38-3.52 (m, 2 H), 1.98-2.15 (m, 2 H) | A | 2.90 | ES+ 296.96 |
| 107 | | (R)-N-(1-cyano-pyrrolidin-3-yl)-2-fluoro-5-(1-methyl-1H-pyrazol-4-yl)benzamide | B | 8.73 (d, J = 6.4 Hz, 1 H), 8.18 (s, 1 H), 7.89 (s, 1 H), 7.67-7.71 (m, 2 H), 7.28 (t, J = 8.8 Hz, 1 H), 4.44-4.48 (m, 1 H), 3.86 (s, 3 H), 3.62-3.66 (m, 1 H), 3.39-3.56 (m, 2 H), 3.28-3.32 (m, 1 H), 2.09-2.17 (m, 1 H), 1.88-1.96 (m, 1 H) | A | 3.15 | ES+ 314.05 |
| 108 | | (R)-N-(1-cyano-pyrrolidin-3-yl)-2-fluoro-4-(pyrimidin-4-yl)benzamide | B | 9.31 (d, J = 1.2 Hz, 1 H), 8.95 (d, J = 5.2 Hz, 1 H), 8.84 (d, J = 6.4 Hz, 1 H), 8.22 (dd, J = 5.2, 1.2 Hz, 1 H), 8.12-8.16 (m, 2 H), 7.75 (t, J = 7.6 Hz, 1 H), 4.44-4.51 (m, 1 H), 3.63-3.67 (m, 1 H), 3.44-3.56 (m, 2 H), 3.28-3.32 (m, 1 H), 2.09-2.18 (m, 1 H), 1.90-1.99 (m, 1 H) | H | 2.97 | ES+ 311.92 |
| 109 | | (R)-N-(1-cyano-pyrrolidin-3-yl)-2-fluoro-4-(imidazo[1,2-a]pyrimidin-6-yl)benzamide | B | 9.46 (d, J = 2.4 Hz, 1 H), 8.98 (d, J = 2.8 Hz, 1 H), 8.76 (d, J = 6.8 Hz, 1 H), 7.94 (d, J = 1.2 Hz, 1 H), 7.80-7.84 (m, 2 H), 7.72-7.74 (m, 2 H), 4.46-4.50 (m, 1 H), 3.63-3.67 (m, 1 H), 3.34-3.56 (m, 2 H), 3.30-3.32 (m, 1 H), 2.10-2.16 (m, 1 H), 1.92-1.97 (m, 1 H) | B | 2.48 | ES+ 351.25 |
| 110 | | (R)-N-(1-cyano-pyrrolidin-3-yl)-2-methoxy-4-(1-methyl-1H-pyrazol-4-yl)benzamide | B | 8.27 (s, 1 H), 8.24 (d, J = 6.8 Hz, 1 H), 7.98 (s, 1 H), 7.64 (d, J = 8.4 Hz, 1 H), 7.28 (d, J = 1.2 Hz, 1 H), 7.22 (dd, J = 8.0, 1.2 Hz, 1 H), 4.44-4.48 (m, 1 H), 3.94 (s, 3 H), 3.87 (s, 3 H), 3.59-3.63 (m, 1 H), 3.43-3.55 (m, 2 H), 3.28-3.31 (m, 1 H), 2.08-2.14 (m, 1 H), 1.91-1.97 (m, 1 H) | B | 3.12 | ES+ 326.19 |

TABLE 7-continued

| Ex | R1 | Name | Synthetic Method | ¹H NMR: (400 MHz, DMSO-d₆) δ ppm | LCMS Method | LCMS RT (min) | MS |
|---|---|---|---|---|---|---|---|
| 111 | | (R)-N-(1-cyano-pyrrolidin-3-yl)-6-(1-methyl-1H-pyrazol-4-yl)nicotinamide | C | 8.93 (d, J = 2.0 Hz, 1 H), 8.71 (d, J = 6.4 Hz, 1 H), 8.38 (s, 1 H), 8.17 (dd, J = 8.0, 2.0 Hz, 1 H), 8.07 (s, 1 H), 7.75 (d, J = 8.4 Hz, 1 H), 4.45-4.52 (m, 1 H), 3.89 (s, 3 H), 3.63-3.67 (m, 1 H), 3.53-3.59 (m, 1 H), 3.43-3.49 (m, 1 H), 3.31-3.33 (m, 1 H), 2.09-2.18 (m, 1 H), 1.91-1.99 (m, 1 H) | A | 2.68 | ES+ 296.96 |
| 112 | | (R)-N-(1-cyano-pyrrolidin-3-yl)-3,5-difluoro-4-(1-methyl-1H-pyrazol-4-yl)benzamide | C | 8.72 (d, J = 6.4 Hz, 1 H), 8.27 (s, 1 H), 7.90 (s, 1 H), 7.67-7.71 (m, 2 H), 4.45-4.49 (m, 1 H), 3.94 (s, 3 H), 3.63-3.67 (m, 1 H), 3.52-3.58 (m, 1 H), 3.43-3.49 (m, 1 H), 3.31-3.32 (m, 1 H), 2.09-2.17 (m, 1 H), 1.92-1.98 (m, 1 H) | B | 3.35 | ES+ 332.59 |
| 113 | | (R)-N-(1-cyano-pyrrolidin-3-yl)-2,6-difluoro-4-(1-methyl-1H-pyrazol-4-yl)benzamide | C | 8.05 (d, J = 6.8 Hz, 1 H), 8.33 (s, 1 H), 8.03 (s, 1 H), 7.42-7.45 (m, 2 H), 4.39-4.46 (m, 1 H), 3.86 (s, 3 H), 3.61-3.65 (m, 1 H), 3.45-3.49 (m, 2 H), 3.21-3.25 (m, 1 H), 2.08-2.17 (m, 1 H), 1.88-1.90 (m, 1 H) | A | 3.15 | ES+ 332.01 |
| 114 | | (R)-N-(1-cyano-pyrrolidin-3-yl)-6-(1-methyl-1H-pyrazol-4-yl)pyrazolo[1,5-a]pyridine-3-carboxamide | C | 9.07 (s, 1 H), 8.56 (s, 1 H), 8.29 (s, 2 H), 8.17 (d, J = 9.2 Hz, 1 H), 8.03 (s, 1 H), 7.74 (d, J = 9.2 Hz, 1 H), 4.45-4.53 (m, 1 H), 3.88 (s, 3 H), 3.64-3.68 (m, 1 H), 3.56-3.58 (m, 1 H), 3.46-3.48 (m, 2 H), 2.12-2.19 (m, 1 H), 1.92-1.98 (m, 1 H) | B | 3.01 | ES+ 336.22 |
| 115 | | (R)-N-(1-cyano-pyrrolidin-3-yl)-2-fluoro-3-methoxy-4-(1-methyl-1H-pyrazol-4-yl)benzamide | C | 8.62 (d, J = 6.8 Hz, 1 H), 8.25 (s, 1 H), 7.97 (s, 1 H), 7.50 (d, J = 8.4 Hz, 1 H), 7.25-7.35 (m, 1 H), 4.42-4.46 (m, 1 H), 3.90 (s, 3 H), 3.85 (s, 3 H), 3.61-3.65 (m, 1 H), 3.41-3.53 (m, 2 H), 3.27-3.31 (m, 1 H), 2.10-2.15 (m, 1 H), 1.90-1.94 (m, 1 H) | B | 3.20 | ES+ 344.21 |
| 116 | | (R)-6-(3-cyano-phenyl)-N-(1-cyanopyrrolidin-3-yl)imidazo[1,2-a]pyridine-2-carboxamide | C | 9.09 (s, 1 H), 8.74 (d, J = 7.2 Hz, 1 H), 8.37 (s, 1 H), 8.25 (s, 1 H), 8.09 (d, J = 8.0 Hz, 1 H), 7.90 (d, J = 7.6 Hz, 1 H), 7.70-7.80 (m, 3 H), 4.51-4.56 (s, 1 H), 3.55-3.64 (m, 2 H), 3.37-3.48 (m, 2 H), 2.02-2.15 (m, 2 H) | A | 3.67 | ES+ 356.96 |

TABLE 7-continued

| Ex | R1 | Name | Synthetic Method | ¹H NMR: (400 MHz, DMSO-d₆) δ ppm | LCMS Method | LCMS RT (min) | MS |
|---|---|---|---|---|---|---|---|
| 117 | 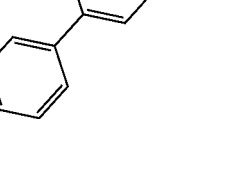 | (R)-6-(4-cyano-phenyl)-N-(1-cyanopyrrolidin-3-yl)imidazo[1,2-a]pyridine-2-carboxamide | C | 9.12 (s, 1 H), 8.74 (d, J = 7.2 Hz, 1 H), 8.39 (s, 1 H), 8.01 (d, J = 8.4 Hz, 1 H), 7.95 (d, J = 8.8 Hz, 1 H), 7.71-7.80 (m, 2 H), 4.51-4.56 (s, 1 H), 3.55-3.64 (m, 2 H), 3.37-3.48 (m, 2 H), 2.02-2.15 (m, 2 H) | A | 3.67 | ES+ 357.03 |
| 118 | 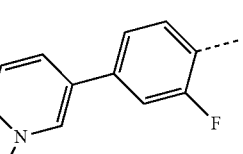 | (R)-N-(1-cyano-pyrrolidin-3-yl)-2-fluoro-4-(imidazo[1,2-a]pyridin-6-yl)benzamide | C | 9.08 (s, 1 H), 8.71 (d, J = 6.0 Hz, 1 H), 7.97 (s, 1 H), 7.64-7.73 (m, 6 H), 4.45-4.48 (m, 1 H), 3.62-3.66 (m, 1 H), 3.46-3.54 (m, 2 H), 3.29-3.31 (m, 1 H), 2.11-2.16 (m, 1 H), 1.91-1.96 (m, 1 H) | A | 3.15 | ES+ 350.04 |
| 119 | 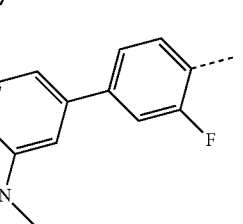 | (R)-N-(1-cyano-pyrrolidin-3-yl)-2-fluoro-4-(2-morpholino-pyridin-4-yl)benzamide | C | 8.74 (d, J = 6.8 Hz, 1H), 8.22 (d, J = 5.2 Hz, 1H), 7.80 (dd, J = 1.6 Hz, 11.6 Hz, 1H), 7.65-7.73 (m, 2H), 7.14 (s, 1H), 7.06 (dd, J = 1.2 Hz, 5.2 Hz, 1H), 4.45-4.49 (m, 1H), 3.71-3.73 (m, 4H), 3.62-3.66 (m, 1H), 3.44-3.56 (m, 5H), 3.29-3.31 (m, 2H), 2.09-2.16 (m, 1H), 1.90-1.95 (m, 1H) | B | 2.68 | ES+ 396.4 |
| 120 | 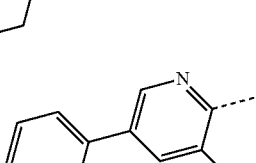 | (R)-N-(1-cyano-pyrrolidin-3-yl)-3-fluoro-5-(1-methyl-1H-indazol-5-yl)picolinamide | C | 9.00 (d, J = 7.2 Hz, 1 H), 8.89 (s, 1 H), 8.25-8.28 (m, 2 H), 8.17 (s, 1H), 7.89 (d, J = 8.8 Hz, 1 H), 7.82 (d, J = 8.8 Hz, 1 H), 4.49-4.54 (m, 1H), 4.10 (s, 3 H), 3.62-3.66 (m, 1 H), 3.52-3.58 (m, 1 H), 3.44-3.49 (m, 1 H), 3.34-3.38 (m, 1 H), 2.12-2.17 (m, 1 H), 1.97-2.02 (m, 1 H) | B | 3.50 | ES+ 365.2 |
| 121 |  | (R)-N-(1-cyano-pyrrolidin-3-yl)-3-fluoro-5-(1-methyl-1H-pyrrolo[2,3-b]pyridin-5-yl)picolinamide | C | 9.00 (d, J = 6.8 Hz, 1 H), 8.90 (s, 1 H), 8.74 (d, J = 2.0 Hz, 1 H), 8.46 (d, J = 2.0 Hz, 1 H), 8.29-8.32 (m, 1 H), 7.64 (d, J = 3.2 Hz, 1 H), 6.58 (d, J = 3.6 Hz, 1 H), 4.49-4.54 (m, 1 H), 3.87 (s, 3 H), 3.62-3.66 (m, 1 H), 3.53-3.58 (m, 1 H), 3.44-3.49 (m, 1 H), 3.34-3.38 (m, 1 H), 2.10-2.17 (m, 1 H), 1.97-2.04 (m, 1 H) | B | 3.52 | ES+ 365.33 |
| 122 | 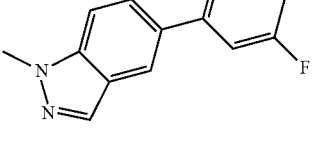 | (R)-N-(1-cyano-pyrrolidin-3-yl)-5-(1,3-dimethyl-1H-pyrazol-4-yl)-3-fluoropicolinamide | C | 8.91 (d, J = 7.2 Hz, 1H), 8.58 (t, J = 1.6 Hz, 1H), 8.22 (s, 1H), 7.88 (dd, J = 1.6 Hz, 12.4 Hz, 1H), 4.47-4.51 (m, 1H), 3.82 (s, 3H), 3.60-3.65 (m, 1H), 3.51-3.57 (m, 1H), 3.42-3.48 (m, 1H), 3.32-3.37 (m, 1H), 2.36 (s, 3H), 2.10-2.15 (m, 1H), 1.91-2.00 (m, 1H) | B | 3.06 | ES+ 329.3 |
| 123 | 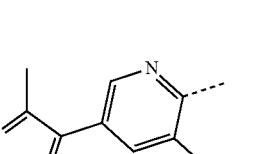 | (R)-3-chloro-N-(1-cyanopyrrolidin-3-yl)-5-(4-fluorophenyl)picolinamide | C | 9.03 (d, J = 6.8 Hz, 1 H), 8.88 (d, J = 1.6 Hz, 1 H), 8.36 (d, J = 2.0 Hz, 1 H), 7.88-7.92 (m, 2 H), 7.39 (t, J = 8.8 Hz, 2 H), 4.46-4.50 (m, 1 H), 3.63-3.67 (m, 1 H), 3.44-3.53 | A | 4.09 | ES+ 345.1 |

TABLE 7-continued

| Ex | R1 | Name | Synthetic Method | ¹H NMR: (400 MHz, DMSO-d₆) δ ppm | LCMS Method | LCMS RT (min) | MS |
|---|---|---|---|---|---|---|---|
| | | | | (m, 2 H), 3.30-3.32 (m, 1 H), 2.12-2.17 (m, 1 H), 1.91-1.96 (m, 1 H) | | | |
| 124 | | (R)-N-(1-cyano-pyrrolidin-3-yl)-6-(1-methyl-1H-pyrazol-4-yl)imidazo[1,2-a]pyridine-2-carboxamide | C | 8.83 (t, J = 1.2 Hz, 1 H), 8.65 (d, J = 7.6 Hz, 1 H), 8.29 (s, 1 H), 8.19 (s, 1 H), 7.88 (d, J = 0.8 Hz, 1 H), 7.57-7.63 (m, 2 H), 4.49-4.54 (m, 1 H), 3.90 (s, 3 H), 3.53-3.62 (m, 2 H), 3.34-3.47 (m, 2 H), 2.00-2.13 (m, 2 H) | A | 2.78 | ES+ 336.3 |
| 125 | | (R)-N-(1-cyano-pyrrolidin-3-yl)-6-(1,3-dimethyl-1H-pyrazol-4-yl)imidazo[1,2-a]pyridine-2-carboxamide | C | 8.63-8.67 (m, 2 H), 8.38 (s, 1 H), 7.99 (s, 1 H), 7.61 (d, J = 9.6 Hz, 1 H), 7.45 (dd, J = 9.2, 1.6 Hz, 1 H), 4.48-4.56 (m, 1H), 3.80 (s, 3 H), 3.54-3.62 (m, 2 H), 3.34-3.47 (m, 2 H), 2.33 (s, 3 H), 1.98-2.18 (m, 2 H) | A | 2.19 | ES+ 350.3 |
| 126 | | (R)-N-(1-cyano-pyrrolidin-3-yl)-5-(1-methyl-1H-pyrazol-4-yl)-1H-indazole-3-carboxamide | C | 13.70 (s, 1 H), 8.69 (d, J = 6.8 Hz, 1 H), 8.25 (s, 1 H), 8.16 (s, 1 H), 7.84 (s, 1 H), 7.59-7.65 (m, 2 H), 4.54-4.58 (m, 1 H), 3.88 (s, 3 H), 3.55-3.66 (m, 2 H), 3.37-3.48 (m, 2 H), 2.11-2.16 (m, 1 H), 2.02-2.08 (m, 1 H) | A | 2.98 | ES+ 336.0 |
| 127 | | (R)-N-(1-cyano-pyrrolidin-3-yl)-6-(1-methyl-1H-pyrazol-4-yl)-1H-indazole-3-carboxamide | C | 13.56 (s, 1 H), 8.67 (d, J = 7.2 Hz, 1 H), 8.26 (s, 1 H), 8.10 (d, J = 8.4 Hz, 1 H), 7.97 (s, 1 H), 7.69 (s, 1 H), 7.48 (d, J = 9.6 Hz, 1 H), 4.52-4.57 (m, 1 H), 3.90 (s, 3 H), 3.51-3.66 (m, 2 H), 3.38-3.48 (m, 2 H), 2.01-2.17 (m, 2 H) | B | 3.03 | ES+ 336.7 |
| 128 | | (R)-N-(1-cyano-pyrrolidin-3-yl)-6-(3,5-dimethyl-isoxazol-4-yl)-1H-indole-2-carboxamide | C | 11.66 (s, 1 H), 8.65 (d, J = 6.8 Hz, 1 H), 7.72 (d, J = 8.0 Hz, 1 H), 7.38 (s, 1 H), 7.24 (s, 1 H), 7.04 (d, J = 8.4 Hz, 1 H), 4.50-4.54 (m, 1 H), 3.65-3.69 (m, 1 H), 3.55-3.60 (m, 1 H), 3.45-3.51 (m, 1 H), 3.32 (s, 1 H), 2.41 (s, 3 H), 2.23 (s, 3 H), 2.13-2.18 (m, 1 H), 1.94-2.01 (m, 1 H) | A | 3.86 | ES+ 350.0 |
| 129 | | (R)-N-(1-cyano-pyrrolidin-3-yl)-6-(1,3-dimethyl-1H-pyrazol-4-yl)-1H-indole-2-carboxamide | C | 11.53 (s, 1 H), 8.57 (d, J = 6.8 Hz, 1 H), 7.86 (s, 1 H), 7.61 (d, J = 8.0 Hz, 1 H), 7.43 (s, 1 H), 7.18 (s, 1 H), 7.12 (d, J = 8.4 Hz, 1 H), 4.49-4.54 (m, 1 H), 3.79 (s, 3 H), 3.65-3.69 (m, 1 H), 3.54-3.60 (m, 1 H), 3.45-3.50 (m, 1 H), 3.31-3.34 (m, 1 H), 2.31 (s, | B | 3.34 | ES+ 349.3 |

TABLE 7-continued

| Ex | R1 | Name | Synthetic Method | ¹H NMR: (400 MHz, DMSO-d₆) δ ppm | LCMS Method | LCMS RT (min) | MS |
|---|---|---|---|---|---|---|---|
| | | | | 3 H), 2.11-2.20 (m, 1 H), 1.94-2.00 (m, 1 H) | | | |
| 130 | | (R)-N-(1-cyano-pyrrolidin-3-yl)-5-(1-methyl-1H-pyrazol-4-yl)-1H-indole-2-carboxamide | C | 11.56 (s, 1 H), 8.59 (d, J = 6.4 Hz, 1 H), 8.06 (s, 1 H), 7.82 (s, 1 H), 7.78 (s, 1 H), 7.40 (s, 2 H), 7.16 (d, J = 2.0 Hz, 1 H), 4.50-4.52 (m, 1 H), 3.86 (s, 3 H), 3.65-3.69 (m, 1 H), 3.55-3.61 (m, 1 H), 3.45-3.50 (m, 1 H), 3.32-3.35 (m, 1 H), 2.13-2.18 (m, 1 H), 1.91-1.99 (m, 1 H) | B | 3.21 | ES+ 335.3 |
| 131 | | (R)-N-(1-cyano-pyrrolidin-3-yl)-2,3-difluoro-4-(1-methyl-1H-pyrazol-4-yl)benzamide | C | 8.74 (d, J = 6.8 Hz, 1 H), 8.28 (d, J = 1.6 Hz, 1 H), 8.01 (s, 1 H), 7.57-7.63 (m, 1 H), 7.37-7.41 (m, 1 H), 4.42-4.49 (m, 1 H), 3.91 (s, 3 H), 3.61-3.65 (m, 1 H), 3.43-3.55 (m, 2 H), 3.28-3.31 (m, 1 H), 2.08-2.18 (m, 1 H), 1.88-1.95 (m, 1 H) | A | 3.30 | ES+ 332.28 |
| 132 | | (R)-N-(1-cyano-pyrrolidin-3-yl)-5-(1-ethyl-1H-pyrazol-4-yl)-4-methyl-picolinamide | C | (MeOD) 8.63 (s, 1 H), 8.06 (s, 1 H), 7.98 (s, 1 H), 7.84 (s, 1 H), 4.63-4.66 (m, 1 H), 4.26-4.32 (q, J = 14.8, 7.2 Hz, 2 H), 3.74-3.78 (m, 1 H), 3.64-3.70 (m, 1 H), 3.54-3.60 (m, 1 H), 3.44-3.48 (m, 1 H), 2.54 (s, 3 H), 2.29-2.34 (m, 1 H), 2.10-2.15 (m, 1 H), 1.53 (t, J = 7.2 Hz, 3 H). | B | 3.33 | ES+ 325.24 |
| 133 | | (R)-N-(1-cyano-pyrrolidin-3-yl)-3-phenoxy-azetidine-1-carboxamide | E | 7.31 (t, J = 7.6 Hz, 2H), 6.98 (t, J = 7.2 Hz, 1H), 6.83 (d, J = 8.0 Hz, 2H), 6.62 (d, J = 6.4 Hz, 1H), 4.97-4.99 (m, 1H), 4.24-4.28 (m, 2H), 4.09-4.14 (m, 1H), 3.73-3.76 (m, 2H), 3.45-3.52 (m, 2H), 3.34-3.40 (m, 1H), 3.22-3.15 (m, 1H), 1.95-2.01 (m, 1H), 1.75-1.80 (m, 1H) | A | 3.95 | ES+ 287.0 |
| 134 | | (R)-3-(1H-benzo[d]imidazol-2-yl)-N-(1-cyano-pyrrolidin-3-yl)azetidine-1-carboxamide | E | 8.32 (s, 1 H), 7.52-7.58 (m, 2 H), 7.15-7.17 (m, 2 H), 6.62 (d, J = 6.8 Hz, 1 H), 4.09-4.23 (m, 5 H), 3.99-4.04 (m, 1 H), 3.46-3.55 (m, 2 H), 3.36-3.42 (m, 1 H), 3.14-3.18 (m, 1 H), 1.98-2.06 (m, 1 H), 1.77-1.85 (m, 1 H) | A | 2.80 | ES+ 310.99 |
| 135 | | (R)-N-(1-cyano-pyrrolidin-3-yl)-4-phenylpiperazine-1-carboxamide | E | 7.20-7.24 (m, 2 H), 6.95-6.97 (m, 2 H), 6.78-6.82 (m, 1 H), 6.65 (d, J = 6.0 Hz, 1 H), 4.16-4.20 (m, 1 H), 3.50-3.55 (m, 1 H), 3.44-3.48 (m, 5 H), 3.36-3.39 (m, 1 H), 3.15-3.19 (m, 1 H), 3.08-3.10 (m, 4 H), 1.91-2.06 (m, 1 H), 1.80-1.88 (m, 1 H) | A | 3.55 | ES+ 300.01 |
| 136 | | N-((R)-1-cyano-pyrrolidin-3-yl)-2-phenylmorpholine-4-carboxamide | E | 7.30-7.41 (m, 5 H), 6.67 (d, J = 6.4 Hz, 1 H), 4.36-4.37 (m, 1 H), 4.16-4.21 (m, 1 H), 3.95-3.98 (m, 2 H), 3.86-3.89 (m, 1 H), 3.44-3.59 (m, 3 H), 3.37-3.41 (m, 1 H), 3.14-3.19 (m, 1 H), 2.83-2.89 (m, 1 | A | 3.54 | ES+ 301.01 |

TABLE 7-continued

| Ex | R1 | Name | Synthetic Method | ¹H NMR: (400 MHz, DMSO-d₆) δ ppm | LCMS Method | LCMS RT (min) | MS |
|---|---|---|---|---|---|---|---|
| | | | | H), 2.64-2.70 (m, 1 H), 1.98-2.06 (m, 1 H), 1.79-1.85 (m, 1 H) | | | |
| 137 | | (R)-4-(2-chloro-6-fluorobenzyl)-N-(1-cyanopyrrolidin-3-yl)-1,4-diazepane-1-carboxamide | E | (CDCl₃) 7.32-7.38 (m, 2 H), 7.21 (t, J = 8.0 Hz, 1 H), 6.25 (d, J = 5.6 Hz, 1 H), 4.38-4.44 (m, 2 H), 3.80 (s, 2 H), 3.65-3.69 (m, 1 H), 3.44-3.55 (m, 6 H), 3.26-3.29 (m, 1 H), 2.75-2.80 (m, 3 H), 2.18-2.23 (m, 1 H), 1.94-2.00 (m, 3 H) | A | 3.95 | ES+ 379.98 |
| 138 | | (R)-4-benzyl-N-(1-cyanopyrrolidin-3-yl)-1,4-diazepane-1-carboxamide | E | 7.23-7.34 (m, 5 H), 6.25 (d, J = 6.4 Hz, 1 H), 4.15-4.19 (m, 1 H), 3.58 (s, 2 H), 3.43-3.52 (m, 2 H), 3.33-3.39 (m, 6 H), 3.14-3.18 (m, 1 H), 2.51-2.55 (m, 3 H), 1.95-2.03 (m, 1 H), 1.79-1.86 (m, 1 H), 1.74-1.78 (m, 2 H) | G | 6.07 | ES+ 328.25 |
| 139 | | (R)-N-(1-cyano-pyrrolidin-3-yl)-1,3,4,9-tetrahydro-2H-pyrido[3,4-b]indole-2-carboxamide | E | 10.83 (s, 1 H), 7.38 (d, J = 8.0 Hz, 1 H), 7.29 (d, J = 7.6 Hz, 1 H), 7.03 (t, J = 7.2 Hz, 1 H), 6.95 (t, J = 7.6 Hz, 1 H), 6.77 (d, J = 6.0 Hz, 1 H), 4.55 (s, 2 H), 4.18-4.22 (m, 1 H), 3.66-3.68 (m, 2 H), 3.47-3.56 (m, 2 H), 3.38-3.42 (m, 1 H), 3.17-3.21 (m, 1 H), 2.68-2.69 (m, 2 H), 1.98-2.07 (m, 1 H), 1.83-1.90 (m, 1 H) | B | 3.64 | ES+ 310.16 |
| 140 | | N-((R)-1-cyano-pyrrolidin-3-yl)-2-((2S,6R)-2,6-dimethyl-morpholino)-5-fluoroiso-nicotinamide | H | 8.87 (d, J = 6.8 Hz, 1H), 8.18 (s, 1H), 6.92 (d, J = 4, 1H), 4.41-4.45 (m 1H), 4.06-4.09 (m, 2H), 3.58-3.65 (m, 3H), 3.44-3.51 (m, 2H), 3.26-3.32 (m, 1H), 2.33-2.41 (m, 2), 2.10-2.15 (m, 1), 1.87-1.92 (m, 1H), 1.15 (d, J = 6 Hz, 6H) | B | 3.53 | ES+ 348.3 |
| 141 | | (R)-N-(1-cyano-pyrrolidin-3-yl)-5-fluoro-2-(isoindolin-2-yl)isonicotinamide | H | 8.90 (d, J = 6.8 Hz, 1H), 8.23 (d, J = 1.6 Hz, 1H), 7.39-7.42 (m, 2H), 7.31-7.34 (m, 2H), 6.67 (d, J = 4 Hz, 1H), 4.75 (s, 4H), 4.45-4.48 (m, 1H), 3.63-3.67 (m, 1H), 3.44-3.54 (m, 2H), 3.29-3.33 (m, 1H), 2.12-2.17 (m, 1H), 1.89-1.94 (m, 1H) | B | 3.84 | ES+ 352.6 |

TABLE 7-continued

| Ex | R1 | Name | Synthetic Method | ¹H NMR: (400 MHz, DMSO-d$_6$) δ ppm | LCMS Method | LCMS RT (min) | MS |
|---|---|---|---|---|---|---|---|
| 142 | | (R)-N-(1-cyano-pyrrolidin-3-yl)-3-fluoro-4-(pyrimidin-2-ylamino)benzamide | G | 9.33 (s, 1H), 8.55 (d, J = 6.4 Hz, 1H), 8.49 (d, J = 4.8 Hz, 2H), 8.026 (t, J = 8.4 Hz, 1H), 7.68-7.74 (m, 2H), 6.92 (t, J = 4.8 Hz, 1H), 4.43-4.49 (m, 1H), 3.62-3.66 (m, 1H), 3.53-3.59 (m, 1H), 3.43-3.48 (m, 1H), 3.28-3.33 (m, 1H), 2.08-2.17 (m, 1H), 1.94-1.99 (m, 1H) | B | 3.07 | ES+ 327.5 |
| 143 | | (R)-N-(1-cyano-pyrrolidin-3-yl)-2-fluoro-4-(pyrrolidin-1-yl)benzamide | H | 7.91-7.93 (m, 1 H), 7.51 (t, J = 8.8 Hz, 1 H), 6.39 (dd, J = 8.8, 2.4 Hz, 1 H), 6.30 (dd, J = 14.8, 2.0 Hz, 1 H), 4.41-4.45 (m, 1 H), 3.58-3.62 (m, 1 H), 3.48-3.54 (m, 1 H), 3.41-3.45 (m, 1 H), 3.25-3.31 (m, 5 H), 2.05-2.12 (m, 1 H), 1.89-1.99 (m, 5 H) | B | 3.88 | ES+ 303.37 |
| 144 | | (R)-N-(1-cyano-pyrrolidin-3-yl)-2,5-difluoro-4-morpholino-benzamide | H | 8.43 (d, J = 6.8, 1 H), 7.37-7.42 (m, 1 H), 6.90-6.95 (m, 1 H), 4.40-4.44 (m, 1 H), 3.73 (t, J = 4.8, 4 H), 3.59-3.63 (m, 1 H), 3.41-3.54 (m, 2 H), 3.26-3.31 (m, 1 H), 3.10 (t, J = 4.4, 4 H), 2.05-2.14 (m, 1 H), 1.86-1.94 (m, 1 H) | B | 3.35 | ES+ 337.00 |
| 145 | | (R)-N-(1-cyano-pyrrolidin-3-yl)-2,5-difluoro-4-(pyrrolidin-1-yl)benzamide | H | 8.07-8.10 (m, 1 H), 7.30-7.42 (m, 1 H), 6.46-6.51 (m, 1 H), 4.38-4.45 (m, 1 H), 3.59-3.64 (m, 1 H), 3.48-3.54 (m, 1 H), 3.40-3.45 (m, 5 H), 3.26-3.31 (m, 1 H), 2.05-2.14 (m, 1 H), 1.87-1.95 (m, 5 H) | B | 4.10 | ES+ 321.30 |
| 146 | | N-((R)-1-cyano-pyrrolidin-3-yl)-2-fluoro-4-((R)-3-methoxypyrrolidin-1-yl)benzamide | H | 7.95-7.97 (m, 1 H), 7.51 (t, J = 8.8 Hz, 1 H), 6.39 (dd, J = 8.8, 2.0 Hz, 1 H), 6.32 (dd, J = 14.4, 2.0 Hz, 1 H), 4.41-4.45 (m, 1 H), 4.08-4.09 (m, 1 H), 3.57-3.61 (m, 1 H), 3.52-3.54 (m, 1 H), 3.40-3.50 (m, 2 H), 3.28-3.32 (m, 4 H), 3.26 (s, 3 H), 2.03-2.13 (m, 3 H), 1.87-1.95 (m, 1 H) | A | 3.63 | ES+ 333.01 |
| 147 | | (R)-N-(1-cyano-pyrrolidin-3-yl)-3-methoxy-4-(pyrimidin-2-ylamino)benzamide | G | 8.54 (d, J = 4.8 Hz, 2 H), 8.46 (d, J = 6.8 Hz, 1 H), 8.35 (d, J = 8.0 Hz, 1 H), 8.20 (s, 1 H), 7.50-7.53 (m, 2 H), 6.94 (t, J = 4.8 Hz, 1 H), 4.47-4.51 (m, 1 H), 3.94 (s, 3 H), 3.63-3.68 (m, 1 H), 3.54-3.60 (m, 1 H), 3.43-3.49 (m, 1 H), 3.36-3.39 (m, 1 H), 2.10-2.17 (m, 1 H), 1.94-2.00 (m, 1 H) | A | 3.49 | ES+ 339.00 |

TABLE 7-continued

| Ex | R1 | Name | Synthetic Method | ¹H NMR: (400 MHz, DMSO-d₆) δ ppm | LCMS Method | LCMS RT (min) | MS |
|---|---|---|---|---|---|---|---|
| 148 | (structure with methoxy, methylpyrimidinyl amino) | (R)-N-(1-cyano-pyrrolidin-3-yl)-3-methoxy-4-((4-methylpyrimidin-2-yl)amino)benzamide | G | 8.39-8.47 (m, 3 H), 8.07 (s, 1 H), 7.48-7.54 (m, 2 H), 6.83 (d, J = 4.8 Hz, 1 H), 4.46-4.50 (m, 1 H), 3.94 (s, 3 H), 3.63-3.67 (m, 1 H), 3.54-3.60 (m, 1 H), 3.43-3.49 (m, 1 H), 3.29-3.34 (m, 1 H), 2.38 (s, 3 H), 2.11-2.18 (m, 1 H), 1.93-2.00 (m, 1 H) | B | 3.55 | ES+ 353.62 |
| 149 | (structure with fluoro, methoxypyrimidinyl amino) | (R)-N-(1-cyano-pyrrolidin-3-yl)-2-fluoro-4-((4-methoxypyrimidin-2-yl)amino)benzamide | G | 10.02 (s, 1 H), 8.34 (d, J = 1.2 Hz, 1 H), 8.29 (d, J = 5.6 Hz, 1 H), 7.89 (d, J = 14.4 Hz, 1 H), 7.54-7.56 (m, 2 H), 6.41 (d, J = 5.6 Hz, 1 H), 4.42-4.46 (m, 1 H), 3.94 (s, 3 H), 3.60-3.64 (m, 1 H), 3.41-3.55 (m, 2 H), 3.27-3.32 (m, 1 H), 2.08-2.13 (m, 1 H), 1.89-1.94 (m, 1 H) | A | 3.71 | ES+ 357.03 |

Example 150 N—((R)-1-cyanopyrrolidin-3-yl)-5-methyl-1-(1-phenylethyl)-1H-pyrazole-3-carboxamide

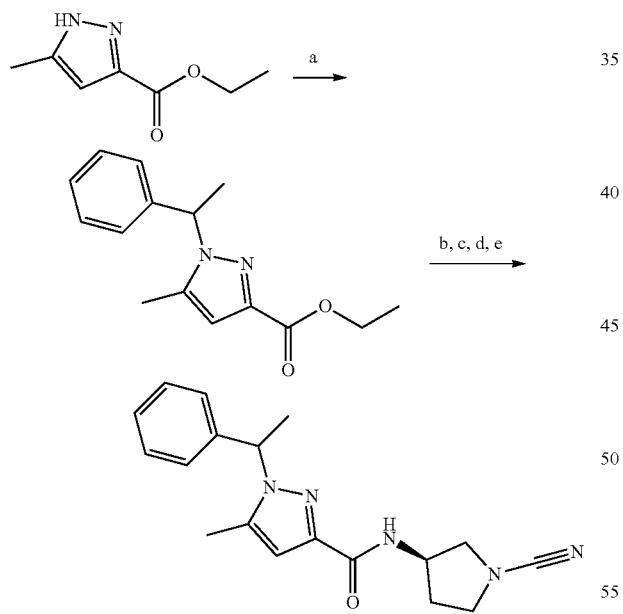

Step a.

To a stirred solution of ethyl 3-methyl-1H-pyrazole-5-carboxylate (1.0 g, 6.49 mmol) in THF (25 ml) was added KOH (0.435 g, 7.78 mmol) and stirred at rt for 15 min. The reaction was treated with (1-bromoethyl)benzene (1.2 g, 6.49 mmol) and heated to 80° C. for 8 h. The resulting reaction mixture was allowed to cool to rt, quickly poured into water (40 ml) and extracted with EtOAc (3×30 ml). The combined organic phase was separated, dried over Na₂SO₄, filtered and concentrated under reduced pressure. The resulting residue was purified by column chromatography yielding undesired regio-isomer ethyl 3-methyl-1-(1-phenylethyl)-1H-pyrazole-5-carboxylate (0.12 g, 0.464 mmol) at 5% EtOAc in hexane and desired regio-isomer ethyl 5-methyl-1-(1-phenylethyl)-1H-pyrazole-3-carboxylate (0.8 g, 3.10 mmol) at 12% EtOAc in hexane. LCMS: Method C, RT 2.20 min, MS: ES+259.32; ¹H NMR (400 MHz, CDCl₃) δ ppm: 7.26-7.34 (m, 2H), 7.12-7.25 (m, 2H), 6.60 (s, 1H), 5.51 (q, J-=7.2 Hz, 1H), 4.42 (q, J=7.2 Hz, 2H), 2.13 (s, 3H), 1.99 (d, J-=6.8 Hz, 3H), 1.41 (t, J=6.8 Hz, 3H).

Steps b-e.

The title compound was synthesised from the intermediate above using a procedure similar to that described for Example 2 to provide the title compound. LCMS: Method B, RT 3.71 min, MS: ES+ 324.38; ¹H NMR (400 MHz, DMSO-d₆) δ ppm 8.19 (d, J=6.4 Hz, 1H), 7.31-7.35 (m, 2H), 7.26-7.27 (m, 1H), 7.16 (d, J=7.2 Hz, 2H), 6.48 (s, 1H), 5.64-5.66 (m, 1H), 4.46-4.48 (m, 1H), 3.58-3.62 (m, 2H), 3.51-3.53 (m, 1H), 3.41-3.46 (m, 1H), 2.16 (s, 3H), 2.08-2.11 (m, 1H), 1.95-2.05 (m, 1H), 1.83 (d, J-6.8 Hz, 3H)

Example 151 (R)—N-(1-cyanopyrrolidin-3-yl)-5-methyl-1-(pyridin-2-ylmethyl)-1H-pyrazole-3-carboxamide

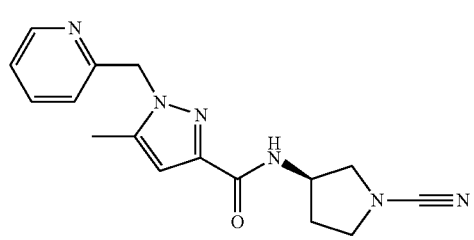 [SMILES: Cc1cc(C(=O)N[C@@H]2CCN(C#N)C2)nn1Cc1ccccn1]

Synthesised using a procedure similar to that described for Example 150. LCMS: Method B, RT 2.82 min, MS: ES+ 311.21; ¹H NMR (400 MHz, DMSO-d₆) δ ppm 8.53 (dd, J=4.8, 0.8 Hz, 1H), 8.32 (d, J=7.2 Hz, 1H), 7.76-7.81 (m, 1H), 7.30-7.33 (m, 1H), 6.98 (d, J=7.6 Hz, 1H), 6.52 (s, 1H), 5.46 (s, 2H), 4.41-4.46 (m, 1H), 3.48-3.58 (m, 2H), 3.38-3.42 (m, 1H), 3.27-3.31 (m, 1H), 2.26 (s, 3H), 2.03-2.06 (m, 1H), 1.91-1.96 (m, 1H).

Example 152 (R)—N-(1-cyanopyrrolidin-3-yl)-2-fluoro-4-(pyridazin-4-yl)benzamide

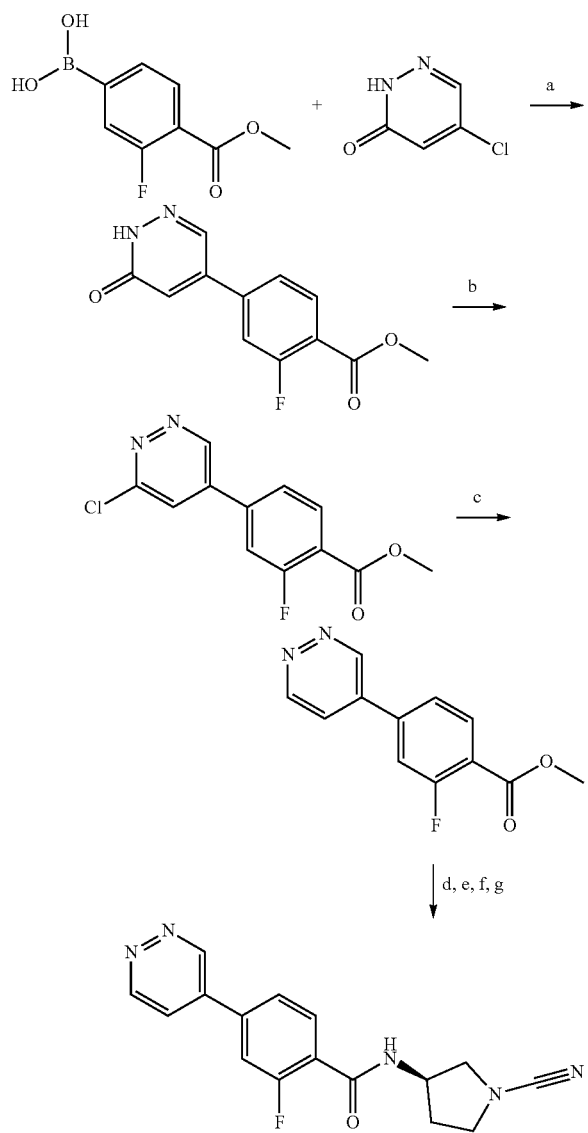

Step a.

A solution of 5-chloropyridazin-3(2H)-one (0.50 g, 3.83 mmol) and 3-fluoro-4-(methoxycarbonyl)phenyl)boronic acid (0.91 g, 4.59 mmol) in 1,4-dioxane:water (9:1, 10 ml) was added $Na_2CO_3$ (0.81 g, 7.66 mmol) at rt. The resulting reaction mixture was degassed for 20 min before adding Pd(dppf)Cl$_2$ (0.14 g, 0.19 mmol) and the reaction mixture was heated at 100° C. for 16 h. The resulting reaction mixture was poured into water (100 ml) and extracted with EtOAc (2×50 ml). The combined organic phase was washed with brine (100 ml). The combined organic phase was dried over $Na_2SO_4$, filtered and concentrated under reduced pressure. The obtained residue was triturated with diethyl ether (2×10 ml) and filtered under vacuum yielding methyl 2-fluoro-4-(6-oxo-1,6-dihydropyridazin-4-yl)benzoate (0.70 g, 2.82 mmol). This material was used directly for the next step without further purification. LCMS: Method C, RT 1.66 min, MS: ES+ 249.22; $^1$H NMR (400 MHz, DMSO-$d_6$) δ ppm 13.24 (s, 1H), 8.35 (d, J=1.60 Hz, 1H), 7.99 (t, J=7.60 Hz, 1H), 7.91 (d, J-12.40 Hz, 1H), 7.80 (d, J-8.00 Hz, 1H), 7.31 (s, 1H), 3.88 (s, 3H).

Step b.

A solution of methyl 2-fluoro-4-(6-oxo-1,6-dihydropyridazin-4-yl)benzoate (0.90 g, 3.62 mmol) in POCl$_3$ (1.06 ml, 1.08 mmol) was heated at 100° C. for 2 h. The resulting reaction mixture was cooled to rt and poured into ice cold water (20 ml). The pH was adjusted to -7-8 using solid NaHCO$_3$. The resulting mixture was extracted with EtOAc (3×100 ml). The combined organic phase was washed with brine (100 ml), dried over Na$_2$SO$_4$, filtered and concentrated under reduced pressure yielding methyl 4-(6-chloropyridazin-4-yl)-2-fluorobenzoate (1.1 g, quantitative). This material was used directly for the next step without further purification. LCMS: Method C, RT 1.96 min, MS: ES+267.26.

Step c.

A solution of methyl 4-(6-chloropyridazin-4-yl)-2-fluorobenzoate (1.10 g, 4.10 mmol) in EtOAc: MeOH (1:1, 20 ml) was prepared in an autoclave. Ammonium formate (0.51 g, 8.21 mmol) and 20% Pd(OH)$_2$ on carbon (0.5 g, 0.71 mmol) was added to the reaction mixture at rt. The reaction mixture was heated at 80° C. for 16 h. The resulting reaction mixture was cooled to rt and carefully filtered through celite hyflow. The celite bed was carefully washed with MeOH (5×30 ml). The combined filtrate was concentrated under reduced pressure. The resulting residue was purified by column chromatography (2% MeOH in DCM) yielding methyl 2-fluoro-4-(pyridazin-4-yl) benzoate (0.17 g, 0.73 mmol). LCMS: Method C, RT 1.69 min, MS: ES+ 233.26; $^1$H NMR (400 MHz, DMSO-$d_6$) δ ppm 9.73-9.74 (m, 1H), 9.36-9.37 (m, 1H), 8.03-8.15 (m, 3H), 7.93-7.94 (m, 1H), 3.90 (s, 3H)

Steps d-g.

The title compound was synthesised from the intermediate above using a procedure similar to that described for steps b-e of Example 2. LCMS: Method A, RT 2.68 min, MS: ES+ 312.32; $^1$H NMR (400 MHz, DMSO-$d_6$) δ ppm 9.72-9.73 (m, 1H), 9.34 (dd, J=5.60, 1.20 Hz, 1H), 8.82 (d, J=6.40 Hz, 1H), 8.11 (dd, J=5.60, 2.80 Hz, 1H), 7.99 (dd, J=11.60, 1.60 Hz, 1H), 7.89 (dd, J=8.40, 2.00 Hz, 1H), 7.74 (t, J=7.60 Hz, 1H), 4.44-4.51 (m, 1H), 3.63-3.70 (m, 1H), 3.39-3.56 (m, 2H), 3.28-3.32 (m, 1H), 2.09-2.18 (m, 1H), 1.89-1.97 (m, 1H)

Example 153 (R)—N-(1-cyanopyrrolidin-3-yl)-1-isobutyl-6-(1-methyl-1H-pyrazol-4-yl)-1H-indazole-3-carboxamide

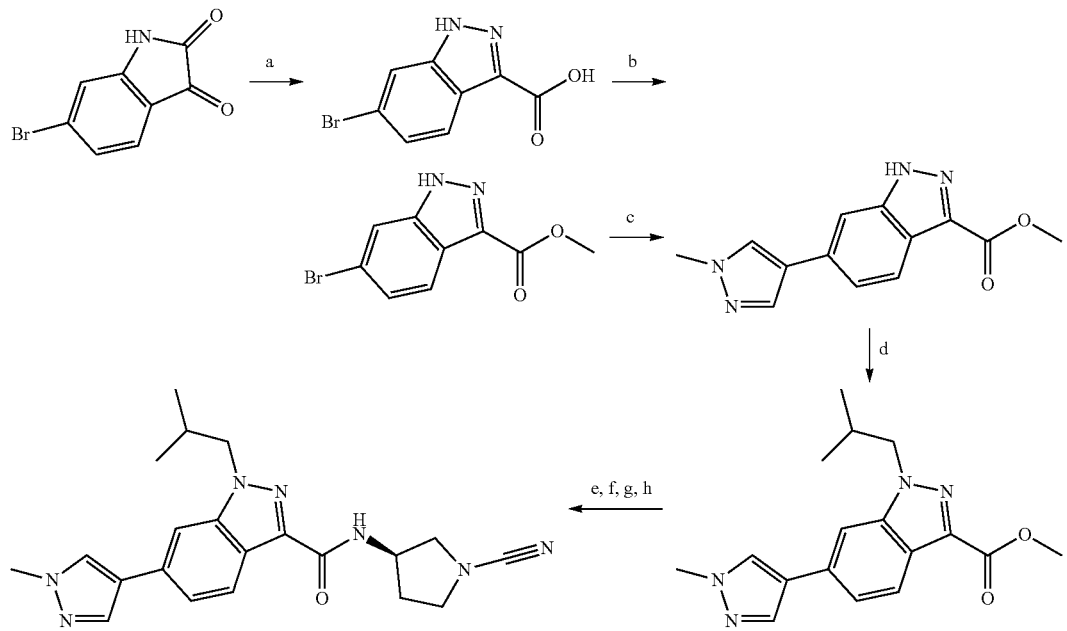

Step a.

To a mixture of 6-bromoindoline-2,3-dione (5 g, 22.12 mmol) in water (55 ml) was added NaOH (0.97 g, 24.3 mmol) at rt. The reaction mixture was stirred at rt for 30 min. A solution of NaNO₂ (1.68 g, 24.3 mmol) in 30 ml water was added dropwise to the reaction mixture at 5° C. over a period of 30 min. The reaction mixture was stirred at 5° C. for 20 min. The resulting reaction mixture was transferred into a dropping funnel and added dropwise to a solution of H₂SO₄ (4.5 ml) in water (55 ml) at a temperature below 10° C. over a period of 25 min. The resulting reaction mixture was stirred at 10° C. for 20 min. A solution of tin (II) chloride (10.06 g, 53.1 mmol) in concentrated HCl (21 ml) was added dropwise to the reaction mixture at 5° C. The reaction mixture was stirred at 5° C. for 2 h. The resulting reaction mixture was filtered off under vacuum. The desired solids were washed with hexane (4×50 ml) and dried under high vacuum to yield 6-bromo-1H-indazole-3-carboxylic acid (5.95 g, 24.9 mmol). LCMS: Method C, RT 1.66 min, MS: ES+ 239.20, 241.20

Step b.

To a solution of 6-bromo-1H-indazole-3-carboxylic acid (5.95 g, 24.9 mmol) in MeOH (95 ml) was added H₂SO₄ (5.8 ml, 58.0 mmol) at rt. The reaction mixture was heated at 90° C. for 3.5 h. The resulting reaction mixture was concentrated under reduced pressure. The obtained residue was dumped in to saturated aqueous NaHCO₃ solution (250 ml) and extracted with EtOAc (4×200 ml). The combined organic layer was washed with brine (2×150 ml), dried over Na₂SO₄, filtered and concentrated under reduced pressure. The resulting residue was purified by column chromatography (11% EtOAc in hexane) yielding methyl 6-bromo-1H-indazole-3-carboxylate (1.81 g, 7.98 mmol). LCMS: Method C, RT 2.08 min, MS: ES+ 255.13, 257.10.

Step c.

To a mixture of 6-bromo-1H-indazole-3-carboxylic acid (0.25 g, 0.98 mmol) in DMF (3 ml) and water (3 ml) was added 1-methyl-4-(4,4,5,5-tetramethyl-1,3,2-dioxaborolan-2-yl)-1H-pyrazole (0.30 g, 2.07 mmol) at rt, followed by NaHCO₃ (0.33 g, 3.92 mmol). The reaction mixture was degassed with N₂ for 15 min, PdCl₂(dppf) (0.071 g, 0.098 mmol) was added to the reaction mixture at rt. The reaction mixture was heated at 140° C. for 1.5 h. The resulting reaction mixture was poured into cold water (150 ml) and extracted with EtOAc (2×100 ml). The combined organic layer was washed with brine (100 ml), dried over Na₂SO₄, filtered and concentrated under reduced pressure to yield methyl 6-(1-methyl-1H-pyrazol-4-yl)-1H-indazole-3-carboxylate (0.31 g, 1.21 mmol). LCMS: Method A, RT 3.29 min, MS: ES+ 256.19.

Step d.

To a solution of methyl 6-(1-methyl-1H-pyrazol-4-yl)-1H-indazole-3-carboxylate (0.31 g, 1.21 mmol) in DMF (7 ml) were added Cs₂CO₃ (0.59 g, 1.81 mmol) and 1-iodo-2-methylpropane (0.16 ml, 1.45 mmol) at rt. The reaction mixture was stirred at rt for 2 h. The reaction mixture was poured into cold water (150 ml) and extracted with EtOAc (2×100 ml). The combined organic layer was washed with brine (100 ml), dried over Na₂SO₄, filtered and concentrated under reduced pressure yielding a mixture of methyl 1-isobutyl-6-(1-methyl-1H-pyrazol-4-yl)-1H-indazole-3-carboxylate (0.027 g, 0.08 mmol) LCMS: Method C, RT 2.24 min, MS: ES+ 313.38, ¹H NMR (400 MHz, DMSO-d₆) δ ppm 8.29 (s, 1H), 8.03 (d, J=4.8 Hz, 2H), 8.0 (s, 1H), 7.57 (dd, J=1.2, 8.4 Hz, 1H), 4.33 (d, J=7.2 Hz, 2H), 3.91 (s, 3H), 3.89 (s, 3H), 2.27-2.33 (m, 1H), 0.88 (d, J=6.4 Hz, 6H) and methyl 2-isobutyl-6-(1-methyl-1H-pyrazol-4-yl)-2H-indazole-3-carboxylate (0.007 g, 0.022 mmol). LCMS: Method C, RT 2.40 min, MS: ES+ 313.43.

Steps e-h.

The title compound was synthesised from the intermediate above using a procedure similar to that described for steps b-e of Example 2. LCMS: Method A, RT 3.98 min, MS: ES+ 392.23; $^1$H NMR (400 MHz, DMSO-$d_6$) δ ppm 8.60 (d, J=7.2 Hz, 1H), 8.28 (s, 1H), 8.09 (d, J=8.4 Hz, 1H), 8.02 (s, 1H), 7.97 (s, 1H), 7.50 (d, J=8.4 Hz, 1H), 4.54-4.58 (m, 1H), 4.30 (d, J=7.2 Hz, 2H), 3.89 (s, 3H), 3.55-3.66 (m, 2H), 3.39-3.47 (m, 2H), 2.33-2.37 (m, 1H), 2.11-2.16 (m, 1H), 2.01-2.06 (m, 1H), 0.90 (d, J=6.4 Hz, 6H).

Example 154 (R)—N-(1-cyanopyrrolidin-3-yl)-6-(3,5-dimethylisoxazol-4-yl)-1-isobutyl-1H-indazole-3-carboxamide

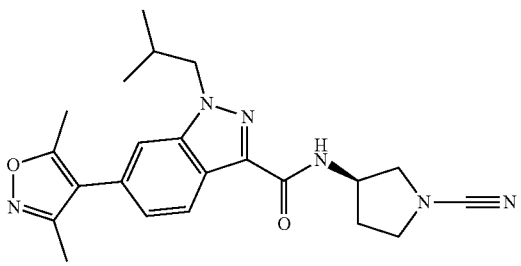 [SMILES: Cc1noc(C)c1-c1ccc2c(C(=O)N[C@@H]3CCN(C#N)C3)nn(CC(C)C)c2c1]

Synthesised using a procedure similar to that described for Example 153 using 3,5-dimethylisoxazole-4-boronic acid (CAS Number 16114-47-9) in step c. LCMS: Method A, RT 4.54 min, MS: ES+ 407.07; 1H NMR (400 MHz, DMSO-$d_6$) δ ppm 8.67 (d, J=6.8 Hz, 1H), 8.21 (d, J=8.0 Hz, 1H), 7.82 (s, 1H), 7.27 (dd, J=8.8, J=1.2 Hz, 1H), 4.57-4.58 (m, 1H), 4.35 (d, J=7.2 Hz, 1H), 3.55-3.66 (m, 2H), 3.33-3.48 (m, 2H), 2.44-2.46 (m, 4H), 2.28-2.33 (m, 4H), 1.99-2.15 (m, 2H), 0.85-0.89 (m, 6H).

Example 155 (R)—N-(1-cyanopyrrolidin-3-yl)-1-(cyclopropylmethyl)-6-(3,5-dimethylisoxazol-4-yl)-1H-indazole-3-carboxamide

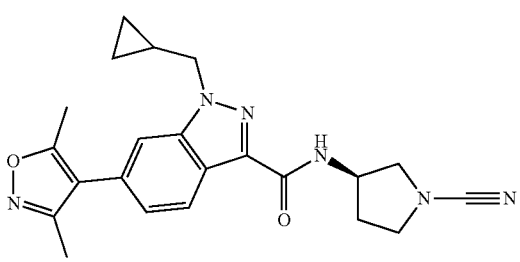 [SMILES: Cc1noc(C)c1-c1ccc2c(C(=O)N[C@@H]3CCN(C#N)C3)nn(CC3CC3)c2c1]

Synthesised using a procedure similar to that described for Example 154 using cyclopropylmethyl bromide (CAS Number 7051-34-5) in step d. LCMS: Method A, RT 4.37 min, MS: ES+ 404.99; $^1$H NMR (400 MHz, DMSO-$d_6$) δ ppm 8.68 (d, J=7.2 Hz, 1H), 8.22 (d, J=8.4 Hz, 1H), 7.83 (s, 1H), 7.28 (dd, J=8.4, 1.2 Hz, 1H), 4.56-4.61 (m, 1H), 4.43-4.45 (m, 2H), 3.56-3.67 (m, 2H), 3.39-3.48 (m, 2H), 2.46 (s, 3H), 2.29 (s, 3H), 2.13-2.18 (m, 1H), 2.03-2.11 (m, 1H), 1.34-1.38 (m, 1H), 0.44-0.54 (m, 4H).

Example 156 (R)—N-(1-cyanopyrrolidin-3-yl)-N-methyl-6-(1-methyl-H-pyrazol-4l-yl)imidazo[1,2-a]pyridine-2-carboxamide

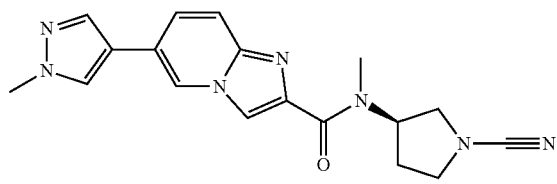 [SMILES: CN(C(=O)c1cn2cc(-c3cnn(C)c3)ccc2n1)[C@@H]1CCN(C#N)C1]

Synthesised using a procedure similar to that described for Example 3 using (R)-tert-butyl 3-(methylamino)pyrrolidine-1-carboxylate (CAS Number 199336-83-9). LCMS: Method A, RT 2.87 min, MS: ES+ 350.17; 1H NMR (400 MHz, DMSO-$d_6$) δ ppm 8.82 (s, 1H), 8.24 (s, 1H), 8.19 (s, 1 H), 7.89 (s, 1H), 7.65 (d, J=9.2 Hz, 1H), 7.58 (dd, J=9.2, 1.2 Hz, 1H), 3.89 (s, 3H), 3.54-3.64 (m, 2H), 3.43-3.47 (m, 3H), 3.37 (s, 3H), 2.07-2.17 (m, 2H).

Example 157 (R)—N-(1-cyanopyrrolidin-3-yl)-N-methyl-5-(1-methyl-1H-pyrazol-4-yl)-1H-indole-2-carboxamide

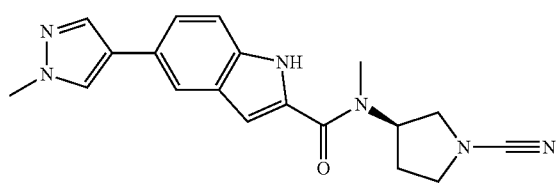 [SMILES: CN(C(=O)c1cc2cc(-c3cnn(C)c3)ccc2[nH]1)[C@@H]1CCN(C#N)C1]

Synthesised using a procedure similar to that described for Example 3 using (R)-tert-butyl 3-(methylamino)pyrrolidine-1-carboxylate (CAS Number 199336-83-9). LCMS: Method A, RT 3.38 min, MS: ES+ 349.11; 1H NMR (400 MHz, DMSO-$d_6$) δ ppm 11.56 (s, 1H), 8.05 (s, 1H), 7.81 (s, 1H), 7.77 (s, 1H), 7.41 (s, 2H), 6.85 (s, 1H), 5.16 (t, J=8.0 Hz, 1H), 3.86 (s, 3H), 3.57-3.66 (m, 2H), 3.40-3.49 (m, 2H), 3.13 (s, 3H), 2.08-2.17 (m, 2H).

Example 158 (R)—N-(1-cyanopyrrolidin-3-yl)-6-(3,5-dimethylisoxazol-4-yl)-N-methyl-1H-benzo[d]imidazole-2-carboxamide

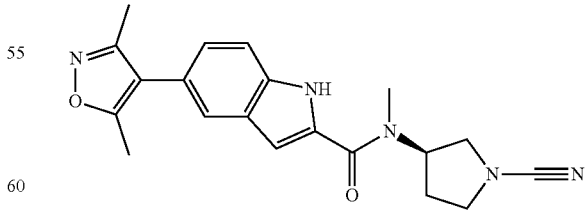

Synthesised using a procedure similar to that described for Example 3 using (R)-tert-butyl 3-(methylamino)pyrrolidine-1-carboxylate (CAS Number 199336-83-9). LCMS: Method B, RT 3.45 min, MS: ES+ 365.3; $^1$H NMR (400 MHz, DMSO-$d_6$) δ ppm 13.02 (s, 1H), 7.49-7.82 (m, 2H), 7.28 (s, 1H), 3.59-3.71 (m, 2H), 3.44-3.54 (m, 3H), 3.02-3.09 (m, 3H), 2.42 (s, 3H), 2.24 (s, 3H), 2.13-2.21 (m, 2H).

Example 159 (R)—N-(1-cyanopyrrolidin-3-yl)-7-(1-methyl-1H-pyrazol-4-yl)imidazo[1,2-a]pyridine-3-carboxamide

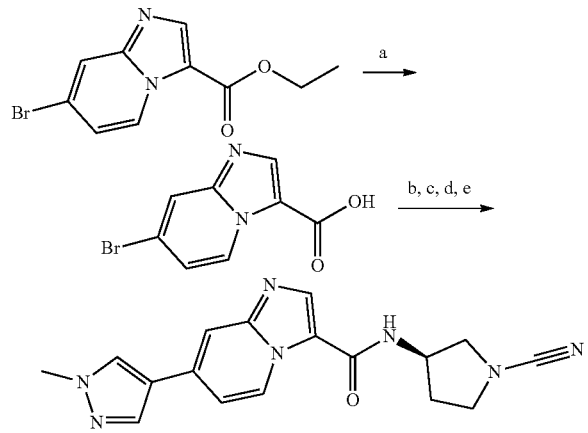

Step a.

To a solution of 7-bromo-imidazo[1,2-a]pyridine-3-carboxylic acid ethyl ester (0.2 g, 0.743 mmol) in THF: water (1:1) (12 ml) was added LiOH.H$_2$O (0.062 g, 1.49 mmol) at 0° C. The reaction mixture was stirred at rt for 6 h. The resulting reaction mixture was acidified to pH 4 by dropwise addition of 10% citric acid solution and stirred for 10 min. The resulting solids were filtered off under vacuum and dried to yield 7-bromoimidazo[1,2-a]pyridine-3-carboxylic acid (0.16 g, 0.666 mmol). LCMS: Method C, RT 1.39 min, MS: ES+ 241.08, 242.99

Steps b-e.

The title compound was synthesised from the intermediate above using a procedure similar to that described for Example 3 to provide the title compound. LCMS: Method B, RT 2.76 min, MS: ES+ 336.32; $^1$H NMR (400 MHz, DMSO-d$_6$) δ ppm 9.33-9.37 (m, 1H), 8.54 (d, J=6.4 Hz, 1H), 8.38 (s, 1H), 8.35 (s, 1H), 8.10 (s, 1H), 7.90 (d, J=0.8 Hz, 1H), 7.40 (dd, J=2 Hz, 7.2 Hz, 1H), 4.51-4.55 (m, 1H), 3.89 (s, 3H), 3.65-3.69 (m, 1H), 3.54-3.60 (m, 1H), 3.44-3.50 (m, 1H), 3.31-3.35 (m, 1H), 2.12-2.21 (m, 1H), 1.94-2.01 (m, 1H)

Example 160 (R)-7-(3-cyanophenyl)-N-(1-cyanopyrrolidin-3-yl)imidazo[,2-a]pyridine-3-carboxamide

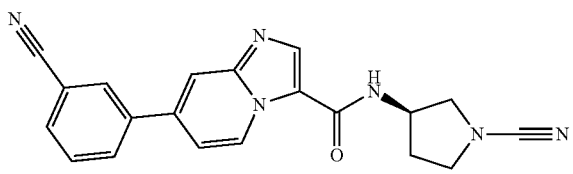 [SMILES: N#Cc1cccc(-c2ccn3c(C(=O)N[C@@H]4CCN(C#N)C4)cnc3c2)c1]

Synthesised using a procedure similar to that described for Example 159. LCMS: Method A, RT 3.69 min, MS: ES+ 357.16; $^1$H NMR (400 MHz, DMSO-d$_6$) δ ppm 9.48 (d, J=7.6 Hz, 1H), 8.68 (d, J=6.8 Hz, 1H), 8.44 (s, 1H), 8.41 (d, J=1.6 Hz, 1H), 8.20-8.25 (m, 2H), 7.91 (d, J=8 Hz, 1H), 7.73 (t, J=7.6 Hz, 1H), 7.62 (dd, J=2 Hz, 7.6 Hz, 1H), 4.53-4.57 (m, 1H), 3.67-3.71 (m, 1H), 3.55-3.61 (m, 1H), 3.47-3.51 (m, 1H), 3.33-3.36 (m, 1H), 2.15-2.20 (m, 1H), 1.96-2.01 (m, 1H)

Example 161 (R)—N-(1-cyanopyrrolidin-3-yl)-N-methyl-7-(2-methylpyridin-4-yl)imidazo[1,2-a]pyridine-3-carboxamide

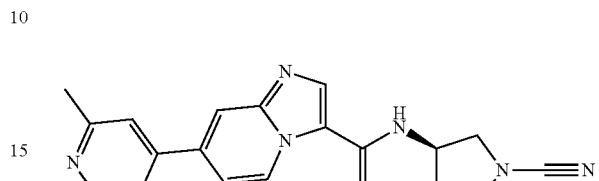

Synthesised using a procedure similar to that described for Example 159. LCMS: Method A, RT 3.04 min, MS: ES+ 361.09; $^1$H NMR (400 MHz, DMSO-d$_6$) δ ppm 9.04 (d, J=7.2 Hz, 1H), 8.57 (d, J=5.2 Hz, 1H), 8.28 (s, 1H), 8.18 (s, 1H), 7.83 (s, 1H), 7.73 (d, J=5.2 Hz, 1H), 7.59 (dd, J=2.0 Hz, 7.6 Hz, 1H), 5.11-5.15 (m, 1H), 3.57-3.69 (m, 2H), 3.35-3.50 (m, 2H), 3.13 (s, 3H), 2.57 (s, 3H), 2.10-2.22 (m, 2H)

Example 162 (R)—N-(1-cyanopyrrolidin-3-yl)-N-methyl-7-(6-methylpyridin-3-yl)imidazo[1,2-a]pyridine-3-carboxamide

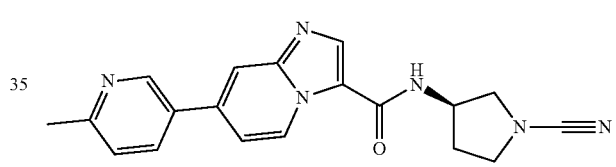

Synthesised using a procedure similar to that described for Example 159. LCMS: Method A, RT 3.15 min, MS: ES+ 361.09; $^1$H NMR (400 MHz, DMSO-d$_6$) δ ppm 9.03 (d, J=7.2 Hz, 1H), 8.97 (d, J=2.0 Hz, 1H), 8.14-8.20 (m, 3H), 7.53 (dd, J=1.6 Hz, 7.2 Hz, 1H), 7.40 (d, J=8.4 Hz, 1H), 5.12-5.15 (m, 1H), 3.57-3.69 (m, 2H), 3.40-3.50 (m, 2H), 3.13 (s, 3H), 2.54 (s, 3H), 2.10-2.21 (m, 2H)

Example 163 (R)—N-(1-cyanopyrrolidin-3-yl)-7-(1,3-dimethyl-1H-pyrazol-4-yl)-N-methylimidazo[1,2-a]pyridine-3-carboxamide

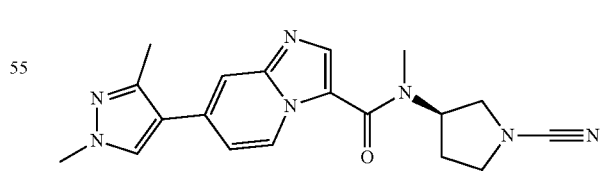

Synthesised using a procedure similar to that described for Example 159. LCMS: Method A, RT 3.06 min, MS: ES+ 364.15; 1H NMR (400 MHz, DMSO-d$_6$) δ ppm 8.94 (d, J=7.2 Hz, 1H), 8.19 (s, 1H), 8.10 (s, 1H), 7.67 (s, 1H), 7.27 (dd, J=7.2, 2 Hz, 1H), 5.08-5.15 (m, 1H), 3.81 (s, 3H), 3.56-3.67 (m, 2H), 3.39-3.47 (m, 2H), 3.11 (s, 3H), 2.41 (s, 3H), 2.08-2.23 (m, 2H).

Example 164 (R)—N-(1-cyanopyrrolidin-3-yl)-7-(2,6-dimethylpyridin-4-yl)-N-methylimidazo[1,2-a]pyridine-3-carboxamide

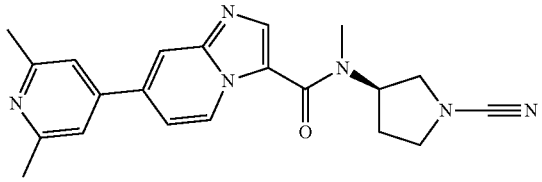 [SMILES: Cc1cc(-c2ccn3c(C(=O)N(C)[C@@H]4CCN(C#N)C4)cnc3c2)cc(C)n1]

Synthesised using a procedure similar to that described for Example 159. LCMS: Method A, RT 3.28 min, MS: ES+ 375.0; H NMR (400 MHz, MeOD) δ ppm 9.11 (d, J=7.6 Hz, 1H), 8.13 (s, 1H), 8.05 (s, 1H), 7.50-7.61 (m, 3H), 5.19-5.26 (m, 1H), 3.68-3.77 (m, 2H), 3.50-3.61 (m, 2H), 3.28 (s, 3H), 2.61 (s, 6H), 2.24-2.35 (m, 2H).

Example 165 (R)—N-(1-cyanopyrrolidin-3-yl)-N-ethyl-7-(2-methylpyridin-4-yl)imidazo[1,2-a]pyridine-3-carboxamide

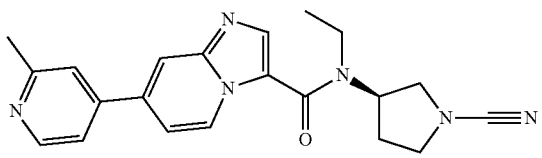 [SMILES: CCN(C(=O)c1cnc2cc(-c3ccnc(C)c3)ccn12)[C@@H]1CCN(C#N)C1]

Synthesised using a procedure similar to that described for Example 159. LCMS: Method A, RT 3.37 min, MS: ES+ 375.0; $^1$H NMR (400 MHz, DMSO-$d_6$) δ ppm 8.96 (d, J=7.1 Hz, 1H), 8.56 (d, J=5.2 Hz, 1H), 8.26 (s, 1H), 8.01 (s, 1H), 7.80 (s, 1H), 7.70 (d, J=5.2 Hz, 1H), 7.52-7.58 (m, 1H), 4.86-4.90 (m, 1H), 3.69-3.73 (m, 1H), 3.38-3.61 (m, 5H), 2.56 (s, 3H), 2.16-2.23 (m, 2H), 1.23 (t, J=6.8 Hz, 3H).

Example 166 (R)—N-(1-cyanopyrrolidin-3-yl)-7-morpholinoimidazo[1,2-a]pyridine-3-carboxamide

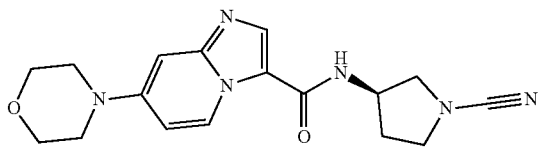 [SMILES: N#CN1CC[C@@H](NC(=O)c2cnc3cc(N4CCOCC4)ccn23)C1]

Synthesised using a procedure similar to that described for Example 91 using 7-bromoimidazo[1,2-a]pyridine-3-carboxylic acid (prepared according to the method described for Example 159, step a). LCMS: Method A, RT 2.92 min, MS: ES+ 341.19; 1H NMR (400 MHz, DMSO-$d_6$) δ ppm 9.16 (d, J=8.0 Hz, 1H), 8.35 (d, J=6.4 Hz, 1H), 8.18 (s, 1H), 7.04 (dd, J=2.4 Hz, 7.6 Hz, 1H), 6.81 (d, J=2.0 Hz, 1H), 4.47-4.51 (m, 1H), 3.73-3.76 (m, 4H), 3.63-3.67 (m, 1H), 3.53-3.59 (m, 1H), 3.44-3.48 (m, 1H), 3.25-3.33 (m, 5H), 2.09-2.18 (m, 1H), 1.91-1.98 (m, 1H).

Example 167 (R)-6-(3-cyanophenyl)-N-(1-cyanopyrrolidin-3-yl)-3-fluoroimidazo[1,2-a]pyridine-2-carboxamide

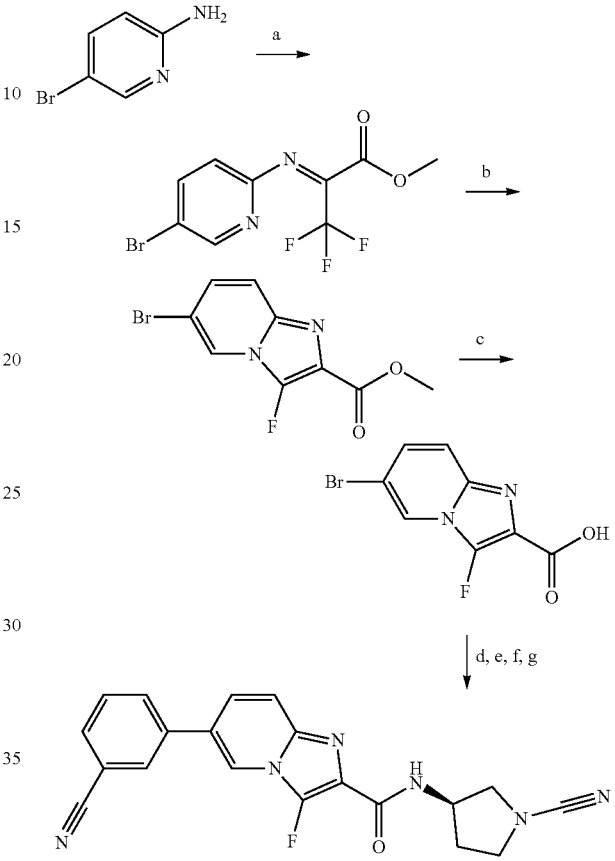

Step a.
To a solution of 5-bromopyridin-2-amine (5 g, 28.9 mmol) in toluene (30 ml) were added methyl 3,3,3-trifluoro-2-oxopropanoate (CAS Number 13089-11-7) (4.5 g, 28.9 mmol) and pyridine (4.65 ml, 57.8 mmol) at rt. The reaction mixture was stirred at rt for 5 min before SOCl$_2$ (3.43 g, 28.9 mmol) was added dropwise to the reaction mixture. The reaction mixture was stirred at rt for 16 h. The resulting reaction mixture was poured into cold water (200 ml) and basified with solid NaHCO$_3$. The resulting mixture was extracted with EtOAc (3×100 ml). The combined organic layer was dried over Na$_2$SO$_4$, filtered and concentrated under reduced pressure. The resulting residue was purified by column chromatography (1% EtOAc in hexane) yielding methyl (Z)-2-((5-bromopyridin-2-yl)imino)-3,3,3-trifluoropropanoate (5 g, 16.07 mmol). LCMS: Method C, RT 2.75 min, MS: ES+ 313.10, 315.10

Step b.
To a solution of methyl (Z)-2-((5-bromopyridin-2-yl)imino)-3,3,3-trifluoropropanoate (5 g, 16.1 mmol) in MeCN (50 ml) was added trimethyl phosphite (2.99 g, 24.1 mmol) at rt. The reaction mixture was heated at 80° C. for 24 h. The resulting reaction mixture was cooled to rt and poured into cold water (150 ml) followed by addition of 5% K$_2$CO$_3$ solution (100 ml). The resulting mixture was extracted with EtOAc (3×100 ml). The combined organic layer was washed with brine (100 ml), dried over Na$_2$SO$_4$, filtered and concentrated under reduced pressure. The resulting residue was purified by column chromatography (25% EtOAc in hexane) yielding methyl 6-bromo-3-fluoroimidazo[1,2-a]pyridine-2-carboxylate (1.5 g, 5.49 mmol). LCMS: Method C, RT 1.94 min, MS: ES+ 273.10, 275.13

Step c.

A mixture of methyl 6-bromo-3-fluoroimidazo[1,2-a]pyridine-2-carboxylate (1.5 g, 5.49 mmol) in concentrated HCl was heated at 100° C. for 2.5 h. The resulting reaction mixture was concentrated under reduced pressure. The obtained residue was azeotropically distilled with DCM (3×10 ml) and dried under reduced pressure to yield 6-bromo-3-fluoroimidazo[1,2-a]pyridine-2-carboxylic acid HCl salt (1.2 g, 4.06 mmol). LCMS: Method C, RT 1.68 min, MS: ES+ 259.30, 261.30

Steps d-g.

The title compound was synthesised from the intermediate above using a procedure similar to that described for Example 3 to provide the title compound. LCMS: Method A, RT 3.80 min, MS: ES+ 374.99; $^1$H NMR (400 MHz, DMSO-$d_6$) δ ppm 8.83 (s, 1H), 8.76 (d, J=7.2 Hz, 1H), 8.36 (s, 1H), 8.16 (d, J=8.0 Hz, 1H), 7.90 (d, J=7.6 Hz, 1H), 7.80 (dd, J=1.6 Hz, 9.6 Hz, 1H), 7.72 (t, J=8.0 Hz, 1H), 7.66 (d, J=9.2 Hz, 1H), 4.50-4.55 (m, 1H), 3.54-3.63 (m, 2H), 3.37-3.47 (m, 2H), 2.01-2.14 (m, 2H).

Compounds in Table 8 were synthesised using a procedure similar to that described for Example 167.

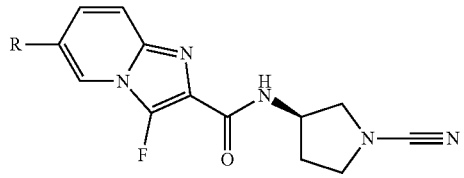

TABLE 8

| Ex | R | Name | $^1$H NMR (400 MHz, DMSO-$d_6$) δ ppm | LCMS Method | LCMS RT (min) | MS |
|---|---|---|---|---|---|---|
| 168 | 1-methyl-1H-pyrazol-4-yl | (R)-N-(1-cyanopyrrolidin-3-yl)-3-fluoro-6-(1-methyl-1H-pyrazol-4-yl)imidazo[1,2-a]pyridine-2-carboxamide | 8.69 (d, J = 7.2 Hz, 1 H), 8.58 (s, 1 H), 8.30 (s, 1 H), 8.04 (s, 1 H), 7.61-7.64 (m, 1 H), 7.54-7.57 (m, 1 H), 4.49-4.54 (m, 1 H), 3.88 (s, 3 H), 3.55-3.62 (m, 2 H), 3.36-3.43 (m, 2 H), 1.99-2.13 (m, 2 H) | A | 2.98 | ES+ 354.2 |
| 169 | 1-ethyl-1H-pyrazol-4-yl | (R)-N-(1-cyanopyrrolidin-3-yl)-6-(1-ethyl-1H-pyrazol-4-yl)-3-fluoroimidazo[1,2-a]pyridine-2-carboxamide | 8.68 (d, J = 7.2 Hz, 1 H), 8.59 (s, 1 H), 8.37 (s, 1 H), 8.05 (s, 1 H), 7.64 (dd, J = 9.2, 2.0 Hz, 1 H), 7.56 (d, J = 9.6 Hz, 1 H), 4.49-4.54 (m, 1 H), 4.14-4.19 (m, 2 H), 3.53-3.62 (m, 2 H), 3.35-3.47 (m, 2 H), 2.01-2.11 (m, 2 H), 1.42 (t, J = 7.2 Hz, 3 H) | B | 3.22 | ES+ 368.2 |
| 170 | 1,3-dimethyl-1H-pyrazol-4-yl | (R)-N-(1-cyanopyrrolidin-3-yl)-6-(1,3-dimethyl-1H-pyrazol-4-yl)-3-fluoroimidazo[1,2-a]pyridine-2-carboxamide | 8.69 (d, J = 7.2 Hz, 1 H), 8.22 (s, 1 H), 8.05 (s, 1 H), 7.58 (d, J = 9.6 Hz, 1 H), 7.47 (dd, J = 9.6, 1.2 Hz, 1 H), 4.49-4.54 (m, 1 H), 3.81 (s, 3 H), 3.53-3.63 (m, 2 H), 3.35-3.47 (m, 2 H), 2.34 (s, 3 H), 2.00-2.13 (m, 2 H) | A | 3.11 | ES+ 368.1 |
| 171 | 3,5-dimethylisoxazol-4-yl | (R)-N-(1-cyanopyrrolidin-3-yl)-6-(3,5-dimethylisoxazol-4-yl)-3-fluoroimidazo[1,2-a]pyridine-2-carboxamide | 8.75 (d, J = 7.2 Hz, 1 H), 8.42 (s, 1 H), 7.63 (d, J = 9.6 Hz, 1 H), 7.40 (dd, J = 10.4, 1.6 Hz, 1 H), 4.50-4.55 (m, 1 H), 3.54-3.63 (m, 2 H), 3.36-3.47 (m, 2 H), 2.45 (s, 3 H), 2.26 (s, 3 H), 2.00-2.14 (m, 2 H) | B | 3.34 | ES+ 369.2 |

Example 172 (R)—N-(1-cyanopyrrolidin-3-yl)-2-fluoro-4-(pyrazolo[1,5-a]pyrimidin-5-yl)benzamide

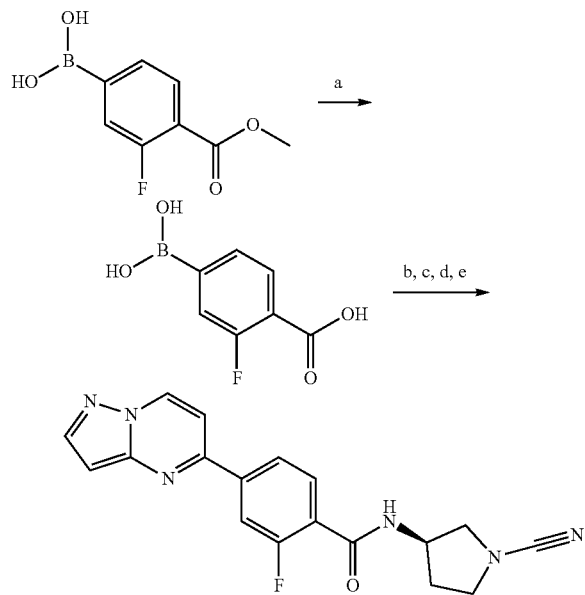

Step a.

To a solution of 3-fluoro-4-(methoxycarbonyl)phenyl) boronic acid (CAS Number 505083-04-5) (0.50 g, 2.50 mmol) in THF: water (5:2, 14 ml) was added LiOH.H₂O (0.32 g, 7.57 mmol) at 0° C. The reaction mixture was stirred at rt for 24 h then heated at 60° C. for 1 h. The resulting reaction mixture was cooled to rt and acidified using 1M HCl solution. The resulting mixture was extracted with EtOAc (3×50 ml). The combined organic phase was dried over Na₂SO₄, filtered and concentrated under reduced pressure yielding 4-borono-2-fluorobenzoic acid (0.42 g, 2.31 mmol). LCMS: Method C, RT 1.32 min, MS: ES-183.20; 1H NMR (400 MHz, DMSO-d₆) δ ppm 13.22 (s, 1H), 8.42 (s, 2H), 7.81 (t, J=7.60 Hz, 1H), 7.65 (d, J=7.60 Hz, 1H), 7.59 (d, J=4.00 Hz, 1H)

Steps b-e.

The title compound was synthesised from the intermediate above using a procedure similar to that described for Example 3 to provide the title compound. LCMS: Method A, RT 3.38 min, MS: ES+ 351.04; ¹H NMR (400 MHz, DMSO-d₆) δ ppm 8.27 (d, J=7.60 Hz, 1H), 8.82 (d, J=6.80 Hz, 1H), 8.29 (d, J=2.40 Hz, 1H), 8.13-8.18 (m, 2H), 7.75-7.77 (m, 2H), 6.83 (d, J=2.40 Hz, 1H), 4.47-4.49 (m, 1H), 3.63-3.67 (m, 1H), 3.40-3.56 (m, 2H), 3.28-3.30 (m, 1H), 2.10-2.17 (m, 1H), 1.91-1.96 (m, 1H)

Example 173 (R)—N-(1-cyanopyrrolidin-3-yl)-5-(4-fluorophenyl)picolinamide

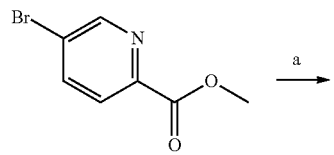

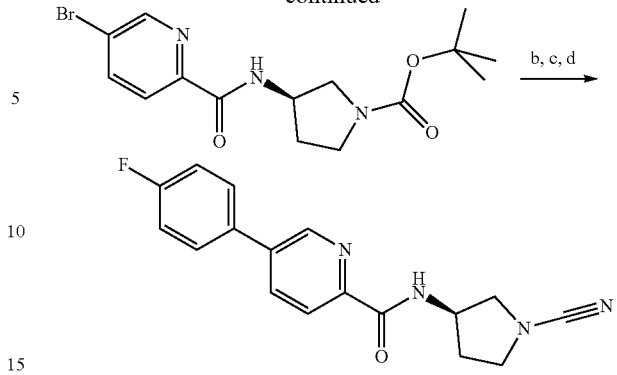

Step a.

To a solution of methyl 5-bromopicolinate (CAS Number 29682-15-3) (1 g, 4.62 mmol) in THF (10 ml) were added DIPEA (1.79 g, 13.9 mmol) and tert-butyl (R)-3-aminopyrrolidine-1-carboxylate (1.03 g, 5.55 mmol) at rt followed by trimethylaluminium (2 M in toluene) (11.5 ml, 2.34 mmol). The reaction mixture was heated at 70° C. for 2 h. The resulting reaction mixture was poured into saturated NH₄Cl solution (150 ml) and the mixture was filtered through celite hyflow. The celite bed was washed with EtOAc (50 ml). The filtrate was extracted with EtOAc (3×100 ml). The combined organic phase was dried over Na₂SO₄, filtered and concentrated under reduced pressure. The resulting residue was purified by column chromatography (20% EtOAc in hexane) yielding tert-butyl (R)-3-(5-bromopicolinamido) pyrrolidine-1-carboxylate (1.2 g, 3.24 mmol), LCMS: Method C, RT 2.34 min, MS: ES+ 314.18, 316.18 [M-56]; ¹H NMR (400 MHz, DMSO-d₆) δ ppm 8.94 (d, J=7.2 Hz, 1H), 8.77-8.78 (m, 1H), 8.26 (dd, J=2, 8 Hz, 1H), 7.96 (d, J=8.4 Hz, 1H), 4.42-4.45 (m, 1H), 3.48-3.58 (m, 1H), 3.37-3.39 (m, 1H), 3.21-3.29 (m, 2H), 1.97-2.06 (m, 2H), 1.40 (s, 9H)

Steps b-d.

The title compound was synthesised from the intermediate above using a procedure similar to that described for steps b-d of Example 3 to provide the title compound. LCMS: Method A, RT 4.15 min, MS: ES+ 311.06; ¹H NMR (400 MHz, DMSO-d₆) δ ppm 9.06 (d, J=7.2 Hz, 1H), 8.94 (d, J=2.0 Hz, 1H), 8.28 (dd, J=2.4, 8.4 Hz, 1H), 8.09 (d, J=8.0 Hz, 1H), 7.85-7.89 (m, 2H), 7.39 (t, J=8.8 Hz, 2H), 4.53-4.57 (m, 1H), 3.54-3.64 (m, 2H), 3.39-3.48 (m, 2H), 2.02-2.16 (m, 2H)

Example 174 N-((cis)-1-cyano-2-methylpyrrolidin-3-yl)-5-(4-fluorophenyl)picolinamide

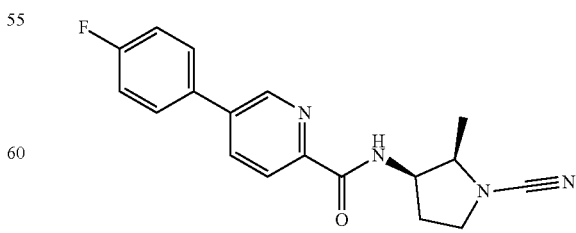

Synthesised as a racemic mixture using a procedure similar to that described for Example 2 using cis-3-amino-1-BOC-2-methylpyrrolidine (CAS Number 1374653-02-7)

in step c. LCMS: Method A, RT 4.35 min, MS: ES+ 324.96; ¹H NMR (400 MHz, DMSO-d₆) δ ppm 8.96 (s, 1H), 8.76 (d, J=8.0 Hz, 1H), 8.29 (d, J=8.0 Hz, 1H), 8.11 (d, J=8.0 Hz, 1H), 7.85-7.89 (m, 2H), 7.39 (t, J=8.8 Hz, 2H), 4.54-4.59 (m, 1H), 3.82-3.87 (m, 1H), 3.63-3.68 (m, 1H), 3.37-3.43 (m, 1H), 2.07-2.21 (m, 2H), 1.08 (t, J=6.4 Hz, 3H).

Example 175 3-chloro-N-((trans)-1-cyano-4-methylpyrrolidin-3-yl)-4-morpholinobenzamide

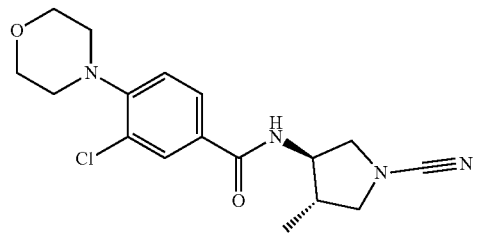 [SMILES: C[C@H]1CN(C#N)C[C@@H]1NC(=O)c1ccc(N2CCOCC2)c(Cl)c1]

Synthesised as a racemic mixture using a procedure similar to that described for Examples 69/70 using 3-chloro-4-morpholinobenzoic acid (CAS Number 26586-20-9) in step e. LCMS: Method B, RT 3.66 min, MS: ES+ 349.10; ¹H NMR (400 MHz, DMSO-d₆) δ ppm 8.52 (d, J=7.2 Hz, 1H), 7.93 (d, J=2.0, 1H), 7.81 (dd, J=8.0, 1.6 Hz, 1H), 7.22 (d, J=8.8 Hz, 1H), 4.09-4.14 (m, 1H), 3.75 (t, J=4.8, 4H), 3.63-3.72 (m, 2H), 3.21-3.25 (m, 1H), 3.06-3.11 (m, 1H), 3.04 (t, J=4.4, 4H), 2.24-2.33 (m, 1H), 1.99 (d, J=6.8, 3H).

Example 176 N-((trans)-1-cyano-4-fluoropyrrolidin-3-yl)-[1,1'-biphenyl]-4-carboxamide

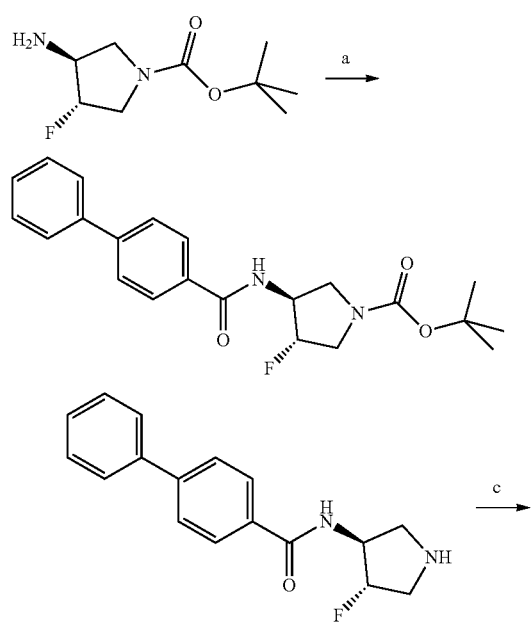

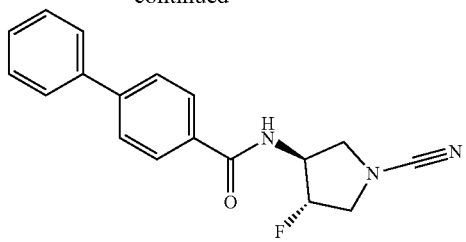

Step a.

To a solution of 4-phenylbenzoic acid (0.110 g, 0.555 mmol) in THF (5 ml) was added DIPEA (0.110 g, 0.852 mmol) and HATU (0.243 g, 0.639 mmol) at rt and stirred for 30 min. Trans-tert-butyl 3-amino-4-fluoropyrrolidine-1-carboxylate (CAS Number 1363382-79-9) (0.100 g, 0.427 mmol) was added to the reaction mixture. The resulting reaction mixture was stirred at rt for 1.5 h. The reaction mixture was poured into saturated NaHCO₃ solution (20 ml) and extracted with EtOAc (2×25 ml). The combined organic layer was dried over Na₂SO₄, filtered and concentrated under reduced pressure. The obtained residue was purified by flash chromatography (10% EtOAc in hexane) yielding trans-tert-butyl 3-([1,1'-biphenyl]-4-carboxamido)-4-fluoropyrrolidine-1-carboxylate (0.170 g, 0.443 mmol). LCMS: Method C, RT 2.52 min, MS: ES-383.45; ¹H NMR (400 MHz, DMSO-d₆) δ ppm 8.72 (d, J=6.4 Hz, 1H), 7.97 (d, J=7.2 Hz, 2H), 7.73-7.82 (m, 4H), 7.48-7.52 (m, 2H), 7.40-7.43 (m, 1H), 4.52-4.54 (m, 1H), 3.63-3.69 (m, 2H), 3.52-3.58 (m, 1H), 3.44-3.50 (m, 2H), 1.44 (s, 9H).

Step b.

A solution of trans-tert-butyl 3-([1,1'-biphenyl]-4-carboxamido)-4-fluoropyrrolidine-1-carboxylate (0.150 g, 0.390 mmol) in formic acid (7.5 ml) was prepared at rt. The resulting reaction mixture was stirred at 50° C. for 3 h. The resulting reaction mixture was evaporated under reduced pressure. The obtained material was co-evaporated with DCM (2×30 ml) and dried under vacuum yielding trans-N-(4-fluoropyrrolidin-3-yl)-[1,1'-biphenyl]-4-carboxamide formic salt (0.140 g, quantitative). LCMS: Method C, RT 1.83 min, MS: ES+ 285.22.

Step c.

The title compound was synthesised from the intermediate above using a procedure similar to that described for step c of Example 1. LCMS: Method H, RT 26.23 min, MS: ES+ 309.92; ¹H NMR (400 MHz, DMSO-d₆) δ ppm 8.75 (d, J=6.4 Hz, 1H), 7.97 (d, J=8.4 Hz, 2H), 7.97 (d, J=8.1 Hz, 2H), 7.73-7.75 (m, 2H), 7.50 (t, J=7.6 Hz, 2H), 7.40-7.44 (m, 1H), 5.12-5.24 (m, 1H), 4.54-4.61 (m, 1H), 3.82-3.89 (m, 1H), 3.65-3.76 (m, 2H), 3.56-3.59 (m, 1H).

Example 177 N-((cis)-1-cyano-4-cyclopropylpyrrolidin-3-yl)-3-fluoro-4-(1-methyl-1H-pyrazol-4-yl)benzamide

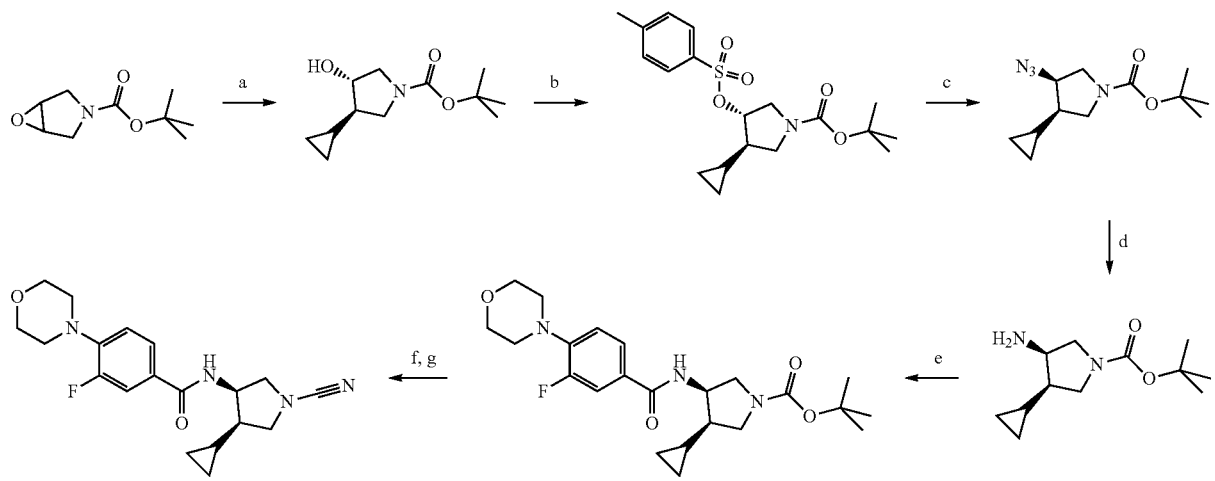

Step a.

A solution of tert-butyl 6-oxa-3-azabicyclo[3.1.0]hexane-3-carboxylate (CAS Number 114214-49-2) (1.00 g, 5.405 mmol) in THF (40 ml) was cooled to −30° C. and treated with copper(I) bromide methyl sulfide complex (0.221 g, 1.078 mmol). A 0.5 M solution of cyclopropylmagnesium bromide in THF (41 ml, 20.5 mmol) was added dropwise to the reaction mixture at −30° C. The reaction mixture was allowed to warm to −10° C. and stirred for 1 h. The resulting mixture was poured into saturated solution of $NH_4Cl$ (500 ml) and extracted with EtOAc (2×70 ml). The combined organic layer was dried over $Na_2SO_4$, filtered and concentrated under reduced pressure. The resulting residue was purified by column chromatography (30% EtOAc in hexane) yielding trans-tert-butyl 3-cyclopropyl-4-hydroxypyrrolidine-1-carboxylate (1.70 g, 7.49 mmol). LCMS: Method A, RT 3.91 min, MS: ES+ 228.00; $^1$H NMR (400 MHz, DMSO-$d_6$) δ ppm: 4.97 (d, J=4.0 Hz, 1H), 3.97-3.99 (m, 1H), 3.59-3.72 (m, 1H), 3.35-3.47 (m, 2H), 3.02-3.07 (m, 2H), 1.37 (s, 9H), 0.55-0.60 (m, 1H), 0.33-0.45 (m, 2H), 0.17-0.23 (m, 1H), 0.06-0.12 (m, 1H).

Step b.

To a solution of trans-tert-butyl 3-cyclopropyl-4-hydroxypyrrolidine-1-carboxylate (1.70 g, 7.49 mmol) in THF (20 ml) was added NaH (60% dispersion in paraffin oil, 0.898 g, 37.42 mmol) at rt. The reaction mixture was stirred at 50° C. for 1 h. The resulting reaction mixture was cooled to rt. A solution of p-toluene sulphonyl chloride (2.800 g, 14.74 mmol) in THF (10 ml) was added dropwise to the reaction mixture and stirred for 16 h. The resulting reaction mixture was poured into water (500 ml) and extracted with EtOAc (2×100 ml). The combined organic layer was dried over $Na_2SO_4$, filtered and concentrated under reduced pressure. The obtained residue was purified by flash chromatography (17% EtOAc in hexane) yielding trans-tert-butyl 3-cyclopropyl-4-(tosyloxy)pyrrolidine-1-carboxylate (1.500 g, 3.94 mmol). LCMS: Method C, RT 2.65 min, MS: ES+326.30 (M-56).

Step c.

To a solution of trans-tert-butyl 3-cyclopropyl-4-(tosyloxy)pyrrolidine-1-carboxylate (1.40 g, 3.67 mmol) in DMF (20 ml) was added $NaN_3$ (4.700 g, 72.31 mmol) at rt. The reaction mixture was heated at 60° C. for 16 h. The resulting reaction mixture was cooled to rt and poured into cold water (400 ml). The resulting mixture was extracted with EtOAc (2×70 ml). The combined organic layer was dried over $Na_2SO_4$, filtered and concentrated under reduced pressure yielding cis-tert-butyl 3-azido-4-cyclopropylpyrrolidine-1-carboxylate (1.00 g, quantitative). This material was used directly for the next step without further purification.

Step d.

To a solution of cis-tert-butyl 3-azido-4-cyclopropylpyrrolidine-1-carboxylate (1.00 g, 3.97 mmol) in MeOH (20 ml) was added 10% Pd on carbon (dry) (1.00 g) at rt. The reaction mixture was purged with hydrogen for 2 h. The resulting reaction mixture was carefully filtered through celite hyflow and the obtained filtrate was concentrated under reduced pressure yielding cis-tert-butyl 3-amino-4-cyclopropylpyrrolidine-1-carboxylate (0.570 g, 2.52 mmol). LCMS: Method A, RT 3.75 min, MS: ES+ 227.00. This material was used directly for the next step without further purification.

Steps e-g.

The title compound was synthesised from the intermediate above using a procedure similar to that described for Example 1. LCMS: Method B, RT 3.64 min, MS: ES+ 354.60; $^1$H NMR (400 MHz, DMSO-$d_6$) δ ppm 8.56 (d, J=8.4 Hz, 1H), 8.24 (d, J=2.0 Hz, 1H), 7.98 (s, 1H), 7.84 (t, J=8.0 Hz, 1H), 7.72-7.78 (m, 2H), 4.64-4.68 (m, 1H), 3.91 (s, 3H), 3.68-3.72 (m, 1H), 3.52-3.57 (m, 1H), 3.37-3.47 (m, 2H), 1.68-1.74 (m, 1H), 0.69-0.85 (m, 1H), 0.39-0.42 (m, 2H), 0.35-0.38 (m, 2H).

Example 178 N-((trans)-1-cyano-4-methoxypyrrolidin-3-yl)-N-methyl-4-(1-methyl-1H-pyrazol-4-yl) benzamide

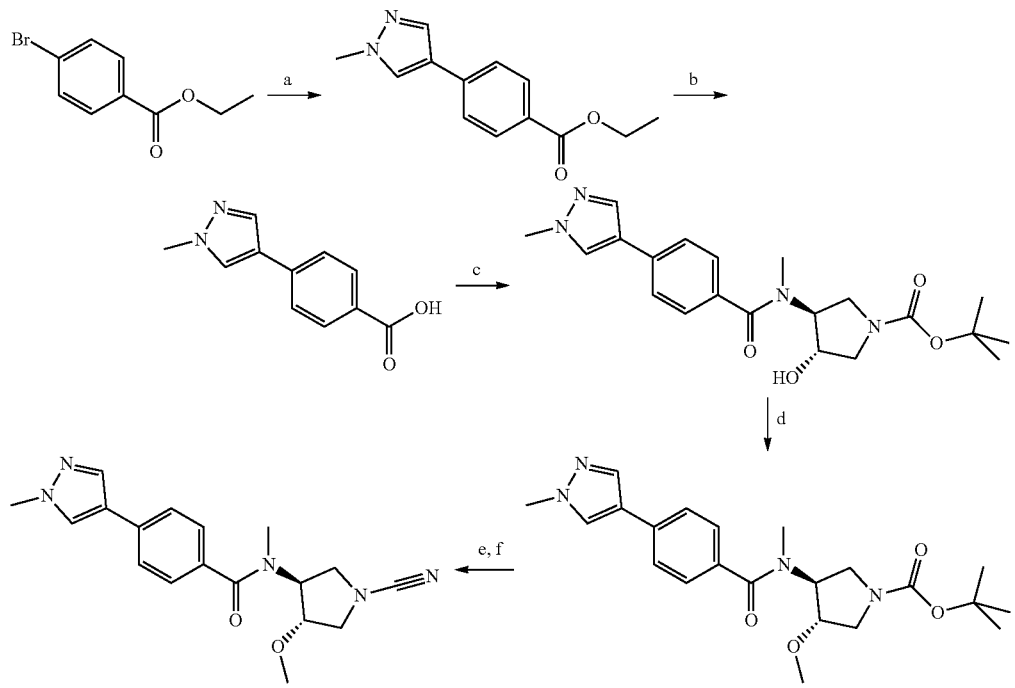

Step a.

To a solution of ethyl 4-bromobenzoate (4.00 g, 17.47 mmol) in 1,4-dioxane (10 ml) was added 1-methyl-4-(4,4,5,5-tetramethyl-1,3,2-dioxaborolan-2-yl)-1H-pyrazole (CAS Number 761446-44-0) (5.44 g, 26.20 mmol) at rt. The resulting reaction mixture was degassed for 30 min before addition of Pd(PPh$_3$)$_4$ (0.201 g, 0.174 mmol) and K$_2$CO$_3$ (4.82 g, 34.93 mmol) at rt. The reaction mixture was heated at 90° C. for 15 h. The resulting reaction mixture was cooled to rt and poured into saturated aqueous NaHCO$_3$ (10 ml). The resulting mixture was extracted with EtOAc (2×100 ml). The combined organic layer was dried over Na$_2$SO$_4$, filtered and concentrated under reduced pressure yielding ethyl 4-(1-methyl-1H-pyrazol-4-yl) benzoate (4.00 g, 17.39 mmol). LCMS: Method C, RT 2.124 min, MS: ES+ 231.10. This material was used directly for the next step without further purification.

Step b.

To a solution of ethyl 4-(1-methyl-1H-pyrazol-4-yl)benzoate (4.00 g, 17.39 mmol) in THF (25 ml) was added a solution of NaOH (1.40 g, 35.0 mmol) in water (10 ml) at rt. The reaction mixture was heated at 80° C. for 15 h. The resulting reaction mixture was cooled to rt and poured into water (20 ml). The resulting mixture was extracted with EtOAc (100 ml). The resulting aqueous layer was acidified with dilute HCl solution. The obtained solids were filtered off and washed with water (20 ml). The obtained solid material was dried under high vacuum yielding 4-(1-methyl-1H-pyrazol-4-yl) benzoic acid (2.500 g, 12.376 mmol). LCMS: Method C, RT 1.586, MS: ES+ 203.01. This material was used directly for the next step without further purification.

Step c.

To a solution of trans-tert-butyl-3-hydroxy-4-(methylamino)pyrrolidine-1-carboxylate (CAS Number 203503-49-5) (0.800 g, 3.703 mmol) in THF (10 ml) was added 4-(1-methyl-1H-pyrazol-4-yl)benzoic acid (0.90 g, 4.44 mmol), HATU (2.80 g, 7.37 mmol) and DIPEA (2 ml, 11.11 mmol) at rt. The reaction mixture was stirred at rt for 3 h. The resulting reaction mixture was poured into water (20 ml) and extracted with EtOAc (4×25 ml). The combined organic layer was dried over Na$_2$SO$_4$, filtered and concentrated under reduced pressure. The resulting residue was purified by flash chromatography (10% MeOH in DCM) yielding trans-tert-butyl 3-hydroxy-4-(N-methyl-4-(1-methyl-1H-pyrazol-4-yl)benzamido)pyrrolidine-1-carboxylate (0.170 g, 0.425 mmol). LCMS: Method C, RT 1.90 min, MS: ES+ 401.65.

Step d.

To a solution of trans-tert-butyl 3-hydroxy-4-(N-methyl-4-(1-methyl-1H-pyrazol-4-yl) benzamido)pyrrolidine-1-carboxylate (0.250 g, 0.625 mmol) in DMF (3 ml) was added NaH (60% dispersion in paraffin oil, 0.061 g, 1.54 mmol) at 0° C. Methyl iodide (0.264 g, 1.86 mmol) was added to the reaction mixture at 0° C. The reaction mixture was stirred at rt for 3 h. The resulting reaction mixture was poured into ice cold water (10 ml) and extracted with EtOAc (2×50 ml). The combined organic layer was dried over Na$_2$SO$_4$, filtered and concentrated under reduced pressure. The resulting residue was purified by flash chromatography (10% MeOH in DCM) yielding trans-tert-butyl 3-methoxy-4-(N-methyl-4-(1-methyl-1H-pyrazol-4-yl)benzamido)pyrrolidine-1-carboxylate (0.250 g, 0.603 mmol). LCMS: Method C, RT 2.08 min, MS: ES+ 415.75.

Steps e, f.

The title compound was synthesised from the intermediate above using a procedure similar to that described for steps b, c of Example 1. LCMS: Method A, RT 3.17 min, MS: ES+ 340.06; $^1$H NMR (400 MHz, DMSO-d$_6$) δ ppm 8.22 (s, 1H), 7.93 (s, 1H), 7.63 (d, J=8.0 Hz, 2H), 7.39 (d, J=7.6 Hz, 2H), 4.09-4.13 (m, 1H), 3.87 (s, 3H), 3.67-3.76 (m, 3H), 3.54-3.58 (m, 1H), 3.42-3.45 (m, 1H), 3.28 (s, 3H), 2.91 (s, 3H).

Example 179 (R)—N-(1-cyanopyrrolidin-3-yl)-5-(1,3-dimethyl-1H-pyrazol-4-yl)picolinamide

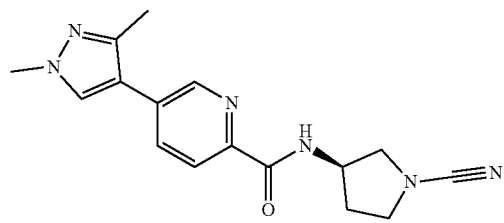 [SMILES: Cc1nn(C)cc1-c1ccc(C(=O)N[C@@H]2CCN(C#N)C2)nc1]

Synthesised using a procedure similar to that described for Example 173. LCMS: Method A, RT 3.01 min, MS: ES+ 311.06; 1H NMR (400 MHz, DMSO-d$_6$) δ ppm 8.96 (d, J=6.8 Hz, 1H), 8.72 (s, 1H), 8.15 (s, 1H), 8.02 (s, 2H), 4.51-4.54 (m, 1H), 3.82 (s, 3H), 3.53-3.64 (m, 2H), 3.38-3.48 (m, 2H), 2.35 (s, 3H), 2.03-2.13 (m, 2H)

Example 180 (R)—N-(1-cyanopyrrolidin-3-yl)-5-(2-methyl-6-(trifluoromethyl)pyrimidin-4-yl)picolinamide

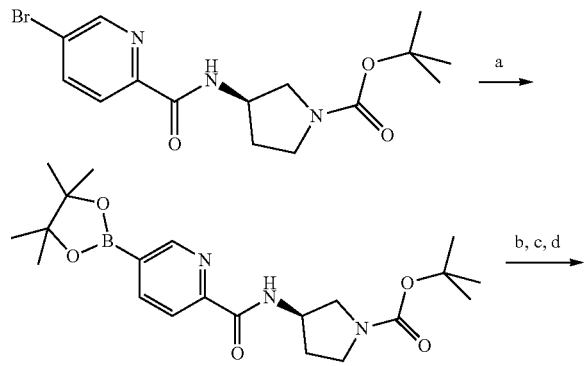

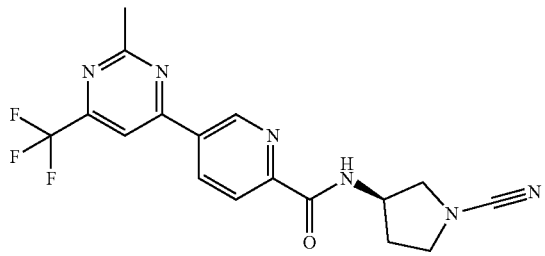

Step a.

To a solution of tert-butyl (R)-3-(5-bromopicolinamido)pyrrolidine-1-carboxylate (0.5 g, 1.35 mmol) (prepared according to the method described for Example 173 step a) in THF (15 ml) was added bis(pinacolato)diboron (0.51 g, 2.02 mmol) at rt. CH$_3$COOK (0.26 g, 2.70 mmol) and X-Phos (0.064 g, 0.13 mmol) were added to the reaction mixture at rt. The reaction mixture was degassed with N$_2$ for 15 min before adding Pd$_2$(dba)$_3$ (0.062 g, 0.067 mmol). The reaction mixture and heated at 90° C. for 6 h. The resulting mixture was poured into water (200 ml) and extracted with EtOAc (3×50 ml). The combined organic phase was washed with brine (200 ml) and dried over Na$_2$SO$_4$, filtered and concentrated under reduced pressure. The resulting residue was purified by column chromatography (10% MeOH in DCM) yielding tert-butyl (R)-3-(5-(4,4,5,5-tetramethyl-1,3,2-dioxaborolan-2-yl)picolinamido)pyrrolidine-1-carboxylate (0.2 g, 0.19 mmol). LCMS: Method A, RT 2.10 min, MS: ES+ 336.07.

Steps b-d.

The title compound was synthesised from the intermediate above using a procedure similar to that described for steps b-d of Example 3 to provide the title compound. LCMS: Method B, RT 4.03 min, MS: ES+ 377.12; $^1$H NMR (400 MHz, DMSO-d$_6$) δ ppm 9.49 (s, 1H), 9.18 (d, J=7.2 Hz, 1H), 8.86 (dd, J=2.0 Hz, 8.4 Hz, 1H), 8.59 (s, 1H), 8.22 (d, J=8.4 Hz, 1H), 4.55-4.59 (m, 1H), 3.55-3.66 (m, 2H), 3.41-3.49 (m, 2H), 2.84 (s, 3H), 2.04-2.18 (m, 2H)

Example 181 (R)—N-(1-cyanopyrrolidin-3-yl)-4-(2,6-dimethylpyrimidin-4-yl)-2-fluorobenzamide

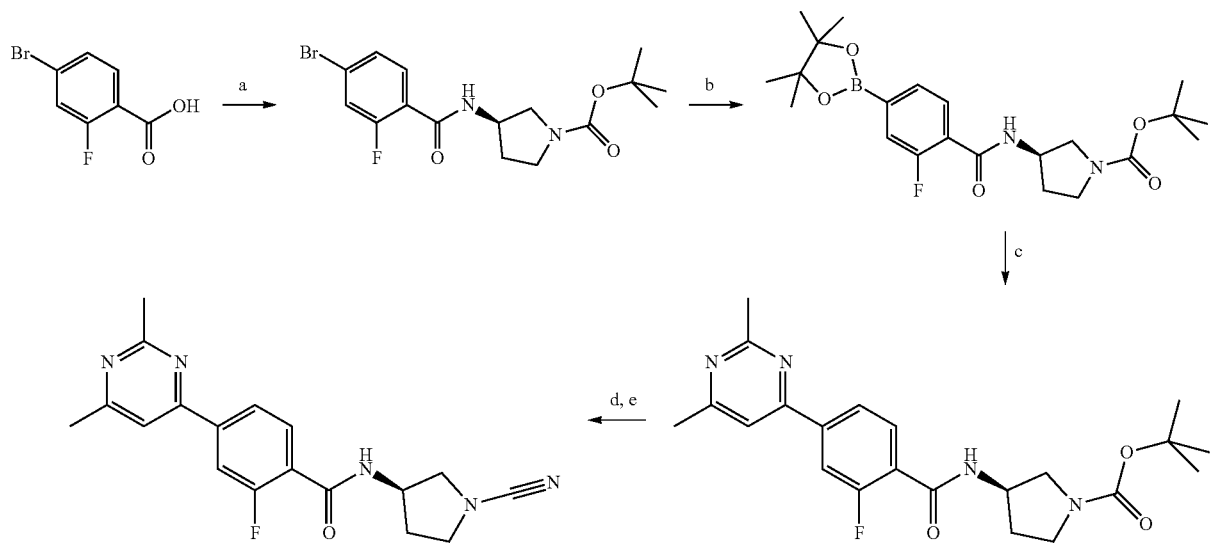

Step a.

To a solution of 4-bromo-2-fluorobenzoic acid (35.0 g, 159.81 mmol) in THF (800 ml) was added DIPEA (82.4 ml, 479 mmol) at 0° C. HATU (91.1 g, 240 mmol) was added to the reaction mixture at 0° C. The reaction mixture was stirred at 0° C. for 45 min. Tert-butyl (R)-3-aminopyrrolidine-1-carboxylate (29.7 g, 160 mmol) was added dropwise to the reaction mixture at 0° C. The resulting reaction mixture was stirred for 15 min at 0° C. and then at rt for 2 h. The resulting mixture was poured into water (1500 ml) and extracted with EtOAc (3×500 ml). The combined organic phase was dried over Na$_2$SO$_4$, filtered and concentrated under reduced pressure. The resulting residue was purified by column chromatography (35% EtOAc in hexane) yielding tert-butyl (R)-3-(4-bromo-2-fluorobenzamido)pyrrolidine-1-carboxylate (50.50 g, 130 mmol). LCMS: Method C, RT 2.37 min, MS: ES+ 387.23; $^1$H NMR (400 MHz, DMSO-d$_6$) δ ppm 8.65 (d, J=6.80 Hz, 1H), 7.65-7.67 (m, 1H), 7.48-7.54 (m, 2H), 4.36-4.39 (m, 1H), 3.47-3.56 (m, 1H), 3.30-3.40 (m, 2H), 3.14-3.18 (m, 1H), 2.05-2.08 (m, 1H), 1.83-1.86 (m, 1H), 1.45 (s, 9H).

Step b.

A solution of tert-butyl (R)-3-(4-bromo-2-fluorobenzamido)pyrrolidine-1-carboxylate (2.75 g, 8.33 mmol) in DMF (10 ml) was added bis(pinacolato)diboron (2.53 g, 9.99 mmol) at rt followed by CH$_3$COOK (2.55 g, 26.0 mmol). The resulting reaction mixture was degassed for 10 min. Pd(dppf)Cl$_2$.CH$_2$Cl$_2$ (0.34 g, 0.41 mmol) was added and the reaction mixture was heated at 100° C. for 6.5 h. The reaction mixture was cooled to rt. The resulting reaction mixture was poured into ice cold water (125 ml) and extracted with DCM (4×25 ml). The combined organic phase was dried over Na$_2$SO$_4$, filtered and concentrated under reduced pressure. The resulting residue was diluted with water (1200 ml) and extracted with DCM (4×100 ml). The combined organic phase was dried over Na$_2$SO$_4$, filtered and concentrated under reduced pressure yielding tert-butyl (R)-3-(2-fluoro-4-(4,4,5,5-tetramethyl-1,3,2-dioxaborolan-2-yl)benzamido)pyrrolidine-1-carboxylate (2.20 g, 5.07 mmol). This material was used directly for the next step without further purification. LCMS: Method C, RT 1.93 min, MS: ES+ 353.30

Step c.

To a solution of tert-butyl (R)-3-(2-fluoro-4-(4,4,5,5-tetramethyl-1,3,2-dioxaborolan-2-yl)benzamido)pyrrolidine-1-carboxylate (0.250 g, 0.576 mmol) in 1,4-dioxane: water (8:2, 10 ml) were added K$_2$CO$_3$ (0.238 g, 1.724 mmol) followed by 4-chloro-2,6-dimethylpyrimidine (CAS Number 4472-45-1) (0.082 g, 0.576 mmol) at rt. The reaction mixture was degassed for 30 min. PdCl$_2$(dppf) (0.042 g, 0.057 mmol) was added to the reaction mixture at rt. The reaction mixture was heated at 100° C. for 3 h. The resulting reaction mixture was cooled to rt and concentrated under reduced pressure. The resulting reaction mixture was poured into water (25 ml) and extracted with EtOAc (2×25 ml). The combined organic phase was dried over Na$_2$SO$_4$, filtered and concentrated under reduced pressure. The obtained residue was purified by flash chromatography (70% EtOAc in hexane) yielding tert-butyl (R)-3-(4-(2,6-dimethylpyrimidin-4-yl)-2-fluorobenzamido)pyrrolidine-1-carboxylate (0.110 g, 0.265 mmol). LCMS: Method C, 2.18, MS: ES+ 415.38

Steps d, e.

The title compound was synthesised from the intermediate above using a procedure similar to that described for steps c, d of Example 3. LCMS: Method B, RT 3.64 min, MS: ES+ 340.10; $^1$H NMR (400 MHz, DMSO-d$_6$) δ ppm 8.79 (d, J=6.80 Hz, 1H), 8.06-8.12 (m, 2H), 7.91 (s, 1H), 7.71-7.75 (m, 1H), 4.46-4.50 (m, 1H), 3.63-3.67 (m, 1H), 3.44-3.56 (m, 2H), 3.27-3.32 (m, 1H), 2.66 (s, 3H), 2.51 (s, 3H), 2.12-2.17 (m, 1H), 1.91-1.96 (m, 1H).

Compounds in Table 9 were synthesised using a procedure similar to that described for Example 181.

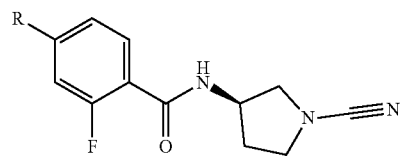

TABLE 9

| Ex | R | Name | $^1$H NMR (400 MHz, DMSO-d$_6$) δ ppm | LCMS Method | LCMS RT (min) | MS |
|---|---|---|---|---|---|---|
| 182 | ![pyrimidine with F and methyl] | (R)-N-(1-cyanopyrrolidin-3-yl)-2-fluoro-4-(5-fluoro-2-methylpyrimidin-4-yl)benzamide | 8.90 (d, J = 3.2 Hz, 1 H), 8.84 (d, J = 6.8 Hz, 1 H), 7.89-7.95 (m, 2 H), 7.77 (t, J = 7.6 Hz, 1 H), 4.47-4.49 (m, 1H), 3.63-3.67 (m, 1 H), 3.34-3.53 (m, 3 H), 2.71 (s, 3 H), 2.12-2.17 (m, 1 H), 1.91-1.95 (m, 1 H) | B | 3.46 | ES+ 344.26 |
| 183 | ![pyrimidine with CF3] | (R)-N-(1-cyanopyrrolidin-3-yl)-2-fluoro-4-(2-(trifluoromethyl)pyrimidin-4-yl)benzamide | 9.19-9.21 (m, 1 H), 8.86-8.89 (m, 1 H), 8.52-8.53 (m, 1 H), 8.20-8.21 (m, 2 H), 7.79-7.81 (m, 1 H), 4.47-4.50 (m, 1H), 3.66-3.67 (m, 1 H), 3.42-3.51 (m, 3 H), 2.14-2.17 (m, 1 H), 1.91-1.97 (m, 1 H) | B | 3.94 | ES+ 380.11 |

TABLE 9-continued

| Ex | R | Name | ¹H NMR (400 MHz, DMSO-d₆) δ ppm | LCMS Method | LCMS RT (min) | MS |
|---|---|---|---|---|---|---|
| 184 | (structure) | (R)-N-(1-cyanopyrrolidin-3-yl)-2-fluoro-4-(2-methyl-3H-pyrrolo[2,3-d]pyrimidin-4-yl)benzamide | 12.12 (s, 1 H), 8.80 (d, J = 6.4 Hz, 1 H), 8.08 (dd, J = 1.6 Hz, 8.0 Hz, 1 H), 7.99 (dd, J = 1.6 Hz, 11.6 Hz, 1 H), 7.77 (t, J = 7.6 Hz, 1 H), 7.62 (d, J = 2.8 Hz, 1 H), 6.86 (d, J = 3.2 Hz, 1 H), 4.48-4.52 (m, 1 H), 3.64-3.68 (m, 1 H), 3.45-3.57 (m, 2 H), 3.33-3.37 (m, 1 H), 2.72 (s, 3 H), 2.11-2.20 (m, 1 H), 1.92-1.97 (m, 1 H) | A | 3.17 | ES+ 365.01 |
| 185 | (structure) | (R)-N-(1-cyanopyrrolidin-3-yl)-2-fluoro-4-(imidazo[1,2-a]pyrazin-3-yl)benzamide | 9.19 (d, J = 1.2 Hz, 1 H), 8.78 (d, J = 6.4 Hz, 1 H), 8.70 (dd, J = 4.8, 1.6 Hz, 1 H), 8.21 (s, 1 H), 8.00 (d, J = 4.8 Hz, 1 H), 7.68-7.79 (m, 3 H), 4.45-4.52 (m, 1 H), 3.63-3.67 (m, 1 H), 3.44-3.56 (m, 2 H), 3.26-3.33 (m, 1 H), 2.10-2.19 (m, 1 H), 1.90-1.98 (m, 1 H) | B | 2.89 | ES+ 351.31 |

Example 186 (R)—N-(1-cyanopyrrolidin-3-yl)-3-fluoro-5-(pyrazolo[1,5-a]pyrimidin-5-yl)picolinamide

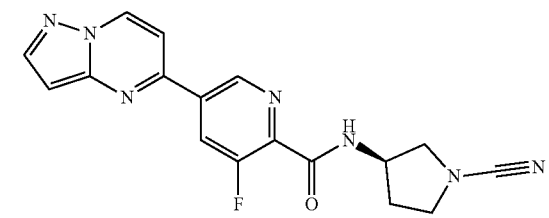 [SMILES: N#CN1CC[C@@H](NC(=O)c2ncc(-c3ccn4nccc4n3)cc2F)C1]

Synthesised using a procedure similar to that described for Example 181, using 5-bromo-3-fluoropicolinic acid (CAS Number 669066-91-5) in step a and 5-chloropyrazolo[1,5-a]pyrimidine (CAS Number 29274-24-6) in step c. LCMS: Method A, RT 3.19 min, MS: ES+ 352.10; ¹H NMR (400 MHz, DMSO-d₆) δ ppm 9.36 (d, J=7.6 Hz, 1H), 9.30 (s, 1H), 9.13 (d, J=6.8 Hz, 1H), 8.63 (dd, J=1.6 Hz, 11.6 Hz, 1H), 8.34 (d, J=2.4 Hz, 1H), 7.85 (d, J=7.6 Hz, 1H), 6.89-6.90 (m, 1H), 4.51-4.53 (m, 1H), 3.63-3.67 (m, 1H), 3.53-3.57 (m, 1H), 3.38-3.46 (m, 1H), 3.36-3.38 (m, 1H), 2.13-2.18 (m, 1H), 1.99-2.02 (m, 1H)

Example 187 (R)—N-(1-cyanopyrrolidin-3-yl)-3-fluoro-5-(imidazo[1,2-a]pyridin-6-yl)picolinamide

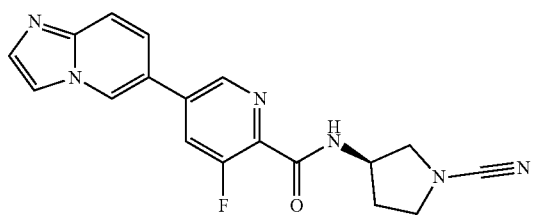 [SMILES: N#CN1CC[C@@H](NC(=O)c2ncc(-c3ccc4nccn4c3)cc2F)C1]

Synthesised using a procedure similar to that described for Example 186. LCMS: Method A, RT 3.02 min, MS: ES+ 351.04; 1H NMR (400 MHz, DMSO-d₆) δ ppm 9.19 (s, 1H), 9.02 (d, J=6.4 Hz, 1H), 8.88 (s, 1H), 8.29 (d, J=12.8 Hz, 1H), 8.00 (s, 1H), 7.73 (s, 2H), 7.67 (s, 1H), 4.05-4.54 (m, 1H), 3.63-3.67 (m, 1H), 3.46-3.58 (m, 2H), 3.36-3.38 (m, 1H), 2.12-2.33 (m, 1H), 1.97-2.04 (m, 1H)

Example 188 (R)—N-(1-cyanopyrrolidin-3-yl)-3-methoxy-3-phenylazetidine-1-carboxamide

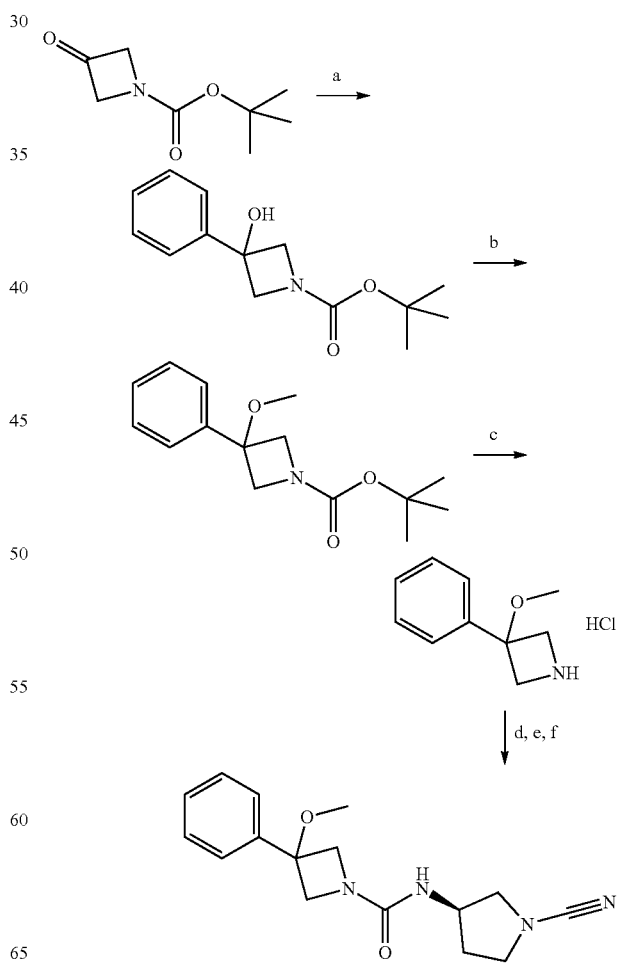

Step a.

To a solution of tert-butyl 3-oxoazetidine-1-carboxylate (CAS Number 398489-26-4) (10 g, 58.41 mmol) in THF (100 ml) was added phenyl magnesium bromide (1 M in THF) (64.2 ml, 64.25 mmol) at 0° C. The reaction mixture was stirred at 0° C. for 2 h and then at rt for 16 h. The reaction mixture was poured into a saturated solution of NH$_4$Cl (150 ml) and extracted with EtOAc (3×30 ml). The combined organic layer was washed with water (2×50 ml), brine (2×50 ml), dried over Na$_2$SO$_4$, filtered and concentrated under reduced pressure. The resulting residue was purified by column chromatography (20% EtOAc in hexane) yielding tert-butyl 3-hydroxy-3-phenylazetidine-1-carboxylate (11.92 g, 47.8 mmol). LCMS: Method C, RT 2.22 min, MS: ES+ 194.1 [M-56], $^1$H NMR (400 MHz, DMSO-d$_6$) δ ppm 7.49 (d, J=7.2 Hz, 2H), 7.38 (t, J=8 Hz, 2H), 7.27-7.31 (m, 1H), 6.33 (s, 1H), 4.03 (s, 4H), 1.41 (s, 9H)

Step b.

To a solution of tert-butyl 3-hydroxy-3-phenylazetidine-1-carboxylate (1 g, 4.01 mmol) in MeCN (40 ml) was added NaH (60% dispersion in paraffin oil, 0.3 g, 7.63 mmol) at rt. The reaction mixture was stirred at rt for 30 min. A solution of methyl iodide (0.75 g, 5.28 mmol) in MeCN (5 ml) was added dropwise to the reaction mixture and stirred for 4 h. The resulting mixture was poured into water (20 ml) and extracted with EtOAc (3×20 ml). The combined organic phase was washed with brine (2×20 ml), dried over Na$_2$SO$_4$, filtered and concentrated under reduced pressure yielding tert-butyl 3-methoxy-3-phenylazetidine-1-carboxylate (1.13 g, 4.29 mmol). LCMS: Method C, RT 2.39 min, MS: ES+ 208.01 [M-56], H NMR (400 MHz, DMSO-d$_6$) δ ppm 7.34-7.50 (m, 5H), 4.03-4.11 (m, 4H), 2.96 (s, 1H), 1.39 (s, 9H)

Step c.

To a solution of tert-butyl 3-methoxy-3-phenylazetidine-1-carboxylate (1.12 g, 4.24 mmol) in 1,4-dioxane (10 ml) was added 4 M HCl in 1,4-dioxane (10 ml) dropwise at rt. The reaction mixture was stirred at rt for 3 h. The resulting reaction mixture was evaporated under reduced pressure and the obtained residue was triturated with n-pentane (20 ml), diethyl ether (20 ml) and dried under vacuum to yield 3-methoxy-3-phenylazetidine HCl salt (0.7 g, 3.5 mmol). LCMS: Method C, RT 1.50 min, MS: ES+ 164.04

Steps d-f.

The title compound was synthesised from the intermediate above using a procedure similar to that described for Example 89. LCMS: Method B, RT 3.38 min, MS: ES+ 301.20; $^1$H NMR (400 MHz, DMSO-d$_6$) δ ppm 7.34-7.46 (m, 5H), 6.65 (d, J=6.4 Hz, 1H), 4.14 (t, J=5.6 Hz, 1H), 4.02-4.07 (m, 4H), 3.44-3.52 (m, 2H), 3.45-3.40 (m, 1H), 3.13-3.16 (m, 1H), 2.98 (s, 3H), 1.95-2.07 (m, 1H), 1.75-1.83 (m, 1H).

Example 189 (R)—N-(1-cyanopyrrolidin-3-yl)-N-methyl-3-phenylazetidine-1-carboxamide

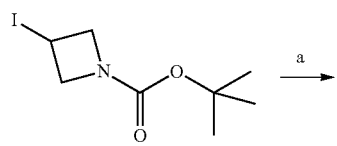

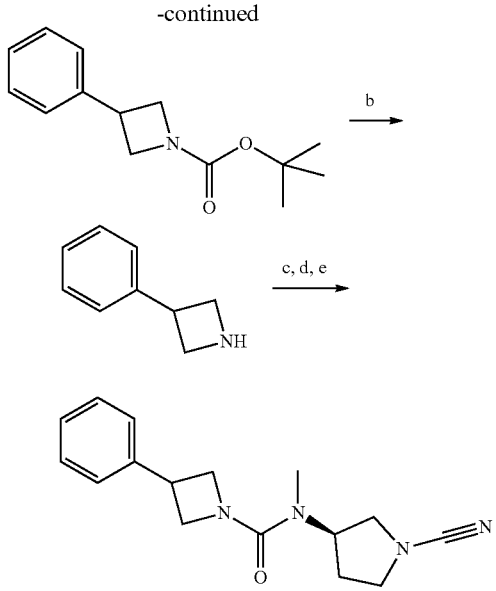

Step a.

A solution of phenylboronic acid (0.65 g, 5.33 mmol) in IPA (4.5 ml) was prepared in a microwaveable glass tube. NiI$_2$ (0.05 g, 0.15 mmol) and trans-2-aminocyclohexanol hydrochloride (0.024 g, 0.15 mmol) were added to the reaction mixture at rt. Sodium bis(trimethylsilyl)amide (1 M in THF) (5.3 ml, 5.28 mmol) was added dropwise to the reaction mixture at rt. N—BOC-3-iodoazetidine (CAS Number 254454-54-1) (0.75 g, 2.65 mmol) was added, the glass tube was sealed and the reaction mixture was subjected to microwave heating at 80° C. for 50 min. The reaction mixture was cooled to rt and evaporated under reduced pressure to yield a black residue. The resulting residue was purified by column chromatography (6% EtOAc in hexane) yielding tert-butyl 3-phenylazetidine-1-carboxylate (1.3 g, 5.57 mmol). LCMS: Method C, RT 2.47 min, MS: ES+ 234.4

Step b.

To a solution of tert-butyl 3-phenylazetidine-1-carboxylate (1.2 g, 5.15 mmol) in DCM was added TFA (3.6 ml) at 0° C. The reaction mixture was stirred at rt for 3 h. The resulting reaction mixture was evaporated under reduced pressure. The residue was azeotropically distilled with diethyl ether (10 ml) and dried under vacuum to yield 3-phenylazetidine TFA salt (0.3 g, 1.21 mmol). This material was used directly for the next step without further purification. LCMS: Method C, RT 1.08 min, MS: ES+ 134.19

Steps c-e.

The title compound was synthesised from the intermediate above using a procedure similar to that described for Example 89 to provide the title compound. LCMS: Method A, RT 3.88 min, MS: ES+ 285.18; $^1$H NMR (400 MHz, DMSO-d$_6$) δ ppm 7.34-7.38 (m, 4H), 7.24-7.27 (m, 1H), 4.59-4.63 (m, 1H), 4.26-4.32 (m, 2H), 3.85-3.91 (m, 2H), 3.75-3.79 (m, 1H), 3.44-3.53 (m, 2H), 3.25-3.40 (m, 2H), 3.71 (s, 3H), 1.91-2.01 (m, 2H).

Example 190 (R)—N-(1-cyanopyrrolidin-3-yl)-3-(4-methoxyphenyl)azetidine-1-carboxamide

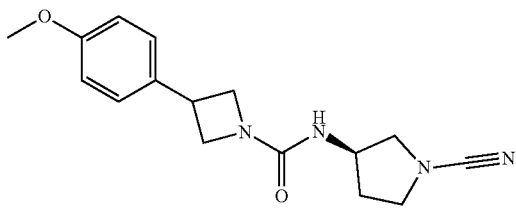 [SMILES: COc1ccc(C2CN(C(=O)N[C@@H]3CCN(C#N)C3)C2)cc1]

Synthesised using a procedure similar to that described for steps a, b of Example 189, using 4-methoxyphenylboronic acid, followed by steps a-c of Example 5. LCMS: Method A, RT 3.44 min, MS: ES+ 301.08; $^1$H NMR (400 MHz, DMSO-$d_6$) δ ppm 7.25 (d, J=8.4 Hz, 2H), 6.91 (d, J=8.8 Hz, 2H), 6.56 (d, J=6.4 Hz, 1H), 4.12-4.20 (m, 3H), 3.74 (s, 3H), 3.53-3.73 (m, 3H), 3.45-3.53 (m, 2H), 3.37-3.41 (m, 1H), 3.13-3.17 (m, 1H), 1.96-2.04 (m, 1H), 1.77-1.83 (m, 1H).

Example 191 (R)-3-(4-chlorophenyl)-N-(1-cyanopyrrolidin-3-yl)azetidine-1-carboxamide

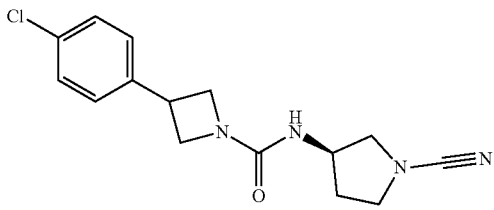 [SMILES: N#CN1CC[C@@H](NC(=O)N2CC(c3ccc(Cl)cc3)C2)C1]

Synthesised using a procedure similar to that described for steps a, b of Example 189, using 4-chlorophenylboronic acid, followed by steps a-c of Example 5. LCMS: Method A, RT 3.86 min, MS: ES+ 304.94; $^1$H NMR (400 MHz, DMSO-$d_6$) δ ppm 7.36-7.43 (m, 4H), 6.59 (d, J=6.4 Hz, 1H), 4.12-4.22 (m, 3H), 3.73-3.79 (m, 3H), 3.45-3.77 (m, 2H), 3.34-3.41 (m, 1H), 3.13-3.17 (m, 1H), 1.98-2.03 (m, 1H), 1.78-1.82 (m, 1H).

Example 192 (R)-3-(3-chlorophenyl)-N-(1-cyanopyrrolidin-3-yl)azetidine-1-carboxamide

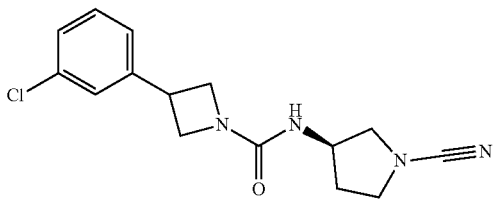 [SMILES: N#CN1CC[C@@H](NC(=O)N2CC(c3cccc(Cl)c3)C2)C1]

Synthesised using a procedure similar to that described for steps a, b of Example 189, using 3-chlorophenylboronic acid, followed by steps a-c of Example 5. LCMS: Method B, RT 3.75 min, MS: ES+ 305.22; $^1$H NMR (400 MHz, DMSO-$d_6$) δ ppm 7.38-7.41 (m, 2H), 7.32 (d, J=7.2 Hz, 2H), 6.58 (d, J=6.8 Hz, 1H), 4.13-4.20 (m, 3H), 3.77-3.78 (m, 3H), 3.45-3.53 (m, 2H), 3.35-3.39 (m, 1H), 3.13-3.17 (m, 1H), 1.96-2.09 (m, 1H), 1.77-1.83 (m, 1H).

Example 193 (3aR,6aR)-1-(3-phenylazetidine-1-carbonyl)hexahydropyrrolo[3,4-b]pyrrole-5(1H)-carbonitrile

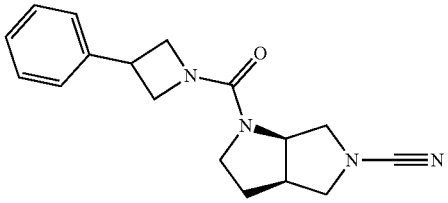 [SMILES: N#CN1C[C@H]2CCN(C(=O)N3CC(c4ccccc4)C3)[C@H]2C1]

Synthesised using a procedure similar to that described for Example 189. LCMS: Method A, RT 3.82 min, MS: ES+ 297.09; 1H NMR (400 MHz, DMSO-$d_6$) δ ppm 7.35-7.39 (m, 4H), 7.24-7.28 (m, 1H), 4.35-4.40 (nm, 1H) 4.20-4.27 (m, 2H), 3.92-3.96 (m, 1H), 3.76-3.86 (m, 3H), 3.50-3.55 (m, 2H), 3.37-3.42 (m, 2H), 3.16-3.23 (m, 1H), 2.87-2.89 (m, 1H), 1.74-1.78 (m, 1H), 1.74-1.78 (m, 1H).

Example 194 (R)-1-(1-cyanopyrrolidin-3-yl)-1-methyl-3-(4-(J -methyl-1H-pyrazol-4-yl)phenyl)urea

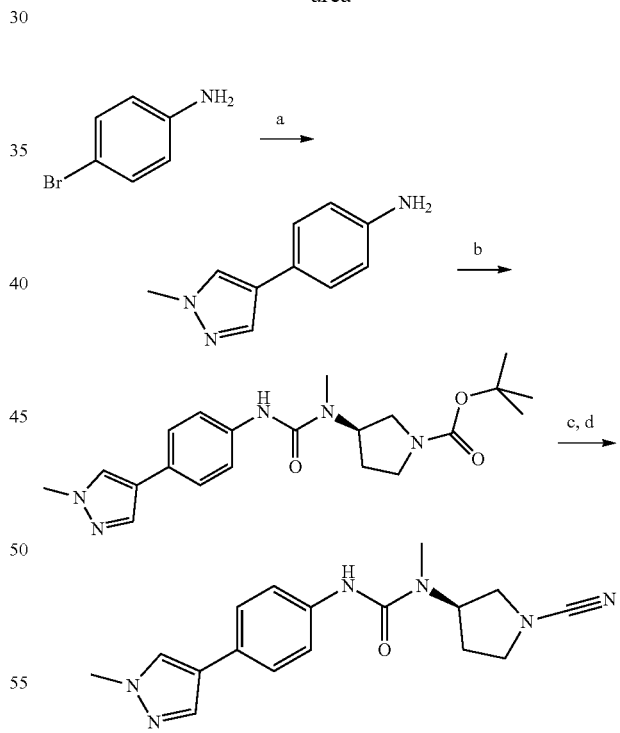

Step a.

To a mixture of 4-bromoaniline (3 g, 17.4 mmol) in DMF: water (8:2) (60 ml) were added 1-methyl-4-(4,4,5,5-tetramethyl-1,3,2-dioxaborolan-2-yl)-1H-pyrazole (CAS Number 761446-44-0) (3.62 g, 17.4 mmol) and Na$_2$CO$_3$ (3.69 g, 34.8 mmol) at rt. The reaction mixture was degassed with N$_2$ for 10 min before adding PdCl$_2$(dppf) (1.27 g, 1.74 mmol). The resulting reaction mixture was heated at 110° C. for 2.5 h. The resulting reaction mixture was poured into cold water (300 ml) and extracted with EtOAc (3×300 ml). The combined organic layer was dried over Na$_2$SO$_4$, filtered and concentrated under reduced pressure to yield 4-(1-methyl-1H-pyrazol-4-yl)aniline (1.8 g, 10.39 mmol). LCMS: Method A, RT 2.84 min, MS: ES+ 173.97, $^1$H NMR (400 MHz, DMSO-d$_6$) δ ppm 7.85 (s, 1H), 7.63 (s, 1H), 7.20 (d, J=8.4 Hz, 2H), 6.54 (d, J=8.8 Hz, 2H), 5.01 (s, 2H), 3.81 (s, 3H).

Step b.

To a solution of 4-(1-methyl-1H-pyrazol-4-yl)aniline (0.5 g, 2.89 mmol) in DCM (10 ml) were added pyridine (0.69 ml, 8.67 mmol) and 4-nitrophenyl chloroformate (0.057 g, 4.33 mmol) at rt. The reaction mixture was stirred at rt for 2 h. (R)-3-(Methylamino)pyrrolidine-1-carboxylic acid tert-butyl ester (0.693 g, 3.46 mmol) was added to the reaction mixture at rt and stirred for a further 16 h. The resulting reaction mixture was poured into cold water (100 ml) and extracted with DCM (3×100 ml). The combined organic layer was washed with 1% citric acid (1×100 ml), brine (100 ml), dried over Na$_2$SO$_4$, filtered and concentrated under reduced pressure to yield tert-butyl (R)-3-(1-methyl-3-(4-(1-methyl-1H-pyrazol-4-yl)phenyl)ureido)pyrrolidine-1-carboxylate (0.6 g, 1.50 mmol). LCMS: Method C, RT 2.07 min, MS: ES+ 400.40.

Steps c, d.

The title compound was synthesised from the intermediate above using a procedure similar to that described for steps b, c of Example 5 to provide the title compound. LCMS: Method A, RT 3.14 min, MS: ES+ 325.03; $^1$H NMR (400 MHz, DMSO-d$_6$) δ ppm 8.35 (s, 1H), 8.02 (s, 1H), 7.77 (s, 1H), 7.41-7.46 (m, 4H), 4.88-4.92 (m, 1H), 3.84 (s, 3H), 3.50-3.56 (m, 2H), 3.35-3.39 (m, 1H), 3.27-3.31 (m, 1H), 2.88 (s, 3H), 1.94-2.03 (m, 2H).

Example 195 (R)-1-(1-cyanopyrrolidin-3-yl)-1-methyl-3-(4-(trifluoromethyl)phenyl)urea

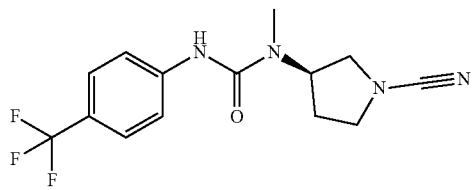 [SMILES: CN(C(=O)Nc1ccc(C(F)(F)F)cc1)[C@@H]1CCN(C#N)C1]

Synthesised using a procedure similar to that described for steps b-d of Example 194. LCMS: Method A, RT 4.14 min, MS: ES+ 312.99; $^1$H NMR (400 MHz, DMSO-d$_6$) δ ppm 8.75 (s, 1H), 7.69 (d, J=8.8 Hz, 2H), 7.59 (d, J=8.4 Hz, 2H), 4.84-4.92 (m, 1H), 3.51-3.57 (m, 2H), 3.42-3.49 (m, 1H), 3.31-3.34 (m, 1H), 2.90 (s, 3H), 1.92-2.08 (m, 2H).

Example 196 (3aR,6aR)-N-(4-chloro-2-fluorophenyl)-5-cyanohexahydropyrrolo[3,4-b]pyrrole-1(2H)-carboxamide

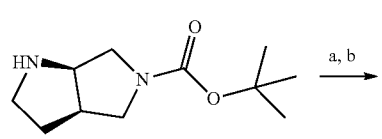

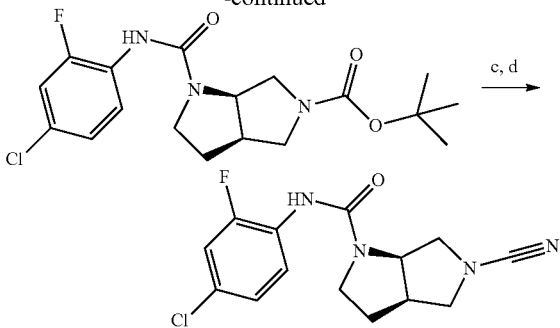

Step a.

To a solution of 4-chloro-2-fluoroaniline (CAS Number 57946-56-2) (0.500 g, 3.434 mmol) in chloroform (10 ml) was added DIPEA (0.891 g, 6.906 mmol) at 0° C. 4-Nitrophenyl chloroformate (0.831 g, 4.122 mmol) was added portion wise to the reaction mixture at 0° C. The reaction mixture was heated to 60° C. for 2.5 h. The resulting reaction mixture was cooled to rt and poured into water (70 ml). The resulting mixture was extracted with DCM (3×40 ml). The combined organic phase was dried over Na$_2$SO$_4$, filtered and concentrated under reduced pressure. The resulting residue was purified by flash chromatography (11% EtOAc in hexane) yielding 4-nitrophenyl (4-chloro-2-fluorophenyl)carbamate (0.230 g, 0.740 mmol).

Step b.

To a solution of 4-nitrophenyl (4-chloro-2-fluorophenyl)carbamate (0.220 g, 0.709 mmol) in pyridine (10 ml) was added tert-butyl (3aR,6aR)-hexahydropyrrolo[3,4-b]pyrrole-5(1H)-carboxylate (CAS Number 370882-39-6) (0.181 g, 0.852 mmol) at rt. The reaction mixture was heated to 130° C. for 8 h. The resulting reaction mixture was cooled to rt and poured into water (100 ml). The resulting mixture was extracted with EtOAc (3×50 ml). The combined organic phase was washed with saturated citric acid (2×50 ml), dried over Na$_2$SO$_4$, filtered and concentrated under reduced pressure. The resulting residue was purified by flash chromatography (43% EtOAc in hexane) yielding tert-butyl (3aR,6aR)-1-((4-chloro-2-fluorophenyl)carbamoyl)hexahydropyrrolo[3,4-b]pyrrole-5(1H)-carboxylate (0.097 g, 0.252 mmol). LCMS: Method C, 2.263, MS: ES-382.59.

Steps c, d.

The title compound was synthesised from the intermediate above using a procedure similar to that described for steps b, c of Example 5 to provide the title compound. LCMS: Method B, RT 3.59 min, MS: ES+ 309.42; $^1$H NMR (400 MHz, DMSO-d6) δ ppm 8.15 (s, 1H), 7.52 (t, J=8.8 Hz, 1H), 7.42 (dd, J=2.4 Hz, 10.4 Hz, 1H), 7.20-7.23 (m, 1H), 4.31-4.34 (m, 1H), 3.50-3.57 (m, 4H), 3.39-3.42 (m, 1H), 3.23-3.27 (m, 1H), 2.93-2.98 (m, 1H), 2.01-2.08 (m, 1H), 1.79-1.84 (m, 1H).

Compounds in Table 10 were synthesised using a procedure similar to general method E as exemplified by either Example 5, Example 89 or Example 196.

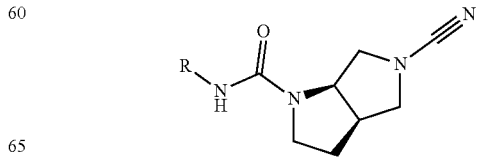

TABLE 10

| Ex | R | Name | Synthetic method | $^1$H NMR: (400 MHz, DMSO-d$_6$) δ ppm | LCMS Method | LCMS RT (min) | MS |
|---|---|---|---|---|---|---|---|
| 197 | | (3aR,6aR)-5-cyano-N-(2-fluoro-4-(trifluoromethoxy)phenyl)hexahydropyrrolo[3,4-b]pyrrole-1(2H)-carboxamide | Example 5 | 8.20 (s, 1 H), 7.60 (t, J = 8.8 Hz, 1 H), 7.41 (dd, J = 10.8, 2.4 Hz, 1 H), 7.19 (d, J = 9.2 Hz, 1 H), 4.34 (t, J = 5.6 Hz, 1 H), 3.51-3.60 (m, 4 H), 3.40-3.43 (m, 1 H), 3.24-3.28 (m, 1 H), 2.94-3.00 (m, 1 H), 2.06-2.09 (m, 1 H), 1.78-1.91 (m, 1 H) | A | 4.27 | ES+ 358.80 |
| 198 | | (3aR,6aR)-5-cyano-N-(4-cyano-2-fluorophenyl)hexahydropyrrolo[3,4-b]pyrrole-1(2H)-carboxamide | Example 89 | 8.37 (s, 1 H), 7.82-7.89 (m, 2 H), 7.60-7.63 (m, 1 H), 4.36 (t, J = 5.2 Hz, 1 H), 3.51-3.61 (m, 4 H), 3.41-3.44 (m, 1 H), 3.24-3.27 (m, 1 H), 2.95-2.98 (m, 1 H), 1.99-2.07 (m, 1 H), 1.79-1.84 (m, 1 H) | A | 3.45 | ES− 298.10 |
| 199 | | (3aR,6aR)-5-cyano-N-(4-cyano-2,5-difluorophenyl)hexahydropyrrolo[3,4-b]pyrrole-1(2H)-carboxamide | Example 89 | 8.55 (s, 1 H), 7.90-7.98 (m, 2 H), 4.36-4.40 (m, 1 H), 3.51-3.63 (m, 4 H), 3.38-3.44 (m, 1 H), 3.20-3.30 (m, 1 H), 2.95-2.97 (m, 1 H), 1.99-2.18 (m, 1 H), 1.77-1.95 (m, 1 H) | A | 3.76 | ES+ 317.90 |
| 200 | | (3aR,6aR)-5-c | Example 89 | 8.15 (s, 1 H), 7.68 (dd, J = 7.6, 2.8 Hz, 1 H), 7.24-7.29 (m, 1 H), 7.14-7.18 (m, 1 H), 4.35 (t, J = 5.6 Hz, 1 H), 3.51-3.58 (m, 4 H), 3.41-3.44 (m, 1 H), 3.22-3.29 (m, 1 H), 2.95-2.97 (m, 1 H), 1.99-2.07 (m, 1 H), 1.79-1.89 (m, 1 H) | B | 3.64 | ES− 307.06 |
| 201 | | (3aR,6aR)-5-cyano-N-(2-fluoro-5-(trifluoromethyl)phenyl)hexahydropyrrolo[3,4-b]pyrrole-1(2H)-carboxamide | Example 89 | 8.30 (s, 1 H), 7.99 (d, J = 6.4 Hz, 1 H), 7.43-7.48 (m, 2 H), 4.35 (t, J = 5.6 Hz, 1 H), 3.51-3.60 (m, 4 H), 3.43-3.46 (m, 1 H), 3.24-3.28 (m, 1 H), 2.96-2.98 (m, 1 H), 2.03-2.08 (m, 1 H), 1.80-1.85 (m, 1 H) | A | 4.22 | ES+ 342.90 |
| 202 | | (3aR,6aR)-5-cyano-N-(5-phenylpyridin-2-yl)hexahydropyrrolo[3,4-b]pyrrole-1(2H)-carboxamide | Example 89 | 9.02 (s, 1 H), 8.57 (d, J = 2 Hz, 1 H), 8.03 (dd, J = 8.8, J = 2.4 Hz, 1 H), 7.96 (d, J = 8.8 Hz, 1 H), 7.68-7.70 (m, 2 H), 7.45-7.49 (m, 2 H), 7.37 (t, J = 7.2 Hz, 1 H), 4.41-4.43 (m, 1 H), 3.51-3.64 (m, 4 H), 3.41-3.44 (m, 1 H), 3.23-3.27 (m, 1 H), 2.93-2.97 (m, 1 H), 1.99-2.08 (m, 1 H), 1.79-1.83 (m, 1 H) | A | 4.11 | ES+ 334.07 |
| 203 | | (3aR,6aR)-5-cyano-N-(4-(trifluoromethyl)phenyl)-hexahydropyrrolo[3,4-b]pyrrole-1(2H)-carboxamide | Example 196 | 8.66 (s, 1 H), 7.74 (d, J = 8.4 Hz, 2 H), 7.59 (d, J = 8.8 Hz, 2 H), 4.36-4.39 (m, 1 H), 3.52-3.61 (m, 4 H), 3.40-3.43 (m, 1 H), 3.24-3.28 (m, 1 H), 2.93-2.97 (m, 1 H), 2.00-2.08 (m, 1 H), 1.81-1.87 (m, 1 H) | A | 4.18 | ES+ 324.90 |

Example 204 (R)-1-(1-cyanopyrrolidin-3-yl)-1-ethyl-3-(4-(trifluoromethyl)phenyl)urea

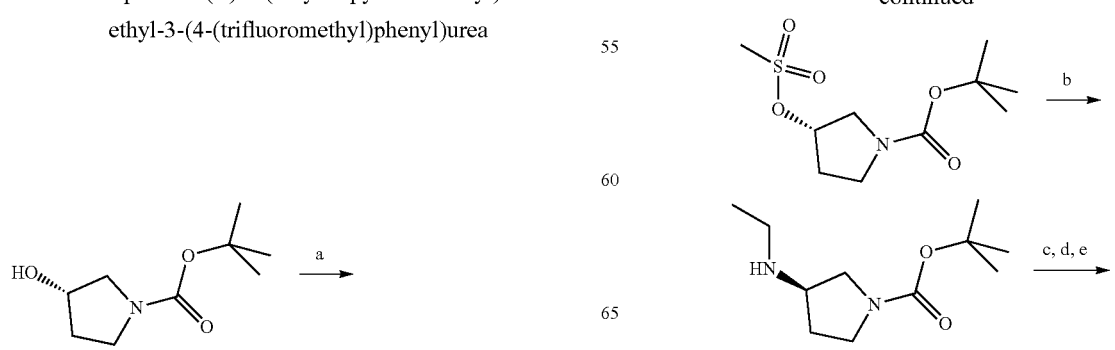

-continued

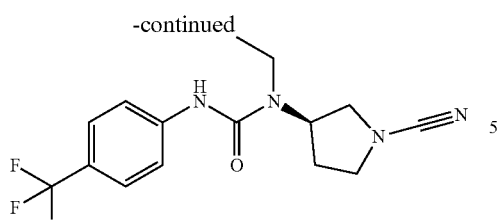

Step a.

To a solution of tert-butyl (S)-3-hydroxypyrrolidine-1-carboxylate (1 g, 5.34 mmol) in DCM (2.5 ml) was added TEA (1.8 ml, 13.3 mmol) at 0° C. followed by mesylchloride (0.62 ml, 8.01 mmol). The reaction mixture was stirred at rt for 1.5 h. The resulting mixture was concentrated under reduced pressure to yield tert-butyl (S)-3-((methylsulfonyl)oxy)pyrrolidine-1-carboxylate (1.5 g, quantitative). This material was used directly for the next step without further purification. LCMS: Method C, RT 2.05 min, MS: ES+ 266.2

Step b.

A mixture of tert-butyl (S)-3-hydroxypyrrolidine-1-carboxylate (0.5 g, 1.88 mmol) in aqueous ethylamine (70% in water) (10 ml) was heated at 90° C. for 16 h. The resulting mixture was concentrated under reduced pressure. The obtained residue was azeotropically distilled with diethyl ether (3×5 ml) and dried under high vacuum to yield tert-butyl (R)-3-(ethylamino)pyrrolidine-1-carboxylate (0.3 g, 1.39 mmol). LCMS: Method C, RT 1.54 min, MS: ES+ 215.29 Steps c-e. The title compound was synthesised from the intermediate above using a procedure similar to that described for steps b-d of Example 194 to provide the title compound. LCMS: Method A, RT 4.42 min, MS: ES+ 327.15; $^1$H NMR (400 MHz, DMSO-$d_6$) δ ppm 8.67 (s, 1H), 7.70 (d, J=8.8 Hz, 2H), 7.59 (d, J=8.8 Hz, 2H), 4.61-4.65 (m, 1H), 3.52-3.57 (m, 2H), 3.31-3.43 (m, 3H), 3.26-3.31 (m, 1H), 2.00-2.08 (m, 2H), 1.08 (t, J1=6.8, 3H).

Example 205 1-(1-cyanopyrrolidin-3-yl)-1-(2-methoxyethyl)-3-(4-(trifluoromethyl)phenyl)urea

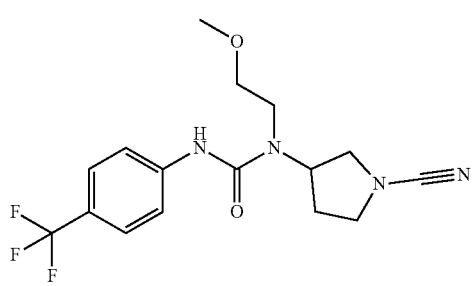 [SMILES: COCCN(C(=O)Nc1ccc(C(F)(F)F)cc1)C1CCN(C#N)C1]

Synthesised using a procedure similar to that described for Example 89 using tert-butyl 3-((2-methoxyethyl)amino)pyrrolidine-1-carboxylate (CAS Number 887587-33-9) in step a. LCMS: Method A, RT 4.66 min, MS: ES+ 357.03; $^1$H NMR (400 MHz, DMSO-$d_6$) δ ppm 8.91 (s, 1H), 7.54 (d, J=8.4 Hz, 2H), 7.43 (d, J=8.8 Hz, 2H), 4.83-4.87 (m, 1H), 3.57-3.79 (m, 4H), 3.56 (s, 3H), 3.37-3.53 (m, 3H), 3.28-3.32 (m, 1H), 2.19-2.25 (m, 1H), 1.97-2.05 (m, 1H).

Example 206 (R)—N-(1-cyanopyrrolidin-3-yl)-N-ethyl-3-fluoro-4-(1-methyl-1H-pyrazol-4-yl)benzamide

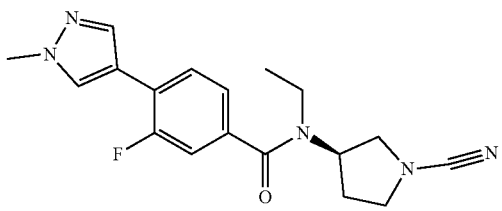 [SMILES: CCN(C(=O)c1ccc(-c2cnn(C)c2)c(F)c1)[C@@H]1CCN(C#N)C1]

Synthesised using a procedure similar to that described for Example 63 using tert-butyl (R)-3-(ethylamino)pyrrolidine-1l-carboxylate (described in the synthesis of Example 204) in step b. LCMS: Method A, RT 3.53 min, MS: ES+ 342.06; 1H NMR (400 MHz, DMSO-$d_6$) δ ppm 8.19 (d, J=2.0 Hz, 1H), 7.94 (s, 1H), 7.78 (t, J=8.0 Hz, 1H), 7.30 (dd, J=11.6, 1.6 Hz, 1H), 7.21 (dd, J=8.0, 1.6 Hz, 1H), 4.39-4.43 (m, 1H), 3.90 (s, 3H), 3.51-3.59 (m, 2H), 3.41-3.47 (m, 2H), 3.28-3.33 (m, 2H), 2.01-2.15 (m, 2H), 1.04-1.10 (m, 3H).

Example 207 (R)—N-(1-cyanopyrrolidin-3-yl)-N-ethyl-3-phenylazetidine-1-carboxamide

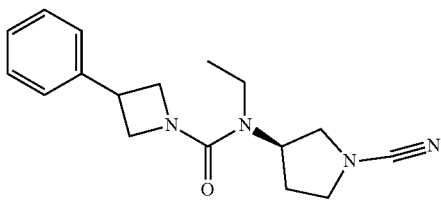 [SMILES: CCN(C(=O)N1CC(c2ccccc2)C1)[C@@H]1CCN(C#N)C1]

Synthesised using a procedure similar to that described for Example 189 using tert-butyl (R)-3-(ethylamino)pyrrolidine-1l-carboxylate (described in the synthesis of Example 204) in step c. LCMS: Method A, RT 4.07 min, MS: ES+ 299.08; $^1$H NMR (400 MHz, CDCl$_3$) δ ppm 7.33-7.41 (m, 4H), 7.29-7.31 (m, 1H), 4.38-4.46 (m, 3H), 4.02-4.06 (m, 2H), 3.77-3.81 (m, 1H), 3.58-3.64 (m, 2H), 3.36-3.47 (m, 2H), 3.17-3.20 (m, 2H), 2.11-2.15 (m, 2H), 1.18-1.21 (m, 3H).

Example 208 (R)-3-(2-oxo-3-(4-phenylthiazol-2-yl)imidazolidin-1-yl)pyrrolidine-1-carbonitrile

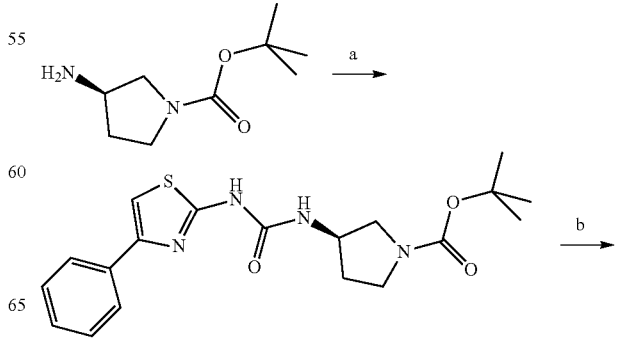

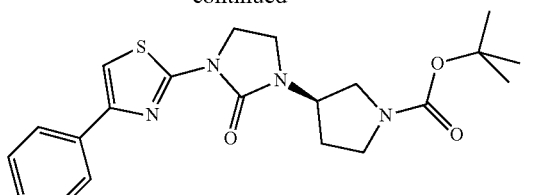

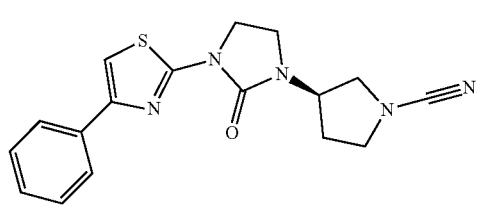

Step a.

To a stirred solution of (R)-3-amino-1N—BOC-pyrrolidine (1.0 g, 5.376 mmol) and DIPEA (1.04 g, 8.06 mmol) in THF (15 ml) was added triphosgene (0.526 g, 1.774 mmol) at 0° C. The reaction mixture was stirred at 0° C. for 2 h. 4-Phenylthiazol-2-amine (0.95 g, 5.376 mmol) was added to the reaction mixture at rt. The reaction mixture was heated at 60° C. for 16 h. The resulting reaction mixture was cooled to rt, quickly poured into water (50 ml) and extracted with EtOAc (2×20 ml). The combined organic phase was separated, dried over $Na_2SO_4$, filtered and concentrated under reduced pressure yielding tert-butyl (R)-3-(3-(4-phenylthiazol-2-yl)ureido)pyrrolidine-1-carboxylate (1.0 g, 2.58 mmol). This material was used directly for the next step without further purification. LCMS: Method C, RT 2.51 min, MS: ES+ 389.4

Step b.

To a stirred solution of tert-butyl (R)-3-(3-(4-phenylthiazol-2-yl)ureido)pyrrolidine-1-carboxylate (0.5 g, 1.29 mmol) in DMF (10 ml) was added $K_2CO_3$ (0.71 g, 5.15 mmol) at rt. The reaction mixture was stirred at rt for 15 min before adding 1,2-dibromoethane (0.29 g, 1.55 mmol). The reaction mixture was heated at 100° C. for 2 h. The resulting reaction mixture was cooled to rt, quickly poured into water (50 ml) and extracted with EtOAc (2×20 ml). The combined organic phase was separated, dried over $Na_2SO_4$, filtered and concentrated under reduced pressure. The resulting residue was purified by column chromatography (35% EtOAc in hexane) yielding tert-butyl (R)-3-(2-oxo-3-(4-phenylthiazol-2-yl)imidazolidin-1-yl)pyrrolidine-1-carboxylate (0.07 g, 0.169 mmol). LCMS: Method C, RT 2.80 min, MS: ES+ 415.4

Steps c, d. The title compound was synthesised from the intermediate above using a procedure similar to that described for steps b, c of Example 5 to provide the title compound. LCMS: Method B, RT 4.47 min, MS: ES+ 340.28; $^1$H NMR (400 MHz, DMSO-$d_6$) δ ppm 7.89 (d, J=7.2 Hz, 2H), 7.56 (s, 1 H), 7.41 (t, J=7.6 Hz, 2H), 7.30 (t, J=7.2 Hz, 1H), 4.90-4.52 (m, 1H), 4.07-4.12 (m, 2H), 3.61-3.65 (m, 2H), 3.41-3.58 (m, 4H), 2.05-2.13 (m, 2H).

Example 209 (R)-3-(2-oxo-3-(4-phenylthiazol-2-yl)tetrahydropyrimidin-1 (2H)-yl)pyrrolidine-1-carbonitrile

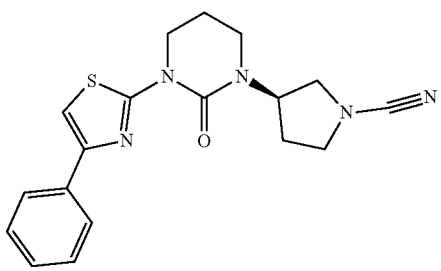 [SMILES: N#CN1CC[C@@H](N2CCCN(c3nc(-c4ccccc4)cs3)C2=O)C1]

Synthesised using a procedure similar to that described for Example 208. LCMS: Method B, RT 4.74 min, MS: ES+ 354.31; 1H NMR (400 MHz, DMSO-$d_6$) δ ppm 7.90 (d, J=7.2 Hz, 2H), 7.54 (s, 1H), 7.39 (t, J=7.4 Hz, 2H), 7.28 (t, J=7.2 Hz, 1H), 4.99-5.03 (m, 1H), 4.08-4.20 (m, 2H), 3.50-3.57 (m, 2H), 3.35-3.43 (m, 4H), 1.98-2.09 (m, 4H).

Example 210 (R)-3-(3-(3-morpholinophenyl)-2-oxoimidazolidin-1-yl)pyrrolidine-1-carbonitrile

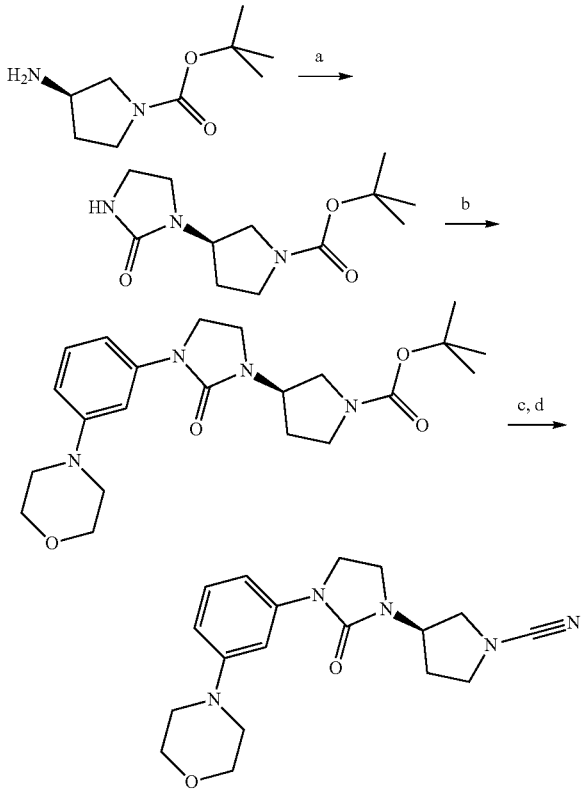

Step a.

To a stirred solution of (R)-3-amino-1N—BOC-pyrrolidine (1.0 g, 5.37 mmol) in THF (12 ml) was added 2-chloroethyl isocyanate (CAS Number 1943-83-5) (0.57 g, 5.37 mmol) at 0° C. The reaction mixture was stirred at rt for 1.5 h. NaH (60% dispersion in paraffin oil, 0.645 g, 16.12 mmol)

was added to the reaction mixture at 0° C. The reaction mixture was heated to 50° C. for 16 h. The resulting reaction mixture was cooled to rt, quickly poured into water (50 ml) and extracted with EtOAc (4×50 ml). The combined organic phase was separated, dried over Na$_2$SO$_4$, filtered and concentrated under reduced pressure. The resulting residue was purified by flash chromatography using (8-9% MeOH in DCM) yielding tert-butyl (R)-3-(2-oxoimidazolidin-1-yl)pyrrolidine-1-carboxylate (1.03 g, 4.062 mmol). LCMS: Method C, RT 1.67 min, MS: ES+ 256.32

Step b.

To a stirred solution of tert-butyl (R)-3-(2-oxoimidazolidin-1-yl)pyrrolidine-1-carboxylate (0.2 g, 0.829 mmol) and 4-(3-bromophenyl)morpholine (CAS Number 197846-82-5) (0.21 g, 0.83 mmol) in toluene (7 ml) was added Cs$_2$CO$_3$ (0.81 g, 2.49 mmol) at rt. The reaction mixture was degassed for 30 min before addition of Pd(OAc)$_2$ (0.019 g, 0.083 mmol) and BINAP (0.103 g, 0.166 mmol). The reaction mixture was heated at 90° C. for 10 h. The resulting reaction mixture was cooled and combined with two other batches prepared on the same scale by an identical method. Excess of solvent was distilled under vacuum and the resulting residue was purified by flash chromatography (54% EtOAc in hexane) yielding tert-butyl (R)-3-(3-(3-morpholinophenyl)-2-oxoimidazolidin-1-yl)pyrrolidine-1-carboxylate (0.267 g, 0.461 mmol). LCMS: Method C, RT 2.22 min, MS: ES+417.70

Steps c, d.

The title compound was synthesised from the intermediate above using a procedure similar to that described for steps b, c of Example 5 to provide the title compound. LCMS: Method B, RT 3.33 min, MS: ES+ 342.58; $^1$H NMR (400 MHz, DMSO-d$_6$) δ ppm 7.23 (s, 1H), 7.15 (t, J=8.0 Hz, 1H), 6.94 (dd, J=1.2 Hz, 8.0 Hz, 1H), 6.61 (dd, J=2.0 Hz, 8.4 Hz, 1H), 4.42-4.49 (m, 1H), 3.72-3.81 (m, 6H), 3.34-3.56 (m, 6H), 3.07 (t, J=6.8 Hz, 4H), 1.97-2.12 (m, 2H).

Example 211 (R)—N-(1-cyanopyrrolidin-3-yl)-4-(pyrimidin-2-yl)-3,4-dihydro-2H-benzo[b][1,4]oxazine-7-carboxamide

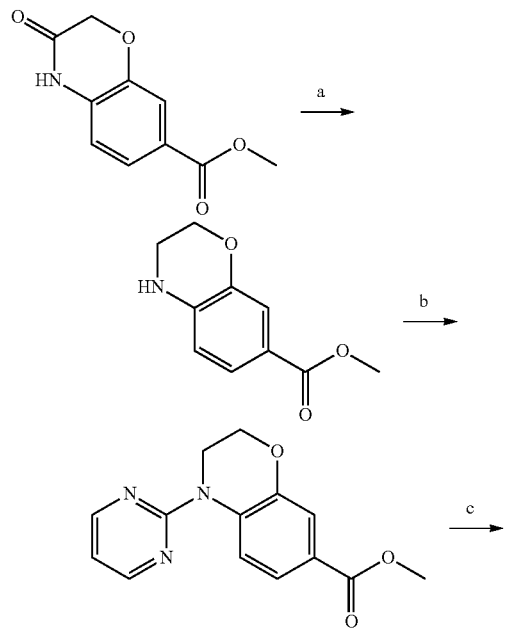

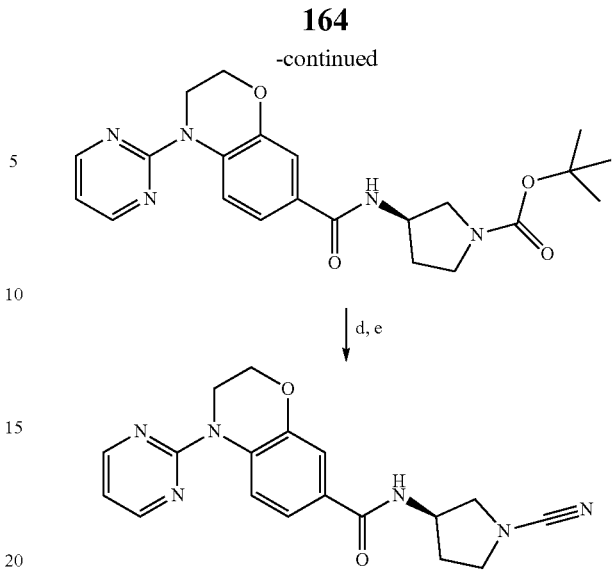

Step a.

To a stirred solution of methyl 3-oxo-3,4-dihydro-2H-benzo[b][1,4]oxazine-7-carboxylate (CAS Number 142166-00-5) (0.7 g, 3.38 mmol) in THF (14 ml) was added borane dimethyl sulphide complex (0.513 g, 6.76 mmol) at 0° C. under nitrogen. The reaction mixture was heated at 60° C. for 3 h. The reaction mixture was cooled to rt. MeOH (2 ml) was added slowly to the reaction mixture at 0° C. and the resulting reaction mixture was heated at 60° C. for 10 min. The excess of solvent was distilled under vacuum. The crude material was purified using flash chromatography The resulting residue was purified by flash chromatography (20% EtOAc in hexane) yielding methyl 3,4-dihydro-2H-benzo[b][1,4]oxazine-7-carboxylate (0.55 g, 2.85 mmol). LCMS: Method C, RT 1.96 min, MS: ES+ 194.1

Step b.

To a stirred solution of methyl 3,4-dihydro-2H-benzo[b][1,4]oxazine-7-carboxylate (0.44 g, 2.28 mmol) and 2-chloropyrimidine (0.782 g, 6.83 mmol) in DMF (13.2 ml) was added Cs$_2$CO$_3$ (2.23 g, 6.83 mmol) at rt under nitrogen atmosphere. The reaction mixture was degassed for 15 min at rt before addition of Pd$_2$(dba)$_3$ (0.021 g, 0.023 mmol) and xantphos (0.04 g, 0.683 mmol). The reaction mixture was heated to 140° C. for 15 h. The resulting reaction mixture was cooled to rt, poured into water (100 ml) and extracted with EtOAc (3×50 ml). The combined organic phase was separated, dried over Na$_2$SO$_4$, filtered and concentrated under reduced pressure. The resulting residue was purified by flash chromatography (10% EtOAc in hexane) yielding methyl 4-(pyrimidin-2-yl)-3,4-dihydro-2H-benzo[b][1,4]oxazine-7-carboxylate (0.29 g, 1.07 mmol). LCMS: Method C, RT 2.25 min, MS: ES+ 272.18

Step c.

To a stirred solution of methyl 4-(pyrimidin-2-yl)-3,4-dihydro-2H-benzo[b][1,4]oxazine-7-carboxylate (0.29 g, 1.07 mmol), (R)-3-amino-1N—BOC-pyrrolidine (0.22 g, 1.18 mmol) and DIPEA (0.276 g, 2.14 mmol) in THF (5.8 ml) was added 2 M TMA in toluene (2.67 ml, 5.34 mmol) at 0° C. The reaction mixture was heated to 80° C. for 2 h. The resulting reaction mixture was cooled to rt and quickly poured into a mixture of EtOAc: water (1:1, 100 ml). The reaction mixture was filtered through a celite bed, the organic phase was separated and aqueous phase was re-extracted using EtOAc (2×25 ml). The combined organic phase was washed with brine (25 ml), separated, dried over Na$_2$SO$_4$, filtered and concentrated under reduced pressure. The resulting residue was purified by column chromatography (70% EtOAc in hexane) yielding tert-butyl (R)-3-(4-(pyrimidin-2-yl)-3,4-dihydro-2H-benzo[b][1,4]oxazine-7-carboxamido)pyrrolidine-1-carboxylate (0.28 g, 0.66 mmol). LCMS: Method C, RT 2.19 min, MS: ES+ 426.28

Steps d, e.

The title compound was synthesised from the intermediate above using a procedure similar to that described for steps d, e of Example 2 to provide the title compound. LCMS: Method A, RT 3.38 min, MS: ES+ 351.11; $^1$H NMR (400 MHz, DMSO-d$_6$) δ ppm 8.58 (d, J=4.4 Hz, 2H), 8.47 (d, J=6.4 Hz, 1H), 8.13 (d, J=8.4 Hz, 1H), 7.37-7.43 (m, 2H), 6.99 (t, J=4.8 Hz, 1H), 4.43-4.47 (m, 1H), 4.30-4.32 (m, 2H), 4.20-4.22 (m, 2H), 3.60-3.64 (m, 1H), 3.52-3.56 (m, 1H), 3.42-3.47 (m, 1H), 3.28-3.32 (m, 1H), 2.08-2.13 (m, 1H), 1.93-1.96 (m, 1H).

Example 212 (R)—N-(1-cyanopyrrolidin-3-yl)-4-(4-cyclopropylpyrimidin-2-yl)-3,4-dihydro-2H-benzo[b][1,4]oxazine-7-carboxamide

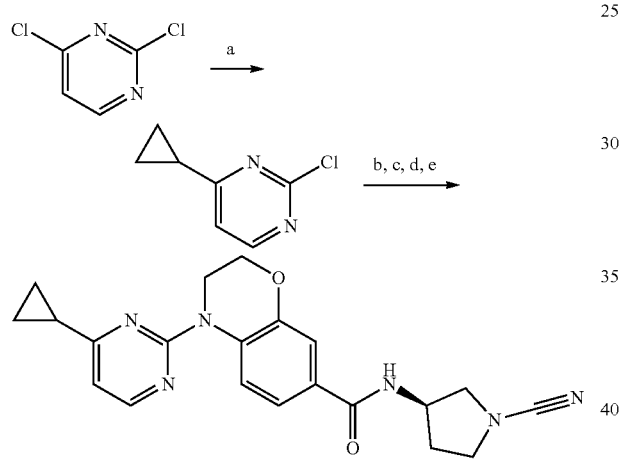

Step a.

To a stirred solution of 2,4-dichloropyrimidine (4.0 g, 26.85 mmol) and cyclopropylboronic acid (2.54 g, 29.54 mmol) in THF (80 ml) was added K$_3$PO$_4$ (14.25 g, 67.13 mmol) at rt. The reaction mixture was degassed for 15 min at rt before addition of Pd(dppf)Cl$_2$ (1.965 g, 2.68 mmol). The reaction mixture was heated at 90° C. for 2 h. The reaction mixture was cooled to rt, quickly poured into water (150 ml) and extracted using EtOAc (3×100 ml). The combined organic phase was washed with brine (100 ml), separated, dried over Na$_2$SO$_4$, filtered and concentrated under reduced pressure. The resulting residue was purified by column chromatography (20% EtOAc in hexane) yielding 2-chloro-4-cyclopropylpyrimidine (1.0 g, 6.47 mmol). LCMS: Method C, RT 2.01 min, MS: ES+ 155.15

Steps b-e.

The title compound was synthesised from the intermediate above using a procedure similar to that described for steps b-e of Example 211 to provide the title compound. LCMS: Method A, RT 4.22 min, MS: ES+ 391.16; $^1$H NMR (400 MHz, DMSO-d$_6$) δ ppm 8.45 (d, J=6.8 Hz, 1H), 8.35 (d, J=4.8 Hz, 1H), 8.10 (d, J=8.4 Hz, 1H), 7.37-7.41 (m, 2H), 6.94 (d, J=5.2 Hz, 1H), 4.44-4.46 (m, 1H), 4.27-4.29 (m, 2H), 4.15-4.18 (m, 2H), 3.60-3.64 (m, 1H), 3.52-3.56 (m, 1H), 3.41-3.47 (m, 1H), 3.28-3.31 (m, 1H), 2.03-2.13 (m, 2H), 1.93-1.97 (m, 1H), 1.00 (s, 4H).

Example 213 (R)—N-(1-cyanopyrrolidin-3-yl)-4-((4-cyclopropylpyrimidin-2-yl)amino)-3-fluorobenzamide

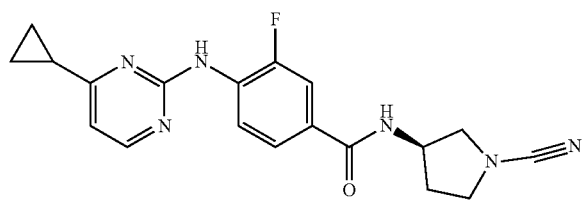 [SMILES: N#CN1CC[C@@H](NC(=O)c2ccc(Nc3nccc(C4CC4)n3)c(F)c2)C1]

Synthesised using a procedure similar to that described for Example 91 using 2-chloro-4-cyclopropylpyrimidine (as described for Example 212) in step b. LCMS: Method B, RT 3.90 min, MS: ES+ 367.23; $^1$H NMR (400 MHz, DMSO-d$_6$) δ ppm 9.06 (s, 1H), 8.54 (d, J=6.4 Hz, 1H), 8.26 (d, J=5.2 Hz, 1H), 8.04 (d, J=8.8 Hz, 1H), 7.68-7.72 (m, 2H), 6.88 (d, J=5.2 Hz, 1H), 4.45-4.49 (m, 1H), 3.62-3.66 (m, 1H), 3.53-3.59 (m, 1H), 3.42-3.48 (m, 1H), 3.30-3.31 (m, 1H), 2.10-2.15 (m, 1H), 1.92-2.03 (m, 2H), 1.01-1.03 (m, 4H).

Example 214 (R)—N-(1-cyanopyrrolidin-3-yl)-4-((4-cyclopropylpyrimidin-2-yl)amino)-2,3-difluorobenzamide

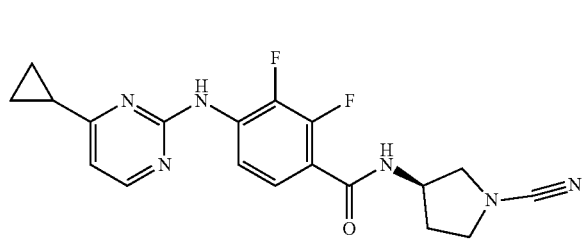 [SMILES: N#CN1CC[C@@H](NC(=O)c2ccc(Nc3nccc(C4CC4)n3)c(F)c2F)C1]

Synthesised using a procedure similar to that described for Example 91 using 2-chloro-4-cyclopropylpyrimidine (as described for Example 212) in step b. LCMS: Method A, RT 4.12 min, MS: ES+ 385.11; H NMR (400 MHz, DMSO-d$_6$) δ ppm 9.35 (s, 1H), 8.65 (d, J=6.4 Hz, 1H), 8.27 (d, J=5.2 Hz, 1H), 7.70-7.74 (m, 1H), 7.33-7.37 (m, 1H), 6.89 (d, J=5.2 Hz, 1H), 4.43-4.47 (m, 1H), 3.61-3.65 (m, 1H), 3.43-3.55 (m, 2H), 3.27-3.31 (m, 1H), 2.08-2.14 (m, 1H), 1.89-2.04 (m, 2H), 0.97-1.05 (m, 4H).

Example 215 (R)—N-(1-cyanopyrrolidin-3-y)-4-(N-methylisobutyramido)picolinamide

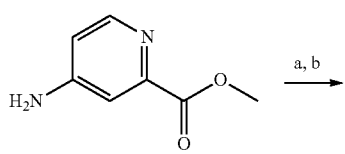

167

-continued

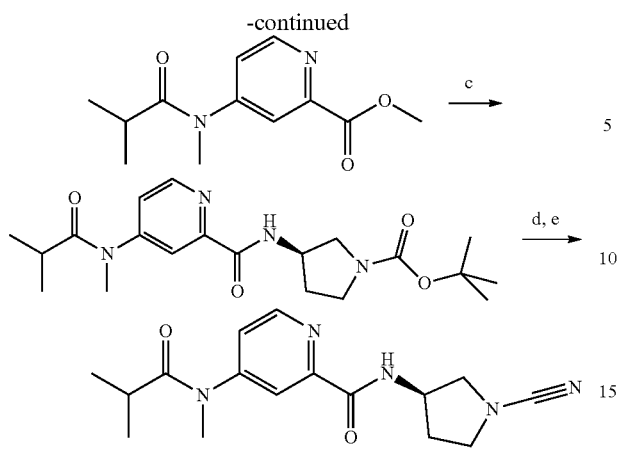

Steps a, b.

Following a procedure similar to that described for steps a, b of Example 62, using methyl 4-aminopicolinate (CAS Number 71469-93-7) in step a, to provide methyl 4-(N-methylisobutyramido) picolinate. LCMS: Method C, RT 1.72 min, MS: ES+ 237.00. This material was used directly for the next step without further purification.

Step c.

To a solution of methyl 4-(N-methylisobutyramido)picolinate (0.150 g, 0.635 mmol) in THF (10 ml) was added DIPEA (0.06 ml, 0.317 mmol) at rt. The reaction mixture was cooled to 0° C. Trimethylaluminum solution (2M in toluene) (1.5 ml, 3.177 mmol) was added to the reaction mixture. The reaction mixture was stirred at 0° C. for 30 min and then treated with (R)-3-amino-1N—BOC-pyrrolidine (0.118 g, 0.633 mmol). The reaction mixture was heated at 90° C. for 2 h. The resulting reaction mixture was cooled to rt and poured into saturated aqueous NaHCO$_3$ solution (50 ml) and extracted with EtOAc (3×50 ml). The combined organic layer was dried over Na$_2$SO$_4$, filtered and concentrated under reduced pressure yielding tert-butyl (R)-3-(4-(N-methylisobutyramido) picolinamido)pyrrolidine-1-carboxylate (0.220 g, 0.564 mmol). LCMS: Method C, RT 2.097 min, MS: ES+ 391.50. This material was used directly for the next step without further purification.

Steps d, e.

The title compound was synthesised from the intermediate above using a procedure similar to that described for steps b, c of Example 1. LCMS: Method B, RT 3.07 min, MS: ES+ 316.10; 1H NMR (400 MHz, DMSO-d$_6$) δ ppm 9.08 (d, J=6.4 Hz, 1H), 8.66 (d, J=5.4 Hz, 1H), 7.97 (d, J=1.6 Hz, 1H), 7.62-7.64 (m, 1H), 4.51-4.55 (m, 1H), 3.50-3.63 (m, 2H), 3.38-3.47 (m, 2H), 3.30 (s, 3H), 2.74-2.78 (m, 1H), 1.99-2.16 (m, 2H), 1.01 (d, J=6.4 Hz, 6H).

Example 216 (R)—N-(1-cyanopyrrolidin-3-yl)-[2,3'-bipyridine]-6'-carboxamide

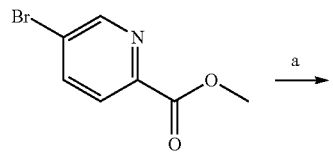

168

-continued

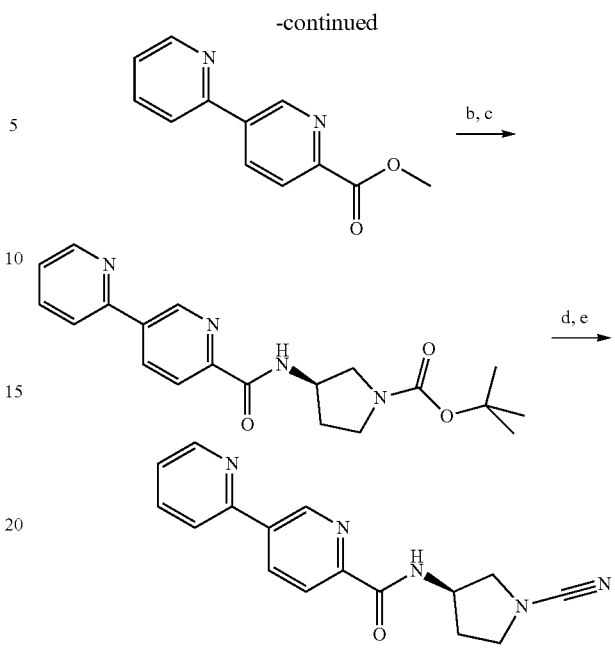

Step a.

To a solution of methyl 5-bromopicolinate (CAS Number 29682-15-3) (0.500 g, 2.314 mmol) in 1,4-dioxane (10 ml) was added 2-(tributylstannyl)pyridine (CAS Number 17997-47-6) (1.00 g, 2.717 mmol) at rt. The reaction mixture was degassed for 10 min before addition of Pd(PPh$_3$)$_4$(0.132 g, 0.114 mmol). The reaction mixture was heated at 110° C. for 16 h. The resulting reaction mixture was poured into water (70 ml) and extracted with EtOAc (2×70 ml). The combined organic layer was dried over Na$_2$SO$_4$, filtered and concentrated under reduced pressure yielding methyl [2,3'-bipyridine]-6'-carboxylate (0.300 g, 1.401 mmol). LCMS: Method C, RT 1.75 min, MS: ES+ 215.19. This material was used directly for the next step without further purification.

Steps b-e.

The title compound was synthesised from the intermediate above using a procedure similar to that described for steps b-e of Example 2. LCMS: Method C, RT 1.76 min, MS: ES+ 294.32; 1H NMR (400 MHz, DMSO-d$_6$) δ ppm 9.33-9.34 (m, 1H), 9.13 (d, J=7.2 Hz, 1H), 8.75-8.77 (m, 1H), 8.64 (dd, J=8.0, 2.0 Hz, 1H), 8.14-8.17 (m, 2H), 7.96-8.01 (m, 1H), 7.47-7.50 (m, 1H), 4.54-4.58 (m, 1H), 3.55-3.65 (m, 2H), 3.40-3.48 (m, 2H), 2.03-2.17 (m, 2H).

Example 217 (R)—N-(1-cyanopyrrolidin-3-yl)-[2,4'-bipyridine]-2'-carboxamide

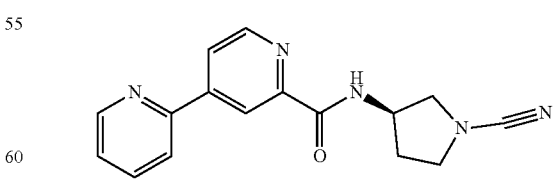

Synthesised using a procedure similar to that described for Example 216 using methyl 4-bromopicolinate (CAS Number 29681-42-3) in step a. LCMS: Method B, RT 3.17 min, MS: ES+294.33; 1H NMR (400 MHz, DMSO-d$_6$) δ ppm 9.11 (d, J=3.2 Hz, 1H), 8.78-8.79 (m, 2H), 8.71 (d, J=1.2 Hz, 1H), 8.29 (dd, J=5.2, 1.6 Hz, 1H), 8.20 (d, J=8.0 Hz, 1H), 7.98-8.03 (m, 1H), 7.52-7.55 (m, 1H), 4.54-4.62 (m, 1H), 3.59-3.64 (m, 1H), 3.55-3.59 (m, 1H), 3.34-3.49 (m, 2H), 2.12-2.19 (m, 1H), 2.02-2.11 (m, 1H).

Example 218 (R)-3-(4-chlorophenyl)-N-(1-cyanopyrrolidin-3-yl)isoxazole-5-carboxamide

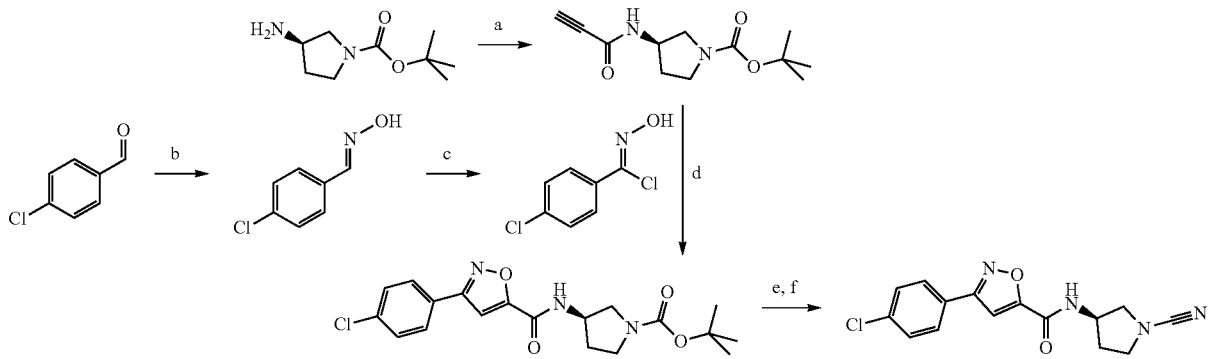

Step a.

To a solution of propiolic acid (0.800 g, 11.4 mmol) in THF (20 ml) was added DIPEA (6.00 ml, 35.1 mmol) and HATU (6.500 g, 17.105 mmol). The reaction mixture was stirred at rt for 30 min and then cooled to 0° C. The reaction mixture was treated with (R)-3-amino-1N—BOC-pyrrolidine (2.120 g, 11.4 mmol) and then stirred at rt for 15 h. The resulting reaction mixture was poured into saturated $NaHCO_3$ solution (50 ml) and extracted with EtOAc (3×30 ml). The combined organic layer was washed with brine (2×50 ml), dried over $Na_2SO_4$, filtered and concentrated under reduced pressure yielding tert-butyl (R)-3-propiolamidopyrrolidine-1-carboxylate (2.200 g, 9.24 mmol). LCMS: Method C, RT 1.88 min, MS: ES+ 239.40. This material was used directly for the next step without further purification.

Step b.

To a solution of 4-chlorobenzaldehyde (5.000 g, 35.5 mmol) in EtOH (50 ml) was added $NH_2OH.HCl$ (2.500 g, 36.0 mmol) at rt. A solution of NaOH (4.300 g, 407 mmol) in water (30 ml) was added to the reaction mixture at rt. The reaction mixture was refluxed for 2 h. The resulting reaction mixture was cooled to rt and acidified using diluted HCl solution to adjust pH ~3-4. The resulting precipitates were collected by filtration and washed with water (200 ml). The resulting solid material was dissolved in EtOAc (100 ml) and washed with saturated aqueous $NaHCO_3$ solution (3×50 ml). The combined organic layer was washed with brine (2×70 ml), dried over $Na_2SO_4$, filtered and concentrated under reduced pressure yielding (E)-4-chlorobenzaldehyde oxime (4.6 g, 29.49 mmol). LCMS: Method C, RT 2.06 min, MS: ES+ 155.90; $^1$H NMR (400 MHz, DMSO-$d_6$) δ ppm 11.36 (s, 1H), 8.15 (s, 1H), 7.61 (d, J=8.4 Hz, 2H), 7.45-7.52 (m, 2H). This material was used directly for the next step without further purification.

Steps c, d.

To a solution of (E)-4-chlorobenzaldehyde oxime (0.700 g, 4.49 mmol) in DCM (20 ml) was added N-chlorosuccinamide (0.900 g, 6.77 mmol) at 0° C. The reaction mixture was stirred at rt for 15 h. The reaction mixture was then cooled to 0° C. TEA (1.2 ml, 9.032 mmol) was added to the reaction mixture and stirred for 5 min. Tert-butyl (R)-3-propiolamidopyrrolidine-1-carboxylate (1.300 g, 5.46 mmol) was added to the reaction mixture at 0° C. The reaction mixture was stirred at rt for 15 h. The resulting reaction mixture was poured into water (100 ml) and extracted with DCM (3×30 ml). The combined organic layer was washed with brine (2×40 ml), dried over $Na_2SO_4$, filtered and concentrated under reduced pressure. The obtained residue was purified by flash chromatography (12-15% EtOAc in hexane) yielding tert-butyl (R)-3-(3-(4-chlorophenyl) isoxazole-5-carboxamido) pyrrolidine-1-carboxylate (0.400 g, 1.023 mmol). LCMS: Method C, RT 2.51 min, MS: ES-390.70.

Steps e, f.

The title compound was synthesised from the intermediate above using a procedure similar to that described for steps b, c of Example 1. LCMS: Method A, RT 4.30 min, MS: ES+ 316.91; $^1$H NMR (400 MHz, DMSO-$d_6$) δ ppm 9.30 (d, J=6.8 Hz, 1H), 7.95-7.98 (m, 2H), 7.71 (s, 1H), 7.61-7.64 (m, 2H), 4.46-4.53 (m, 1H), 3.63-3.67 (m, 1H), 3.53-3.59 (m, 1H), 3.43-3.49 (m, 1H), 3.34-3.38 (m, 1H), 2.10-2.19 (In, 1H), 1.94-2.02 (m, 1H).

Example 219 (R)—N-(1-cyanopyrrolidin-3-yl)-3-(4-(trifluoromethyl)phenyl)isoxazole-5-carboxamide

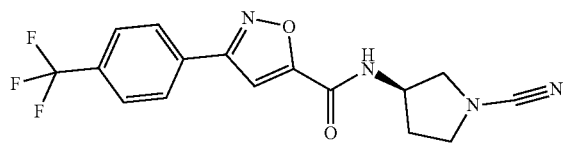 [SMILES: N#CN1CC[C@@H](NC(=O)c2cc(-c3ccc(C(F)(F)F)cc3)no2)C1]

Synthesised using a procedure similar to that described for Example 218 using 4-(trifluoromethyl)benzaldehyde in step a. LCMS: Method A, RT 4.48 min, MS: ES+ 350.91; $^1$H NMR (400 MHz, DMSO-$d_6$) δ ppm 9.35 (d, J=6.4 Hz, 1H), 8.17 (d, J=8.4 Hz, 2H), 7.93 (d, J=8.4 Hz, 2H), 7.80 (s, 1H), 4.47-4.54 (m, 1H), 3.63-3.67 (m, 1H), 3.53-3.59 (m, 1H), 3.42-3.49 (m, 1H), 3.34-3.39 (m, 1H), 2.11-2.19 (m, 1H), 1.94-2.02 (m, 1H).

Example 220 (R)—N-(1-cyanopyrrolidin-3-yl)-3-(3,4-dimethoxyphenyl)isoxazole-5-carboxamide

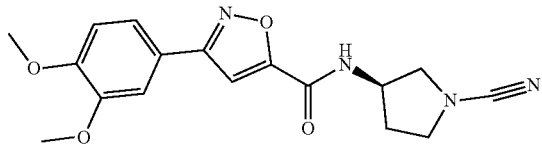 [SMILES: COc1ccc(-c2cc(C(=O)N[C@@H]3CCN(C#N)C3)on2)cc1OC]

Synthesised using a procedure similar to that described for Example 218 using 3,4-dimethoxybenzaldehyde in step a. LCMS: Method A, RT 3.56 min, MS: ES+ 343.12; $^1$H NMR (400 MHz, DMSO-$d_6$) δ ppm 9.24 (d, J=6.8 Hz, 1H), 7.67 (s, 1H), 7.48-7.51 (dd, J=8, 2.4 Hz, 1H), 7.45-7.46 (d, J=2.0 Hz, 1H), 7.10 (d, J=8.4 Hz, 1H), 4.48-4.52 (m, 1H), 3.85 (s, 3H), 3.83 (s, 3H), 3.63-3.67 (m, 1H), 3.53-3.59 (1, 1H), 3.45-3.49 (m, 1H), 3.34-3.38 (m, 1H), 2.10-2.19 (m, 1H), 1.94-2.02 (m, 1H).

Example 221 (R)—N-(1-cyanopyrrolidin-3-yl)-3-(3-methoxyphenyl)isoxazole-5-carboxamide

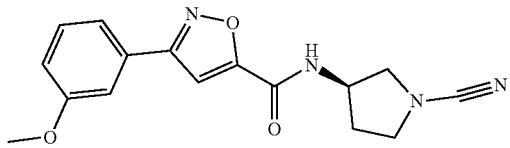 [SMILES: COc1cccc(-c2cc(C(=O)N[C@@H]3CCN(C#N)C3)on2)c1]

Synthesised using a procedure similar to that described for Example 218 using 3-methoxybenzaldehyde in step a. LCMS: Method B, RT 3.76 min, MS: ES+ 313.46; $^1$H NMR (400 MHz, DMSO-$d_6$) δ ppm 9.30 (d, J=6.4 Hz, 1H), 7.72 (s, 1H), 7.44-7.52 (m, 3H), 7.09-7.12 (m, 1H), 4.48-4.52 (m, 1H), 3.84 (s, 3H), 3.63-3.67 (m, 1H), 3.53-3.59 (m, 1H), 3.43-3.49 (m, 1H), 3.34-3.37 (m, 1H), 2.12-2.17 (m, 1H), 1.95-2.00 (m, 1H).

Example 222 N—((R)-1-cyanopyrrolidin-3-yl)-1-phenylpyrrolidine-3-carboxamide

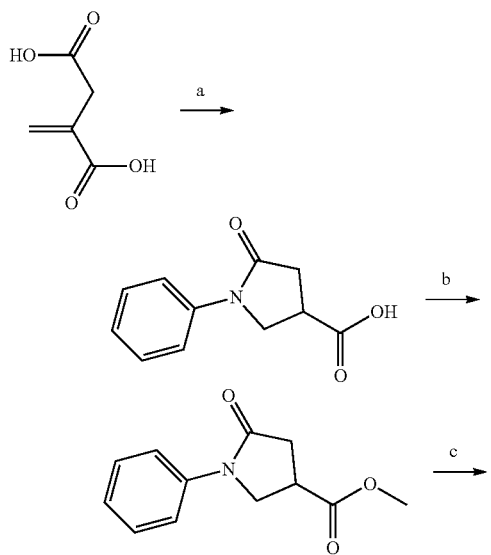

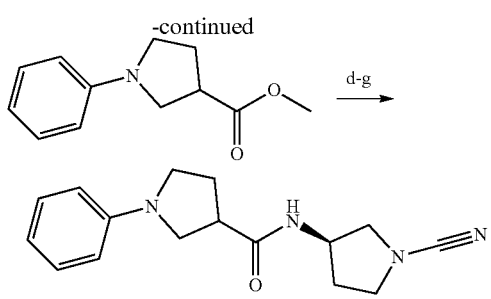

Step a.

To a solution of 2-methylenesuccinic acid (CAS Number 97-65-4) (5.000 g, 38.5 mmol) in water (70 ml) was added aniline (3.000 g, 32.3 mmol) at rt. The reaction mixture was heated at 110° C. for 30 h. The resulting reaction mixture was allowed to cool to rt and basified using 1M NaOH solution (100 ml). The obtained mixture was stirred for 10 min at rt. The resulting precipitates were filtered and the resulting filtrate was acidified using concentrated HCl. The obtained precipitates were collected by filtration and air dried yielding 5-oxo-1-phenylpyrrolidine-3-carboxylic acid (2.000 g, 9.76 mmol). LCMS: Method C, RT 1.70 min, MS: ES+ 206.18; $^1$H NMR (400 MHz, DMSO-$d_6$) δ ppm 12.78 (s, 1H), 7.63-7.66 (m, 2H), 7.36-7.40 (m, 2H), 7.15 (t, J=7.2 Hz, 1H), 4.03-4.08 (m, 1H), 3.95-3.99 (m, 1H), 3.32-3.39 (m, 1H), 2.67-2.82 (m, 2H).

Step b.

To a solution of 5-oxo-1-phenylpyrrolidine-3-carboxylic acid (1.000 g, 4.88 mmol) in MeOH (10 ml) was slowly added SOCl$_2$ (0.658 g, 5.82 mmol) at 0° C. over a period of 30 min. The reaction mixture was stirred at rt for 1 h. The resulting reaction mixture was concentrated under reduced pressure yielding methyl 5-oxo-1-phenylpyrrolidine-3-carboxylate (0.900 g, 4.11 mmol). LCMS: Method C, 1.90 min, MS: ES+ 220.50. This material was used directly for the next step without further purification.

Step c.

To a solution of 5-oxo-1-phenylpyrrolidine-3-carboxylate (1.500 g, 6.85 mmol) in THF (40 ml) was added 9-BBN (0.5 M in THF) (15 ml, 7.50 mmol). The reaction mixture was stirred at rt for 16 h. The resulting reaction mixture was evaporated under reduced pressure and purified by flash chromatography (40% EtOAc in hexane) yielding methyl 1-phenylpyrrolidine-3-carboxylate (0.640 g, 3.12 mmol). LCMS: Method C, RT 2.44 min. MS: ES+ 205.90.

Steps d-g.

The title compound was synthesised from the intermediate above using a procedure similar to that described for steps b-e of Example 2. LCMS: Method B, RT 3.55 min, MS: ES+ 285.28; $^1$H NMR (400 MHz, DMSO-$d_6$) δ ppm 8.36 (d, J=6.8 Hz, 1H), 7.15 (t, J=8.4 Hz, 2H), 6.59 (t, J=7.2 Hz, 1H), 6.52 (d, J=7.6 Hz, 2H), 4.23-4.27 (m, 1H), 3.37-3.55 (m, 4H), 3.24-3.32 (m, 3H), 3.14-3.22 (m, 1H), 3.03-3.09 (m, 1H), 2.01-2.17 (m, 3H), 1.75-1.82 (m, 1H).

Example 223 (R)—N-(1-cyanopyrrolidin-3-yl)-3-fluoro-4-(4-methyl-1H-imidazol-1-yl)benzamide

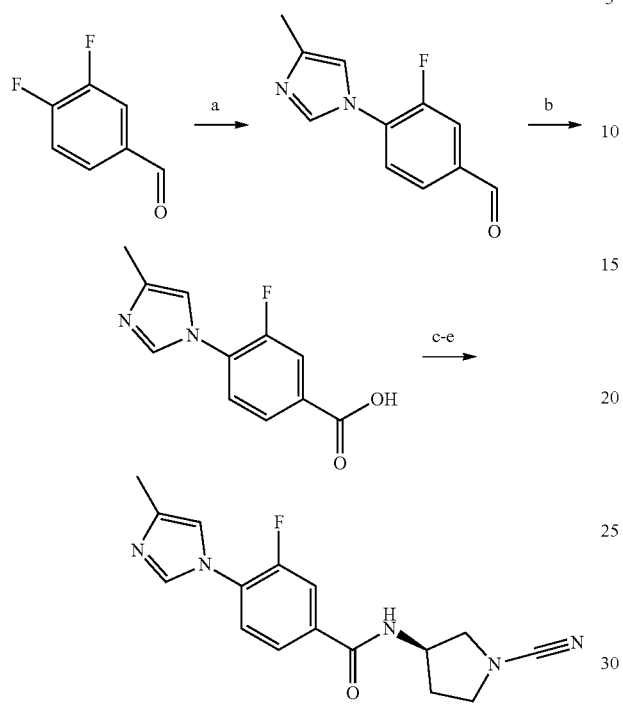

Step a.

To a solution of 3,4-difluorobenzaldehyde (1.000 g, 7.04 mmol) in DMF (10 ml) was added 4-methyl-1H-imidazole (0.580 g, 7.07 mmol) and K$_2$CO$_3$ (1.200 g, 8.70 mmol) at rt. The reaction mixture was heated at 110° C. for 16 h. The resulting reaction mixture was cooled to rt and poured into saturated aqueous NaHCO$_3$ solution (150 ml). The resulting mixture was extracted with EtOAc (3×50 ml). The combined organic phase was dried over Na$_2$SO$_4$, filtered and concentrated under reduced pressure. The resulting residue was purified by column chromatography (30-50% EtOAc in hexane) yielding 3-fluoro-4-(4-methyl-1H-imidazol-1-yl)benzaldehyde (1.300 g, 6.37 mmol). LCMS: Method C, RT 1.38 min, MS: ES+ 205.19; $^1$H NMR (400 MHz, DMSO-d$_6$) δ ppm 10.02 (s, 1H), 8.07 (s, 1H), 7.96 (d, J=1.2 Hz, 1H), 7.89-7.92 (m, 2H), 7.40 (s, 1H), 2.18 (s, 3H).

Step b.

To a solution of 3-fluoro-4-(4-methyl-1H-imidazol-1-yl)benzaldehyde (1.300 g, 6.37 mmol) in MeOH: water (7:1, 16 ml) was added KOH (1.420 g, 25.36 mmol) at rt. The reaction mixture was heated at 65° C. A solution of H$_2$O$_2$ (30% w/w in water) (5.60 ml, 49.41 mmol) was slowly added to the reaction mixture at 65° C. and stirred for 16 h. The resulting reaction mixture was cooled to rt and concentrated under reduced pressure. The resulting mixture was poured into water (200 ml), acidified using 1 M HCl solution and extracted with EtOAc (100 ml). The combined organic phase was dried over Na$_2$SO$_4$, filtered and concentrated under reduced pressure yielding 3-fluoro-4-(4-methyl-1H-imidazol-1-yl) benzaldehyde (0.550 g, 2.50 mmol). LCMS: Method C, RT 1.25 min, MS: ES+221.19. This material was used directly for the next step without further purification.

Steps c-e.

The title compound was synthesised from the intermediate above using a procedure similar to that described for Example 1. LCMS: Method A, RT 3.12 min, MS: ES+ 313.98; $^1$H NMR (400 MHz, DMSO-d$_6$) δ ppm 8.78 (d, J=6.8 Hz, 1H), 8.01 (s, 1H), 7.92-7.96 (dd, J=12.0, 1.6 Hz, 1H), 7.83-7.85 (m, 1H), 7.74-7.78 (m, 1H), 7.36 (s, 1H), 4.47-4.50 (m, 1H), 3.63-3.67 (m, 1H), 3.53-3.59 (m, 1H), 3.45-3.49 (m, 1H), 3.32-3.33 (m, 1H), 2.18 (s, 3H), 2.08-2.16 (m, 1H), 1.93-2.00 (m, 1H).

Example 224 (R)—N-(1-cyanopyrrolidin-3-yl)-3-fluoro-N-methyl-4-(4-methyl-1H-imidazol-1-yl)benzamide

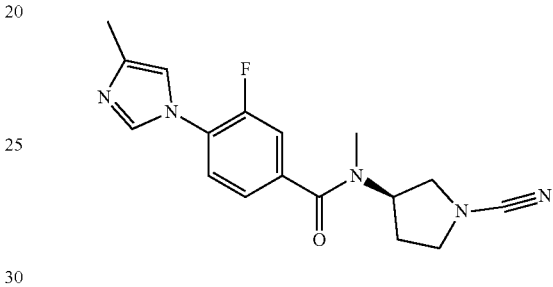

Synthesised using a procedure similar to that described for Example 223 using 1-N—BOC-(3R)-3-(methylamino)pyrrolidine in step c. LCMS: Method A, RT 3.10 min, MS: ES+ 328.02; $^1$H NMR (400 MHz, DMSO-d$_6$) δ ppm 7.97 (s, 1H), 7.69 (t, J=8.0 Hz, 1H), 7.55-7.62 (m, 1H), 7.34-7.42 (m, 1H), 7.32 (s, 1H), 4.32-4.37 (m, 1H), 3.52-3.54 (m, 2H), 3.44-3.47 (m, 2H), 2.89 (s, 3H), 2.18 (s, 3H), 2.02-2.09 (m, 2H).

Example 225 N—((R)-1-cyanopyrrolidin-3-yl)-3-(pyridin-2-yl)pyrrolidine-1-carboxamide

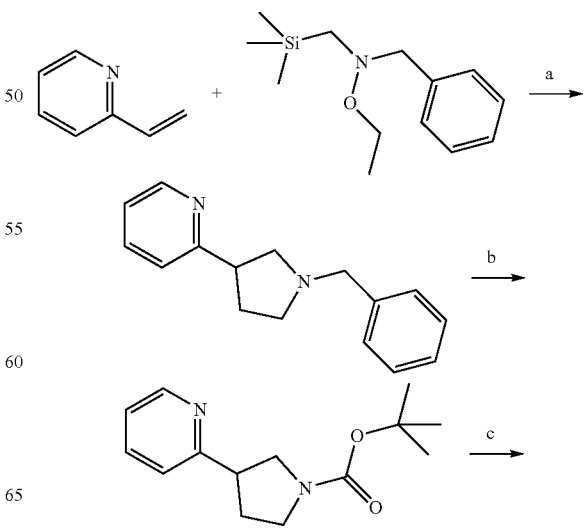

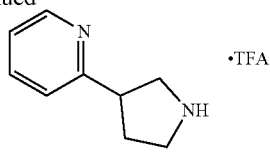

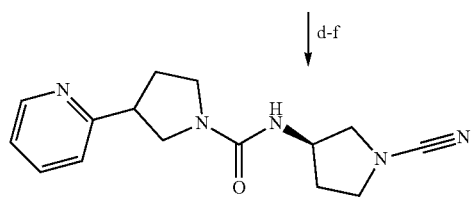

Step a.

To a solution of 2-vinylpyridine (CAS Number 100-69-6) (5.000 g, 47.62 mmol) in DCM (30 ml) was added TFA (0.542 g, 4.75 mmol). The reaction mixture was stirred at rt for 5 min and then treated dropwise with a solution of N-benzyl-1-methoxy-N-((trimethylsilyl)methyl)methanamine (CAS Number 93102-05-7) (16.92 g, 71.39 mmol) in DCM (30 ml) over a period of 45 min. The reaction mixture was stirred at rt for 16 h. The reaction mixture was poured into saturated aqueous NaHCO$_3$ solution (250 ml) and extracted with DCM (3×100 ml). The combined organic phase was dried over Na$_2$SO$_4$, filtered and concentrated under reduced pressure yielding 2-(1-benzylpyrrolidin-3-yl) pyridine (8.00 g, 33.61 mmol). LCMS: Method C, RT 1.52 min, MS: ES+ 239.25. This material was used directly for the next step without further purification.

Step b.

To a solution of 2-(1-benzylpyrrolidin-3-yl)pyridine (5.00 g, 21.01 mmol) in EtOH (50 ml) was added 20% Pd(OH)$_2$ on carbon (50% moisture content) (2.50 g) at rt. Polymethylhydroxylsilane (5.00 ml) was added to the reaction mixture at rt over a period of 10 min. The resulting reaction mixture was stirred at rt for 1 h before addition of BOC anhydride (9.150 g, 41.97 mmol). The reaction mixture was stirred at rt for 16 h. The resulting reaction mixture was filtered through a celite bed and washed with MeOH (50 ml). The combined filtrate was concentrated under reduced pressure. The resulting residue was purified by column chromatography (10% EtOAc in hexane) yielding tert-butyl 3-(pyridin-2-yl) pyrrolidine-1-carboxylate (2.50 g, 10.08 mmol). LCMS: Method C, RT 1.84 min, MS: ES+ 249.40.

Step c.

To a solution of tert-butyl 3-(pyridin-2-yl)pyrrolidine-1-carboxylate (0.500 g, 2.016 mmol) in DCM (4 ml) was added TFA (0.459 g, 4.03 mmol) at rt. The reaction mixture was stirred at rt for 2 h. The resulting reaction mixture was evaporated under reduced pressure. The resulting residue was co evaporated with DCM (3×10 ml) and dried under high vacuum yielding 2-(pyrrolidin-3-yl)pyridine TFA salt (0.260 g, 0.984 mmol). MS: ES+ 149.0. This material was used directly for the next step without further purification.

Steps d-f.

The title compound was synthesised from the intermediate above using a procedure similar to that described for Example 5. LCMS: Method A, RT 2.84 min, MS: ES+ 285.98; $^1$H NMR (400 MHz, DMSO-d$_6$) δ ppm 8.51 (d, J=4.0 Hz, 1H), 7.72-7.77 (m, 1H), 7.34 (d, J=7.6 Hz, 1H), 7.24-7.27 (m, 1H), 6.24 (d, J=6.4 Hz, 1H), 4.09-4.18 (m, 1H), 3.68-3.73 (m, 1H), 3.47-3.57 (m, 4H), 3.36-3.45 (m, 1H), 3.27-3.31 (m, 1H), 3.16-3.19 (m, 2H), 2.19-2.25 (m, 1H), 1.95-2.11 (m, 2H), 1.80-1.88 (m, 1H).

Example 226 N—((R)-1-cyanopyrrolidin-3-yl)-3-(-methyl-1H-pyrazol-4-yl)pyrrolidine-1-carboxamide

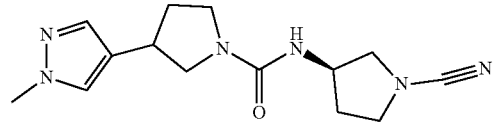 [SMILES: Cn1cc(C2CCN(C(=O)N[C@@H]3CCN(C#N)C3)C2)cn1]

Synthesised using a procedure similar to that described for Example 5 using 1-methyl-4-(pyrrolidin-3-yl)-1H-pyrazole (CAS Number 1211542-11-8) in step a. LCMS: Method H, RT 13.27 min, MS: ES+ 289.07; $^1$H NMR (400 MHz, DMSO-d$_6$) δ ppm 7.54 (s, 1H), 7.31 (s, 1H), 6.18 (d, J=6.4 Hz, 1H), 4.11-4.14 (m, 1H), 3.78 (s, 3H), 3.60-3.64 (m, 1H), 3.45-3.52 (m, 2H), 3.36-3.41 (m, 2H), 3.21-3.28 (m, 1H), 3.15-3.18 (m, 2H), 3.04-3.08 (m, 1H), 2.12-2.14 (m, 1H), 1.95-2.02 (m, 1H), 1.77-1.87 (m, 2H).

Example 227 (R)—N-(1-cyanopyrrolidin-3-yl)-3-(2-methoxypyridin-4-yl)-N-methylisoxazole-5-carboxamide

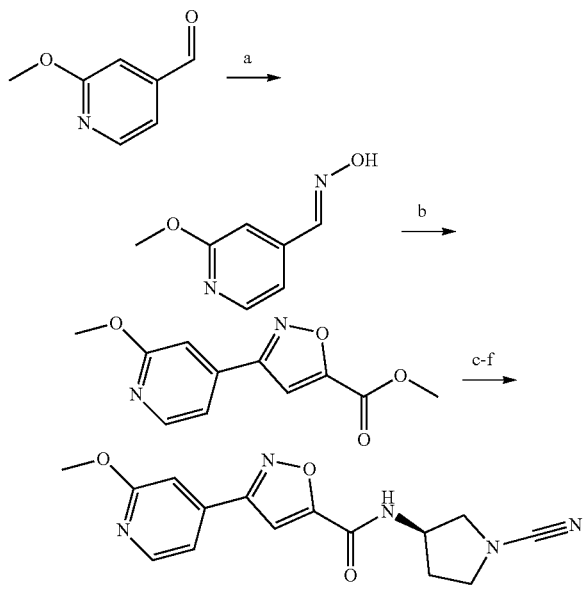

Step a.

To a solution of 2-methoxyisonicotinaldehyde (CAS Number 72716-87-1) (0.500 g, 3.65 mmol) in MeOH (7 ml) was added NH$_2$OH.HCl (0.503 g, 7.29 mmol) at rt. The reaction mixture was heated at 70° C. for 1 h. The resulting reaction mixture was concentrated under reduced pressure yielding (E)-2-methoxyisonicotinaldehyde oxime (1.20 g, quantitative). LCMS: Method A, RT 2.54 min, MS: ES+ 152.91. This material was used directly for the next step without further purification.

Step b.

To a solution of (E)-2-methoxyisonicotinaldehyde oxime (0.600 g, 3.95 mmol) in DMF (7 ml) was added N-chlorosuccinamide (0.787 g, 5.92 mmol) at 0° C. The reaction mixture was stirred at rt for 3 h. 1,8-Diazabicyclo[5.4.0]undec-7-ene (0.900 g, 5.92 mmol) and methyl propiolate (0.500 g, 5.95 mmol) were added to reaction mixture and stirred at rt for 16 h. The resulting mixture was poured into cold water (150 ml) and extracted with EtOAc (2×100 ml). The combined organic layer was washed with brine (100 ml), dried over $Na_2SO_4$, filtered and concentrated under reduced pressure. The resulting residue was purified by flash chromatography (70% EtOAc in hexane) yielding methyl 3-(2-methoxypyridin-4-yl) isoxazole-5-carboxylate (0.330 g, 1.410 mmol). LCMS: Method C, RT 2.17 min, MS: ES+ 235.25.

Steps c-f.

The title compound was synthesised from the intermediate above using a procedure similar to that described for steps b-e of Example 2. LCMS: Method A, RT 3.68 min, MS: ES+ 328.02; $^1$H NMR (400 MHz, DMSO-$d_6$, 80° C.) δ ppm 8.34 (d, J=5.2 Hz, 1H), 7.59 (s, 1H), 7.50 (dd, J=5.6, 1.6 Hz, 1H), 7.34 (s, 1H), 4.50-5.10 (m, 1H), 3.94 (s, 3H), 3.56-3.65 (m, 2H), 3.41-3.51 (m, 2H), 3.04 (s, 3H), 2.10-2.23 (m, 2H).

Example 228 (R)—N-(1-cyanopyrrolidin-3-yl)-2-fluoro-4-(N-methylphenylsulfonamido)benzamide

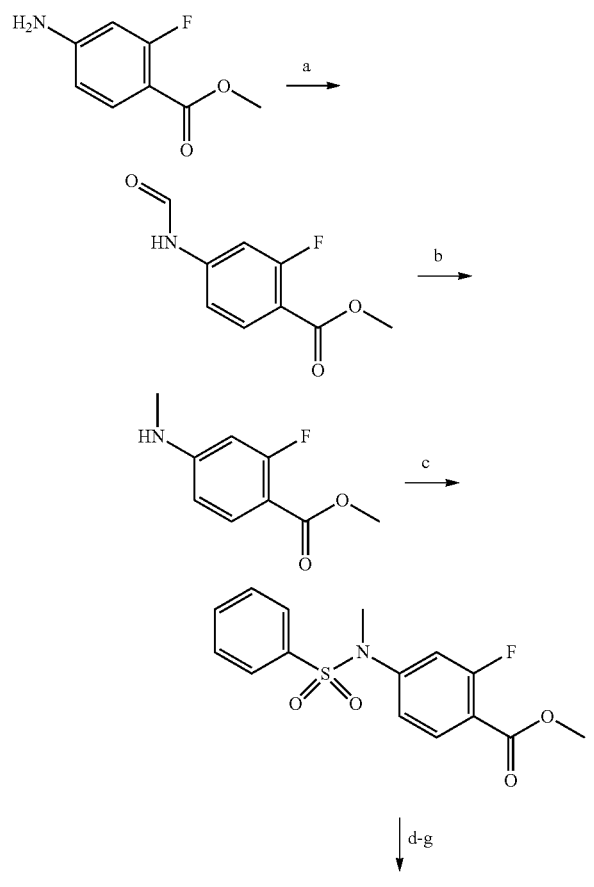

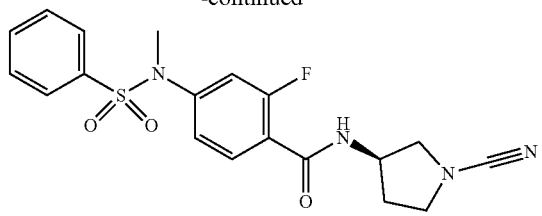

Step a.

A mixture of methyl 4-amino-2-fluorobenzoate (0.300 g, 1.77 mmol) and ethyl formate (10 ml) was heated at 80° C. for 16 h. The resulting reaction mixture was cooled to rt and concentrated under reduced pressure yielding methyl 2-fluoro-4-formamidobenzoate (0.332 g, 1.685 mmol). LCMS: Method C, RT 1.79 min, MS: ES-196.12.

Step b.

To a solution of methyl 2-fluoro-4-formamidobenzoate (0.332 g, 1.68 mmol) in THF (5 ml) was added 1 M solution of $BH_3$.THF complex in THF (8.42 ml, 8.43 mmol) at 0° C. The reaction mixture was stirred at rt for 16 h. The resulting reaction mixture was cooled to 0° C. and acidified with 10% HCl in MeOH (5 ml). The reaction mixture was heated at 50° C. for 1 h. The resulting reaction mixture was cooled to 0° C. and basified using saturated aqueous $NaHCO_3$ solution. The resulting reaction mixture was concentrated under reduced pressure. The obtained residue was poured into water (30 ml) and extracted with EtOAc (2×20 ml). The combined organic layer was dried over $Na_2SO_4$, filtered and concentrated under reduced pressure yielding methyl 2-fluoro-4-(methylamino) benzoate (0.331 g, quantitative). LCMS: Method C, RT 2.031 min. MS: ES+ 184.06. This material was used directly for the next step without further purification.

Step c.

To a solution of methyl 2-fluoro-4-(methylamino)benzoate (0.331 g, 1.81 mmol) in pyridine (3 ml) was added benzenesulphonyl chloride (0.383 g, 2.17 mmol) at 0° C. and stirred for 1 h. The resulting reaction mixture was poured into saturated aqueous citric acid solution (20 ml) and extracted with EtOAc (30 ml). The organic layer was washed with saturated aqueous citric acid solution (2×20 ml). The organic layer was washed with brine (20 ml), dried over $Na_2SO_4$, filtered and concentrated under reduced pressure yielding methyl 2-fluoro-4-(N-methylphenylsulfonamido) benzoate (0.506 g, 1.56 mmol). LCMS: Method C, RT 2.36 min, MS: ES+ 324.19. This material was used directly for the next step without further purification.

Steps d-g.

The title compound was synthesised from the intermediate above using a procedure similar to that described for steps b-e of Example 2. LCMS: Method A, RT 4.00 min, MS: ES+ 402.94; $^1$H NMR (400 MHz, DMSO-$d_6$) δ ppm 8.68 (d, J=6.4 Hz, 1H), 7.72-7.75 (m, 1H), 7.53-7.64 (m, 5H), 7.09-7.15 (m, 2H), 4.41-4.45 (m, 1H), 3.60-3.64 (m, 1H), 3.42-3.53 (m, 2H), 3.26-3.29 (m, 1H), 3.17 (s, 3H), 2.06-2.15 (m, 1H), 1.87-1.93 (m, 1H).

Example 229 (R)—N-(1-cyanopyrrolidin-3-yl)-1-methyl-6-(1-methyl-1H-pyrazol-4-yl)-1H-indole-2-carboxamide

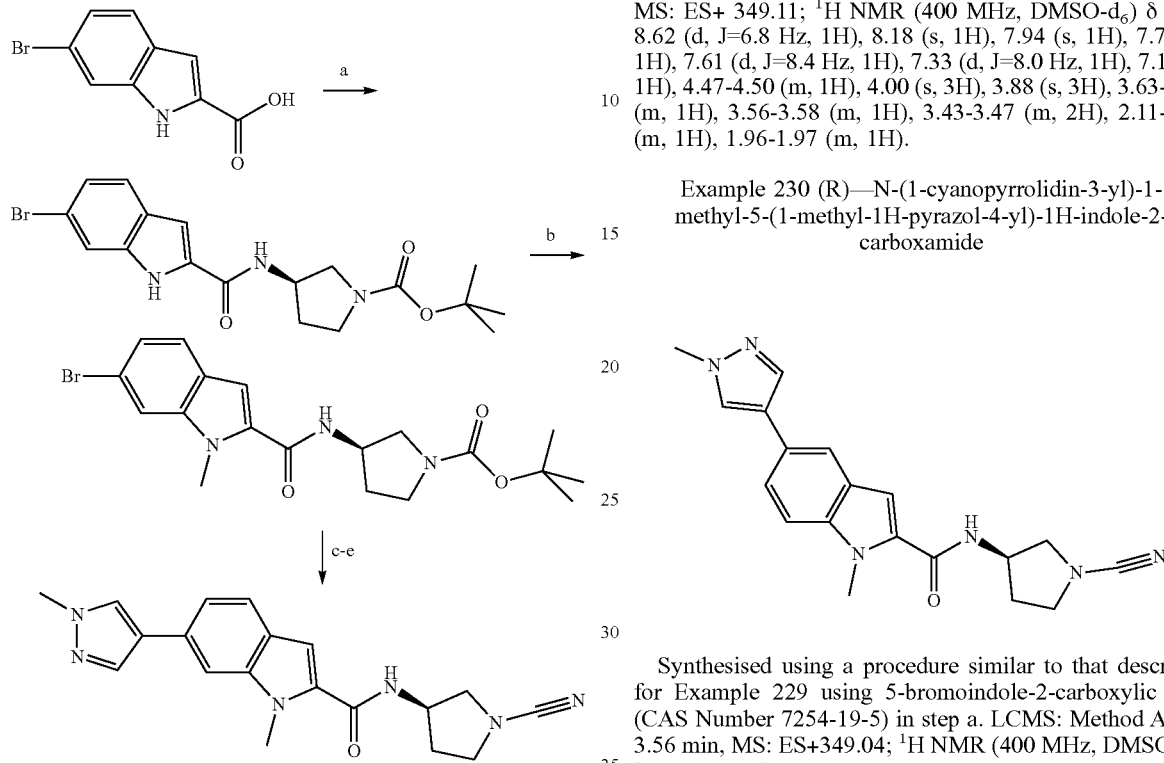

Step a.
To a solution of 6-bromo-1H-indole-2-carboxylic acid (CAS Number 16732-65-3) (0.249 g, 1.04 mmol) in THF (8 ml) was added DIPEA (0.402 g, 3.112 mmol) and HATU (0.394 g, 1.04 mmol) at rt. The reaction mixture was stirred at rt for 10 min. A solution of (R)-3-amino-1N—BOC-pyrrolidine (CAS Number 147081-49-0) (0.193 g, 1.03 mmol) in THF (2 ml) was added dropwise to the reaction mixture at rt. The reaction mixture was stirred at rt for 1 h. The resulting reaction mixture was poured into water (50 ml) and extracted with DCM (2×25 ml). The combined organic layer was washed with brine (20 ml), dried over Na$_2$SO$_4$, filtered and concentrated under reduced pressure. The resulting residue was purified by flash chromatography (40% EtOAc in hexane) yielding tert-butyl (R)-3-(6-bromo-1H-indole-2-carboxamido) pyrrolidine-1-carboxylate (0.400 g, 0.980 mmol). LCMS: Method C, RT 2.24 min, MS: ES+ 408.50, 410.50.

Step b.
To a solution of tert-butyl (R)-3-(6-bromo-1-methyl-1H-indole-2-carboxamido)pyrrolidine-1-carboxylate (0.460 g, 1.130 mmol) in DMF (10 ml) was added Cs$_2$CO$_3$ (0.730 g, 2.239 mmol) and methyl iodide (0.320 g, 2.254 mmol). The reaction mixture was heated at 100° C. for 2.5 h. The resulting reaction mixture was cooled to rt and poured into water (150 ml). The resulting mixture was extracted with DCM (2×25 ml). The combined organic phase was washed with brine (25 ml), dried over Na$_2$SO$_4$, filtered and concentrated under reduced pressure yielding tert-butyl (R)-3-(6-bromo-1-methyl-1H-indole-2-carboxamido) pyrrolidine-1-carboxylate (0.400 g, 0.95 mmol). LCMS: Method C, RT 2.61 min, MS: ES+ 422.30, 424.30. This material was used directly for the next step without further purification.

Steps c-e.
The title compound was synthesised from the intermediate above using a procedure similar to that described for steps b-d of Example 3. LCMS: Method A, RT 3.56 min, MS: ES+ 349.11; $^1$H NMR (400 MHz, DMSO-d$_6$) δ ppm 8.62 (d, J=6.8 Hz, 1H), 8.18 (s, 1H), 7.94 (s, 1H), 7.72 (s, 1H), 7.61 (d, J=8.4 Hz, 1H), 7.33 (d, J=8.0 Hz, 1H), 7.12 (s, 1H), 4.47-4.50 (m, 1H), 4.00 (s, 3H), 3.88 (s, 3H), 3.63-3.67 (m, 1H), 3.56-3.58 (m, 1H), 3.43-3.47 (m, 2H), 2.11-2.14 (m, 1H), 1.96-1.97 (m, 1H).

Example 230 (R)—N-(1-cyanopyrrolidin-3-yl)-1-methyl-5-(1-methyl-1H-pyrazol-4-yl)-1H-indole-2-carboxamide

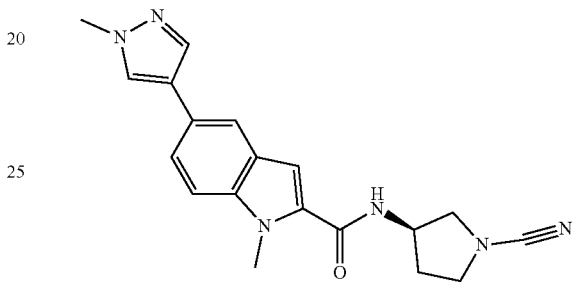

Synthesised using a procedure similar to that described for Example 229 using 5-bromoindole-2-carboxylic acid (CAS Number 7254-19-5) in step a. LCMS: Method A, RT 3.56 min, MS: ES+349.04; $^1$H NMR (400 MHz, DMSO-d$_6$) δ ppm 8.68 (d, J=6.8 Hz, 1H), 8.01 (s, 1H), 7.85 (s, 1H), 7.79 (s, 1H), 7.48-7.53 (m, 2H), 7.11 (s, 1H), 4.46-4.50 (m, 1H), 3.96 (s, 3H), 3.86 (s, 3H), 3.63-3.67 (m, 1H), 3.54-3.60 (m, 1H), 3.43-3.49 (m, 1H), 3.21-3.32 (m, 1H), 2.11-2.16 (m, 1H), 1.94-1.99 (m, 1H).

Example 231 (R)-1-(1-cyanopyrrolidin-3-yl)-3-(2-(isoindolin-2-yl)pyridin-4-yl)-1-methylurea

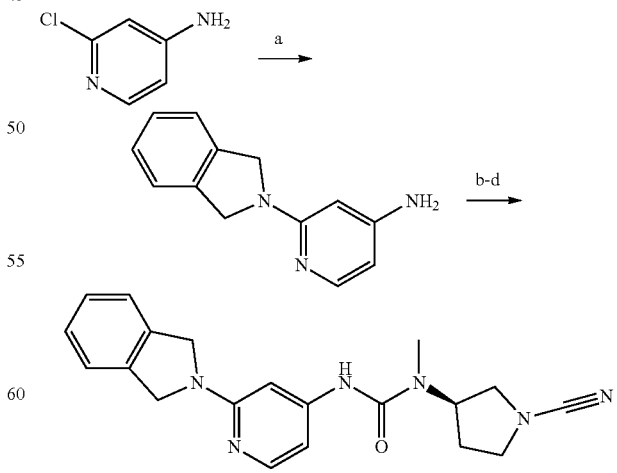

Step a.
To a solution of 2-chloropyridin-4-amine (0.500 g, 3.91 mmol) in toluene (5 ml) was added isoindoline (0.557 g, 4.68 mmol), potassium tert-butoxide (2.070 g, 9.76 mmol) and BINAP (0.243 g, 0.390 mmol) at rt. The reaction mixture was degassed for 5 min before addition of $Pd_2(dba)_3$ (0.178 g, 0.194 mmol) at rt. The reaction mixture was heated at 110° C. for 4 h. The resulting reaction mixture was cooled to rt and poured into water (200 ml). The resulting mixture was extracted with DCM (3×100 ml). The combined organic phase was dried over $Na_2SO_4$, filtered and concentrated under reduced pressure. The resulting residue was purified by flash chromatography (3% MeOH in DCM) yielding 2-(isoindolin-2-yl) pyridin-4-amine (0.700 g, 3.317 mmol). LCMS: Method C, RT 1.68 min, MS: ES+212.13.

Steps b-d.

The title compound was synthesised from the intermediate above using a procedure similar to that described for steps b-d of Example 194. LCMS: Method A, RT 3.83 min, MS: ES+ 363.08; $^1$H NMR (400 MHz, DMSO-$d_6$) δ ppm 8.60 (s, 1H), 7.92 (d, J=5.6 Hz, 1H), 7.39-7.42 (m, 2H), 7.30-7.33 (m, 2H), 6.91 (d, J=1.2 Hz, 1H), 6.82-6.84 (m, 1H), 4.85-4.93 (m, 1H), 4.68 (s, 4H), 3.50-3.58 (m, 2H), 3.36-3.42 (m, 1H), 3.30-3.32 (m, 1H), 2.90 (s, 3H), 1.95-2.07 (m, 2H).

Example 232 (R)—N-(1-cyanopyrrolidin-3-yl)-3-fluoro-1-methyl-5-(1-methyl-1H-pyrazol-4-yl)-1H-indole-2-carboxamide

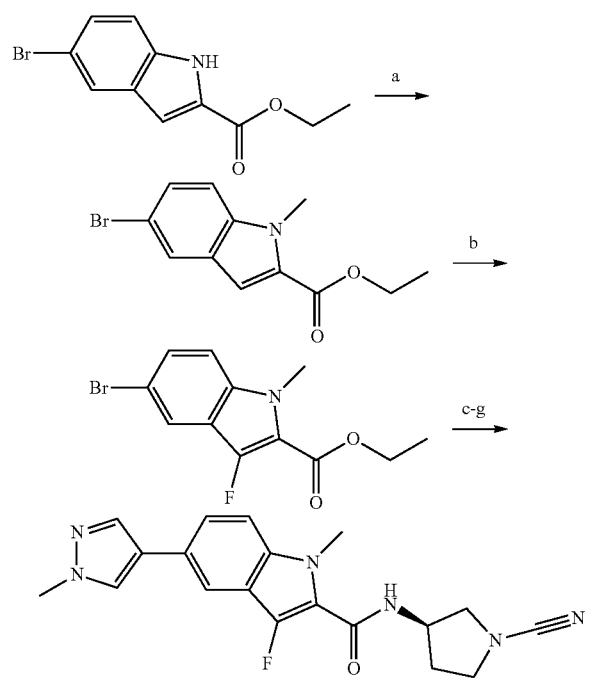

Step a.

To a solution of ethyl 5-bromo-1H-indole-2-carboxylate (CAS Number 16732-70-0) (0.50 g, 1.86 mmol) in DMF (5 ml) was added $K_2CO_3$ (0.521 g, 3.77 mmol) and methyl iodide (0.536 g, 3.77 mmol) at rt. The reaction mixture was heated at 100° C. for 16 h. The resulting reaction mixture cooled to rt and poured into water (50 ml). The resulting mixture was extracted with EtOAc (3×20 ml). The combined organic phase was dried over $Na_2SO_4$, filtered and concentrated under reduced pressure yielding ethyl 5-bromo-1-methyl-1H-indole-2-carboxylate (0.426 g, 1.52 mmol). LCMS: Method C, RT 2.83 min, MS: ES+ 282.10, 284.10. This material was used directly for the next step without further purification.

Step b.

To a solution of ethyl 5-bromo-1-methyl-1H-indole-2-carboxylate (0.200 g, 0.71 mmol) in 1,2-dichloroethane (10 ml) was added 1-fluoro-2,4,6-trimethylpyridinium triflate (CAS Number 107264-00-6) (0.617 g, 2.13 mmol) at rt. The reaction mixture was heated at 100° C. for 16 h. The resulting reaction mixture was cooled to rt and poured into water (30 ml). The resulting mixture was extracted with EtOAc (3×10 ml). The combined organic phase was washed with brine (2×20 ml), dried over $Na_2SO_4$, filtered and concentrated under reduced pressure. The obtained residue was purified by column chromatography (2% EtOAc in hexane) yielding ethyl 5-bromo-3-fluoro-1-methyl-1H-indole-2-carboxylate (0.135 g, 0.450 mmol). LCMS: Method C, RT 2.96 min, MS: ES+300.20, 302.20.

Steps c-g.

The title compound was synthesised from the intermediate above using a procedure similar to that described for Example 2. LCMS: Method A, RT 3.70 min, MS: ES+ 367.07; $^1$H NMR (400 MHz, DMSO-$d_6$) δ ppm 8.64 (d, J=6.0 Hz, 1H), 8.17 (s, 1H), 7.91 (s, 1H), 7.79 (s, 1H), 7.57-7.59 (m, 2H), 4.51-4.52 (m, 1H), 3.86 (s, 3H), 3.83 (s, 3H), 3.64-3.75 (m, 1H), 3.39-3.56 (m, 3H), 2.13-2.18 (m, 1H), 1.94-1.99 (m, 1H).

Example 233 (R)—N-(1-cyanopyrrolidin-3-yl)-7-(1-methyl-1H-pyrazol-4-yl)imidazo[1,5-a]pyridine-3-carboxamide

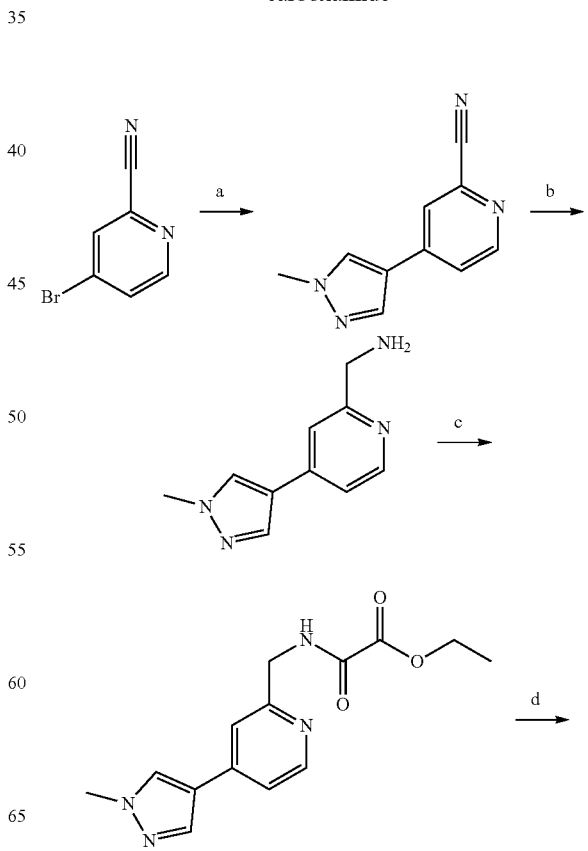

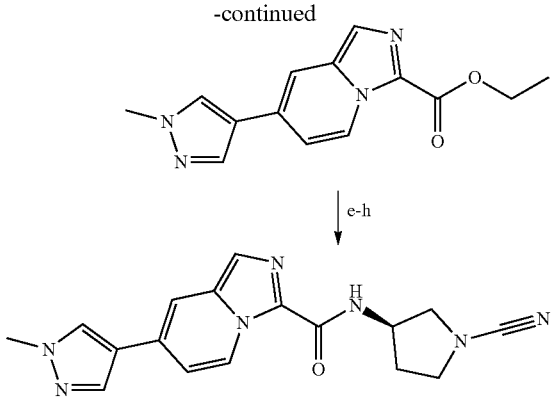

Step a.

To a solution of 4-bromopyridine-2-carbonitrile (CAS Number 62150-45-2) (1.50 g, 8.20 mmol) in 1,4-dioxane: water (9:1, 20 ml) was added 1-methyl-4-(4,4,5,5-tetramethyl-1,3,2-dioxaborolan-2-yl)-1H-pyrazole (1.870 g, 8.99 mmol) and $Cs_2CO_3$ (8.010 g, 24.57 mmol) at rt. The reaction mixture was degassed for 10 min before addition of $PdCl_2$ (dppf) (0.598 g, 0.816 mmol). The reaction mixture was heated at 80° C. for 1 h. The resulting reaction mixture was cooled to rt and poured into water (40 ml). The resulting mixture was extracted with EtOAc (3×75 ml). The combined organic phase was washed with brine (25 ml), dried over $Na_2SO_4$, filtered and concentrated under reduced pressure. The resulting residue was triturated with n-pentane (2×5 ml) and dried under high vacuum yielding 4-(1-methyl-1H-pyrazol-4-yl)picolinonitrile (2.090 g, 11.36 mmol). LCMS: Method C, RT 1.66 min, MS: ES+ 185.19. This material was used directly for the next step without further purification.

Step b.

To a solution of 4-(1-methyl-1H-pyrazol-4-yl)picolinonitrile (0.900 g, 4.891 mmol) in THF (40 ml) was added 1 M solution of $LiAlH_4$ in THF (4.88 ml, 4.891 mmol) at −5° C. The reaction mixture was stirred at rt for 1 h. The reaction mixture was diluted with THF (50 ml), treated with $Na_2SO_4 \cdot 10H_2O$ (15.00 g) and stirred for 20 min. The resulting reaction mixture was filtered and washed with DCM (50 ml). The combined filtrate was concentrated under reduced pressure. To the obtained residue was added 4 M HCl in 1,4-dioxane solution to form corresponding HCl salt. The obtained precipitates were collected by filtration under nitrogen atmosphere and dried under high vacuum yielding (4-(1-methyl-1H-pyrazol-4-yl) pyridin-2-yl) methanamine HCl salt (1.28 g, quantitative). MS: ES+ 189.12. This material was used directly for the next step without further purification.

Step c.

To a solution of (4-(1-methyl-1H-pyrazol-4-yl) pyridin-2-yl)methanamine HCl salt (0.500 g, 2.22 mmol) in DCM (30 ml) was added DIPEA (0.860 g, 6.65 mmol) at 0° C. A solution of ethyl chlorooxoacetate (0.300 g, 2.20 mmol) in DCM (30 ml) was added dropwise to the reaction mixture at 0° C. The reaction mixture was stirred at rt for 1 h. The resulting reaction mixture was poured into water (50 ml) and extracted with DCM (40 ml). The organic layer was washed with brine (20 ml), dried over $Na_2SO_4$, filtered and concentrated under reduced pressure yielding ethyl 2-(((4-(1-methyl-1H-pyrazol-4-yl)pyridin-2-yl)methyl)amino)-2-oxoacetate (0.540 g, 1.87 mmol). LCMS: Method F, RT 4.49 min, MS: ES+ 289.10. This material was used directly for the next step without further purification.

Step d.

A mixture of ethyl 2-(((4-(1-methyl-1H-pyrazol-4-yl) pyridin-2-yl)methyl)amino)-2-oxoacetate (0.540 g, 1.87 mmol) and $P_2O_5$(1.320 g, 9.295 mmol) in $POCl_3$ (11 ml) was heated at 80° C. for 48 h. The resulting reaction mixture was cooled to rt and basified with saturated aqueous $Na_2CO_3$ solution. The obtained mixture was extracted with EtOAc (3×50 ml). The combined organic phase was washed with brine (40 ml), dried over $Na_2SO_4$, filtered and concentrated under reduced pressure. The obtained residue was purified by flash chromatography (80% EtOAc in hexane) yielding ethyl 7-(1-methyl-1H-pyrazol-4-yl)imidazo[1,5-a]pyridine-3-carboxylate (0.070 g, 0.259 mmol). LCMS: Method C, RT 1.78 min, MS: ES+ 271.40.

Steps e-h.

The title compound was synthesised from the intermediate above using a procedure similar to that described for steps b-e of Example 2. LCMS: Method A, RT 3.22 min, MS: ES+ 336.07; $^1$H NMR (400 MHz, DMSO-$d_6$) δ ppm 9.32 (d, J=7.2 Hz, 1H), 8.80 (d, J=7.2 Hz, 1H), 8.28 (s, 1H), 8.01 (s, 1H), 7.93 (s, 1H), 7.51 (s, 1H), 7.26 (d, J=7.2 Hz, 1H), 4.52-4.57 (m, 1H), 3.88 (s, 3H), 3.55-3.64 (m, 2H), 3.38-3.51 (m, 2H), 2.02-2.14 (m, 2H).

Example 234 (R)—N-(1-cyanopyrrolidin-3-yl)-3-(1-phenyl-1H-pyrazol-3-yl)azetidine-1-carboxamide

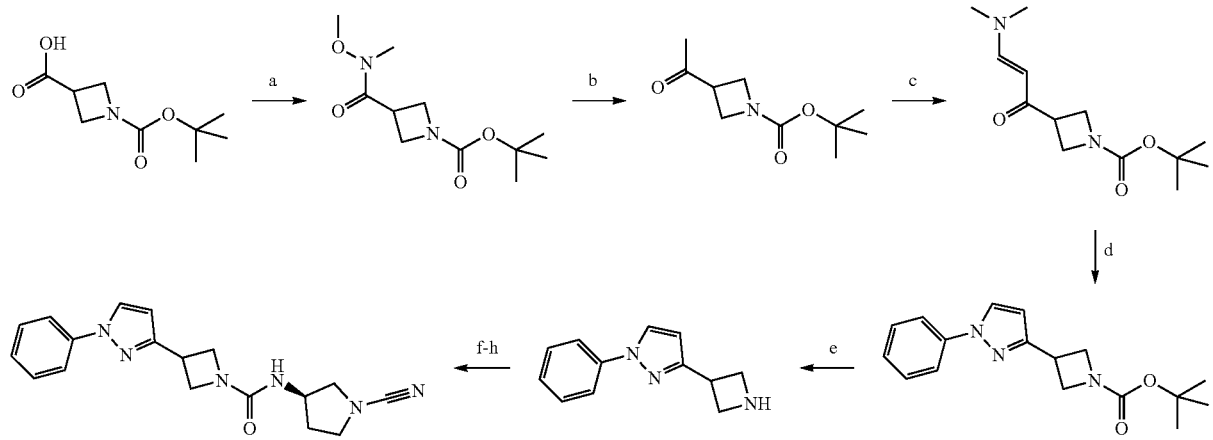

Step a.

To a solution of 1-(tert-butoxycarbonyl)azetidine-3-carboxylic acid (CAS Number 142253-55-2) (3.00 g, 14.92 mmol) in THF (30 ml) was added CDI (2.70 g, 16.67 mmol) at 0° C. The reaction mixture was stirred at rt for 2 h. A solution of N,O-dimethylhydroxylamine hydrochloride (1.90 g, 19.48 mmol) in MeCN (45 ml) was added to the reaction mixture followed by addition of TEA (3.10 ml, 22.39 mmol). The reaction mixture was stirred at rt for 16 h. The resulting reaction mixture was concentrated under reduced pressure and poured into water (200 ml). The obtained mixture was extracted with EtOAc (3×50 ml). The combined organic layer was washed with citric acid solution (100 ml) and brine (100 ml). The combined organic phase was dried over $Na_2SO_4$, filtered and concentrated under reduced pressure yielding tert-butyl 3-(methoxy(methyl)carbamoyl)azetidine-1-carboxylate (3.40 g, 13.93 mmol). LCMS: Method C, RT 1.96 min, MS: ES+ 245.20. This material was used directly for the next step without further purification.

Step b.

A mixture of $CH_3MgBr$ (3 M in diethyl ether) (9.25 ml, 27.75 mmol) in toluene: THF (7:3, 48 ml) was cooled to 0° C. A solution of tert-butyl 3-(methoxy(methyl)carbamoyl) azetidine-1-carboxylate (3.40 g, 13.93 mmol) in THF (20 ml) was added dropwise to the reaction mixture at 0° C. The reaction mixture was stirred at rt for 1 h. The resulting reaction mixture was quenched by slow addition of citric acid solution (50 ml). The resulting reaction mixture was extracted with EtOAc (3×50 ml). The combined organic layer was washed with brine (2×50 ml), dried over $Na_2SO_4$, filtered and concentrated under reduced pressure yielding tert-butyl 3-acetylazetidine-1-carboxylate (2.150 g, 10.80 mmol). LCMS: Method C, RT 1.98 min, MS: ES+ 144.10 (M-56). This material was used directly for the next step without further purification.

Step c.

A mixture of methyl tert-butyl 3-acetylazetidine-1-carboxylate (2.15 g, 10.80 mmol) in N,N-dimethylformamide dimethylacetal (16 ml, 120.6 mmol) was heated at 110° C. for 16 h. The resulting reaction mixture was concentrated under reduced pressure and the obtained residue was purified by flash chromatography (80-100% EtOAc in hexane) yielding tert-butyl (E)-3-(3-(dimethylamino) acryloyl)azetidine-1-carboxylate (1.900 g, 7.48 mmol). LCMS: Method C, RT 1.91 min, MS: ES+255.20.

Step d.

To a solution of tert-butyl (E)-3-(3-(dimethylamino)acryloyl)azetidine-1-carboxylate (0.500 g, 1.97 mmol) in EtOH (6 ml) was added phenylhydrazine (0.280 g, 2.59 mmol) and acetic acid (0.05 ml). The reaction mixture was heated at 60° C. for 4 h. The resulting reaction mixture was cooled to rt and concentrated under reduced pressure. The obtained crude material was purified via flash chromatography to get tert-butyl 3-(1-phenyl-1H-pyrazol-3-yl)azetidine-1-carboxylate (47% EtOAc/hexane) (0.170 g, 0.57 mmol) and tert-butyl 3-(1-phenyl-1H-pyrazol-5-yl)azetidine-1-carboxylate (70% EtOAc/hexane) (0.210 g, 0.70 mmol). The obtained tert-butyl 3-(1-phenyl-1H-pyrazol-3-yl)azetidine-1-carboxylate was used for the next step. LCMS: Method C, RT 2.58 min, MS: ES+300.30; $^1$H NMR (400 MHz, DMSO-$d_6$) δ ppm 8.46 (d, J=2.4 Hz, 1H), 7.81 (dd, J=8.8, 1.2 Hz, 2H), 7.49 (t, J=5.6 Hz, 2H), 7.29 (t, J=7.6 Hz, 1H), 6.56 (d, J=2.4 Hz, 1H), 4.23 (t, J=8.0 Hz, 2H), 3.89-3.96 (m, 2H), 3.85-3.89 (m, 1H), 1.40 (s, 9H).

Step e.

To a solution of tert-butyl 3-(1-phenyl-1H-pyrazol-3-yl) azetidine-1-carboxylate (0.270 g, 0.90 mmol) in 1,4-dioxane (5 ml) was added 4 M HCl in 1,4-dioxane (5 ml) at rt. The reaction mixture was stirred at rt for 3 h. The resulting reaction mixture was concentrated under reduced pressure. The obtained residue was co evaporated with DCM (3×10 ml) and finally dried under high vacuum yielding 3-(azetidin-3-yl)-1-phenyl-1H-pyrazole HCl salt (0.270 g, quantitative). LCMS: Method C, RT 1.53 min, MS: ES+ 200.30. This material was used directly for the next step without further purification.

Steps f-h.

The title compound was synthesised from the intermediate above using a procedure similar to that described for Example 89. LCMS: Method B, RT 3.54 min, MS: ES+ 337.22; $^1$H NMR (400 MHz, DMSO-$d_6$) δ ppm 8.46 (d, J=2.4 Hz, 1H), 7.81 (d, J=8.0 Hz, 2H), 7.48 (t, J=8.0 Hz, 2H), 7.29 (t, J=7.6 Hz, 1H), 6.54-6.57 (m, 2H), 4.13-4.21 (m, 3H), 3.84-3.94 (m, 3H), 3.45-3.54 (m, 2H), 3.35-3.41 (m, 1H), 3.13-3.17 (m, 1H), 1.98-2.03 (m, 1H), 1.77-1.82 (m, 1H).

Example 235 (R)—N-(1-cyanopyrrolidin-3-yl)-3-(1-(pyrazin-2-yl)-1H-pyrazol-3-yl)azetidine-1-carboxamide

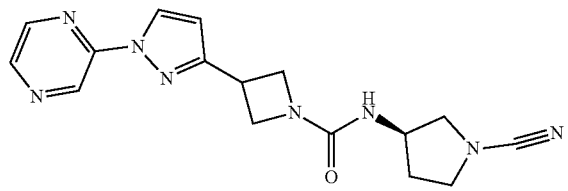 [SMILES: N#CN1CC[C@@H](NC(=O)N2CC(c3ccn(-c4cnccn4)n3)C2)C1]

Synthesised using a procedure similar to that described for steps a-e of Example 134, using 2-hydrazinopyrazine (CAS Number 54608-52-5), followed by steps a-c of Example 5. LCMS: Method A, RT 3.04 min, MS: ES+ 338.94; $^1$H NMR (400 MHz, DMSO-$d_6$) δ ppm 9.17 (d, J=1.2 Hz, 1H), 8.60 (d, J=2.4 Hz, 2H), 8.53-8.54 (m, 1H), 6.69 (d, J=2.4 Hz, 1H), 6.58 (d, J=6.8 Hz, 1H), 4.13-4.16 (m, 3H), 3.89-3.97 (m, 3H), 3.45-3.54 (m, 2H), 3.34-3.41 (m, 1H), 3.14-3.17 (m, 1H), 1.98-2.07 (m, 1H), 1.78-1.83 (m, 1H).

Example 236 (R)—N-(1-cyanopyrrolidin-3-yl)-3-(2-phenylpyrimidin-4-yl)azetidine-1-carboxamide

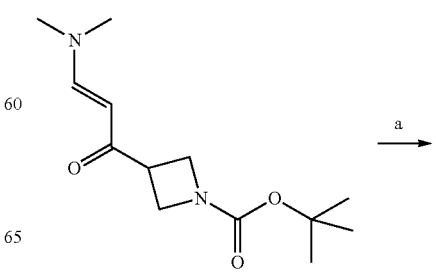

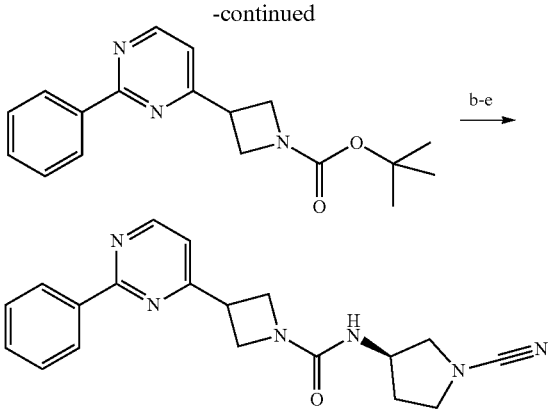

1H), 4.14-4.24 (m, 3H), 3.99-4.09 (m, 3H), 3.45-3.55 (m, 3H), 3.34-3.42 (m, 1H), 3.14-3.17 (m, 1H), 1.99-2.04 (m, 1H), 1.80-1.83 (m, 1H).

Example 238 (R)-3-(benzyloxy)-N-(1-cyanopyrrolidin-3-yl)-3-phenylazetidine-1-carboxamide

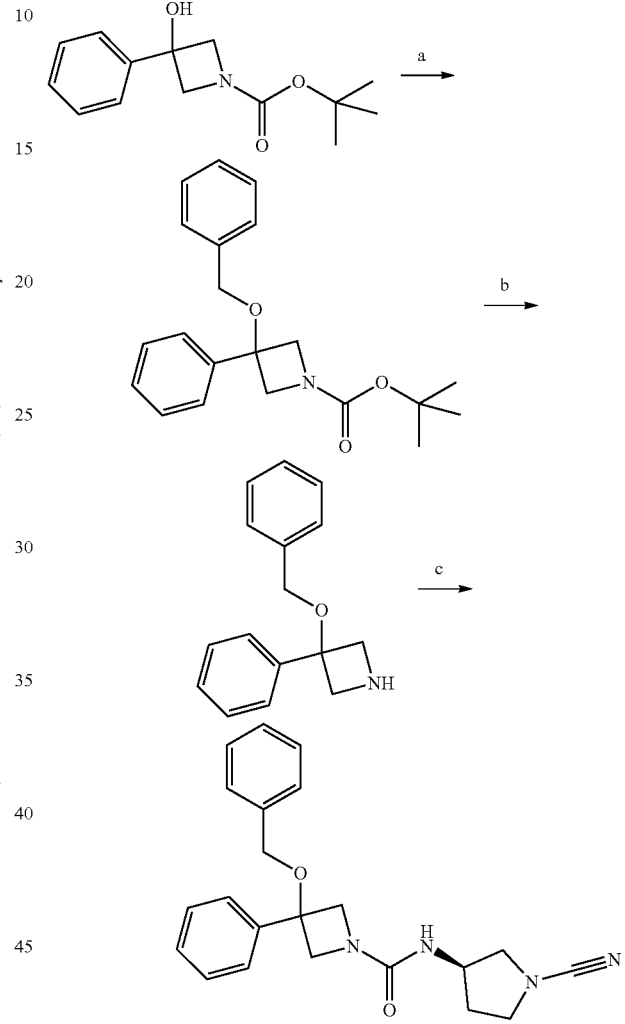

Step a.

To a solution of tert-butyl (E)-3-(3-(dimethylamino)acryloyl)azetidine-1-carboxylate (described in steps a-c of Example 234) (0.900 g, 3.54 mmol) in MeOH (10 ml) was added NaOMe (0.480 g, 8.89 mmol) at rt. Benzamidine hydrochloride hydrate (0.700 g, 4.47 mmol) was added to the reaction mixture at rt. The reaction mixture was refluxed for 5 h. The resulting reaction mixture was cooled to rt and filtered through a celite bed, washed with MeOH (10 ml). The filtrate was concentrated under reduced pressure. The obtained residue was purified by column chromatography (25% EtOAc in hexane) yielding tert-butyl 3-(2-phenylpyrimidin-4-yl)azetidine-1-carboxylate (0.610 g, 1.96 mmol). LCMS: Method C, RT 2.55 min, MS: ES+ 312.13; $^1$H NMR (400 MHz, DMSO-$d_6$) δ ppm 8.83 (d, J=5.2 Hz, 1H), 8.42-8.44 (m, 2H), 7.51-7.55 (m, 3H), 7.39 (d, J=5.2 Hz, 1H), 4.23 10-4.26 (m, 2H), 4.13-4.10 (m, 2H), 3.96-4.01 (m, 1H), 1.42 (s, 9H).

Steps b-e.

The title compound was synthesised using a procedure similar to that described for step e of Example 134, followed by steps a-c of Example 5. LCMS: Method A, RT 3.63 min, MS: ES+349.04; $^1$H NMR (400 MHz, DMSO-$d_6$) δ ppm 8.83-8.84 (m, 1H), 8.41-8.44 (m, 2H), 7.52-7.56 (m, 3H), 7.32-7.40 (m, 1H), 6.63 (d, J=6.4 Hz, 1H), 4.17-4.24 (m, 3H), 3.98-4.10 (m, 3H), 3.46-3.55 (m, 2H), 3.34-3.42 (m, 1H), 3.15-3.17 (m, 1H), 1.99-2.04 (m, 1H), 1.81-1.84 (m, 1H).

Example 237 (R)-3-(2-(4-chlorophenyl)pyrimidin-4-yl)-N-(1-cyanopyrrolidin-3-yl)azetidine-1-carboxamide

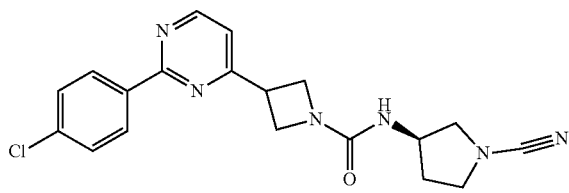 [SMILES: N#CN1CC[C@@H](NC(=O)N2CC(c3ccnc(-c4ccc(Cl)cc4)n3)C2)C1]

Synthesised using a procedure similar to that described for Example 236 using 4-chlorobenzamidine hydrochloride (CAS Number 14401-51-5) in step a. LCMS: Method A, RT 4.18 min, MS: ES+382.97; $^1$H NMR (400 MHz, DMSO-$d_6$) δ ppm 8.45 (d, J=4.8 Hz, 1H), 8.42 (d, J=8.4 Hz, 1H), 7.62 (d, J=8.0 Hz, 2H), 7.43 (d, J=4.4 Hz, 1H), 6.65 (d, J=6.4 Hz, Step a.

To a solution of tert-butyl 3-hydroxy-3-phenylazetidine-1-carboxylate (1.00 g, 4.016 mmol) in DCM (50 ml) was added tetrabutylammonium bromide (0.129 g, 0.400 mmol) and 4 M NaOH solution (40 ml). Benzyl bromide (1.43 ml, 12.05 mmol) was added dropwise to the reaction mixture at rt. The reaction mixture was heated at 80° C. for 16 h. The resulting reaction mixture was cooled to rt and poured into brine (50 ml). The resulting mixture was extracted with DCM (50 ml). The organic layer was washed with brine (100 ml), dried over $Na_2SO_4$, filtered and concentrated under reduced pressure yielding tert-butyl 3-(benzyloxy)-3-phenylazetidine-1-carboxylate (1.80 g, quantitative). LCMS: Method C, RT 2.88 min, MS: ES+ 340.30. This material was used directly for the next step without further purification.

Step b.

To a solution of tert-butyl 3-(benzyloxy)-3-phenylazetidine-1-carboxylate (1.80 g, 5.31 mmol) in DCM (50 ml) was added 4 M HCl in 1,4-dioxane (18 ml) at 0° C. The reaction mixture was stirred at rt for 1 h. The resulting reaction mixture was concentrated under reduced pressure. The obtained residue was co evaporated with DCM (3×50 ml). The obtained material was triturated with diethyl ether (3×40 ml) and finally dried under high vacuum yielding 3-(benzyloxy)-3-phenylazetidine HCl salt (1.17 g, 4.25 mmol). LCMS: Method C, RT 1.72 min, MS: ES+ 240.23; $^1$H NMR (400 MHz, DMSO-$d_6$) δ ppm 9.76 (s, 1H), 9.48 (s, 1H), 7.45-7.53 (m, 5H), 7.33-7.36 (m, 5H), 4.38 (s, 2H), 4.30 (s, 2H), 4.17 (s, 2H). This material was used directly for the next step without further purification.

Steps c-e.

The title compound was synthesised from the intermediate above using a procedure similar to that described for Example 89. LCMS: Method A, RT 4.41 min, MS: ES+ 377.06; $^1$H NMR (400 MHz, DMSO-$d_6$) δ ppm 7.45-7.51 (m, 4H), 7.26-7.40 (m, 6H), 6.69 (d, J=6.8 Hz, 1H), 4.20 (s, 2H), 4.14-4.17 (m, 1H), 4.13 (s, 4H), 3.44-3.53 (m, 2H), 3.35-3.41 (m, 1H), 3.13-3.16 (m, 1H), 1.98-2.03 (m, 1H), 1.76-1.81 (m, 1H).

Example 239 (R)—N-(1-cyanopyrrolidin-3-yl)-1-(4-cyclopropylpyrimidin-2-yl)indoline-5-carboxamide

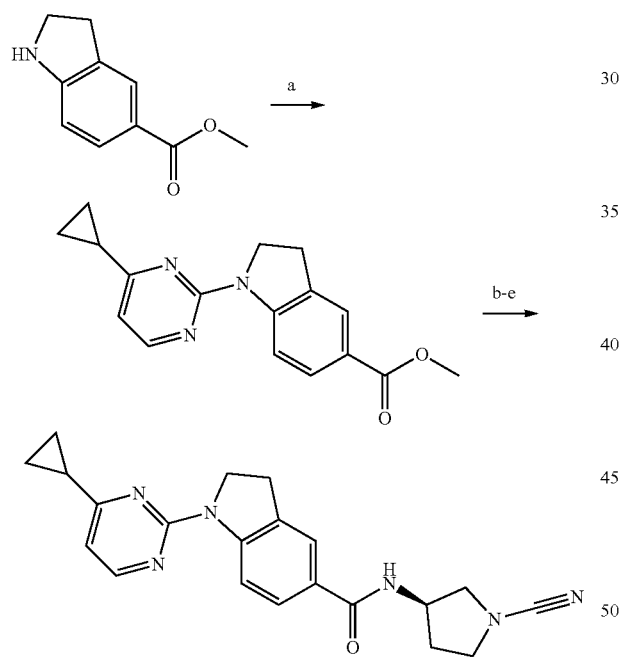

Step a.

To a solution of 2-chloro-4-cyclopropylpyrimidine (1.080 g, 7.01 mmol) in DMF (10 ml) were added methyl indoline-5-carboxylate (CAS Number 339007-88-4) (1.000 g, 5.65 mmol) and Cs$_2$CO$_3$ (5.510 g, 16.90 mmol) at rt. The reaction mixture was degassed for 30 min before addition of Xantphos (0.320 g, 0.553 mmol) and Pd$_2$(dba)$_3$ (0.250 g, 0.273 mmol) at rt. The reaction mixture was heated at 120° C. for 4 h. The resulting reaction mixture was cooled to rt and poured into ice cold water (100 ml) and extracted with EtOAc (3×30 ml). The combined organic layer was washed with ice-cold water (25 ml), dried over Na$_2$SO$_4$, filtered and concentrated under reduced pressure. The resulting residue was triturated with diethyl ether (25 ml) and dried under high vacuum yielding 2-chloro-4-cyclopropylpyrimidine (1.25 g, 4.21 mmol). LCMS: Method C, RT 2.81 min, MS: ES+296.40; $^1$H NMR (400 MHz, CDCl$_3$) δ ppm 8.31-8.35 (m, 2H), 7.89 (dd, J=8.8, 8.8 Hz, 1H), 7.85 (s, 1H), 6.70 (d, J=5.2 Hz, 1H), 4.28 (t, J=8.8 Hz, 2H), 3.90 (s, 3H), 3.21 (t, J=8.8 Hz, 2H), 1.94-1.98 (m, 1H), 1.23-1.28 (m, 2H), 1.11-1.08 (m, 2H). This material was used directly for the next step without further purification.

Steps b-e.

The title compound was synthesised from the intermediate above using a procedure similar to that described for steps b-e of Example 2. LCMS: Method B, RT 4.13 min, MS: ES+ 375.22; $^1$H NMR (400 MHz, CDCl$_3$) δ ppm 8.31-8.35 (m, 2H), 7.60-7.64 (m, 2H), 6.71 (d, J=5.2 Hz, 1H), 6.16 (d, J=6.8 Hz, 1H), 4.71-4.73 (m, 1H), 4.26-4.30 (m, 2H), 3.75-3.80 (m, 1H), 3.54-3.66 (m, 2H), 3.39-3.42 (m, 1H), 3.19-3.24 (m, 2H), 2.27-2.34 (m, 1H), 1.95-2.07 (m, 2H), 1.22-1.27 (m, 2H), 1.19-1.21 (m, 2H).

Example 240 (R)—N-(1-cyanopyrrolidin-3-yl)-1-(4-cyclopropylpyrimidin-2-yl)-N-methylindoline-5-carboxamide

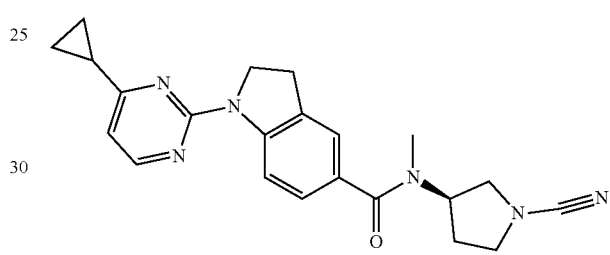

Synthesised using a procedure similar to that described for Example 239 using (R)-tert-butyl 3-(methylamino)pyrrolidine-1-carboxylate (CAS Number 199336-83-9) in step c. LCMS: Method A, RT 4.48 min, MS: ES+ 389.10; $^1$H NMR (400 MHz, CDCl$_3$) δ ppm 8.30-8.34 (m, 2H), 7.26-7.29 (m, 2H), 6.67 (d, J=4.8 Hz, 1H), 5.01-5.03 (m, 1H), 4.27 (t, J=8.8 Hz, 2H), 3.61-3.66 (m, 2H), 3.41-3.48 (m, 2H), 3.21 (t, J=8.8 Hz, 2H), 3.01 (s, 3H), 2.10-2.19 (m, 2H), 1.93-2.00 (m, 1H), 1.21-1.27 (m, 2H), 1.08-1.11 (m, 2H).

Example 241 (3aR,6aR)-5-cyano-N-(3-(2-methylpyridin-4-yl)phenyl)hexahydropyrrolo[3,4-b]pyrrole-1(2H)-carboxamide

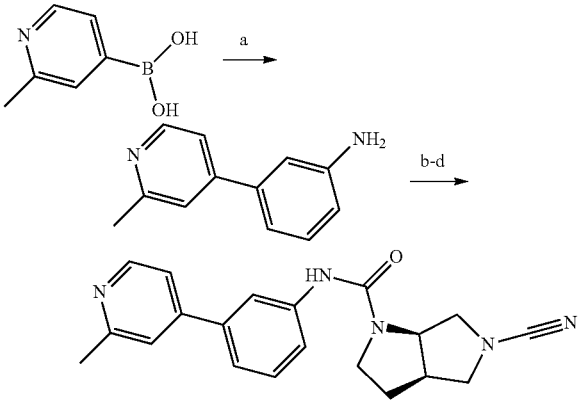

Step a.

To a solution of (2-methylpyridin-4-yl)boronic acid (CAS Number 579476-63-4) (0.500 g, 3.65 mmol) and 3-bromoaniline (0.620 g, 3.60 mmol) in DMF: water (8:2, 10 ml) was added $Cs_2CO_3$ (3.570 g, 10.95 mmol) at rt. The reaction mixture was degassed for 30 min before addition of $Pd(PPh_3)_4$ (0.420 g, 0.363 mmol) at rt. The reaction mixture was heated at 90° C. for 16 h. The resulting reaction mixture was cooled to rt and poured into water (100 ml). The obtained mixture was extracted with EtOAc (2×100 ml). The combined organic phase was dried over $Na_2SO_4$, filtered and concentrated under reduced pressure. The obtained residue was purified by flash chromatography (70% EtOAc in hexane) yielding 3-(2-methylpyridin-4-yl) aniline (0.450 g, 2.445 mmol). LCMS: Method C, RT 0.97 min, MS: ES+ 185.09

Steps b-d.

The title compound was synthesised from the intermediate above using a procedure similar to that described for Example 89, using (3aR,6aR)-5-N—BOC-hexahydro-pyrrolo[3,4-b]pyrrole (CAS Number 370882-39-6) in step b. LCMS: Method B, RT 2.57 min, MS: ES+ 348.16; $^1$H NMR (400 MHz, DMSO-$d_6$) δ ppm 8.49 (d, J=5.6 Hz, 1H), 8.43 (s, 1H), 7.94 (s, 1H), 7.61-7.63 (m, 1H), 7.49 (s, 1H), 7.40-7.42 (m, 1H), 7.34-7.36 (m, 2H), 4.36-4.40 (m, 1H), 3.52-3.60 (m, 4H), 3.41-3.47 (m, 1H), 3.25-3.29 (m, 1H), 2.92-3.97 (m, 1H), 2.45 (s, 3H), 1.99-2.08 (m, 1H), 1.82-1.86 (m, 1H).

Compounds in Table 11 were synthesised using a procedure similar to that described for Example 241.

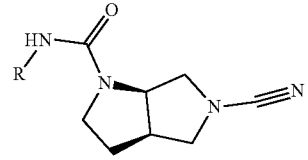

TABLE 11

| Ex | R | Name | $^1$H NMR: (400 MHz, DMSO-$d_6$) δ ppm | LCMS Method | LCMS RT (min) | MS |
|---|---|---|---|---|---|---|
| 242 | 2-methylpyridin-4-yl phenyl | (3aR,6aR)-5-cyano-N-(4-(2-methylpyridin-4-yl)phenyl)hexahydropyrrolo[3,4-b]pyrrole-1(2H)-carboxamide | 8.43-8.46 (m, 2 H), 7.66-7.73 (m, 4 H), 7.55 (s, 1 H), 7.46-7.47 (m, 1 H), 4.37-4.40 (m, 1 H), 3.52-3.61 (m, 4 H), 3.41-3.44 (m, 1 H), 3.25-3.29 (m, 1 H), 2.95-2.97 (m, 1 H), 2.51 (s, 3 H), 2.03-2.09 (m, 1 H), 1.82-1.86 (m, 1 H) | A | 3.39 | ES+ 348.11 |
| 243 | 2-methylpyridin-4-yl 2-fluorophenyl | (3aR,6aR)-5-cyano-N-(2-fluoro-4-(2-methylpyridin-4-yl)phenyl)hexahydropyrrolo[3,4-b]pyrrole-1(2H)-carboxamide | 8.49 (d, J = 5.2 Hz, 1 H), 8.18 (s, 1 H), 7.66-7.75 (m, 3 H), 7.61-7.63 (m, 1 H), 7.56-7.57 (m, 1 H), 4.36-4.38 (m, 1 H), 3.51-3.60 (m, 4 H), 3.42-3.45 (m, 1 H), 3.25-3.28 (m, 1 H), 2.96-2.97 (m, 1 H), 2.53 (s, 3 H), 2.01-2.10 (m, 1 H), 1.81-1.85 (m, 1 H) | A | 3.51 | ES+ 366.01 |
| 244 | 2-methyl-bipyridin-4-yl | (3aR,6aR)-5-cyano-N-(2'-methyl-[3,4'-bipyridin]-6-yl)hexahydropyrrolo[3,4-b]pyrrole-1(2H)-carboxamide | 8.66-8.67 (m, 1 H), 8.47 (d, J = 5.2 Hz, 1 H), 8.13-8.16 (m, 1 H), 8.04-8.06 (m, 1 H), 7.63 (s, 1 H), 7.55 (dd, J = 5.6, 1.6 Hz, 1 H), 4.51-4.55 (m, 1 H), 3.71-3.75 (m, 2 H), 3.59-3.69 (m, 3 H), 3.35-3.38 (m, 1 H), 3.07-3.12 (m, 1 H), 2.61 (s, 3 H), 2.17-2.27 (m, 1 H), 1.96-2.03 (m, 1 H) | A | 3.21 | ES+ 349.04 |
| 245 | 1-methyl-1H-pyrazol-4-yl 2-fluorophenyl | (3aR,6aR)-5-cyano-N-(2-fluoro-4-(1-methyl-1H-pyrazol-4-yl)phenyl)hexahydropyrrolo[3,4-b]pyrrole-1(2H)-carboxamide | 7.98 (s, 1 H), 7.82 (s, 1 H), 7.50 (t, J = 8.4 Hz, 1 H), 7.32-7.37 (m, 2 H), 4.46-4.52 (m, 1 H), 3.93 (s, 3 H), 3.58-3.69 (m, 2 H), 3.50-3.57 (m, 3 H), 3.35-3.36 (m, 1 H), 3.05-3.15 (m, 1 H), 2.18-2.26 (m, 1 H), 1.94-2.02 (m, 1 H) | A | 3.26 | ES+ 354.96 |

Example 246 1-(3-phenyl-1H-pyrazole-5-carbonyl) hexahydropyrrolo[3,4-b]pyrrole-5(1H)-carbonitrile

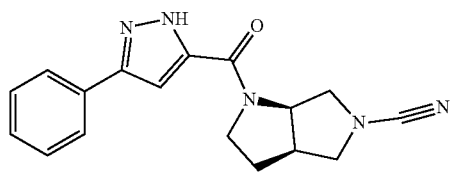 [SMILES: N#CN1C[C@H]2CCN(C(=O)c3cc(-c4ccccc4)n[nH]3)[C@H]2C1]

Example 52 was further subjected to enantiomeric separation using preparative HPLC; mobile phase: (A) hexane (B) IPA: MeOH (50:50), column: CHIRALPAK IC 250× 21.0 mm, 5 m, flow rate: 15 ml/min to provide the title compound. LCMS: Method A, RT 3.56 min, MS: ES+ 308.06; Chiral HPLC: Method X, RT 14.99 min; 1H NMR (400 MHz, DMSO-$d_6$, 80° C.) δ ppm 13.51 (s, 1H), 7.80-7.84 (m, 2H), 7.44-7.48 (m, 2H), 7.37-7.38 (m, 1H), 7.06 (s, 1H), 4.61-5.10 (m, 1H), 3.70-3.98 (m, 2H), 3.60-3.62 (m, 1H), 3.57-3.59 (m, 1H), 3.30-3.33 (m, 2H), 3.02-3.10 (m, 1H), 2.06-2.08 (m, 1H), 1.87-1.88 (m, 1H).

Example 247 (3aR,6aR)-1-(3-phenoxyazetidine-1-carbonyl)hexahydropyrrolo[3,4-b]pyrrole-5(1H)-carbonitrile

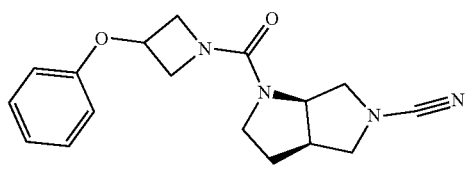 [SMILES: N#CN1C[C@H]2CCN(C(=O)N3CC(Oc4ccccc4)C3)[C@H]2C1]

Synthesised using a procedure similar to that described for Example 89, using (3aR,6aR)-5-N—BOC-hexahydropyrrolo[3,4-b]pyrrole (CAS Number 370882-39-6) in step a. LCMS: Method B, RT 3.53 min, MS: ES+ 313.34; $^1$H NMR (400 MHz, DMSO-$d_6$) δ ppm 7.30 (t, J=8.4 Hz, 2H), 6.97 (t, J=7.6 Hz, 1H), 6.83 (d, J=7.6 Hz, 2H), 4.98-5.01 (m, 1H), 4.40-4.44 (m, 1H), 4.25-4.29 (m, 2H), 3.90-3.94 (m, 1H), 3.78-3.82 (m, 1H), 3.49-3.54 (m, 2H), 3.34-3.40 (m, 3H), 3.18-3.22 (m, 1H), 2.85-2.87 (m, 1H), 1.88-1.95 (m, 1H), 1.75-1.76 (m, 1H).

Example 248 N-(1-cyanopiperidin-3-yl)-[1,1'-biphenyl]-3-carboxamide

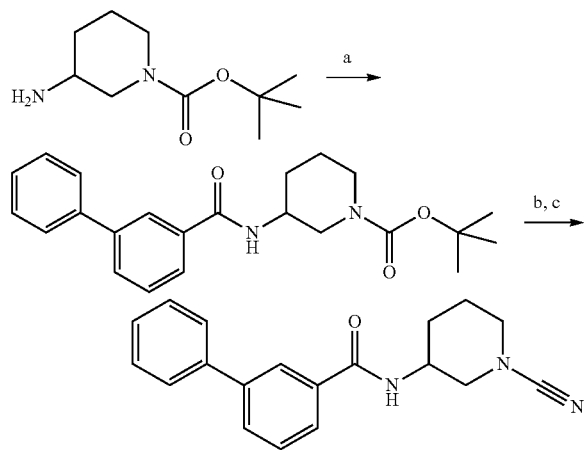

Step a.
To a solution of 3-phenylbenzoic acid (0.2 mmol) in DCM (1 ml) was added HATU (0.2 mmol). The reaction mixture was stirred at 0° C. for 20 min. Tert-butyl 3-aminopiperidine-1-carboxylate (0.2 mmol) and DIPEA (0.6 mmol) were added to the reaction mixture at rt. The reaction mixture was stirred at rt for 16 h. The resulting mixture was concentrated under reduced pressure. The resulting residue was purified by prep-TLC (PE/EtOAc=1:2) yielding tert-butyl 3-([1,1'-biphenyl]-3-ylcarboxamido)piperidine-1-carboxylate. MS: ES+ 381.4.

Steps b, c.
The title compound was synthesised from the intermediate above using a procedure similar to that described for steps b, c of Example 1. LCMS: Method D, RT 2.82 min, MS: ES+ 306.2.

Example 249 1-(3-benzylphenyl)-3-(1-cyanopiperidin-3-yl)urea

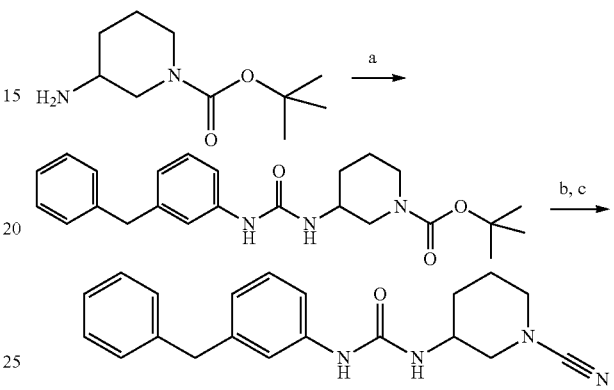

Step a.
To a solution of 1-benzyl-3-isocyanatobenzene (0.2 mmol) in DCM (1 ml) was added tert-butyl 3-aminopiperidine-1-carboxylate (0.2 mmol) and DIPEA (0.6 mmol). The reaction mixture was stirred at rt for 16 h. The resulting mixture was concentrated under reduced pressure. The resulting residue was purified by prep-TLC (PE/EtOAc=1:2) yielding tert-butyl 3-(3-(3-benzylphenyl)ureido)piperidine-1-carboxylate. MS: ES+ 410.5.

Steps b, c.
The title compound was synthesised from the intermediate above using a procedure similar to that described for steps b, c of Example 1. MS: ES+ 335.2.

Example 250 1-(1-cyanopiperidin-3-yl)-3-(3-phenoxyphenyl)urea

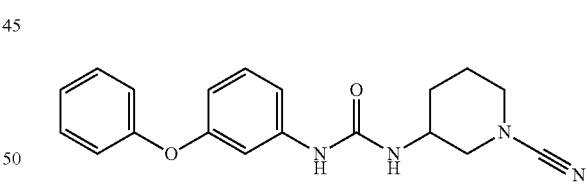

Synthesised using a procedure similar to that described for Example 249. LCMS: Method D, 2.79 min, MS: ES+ 337.2.

Compounds in Table 12 were synthesised using a procedure similar to that described for Example 249 using tert-butyl 3-amino-1-pyrrolidinecarboxylate (CAS number 186550-13-0) in step a.

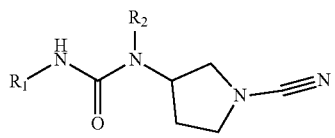

TABLE 12

| Ex | R₁ | R₂ | Name | LCMS Method | LCMS RT (min) | MS |
|---|---|---|---|---|---|---|
| 251 | 2,4-dichlorophenyl | H | 1-(1-cyanopyrrolidin-3-yl)-3-(2,4-dichlorophenyl)urea | D | 2.68 | ES+ 299.0 |
| 251 | 4-(trifluoromethyl)phenyl | H | 1-(1-cyanopyrrolidin-3-yl)-3-(4-(trifluoromethyl)phenyl)urea | D | 2.63 | ES+ 299.0 |
| 253 | 3-benzylphenyl | H | 1-(3-benzylphenyl)-3-(1-cyanopyrrolidin-3-yl)urea | D | 3.06 | ES+ 321.2 |
| 254 | [1,1'-biphenyl]-4-yl | H | 1-([1,1'-biphenyl]-4-yl)-3-(1-cyanopyrrolidin-3-yl)urea | D | 2.68 | ES+ 307.2 |
| 255 | 3-phenoxyphenyl | H | 1-(1-cyanopyrrolidin-3-yl)-3-(3-phenoxyphenyl)urea | D | 3.11 | ES+ 323.2 |
| 256 | 3-benzylphenyl | Me | 3-(3-benzylphenyl)-1-(1-cyanopyrrolidin-3-yl)-1-methylurea | D | 2.91 | ES+ 335.2 |
| 257 | 3-chlorophenyl | Me | 3-(3-chlorophenyl)-1-(1-cyanopyrrolidin-3-yl)-1-methylurea | D | 2.46 | ES+ 279.1 |
| 258 | 3-phenoxyphenyl | Me | 1-(1-cyanopyrrolidin-3-yl)-1-methyl-3-(3-phenoxyphenyl)urea | D | 2.85 | ES+ 337.1 |
| 259 | [1,1'-biphenyl]-4-yl | Me | 3-([1,1'-biphenyl]-4-yl)-1-(1-cyanopyrrolidin-3-yl)-1-methylurea | D | 2.83 | ES+ 321.2 |

TABLE 12-continued

| Ex | R$_1$ | R$_2$ | Name | LCMS Method | LCMS RT (min) | MS |
|---|---|---|---|---|---|---|
| 260 | 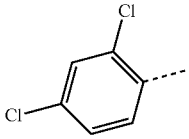 | Me | 1-(1-cyanopyrrolidin-3-yl)-3-(2,4-dichlorophenyl)-1-methylurea | D | 2.70 | ES+ 313.0 |
| 261 | 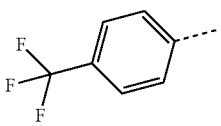 | Me | 1-(1-cyanopyrrolidin-3-yl)-1-methyl-3-(4-(trifluoromethyl)phenyl)urea | D | 2.70 | ES+ 313.0 |

Biological Activity of Compounds of the Invention
Abbreviations:
TAMRA carboxytetramethylrhodamine
PCR polymerase chain reaction
PBS phosphate buffered saline
EDTA ethylenediaminetetraacetic acid
Tris 2-amino-2-(hydroxymethyl)-1,3-propanediol
NP-40 Nonidet P-40, octylphenoxypolyethoxyethanol
BSA bovine serum albumin
PNS peripheral nervous system
BH3 Bcl-2 homology domain 3
PTEN phosphatase and tensin homologue
In Vitro USP30 FP Inhibition Assay
USP30 Biochemical Kinetic Assay.

Reactions were performed in duplicate in black 384 well plates (small volume, Greiner 784076) in a final reaction volume of 21 µl. USP30 CD (57-517, #64-0057-050 Ubiquigent) was diluted in reaction buffer (40 mM Tris, pH 7.5, 0.005% Tween 20, 0.5 mg/ml BSA, 5 mM—beta-mercaptoethanol) to the equivalent of 0, 0.005, 0.01, 0.05, 0.1 and 0.5 l/well. Buffer was optimised for optimal temperature, pH, reducing agent, salts, time of incubation, and detergent. Reactions were initiated by the addition of 50 nM of TAMRA labelled peptide linked to ubiquitin via an isopeptide bond as fluorescence polarisation substrate. Reactions were incubated at room temperature and read every 2 min for 120 min. Readings were performed on a Pherastar Plus (BMG Labtech). λ Excitation 540 nm; λ Emission 590 nm.

USP30 Biochemical IC50 Assay

Dilution plates were prepared at 21 times the final concentration (2100 µM for a final concentration of 100 µM) in 50% DMSO in a 96-well polypropylene V-bottom plate (Greiner #651201). A typical 8-point dilution series would be 100, 30, 10, 3, 1, 0.3, 0.1, 0.03 µM final. Reactions were performed in duplicate in black 384 well plates (small volume, Greiner 784076) in a final reaction volume of 21 µl. Either 1 µl of 50% DMSO or diluted compound was added to the plate. USP30 was diluted in reaction buffer (40 mM Tris, pH 7.5, 0.005% Tween 20, 0.5 mg/ml BSA, 5 mM—beta-mercaptoethanol) to the equivalent of 0.05 l/well and 10 µl of diluted USP30 was added to the compound. Enzyme and compound were incubated for 30 min at room temp. Reactions were initiated by the addition of 50 nM of TAMRA labelled peptide linked to ubiquitin via an isopeptide bond as fluorescence polarisation substrate. Reactions were read immediately after addition of substrate and following a 2 hr incubation at room temperature. Readings were performed on a Pherastar Plus (BMG Labtech). λ Excitation 540 nm; λ Emission 590 nm.

In Vitro USP30 FI Inhibition Assay
USP30 Biochemical Fluorescence Intensity Kinetic Assay.

Reactions were performed in duplicate in black 384 well plates (small volume, Greiner 784076) in a final reaction volume of 21 µl. USP30 CD (Boston Biochem E-582 or 57-517, #64-0057-050 Ubiquigent) was diluted in reaction buffer (40 mM Tris, pH 7.5, 0.005% Tween 20, 0.5 mg/ml BSA, 5 mM—beta-mercaptoethanol) to the equivalent of 0, 0.0005, 0.001, 0.005, and 0.01 µl/well. Buffer was optimised for optimal temperature, pH, reducing agent, salts, time of incubation, and detergent. Reactions were initiated by the addition of Ubiquitin-Rhodamine 110 (U-555, Boston Biochem) at a final concentration of 100 nM. Reactions were incubated at room temperature and read every 2 min for 120 min. Readings were performed on a Pherastar Plus (BMG Labtech). λ Excitation 487 nm; λ Emission 535 nm.

USP30 Biochemical Fluorescence Intensity IC$_{50}$ Assay

Dilution plates were prepared at 21 times the final concentration (2100 µM for a final concentration of 100 µM) in 50% DMSO in a 96-well polypropylene V-bottom plate (Greiner #651201). A typical 8-point dilution series would be 100, 30, 10, 3, 1, 0.3, 0.1, 0.03 µM final. Reactions were performed in duplicate in black 384 well plates (small volume, Greiner 784076) in a final reaction volume of 21 µl. Either 1 µl of 50% DMSO or diluted compound was added to the plate. USP30 was diluted in reaction buffer (40 mM Tris, pH 7.5, 0.005% Tween 20, 0.5 mg/ml BSA, 5 mM—beta-mercaptoethanol) to the equivalent of 0.001 µl/well and 10 µl of diluted USP30 was added to the compound. Enzyme and compound were incubated for 30 min at room temp. Reactions were initiated by the addition of Ubiquitin-Rhodamine 110 (U-555; Boston Biochem) at a final concentration of 100 nM. Reactions were read immediately after addition of substrate and following a 2 h incubation at room temperature. Readings were performed on a Pherastar Plus (BMG Labtech). 2 Excitation 487 nm; 2 Emission 535 nm.

Activity of Exemplary Compounds in USP30 Biochemical FP or FI IC50 Assay

Ranges
A<0.1 µM;
0.1<B<1 µM;
1 µM<C<10 µM;
10 µM<D<30 µM

| Example | IC50 range |
|---------|------------|
| 1 | B |
| 2 | A |
| 3 | A |
| 4 | B |
| 5 | B |
| 6 | B |
| 7 | B |
| 8 | A |
| 9 | B |
| 10 | B |
| 11 | C |
| 12 | B |
| 13 | A |
| 14 | A |
| 15 | C |
| 16 | C |
| 17 | C |
| 18 | C |
| 19 | B |
| 20 | C |
| 21 | C |
| 22 | B |
| 23 | B |
| 24 | C |
| 25 | C |
| 26 | C |
| 27 | B |
| 28 | C |
| 29 | B |
| 30 | B |
| 31 | B |
| 32 | B |
| 33 | B |
| 34 | B |
| 35 | A |
| 36 | A |
| 37 | A |
| 38 | A |
| 39 | A |
| 40 | A |
| 41 | B |
| 42 | B |
| 43 | B |
| 44 | A |
| 45 | B |
| 46 | B |
| 47 | C |
| 48 | C |
| 49 | B |
| 50 | B |
| 51 | A |
| 52 | B |
| 53 | B |
| 54 | B |
| 55 | B |
| 56 | B |
| 57 | B |
| 58 | B |
| 59 | B |
| 60 | C |
| 61 | B |
| 62 | B |
| 63 | B |
| 64 | B |
| 65 | B |
| 66 | B |
| 67 | B |
| 68 | B |
| 69 | C |
| 70 | A |
| 71 | B |
| 72 | A |
| 73 | B |
| 74 | B |
| 75 | B |
| 76 | A |
| 77 | A |
| 78 | A |
| 79 | A |
| 80 | A |
| 81 | A |
| 82 | B |
| 83 | B |
| 84 | B |
| 85 | A |
| 86 | A |
| 87 | B |
| 88 | B |
| 89 | B |
| 90 | A |
| 91 | A |
| 92 | B |
| 93 | A |
| 94 | C |
| 95 | A |
| 96 | B |
| 97 | A |
| 98 | A |
| 99 | B |
| 100 | A |
| 101 | B |
| 102 | A |
| 103 | B |
| 104 | B |
| 105 | A |
| 106 | B |
| 107 | B |
| 108 | B |
| 109 | B |
| 110 | B |
| 111 | B |
| 112 | A |
| 113 | B |
| 114 | B |
| 115 | B |
| 116 | A |
| 117 | B |
| 118 | A |
| 119 | A |
| 120 | A |
| 121 | A |
| 122 | B |
| 123 | A |
| 124 | B |
| 125 | B |
| 126 | A |
| 127 | B |
| 128 | A |
| 129 | A |
| 130 | A |
| 131 | A |
| 132 | B |
| 133 | B |
| 134 | B |
| 135 | B |
| 136 | B |
| 137 | B |
| 138 | B |
| 139 | B |
| 140 | B |
| 141 | B |
| 142 | A |
| 143 | A |
| 144 | B |
| 145 | A |
| 146 | B |
| 147 | B |
| 148 | B |
| 149 | A |
| 150 | B |
| 151 | B |
| 152 | B |
| 153 | B |
| 154 | A |
| 155 | A |
| 156 | B |

| Example | IC50 range |
|---|---|
| 157 | A |
| 158 | B |
| 159 | B |
| 160 | A |
| 161 | B |
| 162 | B |
| 163 | B |
| 164 | B |
| 165 | B |
| 166 | B |
| 167 | A |
| 168 | B |
| 169 | B |
| 170 | B |
| 171 | B |
| 172 | A |
| 173 | A |
| 174 | B |
| 175 | A |
| 176 | B |
| 177 | B |
| 178 | B |
| 179 | B |
| 180 | B |
| 181 | A |
| 182 | A |
| 183 | B |
| 184 | A |
| 185 | A |
| 186 | B |
| 187 | B |
| 188 | B |
| 189 | B |
| 190 | A |
| 191 | A |
| 192 | A |
| 193 | B |
| 194 | B |
| 195 | B |
| 196 | B |
| 197 | A |
| 198 | B |
| 199 | B |
| 200 | B |
| 201 | A |
| 202 | A |
| 203 | A |
| 204 | A |
| 205 | B |
| 206 | B |
| 207 | B |
| 208 | B |
| 209 | B |
| 210 | B |
| 211 | B |
| 212 | A |
| 213 | A |
| 214 | A |
| 215 | B |
| 216 | B |
| 217 | B |
| 218 | A |
| 219 | B |
| 220 | B |
| 221 | A |
| 222 | B |
| 223 | A |
| 224 | B |
| 225 | C |
| 226 | C |
| 227 | B |
| 228 | B |
| 229 | B |
| 220 | A |
| 231 | B |
| 232 | A |
| 233 | B |
| 234 | A |
| 235 | B |
| 236 | B |
| 237 | A |
| 238 | A |
| 239 | A |
| 240 | A |
| 241 | A |
| 242 | A |
| 243 | B |
| 244 | A |
| 245 | B |
| 246 | B |
| 247 | B |
| 248 | C |
| 249 | D |
| 250 | C |
| 251 | B |
| 252 | B |
| 253 | B |
| 254 | A |
| 255 | A |
| 256 | B |
| 257 | B |
| 258 | A |
| 259 | A |
| 260 | B |
| 261 | B |
| 262 | A |
| 263 | B |
| 264 | B |
| 265 | C |
| 266 | B |
| 267 | B |
| 268 | B |
| 269 | C |
| 270 | B |
| 271 | A |
| 272 | A |
| 273 | B |

1. A compound having the formula (I)

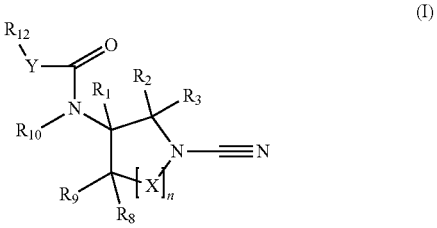

or a pharmaceutically acceptable salt thereof, wherein:

n is 1 or 2;

when n is 1, X is $CR^4R^5$ and when n is 2, X is $CR^6R^7CR^4R^5$ (wherein $CR^4R^5$ is adjacent to heterocycle N atom);

$R^2$ represents a hydrogen atom, cyano, an optionally substituted $C_1$-$C_6$ alkyl, an optionally substituted $C_1$-$C_6$ alkoxy group, an optionally substituted 4 to 10 membered heteroaryl, heterocyclyl, aryl or 3 to 8 membered cycloalkyl ring;

$R^1$, $R^3$, $R^4$ and $R^5$ each independently represent a hydrogen atom, cyano, an optionally substituted $C_1$-$C_3$ alkyl or an optionally substituted $C_1$-$C_3$ alkoxy group;

$R^6$, $R^7$ and $R^8$ each independently represent a hydrogen atom, a fluorine atom, cyano, an optionally substituted $C_1$-$C_3$ alkyl or an optionally substituted $C_1$-$C_3$ alkoxy group;

$R^9$ represents a hydrogen atom, a fluorine atom, cyano, an optionally substituted $C_1$-$C_6$ alkyl, an optionally substituted $C_1$-$C_3$ alkoxy group, an optionally substituted 4 to 10 membered heteroaryl, heterocyclyl, aryl or 3 to 8 membered cycloalkyl ring, or forms an optionally substituted heterocyclic ring with $R^{10}$ wherein the ring optionally comprises one or more additional heteroatoms;

$R^{10}$ represents a hydrogen atom, $C_{1-6}$ alkyl, or forms an optionally substituted heterocyclic ring with $R^9$ or $R^{11}$ wherein the ring optionally comprises one or more additional heteroatoms;

Y represents a covalent bond, $NR^{11}$ or optionally substituted $C_1$-$C_3$ alkyl;

$R^{11}$ represents a hydrogen atom, an optionally substituted $C_1$-$C_6$ alkyl, a 4 to 10 membered heteroaryl, heterocyclyl, aryl or 3 to 8 membered cycloalkyl ring or forms an optionally substituted heterocyclic ring with $R^{10}$ wherein the ring optionally comprises one or more additional heteroatoms;

$R^{12}$ represents a substituted 4 to 10 membered heteroaryl, heterocyclyl, aryl or 3 to 8 membered cycloalkyl ring; and where the compound is not of the formula:

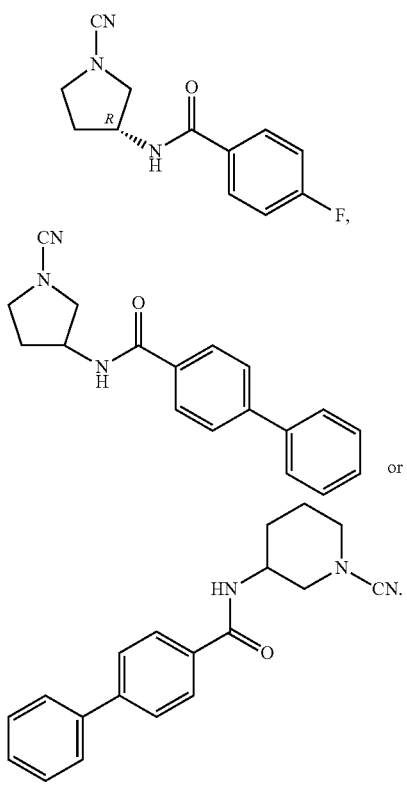

2. The compound according to paragraph 1, wherein $R^{12}$ represents a 4 to 10 membered heteroaryl, aryl, heterocyclyl, or 3 to 8 membered cycloalkyl ring substituted with one or more of $Q^1$-$(R^{13})_p$, wherein:

p is 0 or 1;

$Q^1$ represents a halogen atom, cyano, oxo, a covalent bond, $-NR^{14}-$, $-NR^{14}R^{15}$, $-CONR^{14}-$, $-NR^{14}CO-$, an oxygen atom, $-CO-$, $-S(O)_q-$, $-SO_2NR^{14}$, $-C_1$-$C_6$ alkoxy, $C_1$-$C_6$ haloalkoxy, $C_1$-$C_6$ hydroxyalkyl, $-SO_2R^{14}$, $-NR^{14}COR^{15}$, $-NR^{14}CONR^{15}R^{16}$, $-NR^{14}SO_2NR^{15}R^{16}$, $-CONR^{14}R^{15}$, $-CO_2R^{14}$, $-NR^{14}CO_2R^{15}$, $-SO_2NR^{14}R^{15}$, $-C(O)R^{14}$ and $-NR^{14}SO_2R^{15}$, $NO_2$, or an optionally substituted $C_1$-$C_6$ alkylene, $-C_2$-$C_6$ alkenylene or $-C_1$-$C_6$ alkyl group;

q is 0, 1 or 2;

$R^{14}$, $R^{15}$ and $R^{16}$ each independently represent a hydrogen atom or an optionally substituted $C_1$-$C_6$ alkyl, or an optionally substituted $C_1$-$C_6$ alkylene group;

when p is 1, $R^{13}$ represents an optionally substituted 4 to 10 membered heteroaryl, heterocyclyl, aryl or 3 to 8 membered cycloalkyl ring (when p is 0, $Q^1$ is present and $R^{13}$ is absent).

3. The compound according to paragraph 2, wherein $R^{13}$ represents a 4 to 10 membered heteroaryl, heterocyclyl, aryl, or 3 to 8 membered cycloalkyl ring substituted with one or more substituents selected from halogen, optionally substituted $C_1$-$C_6$ haloalkyl, optionally substituted $C_1$-$C_6$ alkoxy, $C_1$-$C_6$ haloalkoxy, optionally substituted $C_1$-$C_6$ alkyl, optionally substituted $C_2$-$C_6$ alkenyl, optionally substituted $C_2$-$C_6$ alkynyl, $C_1$-$C_6$ hydroxyalkyl, oxo, cyano, optionally substituted heterocyclyl, optionally substituted cycloalkyl, optionally substituted heteroaryl, optionally substituted aryl, -$Q^2$-$R^{17}$, -$Q^2$-$NR^{17}CONR^{18}R^{19}$, -$Q^2$-$NR^{17}R^{18}$, -$Q^2$-$COR^{17}$, -$Q^2$-$NR^{17}COR^{18}$, -$Q^2$-$NR^{17}CO_2R^{18}$, -$Q^2$-$SO_2R^{17}$, $Q^2$-$CONR^{17}R^{18}$, -$Q^2$-$CO_2R^{17}$, -$Q^2$-$SO_2NR^{17}R^{18}$ and -$Q^2$-$NR^{17}SO_2R^{18}$; wherein $Q^2$ represents a covalent bond, an oxygen atom, $-CO-$, or a $C_1$-$C_6$ alkylene or $C_2$-$C_6$ alkenylene group; and $R^{16}$, $R^{17}$, $R_{18}$ each independently represent hydrogen, optionally substituted $C_1$-$C_6$ alkyl, optionally substituted heterocyclyl, optionally substituted heteroaryl, optionally substituted aryl, or an optionally substituted cycloalkyl.

4. The compound according to any preceding paragraph, wherein $R^{12}$ is selected from the group consisting of phenyl, pyrrolidinyl, thiazolyl, pyridinyl, dihydropyridinyl, isoxazolyl, oxazolyl, imidazolyl, pyrazolyl, pyridazinyl, pyrimidinyl, indolyl, benzimidazolyl and quinolinyl.

5. The compound according to paragraph 1, having the structure of formula (II)

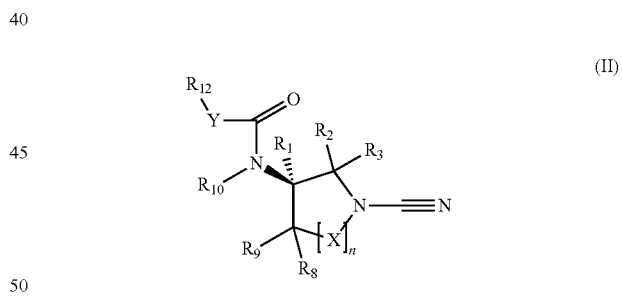

(II)

or a pharmaceutically acceptable salt thereof, wherein n, X, $R^1$, $R^2$, $R^3$, $R^8$, $R^9$, $R^{10}$, $R^{12}$ and Y are defined in claims 1 to 4 for compounds of formula (I).

6. The compound according to paragraph 1, having the structure of formula (IID)

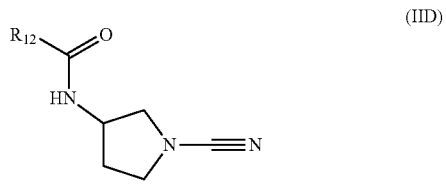

(IID)

or a pharmaceutically acceptable salt thereof, wherein:

$R^{12}$ represents a 4 to 10 membered heteroaryl, heterocyclyl, aryl or 3 to 8 membered cycloalkyl ring substituted with one or more of $Q^1$-$(R^3)$P;

p is 0 or 1;

$Q^1$ represents halogen atom, cyano, oxo, a covalent bond, —$NR^4$—, —$NR^{14}R^{15}$, —$CONR^4$—, —$NR^{14}CO$—, an oxygen atom, —CO—, —$S(O)_q$—, $C_1$-$C_6$ alkoxy, $C_1$-$C_6$ haloalkoxy, $C_1$-$C_6$ hydroxyalkyl, —$SO_2R^{14}$, —$NR^{14}R^{15}$, —$NR^{14}COR^{15}$, —$NRCONR^{14}R^{15}$, —$CONR^{14}R^{15}$, —$CO_2R^{14}$, —$NR^{14}CO_2R^{15}$, —$SO_2NR^{14}R^{15}$, —$CONR^{14}$, —$C(O)R^4$ and —$NR^{14}SO_2R^{15}$ or an optionally substituted $C_1$-$C_6$ alkylene, —$C_2$-$C_6$ alkenylene or —$C_1$-$C_6$ alkyl group; and $R^{13}$ represents an optionally substituted 4 to 10 membered heteroaryl, heterocyclyl, aryl or 3 to 8 membered cycloalkyl ring.

7. The compound according to paragraph 6, wherein:

$R^{12}$ represents a 5 or 6 membered aryl or heteroaryl which is substituted with one or two of $Q^1$-$(R^3)$;

p is 0 or 1;

$Q^1$ represents a halogen atom, a covalent bond, $C_1$-$C_3$ alkoxy or $C_1$-$C_3$ alkyl; and $R^{13}$ represents a 5 or 6 membered aryl, heteroaryl or heterocyclyl ring, wherein the ring is optionally substituted with $C_1$-$C_3$ alkyl.

8. The compound of formula (I) as defined in paragraph 1, selected from the group consisting of:

(R)—N-(1-cyanopyrrolidin-3-yl)-5-phenylpicolinamide
(R)—N-(1-cyanopyrrolidin-3-yl)-3-methoxy-4-(1-methyl-1H-pyrazol-4-yl)benzamide
2'-chloro-N-(1-cyanopyrrolidin-3-yl)-[1,1'-biphenyl]-4-carboxamide
6-(benzyl(methyl)amino)-N-(1-cyanopyrrolidin-3-yl)nicotinamide
(R)—N-(1-cyanopyrrolidin-3-yl)-3-phenylazetidine-1-carboxamide
N—((R)-1-cyanopyrrolidin-3-yl)-4-((2S,6R)-2,6-dimethylmorpholino)-3-fluorobenzamide
N-(1-cyanopyrrolidin-3-yl)-4-phenylthiazole-2-carboxamide
3-(3-chlorophenyl)-N-(1-cyanopyrrolidin-3-yl)isoxazole-5-carboxamide
N-(1-cyanopyrrolidin-3-yl)-1-phenyl-1H-imidazole-4-carboxamide
N-(1-cyanopyrrolidin-3-yl)-1-(2,4-difluorobenzyl)-5-oxopyrrolidine-3-carboxamide
N-(1-cyanopyrrolidin-3-yl)-5-oxo-1-phenylpyrrolidine-3-carboxamide
N-(1-cyanopyrrolidin-3-yl)-4-(3,5-dimethylisoxazol-4-yl)benzamide
3'-chloro-N-(1-cyanopyrrolidin-3-yl)-[1,1'-biphenyl]-4-carboxamide
N-(1-cyanopyrrolidin-3-yl)-2'-methoxy-[1,1'-biphenyl]-4-carboxamide
N-(1-cyanopyrrolidin-3-yl)-4-phenoxybenzamide
2-([1,1'-biphenyl]-4-yl)-N-(1-cyanopyrrolidin-3-yl)acetamide
N-(1-cyanopyrrolidin-3-yl)-2-phenylquinoline-4-carboxamide
6-(4-carbamoylpiperidin-1-yl)-N-(1-cyanopyrrolidin-3-yl)nicotinamide
N-(1-cyanopyrrolidin-3-yl)-6-(4-(2,4-difluorophenyl)piperazin-1-yl)nicotinamide
ethyl 4-(5-((1-cyanopyrrolidin-3-yl)carbamoyl)pyridin-2-yl)piperazine-1-carboxylate
N-(1-cyanopyrrolidin-3-yl)-6-(2-(pyridin-3-yl)pyrrolidin-1-yl)nicotinamide
N-(1-cyanopyrrolidin-3-yl)-6-(4-phenoxypiperidin-1-yl)nicotinamide
N-(1-cyanopyrrolidin-3-yl)-6-(4-(pyridin-4-yl)piperidin-1-yl)nicotinamide
6-(benzyl(methyl)amino)-N-(1-cyanopyrrolidin-3-yl)picolinamide
N-(1-cyanopyrrolidin-3-yl)-6-(3,4-dihydroisoquinolin-2(1H)-yl)picolinamide
N-(1-cyanopyrrolidin-3-yl)-6-(4-phenoxypiperidin-1-yl)picolinamide
N-(1-cyanopyrrolidin-3-yl)-2-(3,4-dihydroisoquinolin-2(1H)-yl)isonicotinamide
2-(4-acetyl-1,4-diazepan-1-yl)-N-(1-cyanopyrrolidin-3-yl)isonicotinamide
(R)—N-(1-cyanopyrrolidin-3-yl)-6-phenylpicolinamide
(R)—N-(1-cyanopyrrolidin-3-yl)-4-phenylpicolinamide
(R)—N-(1-cyanopyrrolidin-3-yl)-4-morpholinobenzamide
(R)—N-(1-cyanopyrrolidin-3-yl)-3-fluoro-4-morpholinobenzamide
(R)—N-(1-cyanopyrrolidin-3-yl)-3-phenylisoxazole-5-carboxamide
(R)—N-(1-cyanopyrrolidin-3-yl)-5-(pyridin-4-yl)isoxazole-3-carboxamide
(R)—N-(1-cyanopyrrolidin-3-yl)-[1,1'-biphenyl]-4-carboxamide
(R)-6-(4-chlorophenyl)-N-(1-cyanopyrrolidin-3-yl)nicotinamide
(R)-2-(2-chlorophenyl)-N-(1-cyanopyrrolidin-3-yl)thiazole-5-carboxamide
(R)-4-(3-chloropyridin-4-yl)-N-(1-cyanopyrrolidin-3-yl)benzamide
(R)-4-(3-chloropyridin-4-yl)-N -(1-cyanopyrrolidin-3-yl)-3-methoxybenzamide
(R)—N-(1-cyanopyrrolidin-3-yl)-3-methoxy-4-(2-methylpyridin-4-yl)benzamide
(R)—N-(1-cyanopyrrolidin-3-yl)-3-methoxy-4-(2-morpholinopyridin-4-yl)benzamide
(R)—N-(1-cyanopyrrolidin-3-yl)-4-fluoro-3-(pyridin-4-yl)benzamide
(R)—N-(1-cyanopyrrolidin-3-yl)-4-fluoro-3-(1-methyl-1H-pyrazol-4-yl)benzamide
(R)—N-(1-cyanopyrrolidin-3-yl)-4-(1-methyl-1H-pyrazol-4-yl)benzamide
(R)—N-(1-cyanopyrrolidin-3-yl)-5-(1-methyl-1H-pyrazol-4-yl)pyrimidine-2-carboxamide
N—((R)-1-cyanopyrrolidin-3-yl)-3-phenylpyrrolidine-1-carboxamide
(S)—N-(1-cyanopyrrolidin-3-yl)-4-(pyridin-4-yl)benzamide
(S)—N-(1-cyanopyrrolidin-3-yl)-6-phenylpicolinamide
(R)-4-(3-chloropyridin-4-yl)-N-(1-cyanopyrrolidin-3-yl)-N-methylbenzamide
(R)-1-(1-cyanopyrrolidin-3-yl)-3-(imidazo[1,2-a]pyridin-2-yl)-1-methylurea
(3aR,6aR)-1-([1,1'-biphenyl]-3-carbonyl)hexahydropyrrolo[3,4-b]pyrrole-5 (1H)-carbonitrile
(3aR,6aR)-1-(3-phenyl-1H-pyrazole-5-carbonyl)hexahydropyrrolo[3,4-b]pyrrole-5(1H)-carbonitrile
(3aR,6aR)-1-(3-phenylisoxazole-5-carbonyl)hexahydropyrrolo[3,4-b]pyrrole-5(1H)-carbonitrile
(3aR,6aR)-1-(1-phenyl-1H-imidazole-4-carbonyl)hexahydropyrrolo[3,4-b]pyrrole-5(1H)-carbonitrile
(3aR,6aR)-1-(3-(4-methoxyphenyl)-1H-pyrazole-5-carbonyl)hexahydropyrrolo[3,4-b]pyrrole-5(1H)-carbonitrile (3aR,6aR)-1-(3-(4-methoxyphenyl)isoxazole-5-carbonyl)hexahydropyrrolo[3,4-b]pyrrole-5(1H)-carbonitrile (3aR,6aR)-1-(4-fluoro-3-(pyridin-4-yl)benzoyl)hexahydropyrrolo[3,4-b]pyrrole-5(1H)-carbonitrile (3aR,6aR)-1-(4-fluoro-3-(1-methyl-1H-pyrazol-4-yl)benzoyl)hexahydropyrrolo[3,4-b]pyrrole-5 (H)-carbonitrile (3aR,6aR)-1-(4-(3-chloropyridin-4-yl)-3-methoxybenzoyl)hexahydropyrrolo[3,4-b]pyrrole-5(1H)-carbonitrile (3aR,6aR)-1-(3-methoxy-4-(1-methyl-1H-pyrazol-4-yl)benzoyl)hexahydropyrrolo[3,4-b]pyrrole-5(1H)-carbonitrile (3aR,6aR)-1-(2-oxo-6-phenyl-1,2-dihydropyridine-3-carbonyl)hexahydropyrrolo[3,4-b]pyrrole-5(1H)-carbonitrile (R)—N-(1-cyanopyrrolidin-3-yl)-3-(N-methylisobutyramido)benzamide (R)—N-(1-cyanopyrrolidin-3-yl)-5-phenylpyrimidine-2-carboxamide (R)—N-(1-cyanopyrrolidin-3-yl)-3-(pyridin-4-yl)isoxazole-5-carboxamide (R)—N-(1-cyanopyrrolidin-3-yl)-3-(pyridin-3-yl)isoxazole-5-carboxamide (R)—N-(1-cyanopyrrolidin-3-yl)-3-(pyridin-2-yl)isoxazole-5-carboxamide N-(1-cyanopyrrolidin-3-yl)-5-phenylpyridazine-3-carboxamide N-(1-cyanopyrrolidin-3-yl)-N-methyl-[1,1'-biphenyl]-4-carboxamide N -((3S,4R)-1-cyano-4-methylpyrrolidin-3-yl)-2-phenylthiazole-5-carboxamide N-((3R,4S)-1-cyano-4-methylpyrrolidin-3-yl)-2-phenylthiazole-5-carboxamide N-((3S,4R)-1-cyano-4-methylpyrrolidin-3-yl)-5-phenylthiazole-2-carboxamide N-((3R,4S)-1-cyano-4-methylpyrrolidin-3-yl)-5-phenylthiazole-2-carboxamide (R)—N-(1-cyanopyrrolidin-3-yl)-2-(isoindolin-2-yl)isonicotinamide (R)—N-(1-cyanopyrrolidin-3-yl)-2-(3,4-dihydroisoquinolin-2(1H)-yl)isonicotinamide (R)—N-(1-cyanopyrrolidin-3-yl)-2-fluoro-4-(4-methyl-1H-imidazol-1-yl)benzamide (R)—N-(1-cyanopyrrolidin-3-yl)-3-fluoro-4-(1-methyl-1H-pyrazol-4-yl)benzamide (R)—N-(1-cyanopyrrolidin-3-yl)-2-fluoro-4-(1-methyl-1H-pyrazol-4-yl)benzamide (R)—N-(1-cyanopyrrolidin-3-yl)-2,5-difluoro-4-(1-methyl-1H-pyrazol-4-yl)benzamide (R)—N-(1-cyanopyrrolidin-3-yl)-4-(1,3-dimethyl-1H-pyrazol-4-yl)-3-fluorobenzamide (R)—N-(1-cyanopyrrolidin-3-yl)-4-(1,3-dimethyl-1H-pyrazol-4-yl)-2-fluorobenzamide (R)—N-(1-cyanopyrrolidin-3-yl)-4-(1-ethyl-1H-pyrazol-4-yl)-2-fluorobenzamide (R)—N-(1-cyanopyrrolidin-3-yl)-2-fluoro-4-(1-(2-methoxyethyl)-1H-pyrazol-4-yl)benzamide (R)—N-(1-cyanopyrrolidin-3-yl)-6-(1-methyl-1H-pyrazol-4-yl)-1H-benzo[d]imidazole-2-carboxamide (R)—N-(1-cyanopyrrolidin-3-yl)-6-(1-methyl-1H-pyrazol-4-yl)-1H-indole-2-carboxamide (R)—N-(1-cyanopyrrolidin-3-yl)-2-fluoro-4-(5-(trifluoromethyl)-1H-pyrazol-4-yl)benzamide (R)—N-(1-cyanopyrrolidin-3-yl)-2-fluoro-4-(1-methyl-1H-indazol-5-yl)benzamide (R)—N-(1-cyanopyrrolidin-3-yl)-3-fluoro-N-methyl-4-(1-methyl-1H-pyrazol-4-yl)benzamide (R)—N-(1-cyanopyrrolidin-3-yl)-N-methyl-6-(1-methyl-1H-pyrazol-4-yl)-1H-benzo[d]imidazole-2-carboxamide (R)—N-(1-cyanopyrrolidin-3-yl)-N-methyl-3-phenoxyazetidine-1-carboxamide (3aR,6aR)-5-cyano-N-(2-fluoro-4-(trifluoromethyl)phenyl)hexahydropyrrolo[3,4-b]pyrrole-1 (2H)-carboxamide (R)—N-(1-cyanopyrrolidin-3-yl)-2-fluoro-4-(pyrimidin-2-ylamino)benzamide N-((3R,4S)-1-cyano-4-methylpyrrolidin-3-yl)-2-fluoro-4-((R)-3-methoxypyrrolidin-1-yl)benzamide 2-(2-chlorophenyl)-N-((3R,4R)-1-cyano-4-hydroxypyrrolidin-3-yl)thiazole-5-carboxamide N-(1-cyano-3-methylpyrrolidin-3-yl)-2-fluoro-4-(1-methyl-1H-pyrazol-4-yl)benzamide (R)—N-(1-cyanopyrrolidin-3-yl)-5-(4-methoxyphenyl)-1H-pyrazole-3-carboxamide (R)—N-(1-cyanopyrrolidin-3-yl)-5-(pyridin-2-yl)-1H-pyrazole-3-carboxamide (R)—N-(1-cyanopyrrolidin-3-yl)-5-(2-methoxyphenyl)-1H-pyrazole-3-carboxamide (R)—N-(1-cyanopyrrolidin-3-yl)-5-(2-fluorophenyl)-1H-pyrazole-3-carboxamide (R)—N-(1-cyanopyrrolidin-3-yl)-6-morpholinonicotinamide (R)—N-(1-cyanopyrrolidin-3-yl)-3-(4-methoxyphenyl)isoxazole-5-carboxamide (R)—N-(1-cyanopyrrolidin-3-yl)-1H-indazole-3-carboxamide (R)—N-(1-cyanopyrrolidin-3-yl)-5-phenyl-1H-pyrazole-3-carboxamide (R)—N-(1-cyanopyrrolidin-3-yl)-5-(pyridin-3-yl)-1H-pyrazolc-3-carboxamide (R)—N-(1-cyanopyrrolidin-3-yl)-2-fluoro-3-(1-methyl-1H-pyrazol-4-yl)benzamide (R)—N-(1-cyanopyrrolidin-3-yl)-2-fluoro-4-(2-methylpyrimidin-4-yl)benzamide (R)—N-(1-cyanopyrrolidin-3-yl)-5-(1-methyl-1H-pyrazol-4-yl)picolinamide (R)—N-(1-cyanopyrrolidin-3-yl)-2-fluoro-5-(1-methyl-1H-pyrazol-4-yl)benzamide (R)—N-(1-cyanopyrrolidin-3-yl)-2-fluoro-4-(pyrimidin-4-yl)benzamide (R)—N-(1-cyanopyrrolidin-3-yl)-2-fluoro-4-(imidazo[1,2-a]pyrimidin-6-yl)benzamide (R)—N-(1-cyanopyrrolidin-3-yl)-2-methoxy-4-(1-methyl-1H-pyrazol-4-yl)benzamide (R)—N-(1-cyanopyrrolidin-3-yl)-6-(1-methyl-1H-pyrazol-4-yl)nicotinamide (R)—N-(1-cyanopyrrolidin-3-yl)-3,5-difluoro-4-(1-methyl-1H-pyrazol-4-yl)benzamide (R)—N-(1-cyanopyrrolidin-3-yl)-2,6-difluoro-4-(1-methyl-1H-pyrazol-4-yl)benzamide (R)—N-(1-cyanopyrrolidin-3-yl)-6-(1-methyl-1H-pyrazol-4-yl)pyrazolo[1,5-a]pyridine-3-carboxamide (R)—N-(1-cyanopyrrolidin-3-yl)-2-fluoro-3-methoxy-4-(1-methyl-1H-pyrazol-4-yl)benzamide (R)-6-(3-cyanophenyl)-N-(1-cyanopyrrolidin-3-yl)imidazo[1,2-a]pyridine-2-carboxamide (R)-6-(4-cyanophenyl)-N-(1-cyanopyrrolidin-3-yl)imidazo[1,2-a]pyridine-2-carboxamide (R)—N-(1-cyanopyrrolidin-3-yl)-2-fluoro-4-(imidazo[1,2-a]pyridin-6-yl)benzamide (R)—N-(1-cyanopyrrolidin-3-yl)-2-fluoro-4-(2-morpholinopyridin-4-yl)benzamide (R)—N-(1-cyanopyrrolidin-3-yl)-3-fluoro-5-(1-methyl-1H-indazol-5-yl)picolinamide (R)—N-(1-cyanopyrrolidin-3-yl)-3-fluoro-5-(1-methyl-1H-pyrrolo[2,3-b]pyridin-5-yl)picolinamide (R)—N-(1-cyanopyrrolidin-3-yl)-5-(1,3-di methyl-1H-pyrazol-4-yl)-3-fluoropicolinamide
(R)-3-chloro-N-(1-cyanopyrrolidin-3-yl)-5-(4-fluorophenyl)picolinamide
(R)—N-(1-cyanopyrrolidin-3-yl)-6-(1-methyl-1H-pyrazol-4-yl)imidazo[1,2-a]pyridine-2-carboxamide
(R)—N-(1-cyanopyrrolidin-3-yl)-6-(1,3-dimethyl-1H-pyrazol-4-yl)imidazo[1,2-a]pyridine-2-carboxamide
(R)—N-(1-cyanopyrrolidin-3-yl)-5-(1-methyl-1H-pyrazol-4-yl)-1H-indazole-3-carboxamide
(R)—N-(1-cyanopyrrolidin-3-yl)-6-(1-methyl-1H-pyrazol-4-yl)-1H-indazole-3-carboxamide
(R)—N-(1-cyanopyrrolidin-3-yl)-6-(3,5-dimethylisoxazol-4-yl)-1H-indole-2-carboxamide
(R)—N-(1-cyanopyrrolidin-3-yl)-6-(1,3-dimethyl-1H-pyrazol-4-yl)-1H-indole-2-carboxamide
(R)—N-(1-cyanopyrrolidin-3-yl)-5-(1-methyl-1H-pyrazol-4-yl)-1H-indole-2-carboxamide
(R)—N-(1-cyanopyrrolidin-3-yl)-2,3-difluoro-4-(1-methyl-1H-pyrazol-4-yl)benzamide
(R)—N-(1-cyanopyrrolidin-3-yl)-5-(1-ethyl-1H-pyrazol-4-yl)-4-methylpicolinamide
(R)—N-(1-cyanopyrrolidin-3-yl)-3-phenoxyazetidine-1-carboxamide
(R)-3-(1H-benzo[d]imidazol-2-yl)-N-(1-cyanopyrrolidin-3-yl)azetidine-1-carboxamide
(R)—N-(1-cyanopyrrolidin-3-yl)-4-phenylpiperazine-1-carboxamide
N—((R)-1-cyanopyrrolidin-3-yl)-2-phenylmorpholine-4-carboxamide
(R)-4-(2-chloro-6-fluorobenzyl)-N-(1-cyanopyrrolidin-3-yl)-1,4-diazepane-1-carboxamide
(R)-4-benzyl-N-(1-cyanopyrrolidin-3-yl)-1,4-diazepane-1-carboxamide
(R)—N-(1-cyanopyrrolidin-3-yl)-1,3,4,9-tetrahydro-2H-pyrido[3,4-b]indole-2-carboxamide
N—((R)-1-cyanopyrrolidin-3-yl)-2-((2S,6R)-2,6-dimethylmorpholino)-5-fluoroisonicotinamide
(R)—N-(1-cyanopyrrolidin-3-yl)-5-fluoro-2-(isoindolin-2-yl)isonicotinamide
(R)—N-(1-cyanopyrrolidin-3-yl)-3-fluoro-4-(pyrimidin-2-ylamino)benzamide
(R)—N-(1-cyanopyrrolidin-3-yl)-2-fluoro-4-(pyrrolidin-1-yl)benzamide
(R)—N-(1-cyanopyrrolidin-3-yl)-2,5-difluoro-4-morpholinobenzamide
(R)—N-(1-cyanopyrrolidin-3-yl)-2,5-difluoro-4-(pyrrolidin-1-yl)benzamide
N—((R)-1-cyanopyrrolidin-3-yl)-2-fluoro-4-((R)-3-methoxypyrrolidin-1-yl)benzamide
(R)—N-(1-cyanopyrrolidin-3-yl)-3-methoxy-4-(pyrimidin-2-ylamino)benzamide
(R)—N-(1-cyanopyrrolidin-3-yl)-3-methoxy-4-((4-methylpyrimidin-2-yl)amino)benzamide
(R)—N-(1-cyanopyrrolidin-3-yl)-2-fluoro-4-((4-methoxypyrimidin-2-yl)amino)benzamide
N—((R)-1-cyanopyrrolidin-3-yl)-5-methyl-1-(1-phenylethyl)-1H-pyrazole-3-carboxamide
(R)—N-(1-cyanopyrrolidin-3-yl)-5-methyl-1-(pyridin-2-ylmethyl)-1H-pyrazole-3-carboxamide
(R)—N-(1-cyanopyrrolidin-3-yl)-2-fluoro-4-(pyridazin-4-yl)benzamide
(R)—N-(1-cyanopyrrolidin-3-yl)-1-isobutyl-6-(1-methyl-1H-pyrazol-4-yl)-1H-indazole-3-carboxamide
(R)—N-(1-cyanopyrrolidin-3-yl)-6-(3,5-dimethylisoxazol-4-yl)-1-isobutyl-1H-indazole-3-carboxamide
(R)—N-(1-cyanopyrrolidin-3-yl)-1-(cyclopropylmethyl)-6-(3,5-dimethylisoxazol-4-yl)-1H-indazole-3-carboxamide
(R)—N-(1-cyanopyrrolidin-3-yl)-N-methyl-6-(1-methyl-1H-pyrazol-4-yl)imidazo[1,2-a]pyridine-2-carboxamide
(R)—N-(1-cyanopyrrolidin-3-yl)-N-methyl-5-(1-methyl-1H-pyrazol-4-yl)-1H-indole-2-carboxamide
(R)—N-(-cyanopyrrolidin-3-yl)-6-(3,5-dimethylisoxazol-4-yl)-N-methyl-1H-benzo[d]imidazole-2-carboxamide
(R)—N-(1-cyanopyrrolidin-3-yl)-7-(1-methyl-1H-pyrazol-4-yl)imidazo[1,2-a]pyridine-3-carboxamide
(R)-7-(3-cyanophenyl)-N-(1-cyanopyrrolidin-3-yl)imidazo[1,2-a]pyridine-3-carboxamide
(R)—N-(1-cyanopyrrolidin-3-yl)-N-methyl-7-(2-methylpyridin-4-yl)imidazo[1,2-a]pyridine-3-carboxamide
(R)—N-(1-cyanopyrrolidin-3-yl)-N-methyl-7-(6-methylpyridin-3-yl)imidazo[1,2-a]pyridine-3-carboxamide
(R)—N-(1-cyanopyrrolidin-3-yl)-7-(1,33-dimethyl-1H-pyrazol-4-yl)-N-methylimidazo[1,2-a]pyridine-3-carboxamide
(R)—N-(1-cyanopyrrolidin-3-yl)-7-(2,6-dimethylpyridin-4-yl)-N-methylimidazo[1,2-a]pyridine-3-carboxamide
(R)—N-(1-cyanopyrrolidin-3-yl)-N-ethyl-7-(2-methylpyridin-4-yl)imidazo[1,2-a]pyridine-3-carboxamide
(R)—N-(1-cyanopyrrolidin-3-yl)-7-morpholinoimidazo[1,2-a]pyridine-3-carboxamide
(R)-6-(3-cyanophenyl)-N-(1-cyanopyrrolidin-3-yl)-3-fluoroimidazo[1,2-a]pyridine-2-carboxamide
(R)—N-(1-cyanopyrrolidin-3-yl)-3-fluoro-6-(1-methyl-1H-pyrazol-4-yl)imidazo[1,2-a]pyridine-2-carboxamide
(R)—N-(1-cyanopyrrolidin-3-yl)-6-(1-ethyl-1H-pyrazol-4-yl)-3-fluoroimidazo[1,2-a]pyridine-2-carboxamide
(R)—N-(1-cyanopyrrolidin-3-yl)-6-(1,3-dimethyl-1H-pyrazol-4-yl)-3-fluoroimidazo[1,2-a]pyridine-2-carboxamide
(R)—N-(1-cyanopyrrolidin-3-yl)-6-(3,5-dimethylisoxazol-4-yl)-3-fluoroimidazo[1,2-a]pyridine-2-carboxamide
(R)—N-(1-cyanopyrrolidin-3-yl)-2-fluoro-4-(pyrazolo[1,5-a]pyrimidin-5-yl)benzamide
(R)—N-(1-cyanopyrrolidin-3-yl)-5-(4-fluorophenyl)picolinamide
N-((2R,3R)-1-cyano-2-methylpyrrolidin-3-yl)-5-(4-fluorophenyl)picolinamide
3-chloro-N-((3R,4S)-1-cyano-4-methylpyrrolidin-3-yl)-4-morpholinobenzamide
N-((3R,4R)-1-cyano-4-fluoropyrrolidin-3-yl)-[1,1'-biphenyl]-4-carboxamide
N-((3R,4R)-1-cyano-4-cyclopropylpyrrolidin-3-yl)-3-fluoro-4-(1-methyl-1H-pyrazol-4-yl)benzamide
N-((3S,4S)-1-cyano-4-methoxypyrrolidin-3-yl)-N-methyl-4-(1-methyl-1H-pyrazol-4-yl)benzamide
(R)—N-(1-cyanopyrrolidin-3-yl)-5-(1,3-dimethyl-1H-pyrazol-4-yl)picolinamide
(R)—N-(1-cyanopyrrolidin-3-yl)-5-(2-methyl-6-(trifluoromethyl)pyrimidin-4-yl)picolinamide
(R)—N-(1-cyanopyrrolidin-3-yl)-4-(2,6-dimethylpyrimidin-4-yl)-2-fluorobenzamide
(R)—N-(1-cyanopyrrolidin-3-yl)-2-fluoro-4-(5-fluoro-2-methylpyrimidin-4-yl)benzamide
(R)—N-(1-cyanopyrrolidin-3-yl)-2-fluoro-4-(2-(trifluoromethyl)pyrimidin-4-yl)benzamide
(R)—N-(1-cyanopyrrolidin-3-yl)-2-fluoro-4-(2-methyl-3H-pyrrolo[2,3-d]pyrimidin-4-yl)benzamide
(R)—N-(1-cyanopyrrolidin-3-yl)-2-fluoro-4-(imidazo[1,2-a]pyrazin-3-yl)benzamide
(R)—N-(1-cyanopyrrolidin-3-yl)-3-fluoro-5-(pyrazolo[1,5-a]pyrimidin-5-yl)picolinamide
(R)—N-(1-cyanopyrrolidin-3-yl)-3-fluoro-5-(imidazo[1,2-a]pyridin-6-yl)picolinamide (R)—N-(1-cyanopyrrolidin-3-yl)-3-methoxy-3-phenylazetidine-1-carboxamide
(R)—N-(1-cyanopyrrolidin-3-yl)-N-methyl-3-phenylazetidine-1-carboxamide
(R)—N-(1-cyanopyrrolidin-3-yl)-3-(4-methoxyphenyl)azetidine-1-carboxamide
(R)-3-(4-chlorophenyl)-N-(1-cyanopyrrolidin-3-yl)azetidine-1-carboxamide
(R)-3-(3-chlorophenyl)-N-(1-cyanopyrrolidin-3-yl)azetidine-1-carboxamide
(3aR,6aR)-1-(3-phenylazetidine-1-carbonyl)hexahydropyrrolo[3,4-b]pyrrole-5 (1H)-carbonitrile
(R)-1-(1-cyanopyrrolidin-3-yl)-1-methyl-3-(4-(1-methyl-1H-pyrazol-4-yl)phenyl)urea
(R)-(1-(1-cyanopyrrolidin-3-yl)-1-methyl-3-(4-(trifluoromethyl)phenyl)urea
(3aR,6aR)-N-(4-chloro-2-fluorophenyl)-5-cyanohexahydropyrrolo[3,4-b]pyrrole-1(2H)-carboxamide
(3aR,6aR)-5-cyano-N-(2-fluoro-4-(trifluoromethoxy)phenyl)hexahydropyrrolo[3,4-b]pyrrole-1(2H)-carboxamide
(3aR,6aR)-5-cyano-N-(4-cyano-2-fluorophenyl)hexahydropyrrolo[3,4-b]pyrrole-1(2H)-carboxamide
(3aR,6aR)-5-cyano-N-(4-cyano-2,5-difluorophenyl)hexahydropyrrolo[3,4-b]pyrrole-1(2H)-carboxamide
(3aR,6aR)-N-(5-chloro-2-fluorophenyl)-5-cyanohexahydropyrrolo[3,4-b]pyrrole-1 (2H)-carboxamide
(3aR,6aR)-5-cyano-N-(2-fluoro-5-(trifluoromethyl)phenyl)hexahydropyrrolo[3,4-b]pyrrole-1(2H)-carboxamide
(3 aR, 6aR)-5-cyano-N-(5-phenylpyridin-2-yl)hexahydropyrrolo[3,4-b]pyrrole-1 (2H)-carboxamide
(3aR,6aR)-5-cyano-N-(4-(trifluoromethyl)phenyl)hexahydropyrrolo[3,4-b]pyrrole-1(2H)-carboxamide
(R)-1-(1-cyanopyrrolidin-3-yl)-1-ethyl-3-(4-(trifluoromethyl)phenyl)urea
1-(1-cyanopyrrolidin-3-yl)-1-(2-methoxyethyl)-3-(4-(trifluoromethyl)phenyl)urea
(R)—N-(1-cyanopyrrolidin-3-yl)-N-ethyl-3-fluoro-4-(-methyl-1H-pyrazol-4-yl)benzamide
(R)—N-(1-cyanopyrrolidin-3-yl)-N-ethyl-3-phenylazetidine-1-carboxamide
(R)-3-(2-oxo-3-(4-phenylthiazol-2-yl)imidazolidin-1-yl)pyrrolidine-1-carbonitrile
(R)-3-(2-oxo-3-(4-phenylthiazol-2-yl)tetrahydropyrimidin-1(2H)-yl)pyrrolidine-1-carbonitrile
(R)-3-(3-(3-morpholinophenyl)-2-oxoimidazolidin-1-yl)pyrrolidine-1-carbonitrile
(R)—N-(1-cyanopyrrolidin-3-yl)-4-(pyrimidin-2-yl)-3,4-dihydro-2H-benzo[b][1,4]oxazine-7-carboxamide
(R)—N-(1-cyanopyrrolidin-3-yl)-4-(4-cyclopropylpyrimidin-2-yl)-3,4-dihydro-2H-benzo[b][1,4]oxazine-7-carboxamide
(R)—N-(1-cyanopyrrolidin-3-yl)-4-((4-cyclopropylpyrimidin-2-yl)amino)-3-fluorobenzamide
(R)—N-(1-cyanopyrrolidin-3-yl)-4-((4-cyclopropylpyrimidin-2-yl)amino)-2,3-difluorobenzamide
(R)—N-(1-cyanopyrrolidin-3-yl)-4-(N-methylisobutyramido)picolinamide
(R)—N-(1-cyanopyrrolidin-3-yl)-[2,3'-bipyridine]-6'-carboxamide
(R)—N-(1-cyanopyrrolidin-3-yl)-[2,4'-bipyridine]-2'-carboxamide
(R)-3-(4-chlorophenyl)-N-(1-cyanopyrrolidin-3-yl)isoxazole-5-carboxamide
(R)—N-(1-cyanopyrrolidin-3-yl)-3-(4-(trifluoromethyl)phenyl)isoxazole-5-carboxamide
(R)—N-(1-cyanopyrrolidin-3-yl)-3-(3,4-dimethoxyphenyl)isoxazole-5-carboxamide
(R)—N-(1-cyanopyrrolidin-3-yl)-3-(3-methoxyphenyl)isoxazole-5-carboxamide
N—((R)-1-cyanopyrrolidin-3-yl)-1-phenylpyrrolidine-3-carboxamide
(R)—N-(1-cyanopyrrolidin-3-yl)-3-fluoro-4-(4-methyl-1H-imidazol-1-yl)benzamide
(R)—N-(1-cyanopyrrolidin-3-yl)-3-fluoro-N-methyl-4-(4-methyl-1H-imidazol-1-yl)benzamide
N—((R)-1-cyanopyrrolidin-3-yl)-3-(pyridin-2-yl)pyrrolidine-1-carboxamide
N—((R)-1-cyanopyrrolidin-3-yl)-3-(1-methyl-1H-pyrazol-4-yl)pyrrolidine-1-carboxamide
(R)—N-(1-cyanopyrrolidin-3-yl)-3-(2-methoxypyridin-4-yl)-N -methylisoxazole-5-carboxamide
(R)—N-(1-cyanopyrrolidin-3-yl)-2-fluoro-4-(N-methylphenylsulfonamido)benzamide
(R)—N-(1-cyanopyrrolidin-3-yl)-1-methyl-6-(1-methyl-1H-pyrazol-4-yl)-1H-indole-2-carboxamide
(R)—N-(1-cyanopyrrolidin-3-yl)-1-methyl-5-(1-methyl-1H-pyrazol-4-yl)-1H-indole-2-carboxamide
(R)-1-(1-cyanopyrrolidin-3-yl)-3-(2-(isoindolin-2-yl)pyridin-4-yl)-1-methylurea
(R)—N-(1-cyanopyrrolidin-3-yl)-3-fluoro-1-methyl -5-(1-methyl-1H-pyrazol -4-yl)-1H-indole-2-carboxamide
(R)—N-(1-cyanopyrrolidin-3-yl)-7-(1-methyl-1H-pyrazol-4-yl)imidazo[1,5-a]pyridine-3-carboxamide
(R)—N-(1-cyanopyrrolidin-3-yl)-3-(1-phenyl-1H-pyrazol-3-yl)azetidine -1-carboxamide
(R)—N-(1-cyanopyrrolidin-3-yl)-3-(1-(pyrazin-2-yl)-1H-pyrazol-3-yl)azetidine-1-carboxamide
(R)—N-(1-cyanopyrrolidin-3-yl)-3-(2-phenylpyrimidin-4-yl)azetidine-1-carboxamide
(R)-3-(2-(4-chlorophenyl)pyrimidin-4-yl)-N-(1-cyanopyrrolidin-3-yl)azetidine-1-carboxamide
(R)-3-(benzyloxy)-N-(1-cyanopyrrolidin-3-yl)-3-phenylazetidine-1-carboxamide
(R)—N-(1-cyanopyrrolidin-3-yl)-1-(4-cyclopropylpyrimidin-2-yl)indoline-5-carboxamide
(R)—N-(1-cyanopyrrolidin-3-yl)-1-(4-cyclopropylpyrimidin-2-yl)-N-methylindoline-5-carboxamide
(3aR,6aR)-5-cyano-N-(3-(2-methylpyridin-4-yl)phenyl)hexahydrpyrrolo[3,4-b]pyrrole-1(2H)-carboxamide
(3aR,6aR)-5-cyano-N -(4-(2-methylpyridin-4-yl)phenyl)hexahydropyrrolo[3,4-b]pyrrole-1(2H)-carboxamide
(3aR,6aR)-5-cyano-N-(2-fluoro-4-(2-methylpyridin-4-yl)phenyl)hexahydropyrrolo[3,4-b]pyrrole-1(2H)-carboxamide
(3aR,6aR)-5-cyano-N-(2'-methyl-[3,4'-bipyridin]-6-yl)hexahydropyrrolo[3,4-b]pyrrole-1(2H)-carboxamide
(3aR,6aR)-5-cyano-N-(2-fluoro-4-(1-methyl-1H-pyrazol-4-yl)phenyl)hexahydropyrrolo[3,4-b]pyrrole-1 (2H)-carboxamide
1-(3-phenyl-1H-pyrazole-5-carbonyl)hexahydropyrrolo[3,4-b]pyrrole-5 (1H)-carbonitrile
(3aR,6aR)-1-(3-phenoxyazetidine-1-carbonyl)hexahydropyrrolo[3,4-b]pyrrole-5 (1H)-carbonitrile
N-(1-cyanopiperidin-3-yl)-[1,1'-biphenyl]-3-carboxamide
1-(3-benzylphenyl)-3-(1-cyanopiperidin-3-yl)urea
1-(1-cyanopiperidin-3-yl)-3-(3-phenoxyphenyl)urea
1-(1-cyanopyrrolidin-3-yl)-3-(2,4-dichlorophenyl)urea
1-(1-cyanopyrrolidin-3-yl)-3-(4-(trifluoromethyl)phenyl)urea
1-(3-benzylphenyl)-3-(1-cyanopyrrolidin-3-yl)urea
1-([1,1'-biphenyl]-4-yl)-3-(1-cyanopyrrolidin-3-yl)urea
1-(1-cyanopyrrolidin-3-yl)-3-(3-phenoxyphenyl)urea
3-(3-benzylphenyl)-1-(1-cyanopyrrolidin-3-yl)-1-methylurea 3-(3-chlorophenyl)-1-(1-cyanopyrrolidin-3-yl)-1-methylurea
1-(1-cyanopyrrolidin-3-yl)-1-methyl-3-(3-phenoxyphenyl)urea
3-([1,1'-biphenyl]-4-yl)-1-(1-cyanopyrrolidin-3-yl)-1-methylurea
1-(1-cyanopyrrolidin-3-yl)-3-(2,4-dichlorophenyl)-1-methylurea
1-(1-cyanopyrrolidin-3-yl)-1-methyl-3-(4-(trifluoromethyl)phenyl)urea
(R)—N-(1-cyanopyrrolidin-3-yl)-6-(3,5-dimethylisoxazol-4-yl)-N-methyl-1H-indole-2-carboxamide
(R)—N-(1-cyanopyrrolidin-3-yl)-N-methyl-5-(1-methyl-1H-pyrazol-4-yl)-1H-pyrrolo[2,3-c]pyridine-2-carboxamide
N—((R)-1-cyanopyrrolidin-3-yl)-N-methyl-2-phenylmorpholine-4-carboxamide
(R)—N-(1-cyanopyrrolidin-3-yl)-N-methylindoline-1-carboxamide
(R)-1-(1-cyanopyrrolidin-3-yl)-1-methyl-3-(6-(trifluoromethyl)pyridin-3-yl)urea
(R)-3-(5-chloropyridin-2-yl)-1-(1-cyanopyrrolidin-3-yl)-1-methylurea
(3aR,6aR)-1-(3-chloro-4-morpholinobenzoyl)hexahydropyrrolo[3,4-b]pyrrole-5 (1H)-carbonitrile
(3aR,6aR)-1-(indoline-1-carbonyl)hexahydropyrrolo[3,4-b]pyrrole-5(1H)-carbonitrile
(R)—N-(1-cyanopyrrolidin-3-yl)-3-(2-methylpyridin-4-yl)isoxazole-5-carboxamide
(R)—N-(1-cyanopyrrolidin-3-yl)-3-(3,4-dimethylphenyl)isoxazole-5-carboxamide
(R)—N-(1-cyanopyrrolidin-3-yl)-3-(2,4-difluorophenyl)isoxazole-5-carboxamide
(R)—N-(1-cyanopyrrolidin-3-yl)-N -methyl-3-(2-methylpyridin-4-yl)isoxazole-5-carboxamide 9. A pharmaceutical composition comprising a compound of formula (I) as defined in any one of paragraphs 1 to 8 in combination with one or more pharmaceutically acceptable excipients.

10. A compound of formula (I) or a pharmaceutically acceptable salt thereof as defined in any one of paragraphs 1 to 8, or a composition as defined in claim 9, for use in therapy.

11. A compound of formula (I) or a pharmaceutically acceptable salt thereof as defined in any one of paragraphs 1 to 8, or a composition as defined in claim 9, for use in the treatment of a condition involving mitochondrial dysfunction.

12. A compound or composition for use according to paragraph 11, wherein the condition involving mitochondrial dysfunction is selected from a neurodegenerative disease; mitochondrial myopathy, encephalopathy, lactic acidosis, and stroke-like episodes (MELAS) syndrome; Leber's hereditary optic neuropathy (LHON); cancer; neuropathy, ataxia, retinitis pigmentosa-maternally inherited Leigh syndrome (NARP-MILS); Danon disease; diabetes; metabolic disorders; ischemic heart disease leading to myocardial infarction; psychiatric diseases, for example schizophrenia; multiple sulfatase deficiency (MSD); mucolipidosis II (ML II); mucolipidosis III (ML III); mucolipidosis IV (ML IV); GM1-gangliosidosis (GM1); neuronal ceroid-lipofuscinoses (NCL1); Alpers disease; Barth syndrome; Beta-oxidation defects; carnitine-acyl-carnitine deficiency; carnitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastrointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; and very long-chain acyl-CoA dehydrogenase (VLCAD) deficiency.

13. A compound or composition for use according to paragraph 11, wherein the condition involving mitochondrial dysfunction is a central nervous system disorder.

14. A compound of formula (I) or a pharmaceutically acceptable salt thereof as defined in any one of paragraphs 1 to 8, or a composition as defined in paragraph 9, for use in the treatment of a cancer.

15. A method of treatment or prevention of a condition involving mitochondrial dysfunction, or a cancer, the method comprising administering to a subject an effective amount of a compound defined in any one of paragraph 1 to 8, or a pharmaceutical composition according to paragraph 9.

16. A compound of formula (IA) or a pharmaceutically acceptable salt thereof, for use in the treatment of a condition involving mitochondrial dysfunction, or a cancer,

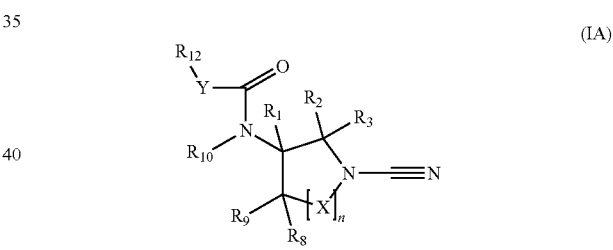

(IA)

wherein
n is 1 or 2;
when n is 1, X is $CR^4R^5$ and when n is 2, X is $CR^6R^7CR^R$ (wherein $CR^4R^5$ is adjacent to heterocycle N atom);
$R^2$ represents a hydrogen atom, cyano, an optionally substituted $C_1$-$C_6$ alkyl, an optionally substituted $C_1$-$C_6$ alkoxy group, an optionally substituted 4 to 10 membered heteroaryl, heterocyclyl, aryl or 3 to 8 membered cycloalkyl ring;
$R^1$, $R^3$, $R^4$ and $R^5$ each independently represent a hydrogen atom, cyano, an optionally substituted $C_1$-$C_3$ alkyl or an optionally substituted $C_1$-$C_3$ alkoxy group;
$R^6$, $R^7$ and $R^8$ each independently represent a hydrogen atom, a fluorine atom, cyano, an optionally substituted $C_1$-$C_3$ alkyl or an optionally substituted $C_1$-$C_3$ alkoxy group;
$R^9$ represents a hydrogen atom, a fluorine atom, cyano, an optionally substituted $C_1$-$C_6$ alkyl, an optionally substituted $C_1$-$C_3$ alkoxy group, an optionally substituted 4 to 10 membered heteroaryl, heterocyclyl, aryl or 3 to 8 membered cycloalkyl ring, or forms an optionally substituted heterocyclic ring with $R^{10}$ wherein the ring optionally comprises one or more additional heteroatoms;

$R^{10}$ represents a hydrogen atom, $C_{1-6}$ alkyl, or forms an optionally substituted heterocyclic ring with $R^9$ or $R^{11}$ wherein the ring optionally comprises one or more additional heteroatoms;

Y represents a covalent bond, $NR^{11}$ or optionally substituted $C_1$-$C_3$ alkyl;

$R^{11}$ represents a hydrogen atom, an optionally substituted $C_1$-$C_6$ alkyl, a 4 to 10 membered heteroaryl, heterocyclyl, aryl or 3 to 8 membered cycloalkyl ring, or forms an optionally substituted heterocyclic ring with $R^{10}$ wherein the ring optionally comprises one or more additional heteroatoms;

$R^{12}$ represents an optionally substituted 4 to 10 membered heteroaryl, heterocyclyl, aryl or 3 to 8 membered cycloalkyl ring.

The invention claimed is:

1. A compound of formula (II):

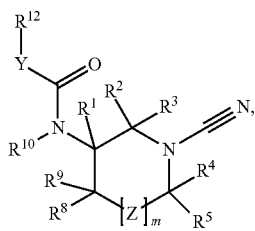

(II)

a tautomer thereof, or a pharmaceutically acceptable salt of said compound or tautomer, wherein:

m is 0 or 1;

when m is 1, Z is —$C(R^6)(R^7)$-;

$R^1$, $R^2$, $R^3$, $R^4$, $R^5$, $R^6$, $R^7$, $R^8$, and $R^9$, each independently represent hydrogen;

$R^{10}$ represents hydrogen or $C_{1-6}$ alkyl;

$R^{12}$ is selected from azetidinyl and pyrrolidinyl, and Y is a covalent bond which is attached to the nitrogen of the azetidinyl or pyrrolidinyl ring;

wherein $R^{12}$ is substituted with one -$Q^1$-$(R^{13})_p$, wherein:

p is 1;

$Q^1$ is selected from a covalent bond, an oxygen atom, —$NR^{14}$—, and $C_1$-$C_3$ alkylene;

$R^{14}$ represents hydrogen or $C_1$-$C_3$ alkyl;

$R^{13}$ represents phenyl;

wherein $R^{13}$ may be optionally substituted with one or more substituents selected from halogen, $C_1$-$C_6$ haloalkyl, $C_1$-$C_6$ alkoxy, $C_1$-$C_6$ haloalkoxy, $C_1$-$C_6$ alkyl, cyano, -$Q^2$-$COR^{17}$, $Q^2$-$CONR^{17}R^{18}$-$Q^2$-$CO_2R^{17}$ and cyclopropyl;

$Q^2$ represents a covalent bond; and $R^{17}$ and $R^{18}$ each independently represent hydrogen or $C_1$-$C_6$ alkyl.

2. The compound according to claim 1, wherein m is 0.

3. The compound according to claim 1, having the structure of formula (III)

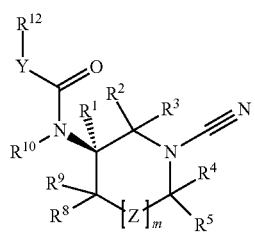

(III)

a tautomer thereof, or a pharmaceutically acceptable salt of said compound or tautomer.

4. A pharmaceutical composition comprising an effective amount of a compound according to claim 1, a tautomer thereof, or a pharmaceutically acceptable salt of said compound or tautomer, together with one or more pharmaceutically acceptable excipients.

* * * * *